(12) United States Patent
Shinde et al.

(10) Patent No.: US 11,109,595 B2
(45) Date of Patent: *Sep. 7, 2021

(54) MICROALGAE-BASED COMPOSITIONS FOR BENEFITING PLANTS AND METHODS OF APPLICATION

(71) Applicant: HELIAE DEVELOPMENT, LLC, Gilbert, AZ (US)

(72) Inventors: Sandip Shinde, Gilbert, AZ (US); Manikandadas Mathilakathu Madathil, Gilbert, AZ (US); Laura Carney, Chandler, AZ (US)

(73) Assignee: Heliae Development, LLC, Gilbert, AZ (US)

( * ) Notice: Subject to any disclaimer, the term of this patent is extended or adjusted under 35 U.S.C. 154(b) by 78 days.

This patent is subject to a terminal disclaimer.

(21) Appl. No.: 16/333,594

(22) PCT Filed: Sep. 15, 2017

(86) PCT No.: PCT/US2017/051678
§ 371 (c)(1),
(2) Date: Mar. 14, 2019

(87) PCT Pub. No.: WO2018/053211
PCT Pub. Date: Mar. 22, 2018

(65) Prior Publication Data
US 2020/0060283 A1 Feb. 27, 2020

Related U.S. Application Data

(60) Provisional application No. 62/395,178, filed on Sep. 15, 2016, provisional application No. 62/395,051, filed on Sep. 15, 2016, provisional application No. 62/395,061, filed on Sep. 15, 2016, provisional application No. 62/395,181, filed on Sep. 15, 2016, provisional application No. 62/395,182, filed on Sep. 15, 2016, provisional application No. 62/395,070, filed on Sep. 15, 2016, provisional application No. 62/395,072, filed on Sep. 15, 2016, provisional application No. 62/395,069, filed on Sep. 15, 2016, provisional application No. 62/395,066, filed on Sep. 15, 2016, provisional application No. 62/410,957, filed on Oct. 21, 2016, provisional application No. 62/410,931, filed on Oct. 21, 2016, provisional application No. 62/410,968, filed on Oct. 21, 2016, provisional application No. 62/410,949, filed on Oct. 21, 2016, provisional application No. 62/410,980, filed on Oct. 21, 2016, provisional application No. 62/411,131, filed on Oct. 21, 2016, provisional application No. 62/411,151, filed on Oct. 21, 2016, provisional application No. 62/410,942, filed on Oct. 21, 2016, provisional application No. 62/462,642, filed on Feb. 23, 2017, provisional application No. 62/462,684, filed on Feb. 23, 2017, provisional application No. 62/462,619, filed on Feb. 23, 2017, provisional application No. 62/462,608, filed on Feb. 23, 2017, provisional application No. 62/462,654, filed on Feb. 23, 2017.

(30) Foreign Application Priority Data

Jun. 16, 2017 (WO) ................ PCT/US2017/037878
Jun. 16, 2017 (WO) ................ PCT/US2017/037880

(51) Int. Cl.
*A01N 63/00* (2020.01)

(52) U.S. Cl.
CPC .................................. *A01N 63/00* (2013.01)

(58) Field of Classification Search
None
See application file for complete search history.

(56) References Cited

U.S. PATENT DOCUMENTS

| | | | |
|---|---|---|---|
| 4,863,955 A | 9/1989 | Moore | |
| 9,386,774 B2* | 7/2016 | Shinde | C12N 1/12 |
| 10,357,038 B2* | 7/2019 | Shinde | A01N 65/00 |
| 10,517,303 B2* | 12/2019 | Shinde | C12N 1/12 |
| 10,631,543 B2* | 4/2020 | Carney | A01G 22/05 |
| 10,645,937 B2* | 5/2020 | Carney | A01N 65/03 |
| 10,694,751 B2* | 6/2020 | Carney | A01N 63/30 |
| 10,701,941 B2* | 7/2020 | Carney | A01N 63/10 |
| 2014/0090431 A1* | 4/2014 | Blotsky | C05F 11/08 71/11 |

(Continued)

FOREIGN PATENT DOCUMENTS

| | | |
|---|---|---|
| CN | 102010829 | 4/2011 |
| CN | 102173922 | 9/2011 |

(Continued)

OTHER PUBLICATIONS

Kulik, et al, "The potential for Using Cyanobacteria (blue-green algae) and algae in the biological control of plant pathogenic bateria and funfi", Eurpean Journal of Plant Patho, Springer Netherlands, NL, vol. 101, No. 6, Jan. 1, 1995, pp. 585-599.

An-Dong Gong, et al, "The Shewanella algae strain TM8 Produces Volatiles with Strong Inhibition Activity Against *Aspergillus* Pathogens and Aflatoxins" Frontiers in Microbiology, vol. 6, Oct. 6, 2015.

Sowmyalakshmi, et al, "Extracts of the Marine Brown Macroalga, Ascophyllum Nodosum. Induce Jasmonic Acid Dependent Systemic Resistance in *Arabidopsis thaliana* Against *Pseudomonas syringae* pv. Tomato DC3000 and Sclerotinia Sclerotiorum" European Journal of Plant Pathology Kluwer Academic Publisher, CO, vol. 131, No. 2, May 21, 2011, pp. 237-248.

(Continued)

*Primary Examiner* — Alton N Pryor
(74) *Attorney, Agent, or Firm* — Heliae Development LLC; Adam Lunceford; Veronica-Adele R. Cao

(57) ABSTRACT

The invention relates to compositions and methods for improving characteristics of plants and soil by administering an effective amount of a microalgae-based composition in low concentration applications.

20 Claims, 14 Drawing Sheets

(56) References Cited

U.S. PATENT DOCUMENTS

2014/0298717 A1* 10/2014 Ayers .................. C05D 9/02
47/1.4

FOREIGN PATENT DOCUMENTS

| CN | 104987262 | | 10/2015 |
|---|---|---|---|
| CN | 105601452 | | 5/2016 |
| JP | 60069183 A | * | 4/1985 |
| RU | 2013149189 | | 5/2015 |
| RU | 2562544 C2 | * | 9/2015 |

OTHER PUBLICATIONS

De Mule et al, "Bioactive Compounds from Nostoc-Muscorum Cyanbacteria", Cytobios: The prestige Interntional Journal of Cell Biology, Cambridge, vol. 66, No. 266-267, Jan. 1, 1991, pp. 169-172.

Biondi et al, "Evaluation of Nostoc Strain ATCC 53789 as a Potential Source of Natural Pesticides", Applied and Environmental Microbiolofy, vol. 70, No. 6, Jun. 1, 2004, pp. 3313-3320.

Ramahandra et al, "Enchancement of Secondary Metabolite Production in Hairy Root Cultures of Beta Culgaris and Tagetes Patula under the Influence of Microalgal Elicitors", Food Biotechnology, Dekker, New York,NY, USA, vol. 15, No. 1, Jan. 1, 2001, pp. 35-46.

Hussain, et al, "RootColonization and Phytostimulation by Phytohormones Producing Entophytic *Nostoc* sp AH-12", Current Microbiology, Springer, Boston, vol. 67, No. 5, Oct. 31, 2013, pp. 624-630.

Issa et al, "Effect of Biological Treatments on Growth and Some Metabolic Activities of Barley Plants Gown in Saline Soil", Microbiological Research, Fischer, Jena, DE, vol. 149, No. 3, Jan. 1, 194, pp. 317-320.

Adan Treo et al, "Recycling Wast Debris of Immobilized Microalgae and Plant Growth-Promoting Bacteria from Wastewater Treatment as a Resource to Improce Fertility of Eroded Desert Soil", Environmnetal and Experimental Botany, Elsevier, Amsterdam,NL, vol. 75, Aug. 21, 2011, pp. 66-73.

Grzesik et al, "Improvements in Germination, Growth, and Metabolic Activity of Corn Seedlings b Grain Conditioning and Root Application with Cyanobacteria and Microalgae", Polish Journal of Environmental Studies, vol. 23, No. 4, 2014, pp. 1147-1153, p. 1149.

International Search Report of PCT/US2014/051678.

* cited by examiner

MICROALGAE-BASED COMPOSITIONS FOR BENEFITING PLANTS AND METHODS OF APPLICATION

CROSS REFERENCE TO RELATED APPLICATIONS

This application claims the benefit of International Patent Application PCT/US2017/037878, filed Jun. 16, 2017, entitled Microalgae-Based Composition, and Methods of its Preparation and Application to Plants: International Patent Application PCT/US2017/037880, filed Jun. 16, 2017, entitled Microalgae-Based Compositions for Benefiting Plants and Methods of Application; U.S. Provisional Application No. 62/395,178, filed Sep. 15, 2016, entitled Microalgae Based Composition for Benefiting Plants and Methods of Application; U.S. Provisional Application No. 62/410,931, filed Oct. 21, 2016, entitled Microalgae Based Compositions for Benefiting Plants and Methods of Application; U.S. Provisional Application No. 62/462,654, filed Feb. 23, 2017, entitled Microalgae Based Compositions for Benefiting Plants and Methods of Application; U.S. Provisional Application No. 62/395,051, filed Sep. 15, 2016, entitled Extracted *Chlorella* Oil and Biomass Compositions for Plants and Methods of Application; U.S. Provisional Application No. 62/462,684, filed Feb. 23, 2017, entitled Extracted *Chlorella* Oil and Biomass Compositions for Plants and Methods of Application; U.S. Provisional Application No. 62/395,061 filed Sep. 15, 2016, entitled *Galdieria* Based Compositions for Plants and Methods of Application; U.S. Provisional Application No. 62/395,066 filed Sep. 15, 2016, entitled *Haematococcus* Whole Biomass and Extracted Oil Based Compositions for Plants and Methods of Applications; U.S. Provisional Application No. 62/395,069, filed Sep. 15, 2016, entitled *Isochrysis* Based Compositions for Plants and Methods of Application; U.S. Provisional Application No. 62/410,942 filed Oct. 21, 2016, entitled *Isochrysis* Based Composition for Plants and Methods of Application; U.S. Provisional Application No. 62/462,619, filed Feb. 23, 2017, entitled *Isochrysis* Based Compositions for Plants and Methods of Application; U.S. Provisional Application No. 62/395,181, filed Sep. 15, 2016, entitled *Nannochloropsis* Based Compositions for Plants and Methods of Application; U.S. Provisional Application No. 62/410,949, filed Oct. 21, 2016, entitled *Nannochloropsis* Based Compositions for Plants and Methods of Application; U.S. Provisional Patent Application No. 62/395,182, filed Sep. 15, 2016, entitled *Porphyridium* Based Compositions for Plants and Methods of Application; U.S. Provisional Patent Application No. 62/410,957, filed Oct. 21, 2016, entitled *Porphyridium* Based Compositions for Plants and Methods of Application; U.S. Provisional Patent Application No. 62/395,070, filed Sep. 15, 2016, entitled *Schizochytrium* Based Compositions for Plants and Methods of Application; U.S. Provisional Patent Application No. 62/410,968, filed Oct. 21, 2016, entitled *Schizochytrium* Based Compositions for Plants and Methods of Application; U.S. Provisional Patent Application No. 62/462,642, filed Feb. 23, 2017, entitled *Schizochytrium* Based Compositions for Plants and Methods of Application; U.S. Provisional Patent Application No. 62/395,072 filed Sep. 15, 2016, entitled *Tetraselmis* Based Compositions for Plants and Methods of Application; U.S. Provisional Patent Application No. 62/410,980 filed Oct. 21, 2016, entitled Pavlova Based Compositions for Benefiting Plants and Methods of Application; U.S. Provisional Patent Application No. 62/411,131, filed Oct. 21, 2016, entitled *Spirulina* Based Compositions for Benefiting Plants and Methods of Application; U.S. Patent Application No. 62/462,608, filed Feb. 23, 2017, entitled *Scenedesmus* Based Compositions for Benefiting Plants and Methods of Application and U.S. Patent Application No. 62/411,151, filed Oct. 21, 2016, entitled *Scenedesmus* Based Compositions for Benefiting Plants and Methods of Application. The entire contents of all of the foregoing applications are hereby incorporated by reference herein.

BACKGROUND

Seed emergence occurs as an immature plant breaks out of its seed coat, typically followed by the rising of a stem out of the soil. The first leaves that appear on many seedlings are the so-called seed leaves, or cotyledons, which often bear little resemblance to the later leaves. Shortly after the first true leaves, which are more or less typical of the plant, appear, the cotyledons will drop off Germination of seeds is a complex physiological process triggered by imbibition of water after possible dormancy mechanisms have been released by appropriate triggers. Under favorable conditions rapid expansion growth of the embryo culminates in rupture of the covering layers and emergence of the radical. A number of agents have been proposed as modulators of seed emergence. Temperature and moisture modulation are common methods of affecting seed emergence. Addition of nutrients to the soil has also been proposed to promote emergence of seeds of certain plants.

Additionally, whether at a commercial or home garden scale, growers are constantly striving to optimize the yield and quality of a crop to ensure a high return on the investment made in every growing season. As the population increases and the demand for raw plant materials goes up for the food and renewable technologies markets, the importance of efficient agricultural production intensifies. The influence of the environment on a plant's health and production has resulted in a need for strategies during the growth season which allow the plants to compensate for the influence of the environment and maximize production. Addition of nutrients to the soil or application to the foliage has been proposed to promote yield and quality in certain plants. The effectiveness can be attributable to the ingredients or the method of preparing the product. Increasing the effectiveness of a product can reduce the amount of the product needed and increase efficiency of the agricultural process. Therefore, there is a need in the art for methods of enhancing the yield and quality of plants and plant-associated soils.

SUMMARY

Compositions and methods are described herein improving at least one plant and/or soil characteristic. The compositions can include cells (i.e., biomass) or extracts from the microalgae in various states, such as but not limited to, cells with reduced protein content, whole cells, lysed cells, dried cells, excreted products (e.g., excreted polysaccharides [EPS]), extracted oil, extracted protein, cells that have been subjected to an oil or protein extraction process, and combinations thereof. In this respect, an "extract°" in the context of the invention can mean biomass that has been subjected to extraction of one or more fractions, such as one or more lipid fractions and/or it can mean a lipid fraction, a protein faction, or other fraction that has been extracted from "whole" biomass/cells. The composition can include microalgae derived products as the primary or sole active ingredient, or in combination with other active ingredients such as, but not limited to, extracts or biomass from macroalgae (e.g., kelp such as *Ascophyllum nodosum, Kappaphycus alvarezii*, or one or more extracts thereof). The compositions can be in the form of a liquid or dry form (powder, or the like). The compositions can be stabilized through the addition of stabilizers suitable for plants, pasteurization, and combinations thereof. The methods can include applying the compositions to plants or seeds in a variety of methods, such as but not limited to, soil application, foliar application, seed treatments (such as seed coating), and/or hydroponic application. The methods can include single or multiple applications of the compositions, and can also include low concentrations of microalgae cells (i.e., biomass), excreted products, or extracts.

In one non-limiting embodiment, a method of plant enhancement can include administering to a plant, seedling, or seed a composition treatment comprising 0.001-0.1% by weight of microalgae biomass to enhance at least one plant characteristic, which in some embodiments is whole microalgae biomass. "Whole microalgae biomass" means a composition wherein substantially all of the components of the microalgae cells produced in the composition during culturing/growth remain present (e.g., in certain aspects of the invention at least about 90"o of the cellular components, at least about 95% of the cellular components, or at least about 99% of the cellular components produced during growth/culturing remain present). This kind of composition ("whole microalgae biomass") is distinct from, for example, a composition formed from an extract taken from a microalgae composition, which might be composed primarily or entirely of one or more microalgae-derived oils or proteins.

"Microalgae biomass" means any composition wherein a majority of the cellular components of the whole microalgae biomass are maintained in the composition (by number of components, but not necessarily by weight). Thus, for example, a collection of microalgae cells that is subjected to an oil extraction would be considered microalgae biomass, but not be considered whole microalgae biomass. A microalgae biomass subjected to processing to remove one or more of its cellular components also may be referred to as a "post-extraction microalgae biomass".

In some embodiments, the composition can be applied when the plant is under at least one of salt stress and temperature stress conditions. In some embodiments, the microalgae biomass can have been subjected to a protein extraction process. In some embodiments, the microalgae biomass can have been subjected to an oil extraction process. In some embodiments, the microalgae can include at least one from the group consisting of *Botryococcus, Scenedesmus, Pavlova, Phaeodactylum, Nannochloropsis, Spirulina, Galdieria, Haematococcus, Isochrysis, Porphyridium, Schizochytrium*, and *Tetraselmis*.

In another non-limiting embodiment, a composition can include microalgae biomass, in a concentration in the range of 0.001-0.1% by weight. For sake of illustration, a composition can have a microalgae biomass concentration within a narrower range of concentrations such as 0.002%-0.09%, such as 0.003%-0.085%, 0.004%-0.08%, 0.005%-0.075%, 0.0075%-0.075%, 0.008%-0.08%, 0.009%-0.09%, 0.01%-0.1%, 0.015%-0.09%, 0.02%-0.08%, 0.025%-0.075%, or any similar amount within these ranges such as a range with a lower end of 0.001%, 0.003%, 0.005%>, 0.007%, 0.009%, 0.01%, 0.02%, 0.03%, 0.04%, or 0.05% and an upper end of the range of 0.1%, 0.09%, 0.085%, 0.08%, 0.075%, 0.07%, or 0.05%.

In another non-limiting embodiment, a method of preparing a composition can include diluting the concentration of microalgae biomass to a concentration in the range of 0.001-0.1<% by weight or that is within the range 0.002%-0.09%, such as 0.003%-0.085%, 0.004%-0.08%, 0.005%-0.075%, 0.0075%-0.075%, 0.008%-0.08%, 0.009%-0.09%, 0.01%-0.1%, 0.015%-0.09%, 0.02%-0.08%, 0.025%-0.075%, or any similar amount within these ranges such as a range with a lower end of 0.001%, 0.003%, 0.005%, 0.007%, 0.009%, 0.01%, 0.02%, 0.03%, 0.04%, or 0.05% and an upper end of the range of 0.1%, 0.09%, 0.085%, 0.08%, 0.075%, 0.07%, or 0.05%.

In another non-limiting embodiment, a method of preparing a composition can include: subjecting microalgae cells to an oil extraction process; separating the extracted oil from the extracted biomass; and diluting the concentration of extracted biomass to a concentration in the range of 0.001-0.1% by weight or that is in a range such as 0.002%-0.09%, such as 0.003%-0.085%, 0.004%-0.08%, 0.005%-0.075%, 0.0075%-0.075%, 0.008%-0.08%, 0.009%-0.09%, 0.01%-0.1%, 0.015%-0.09%, 0.02%-0.08%, 0.025%-0.075%, or any similar amount within these ranges such as a range with a lower end of 0.001%, 0.003%, 0.005%, 0.007%, 0.009%, 0.01%, 0.02%, 0.03%, 0.04%, or 0.05% and an upper end of the range of 0.1%, 0.09%, 0.085%, 0.08%, 0.075%, 0.07%, or 0.05%.

In one non-limiting embodiment, a method of plant enhancement can include administering to a plant, seedling, or seed a composition treatment comprising 0.0001-0.01% by weight of extracted microalgae oil (or in one of the narrower ranges described above, such as 0.001-0.01%, 0.005-0.01%, 0.0075-0.01%, or 0.009-0.01%) to enhance at least one plant characteristic. In some embodiments, the composition can be applied when the plant is under at least one of salt stress and temperature stress conditions. In some embodiments, the microalgae cells can have a low protein content. In some embodiments, the microalgae can include at least one from the group consisting of *Botryococcus, Scenedesmus, Pavlova, Phaeodactylum, Spirulina, Galdieria, Chlorella, Haematococcus, Isochrysis, Nannochloropsis, Porphyridium, Schizochytrium*, and *Tetraselmis*.

In another non-limiting embodiment, a composition can include extracted microalgae oil, in a concentration in the range of 0.0001-0.01% by weight (or one of the other ranges described above).

In another non-limiting embodiment, a method of preparing a composition can include: subjecting microalgae cells to an oil extraction process; separating the extracted oil from the extracted biomass; and diluting the concentration of extracted oil to a concentration in the range of 0.0001-0.01% by weight (or one of the narrower ranges described above).

In one non-limiting embodiment, a method of plant enhancement can include administering to a plant, seedling, or seed, or to soil associated with the plant (or another medium associated with the plant, such as a hydroponic medium), a composition treatment comprising 0.001-0.1% by weight of extracted microalgae protein from at least one from the group consisting of *Galdieria, Porphyridium*, and *Spirulina* to enhance at least one plant characteristic. In some embodiments, the composition can be applied when the plant is under at least one of salt stress and temperature stress conditions.

In another non-limiting embodiment, a composition can include extracted microalgae protein, in a concentration in the range of 0.001-0.1% by weight or in one of the narrower ranges provided above such as 0.002%-0.090% such as 0.003%-0.085%, 0.004%-0.08%>, 0.005%-0.075%, 0.0075%-0.075%, 0.008%-0.08%, 0.009%-0.09%, 0.01%-0.1%, 0.015%-0.09%, 0.02%-0.08%, 0.025%-0.075%, or any similar amount within these ranges such as a range with a lower end of 0.001%, 0.003%, 0.005%, 0.007%, 0.009%, 0.01%, 0.02%, 0.03%, 0.04%, or 0.05% and an upper end of the range of 0.1%, 0.09%, 0.085%, 0.08%, 0.075%, 0.07%, or 0.05%.

In another non-limiting embodiment, a method of preparing a composition can include: subjecting microalgae cells to a protein extraction process; separating the extracted protein fraction; and diluting the concentration of extracted protein fraction to a concentration in the range of 0.001-0.1% by weight or one of the narrower ranges provided above.

In one non-limiting embodiment, a method of plant enhancement can include administering to a plant, seedling, or seed a composition treatment comprising 0.001-0.1% by weight of EPS from *Porphyridium* (or a concentration such as 0.002%-0.09%, such as 0.003%-0.085%, 0.004%-0.08%, 0.005%-0.075%, 0.0075%-0.075%, 0.008%-0.08%, 0.009%-0.09%, 0.01%-0.1%, 0.015%-0.09%, 0.02%-0.08%, 0.025%-0.075%, or any similar amount within these ranges such as a range with a lower end of 0.001%, 0.003%, 0.005%, 0.007%, 0.009%, 0.01%, 0.02%, 0.03%, 0.04%, or 0.05% and an upper end of the range of 0.1%, 0.09%, 0.085%, 0.08%, 0.075%, 0.07%, or 0.05%) to enhance at least one plant and/or soil characteristic. In some embodiments, the composition can be applied when the plant is under at least one of salt stress and temperature stress conditions.

In another non-limiting embodiment, a composition can include EPS from *Porphyridium*, in a concentration in the range of 0.001-0.1% by weight or one of the narrower ranges described elsewhere herein.

In another non-limiting embodiment, a method of preparing a composition can include: isolating EPS from a culture of *Porphyridium*; and diluting the concentration of isolated EPS to a concentration in one of the disclosed ranges provided herein, such as in the range of 0.001-0.1% by weight.

In another non-limiting embodiment, a method of plant enhancement can include administering to a plant, seedling, or a seed a composition treatment comprising 10% by weight of microalgae biomass to soil at an application rate in the range of 0.5-20 liters per acre to enhance at least one plant and/or soil characteristic. In an exemplary embodiment, the application rate can be in the range of 3.7 to 15 liters per acre. In some embodiments, the microalgae can comprise at least one microalgae from the group consisting of *Aurantiachytrium, Spirulina, Isachrysis*, and *Scenedesmus*.

DETAILED DESCRIPTION

Figure 1:
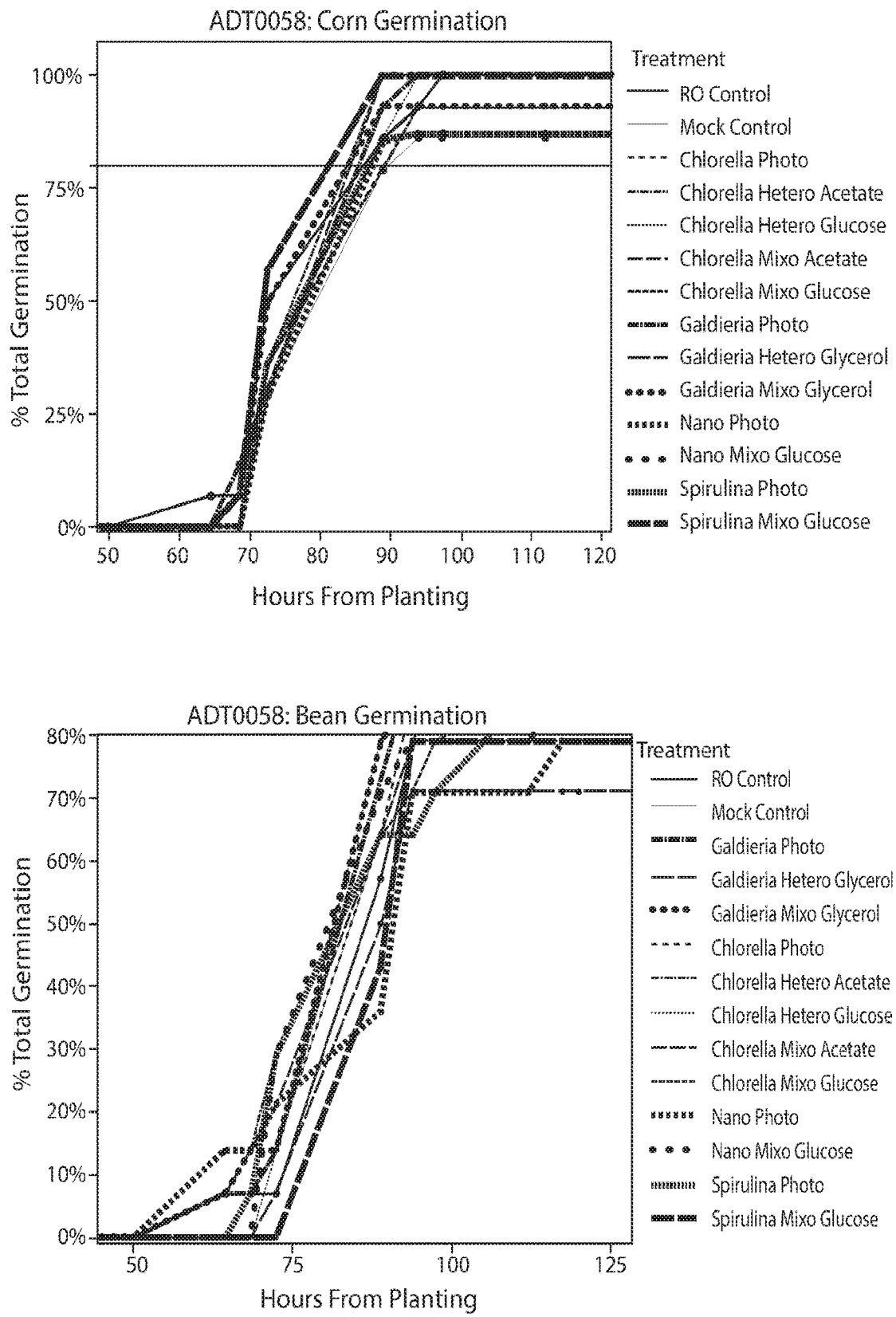
FIG. 1 depicts results of experiments involving microalgae-based compositions on corn, bean and pepper seed germination.
Figure 1:
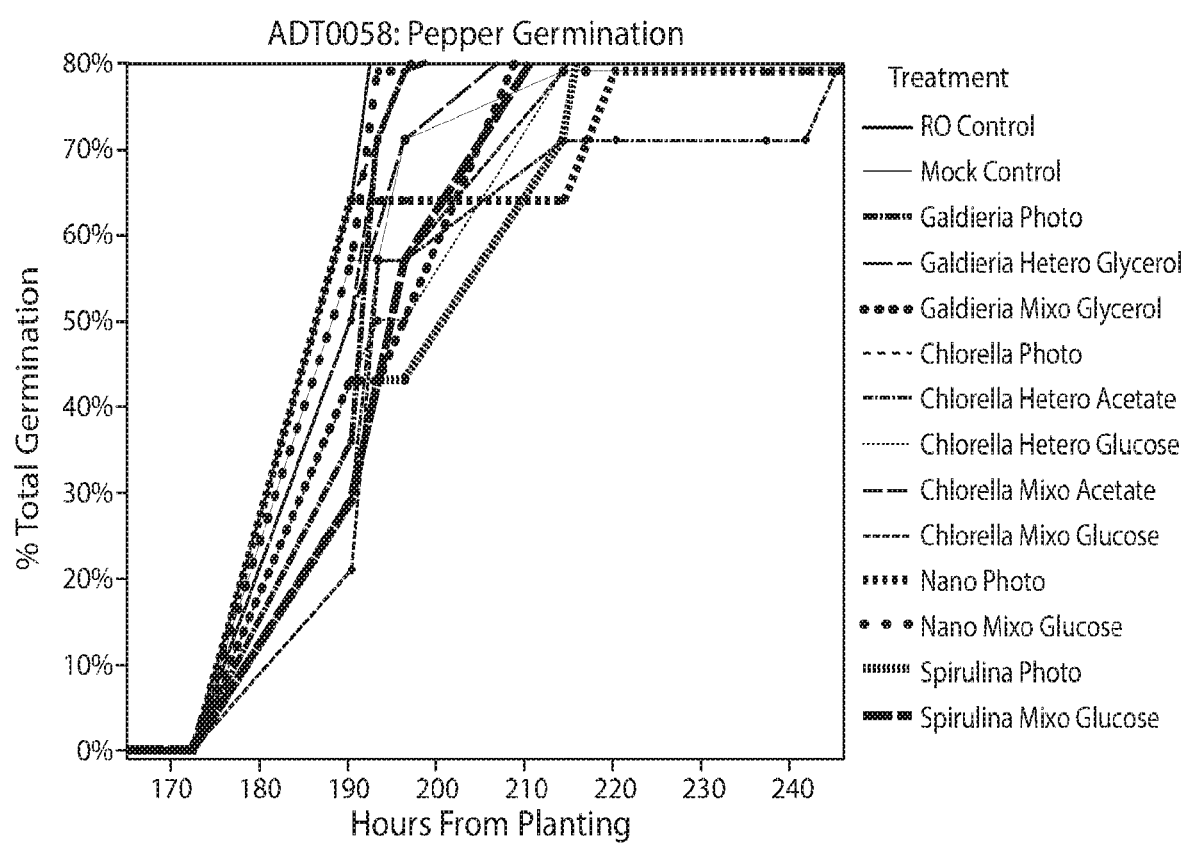

Many plants can benefit from the application of liquid compositions that provide a bio-stimulatory effect. Non-limiting examples of plant families that can benefit from such compositions include plants from the following: Solanaceae, Fabaceae (Leguminosae), Poaceae, Roasaceae, Vitaceae, Brassicaeae (Cruciferae), Caricaceae, Malvaceae, Sapindaceae, Anacardiaceae, Rutaceae, Moraceae, Convolvulaceae, Lamiaceae, Verbenaceae, Pedaliaceae, Asteraceae (Compositae), Apiaceae (Umbelliferae), Araliaceae, Oleaceae, Ericaceae, Actinidaceae, Cactaceae, Chenopodiaceae, Polygonaceae, Theaceae, Lecythidaceae, Rubiaceae, Papveraceae, Illiciaceae Grossulariaceae, Myrtaceae, Juglandaceae, Bertulaceae, Cucurbitaceae, Asparagaceae (Liliaceae), Alliaceae (Liliceae), Bromeliaceae, Zingieraceae, Muscaceae, Areaceae, Dioscoreaceae, Myristicaceae, Annonaceae, Euphorbiaceae, Laurasia, Piperaceae, and Proteaceae. A biostimulatory effect can mean an effect that results directly in promotion of plant growth, plant quality, plant health, plant pest and/or disease resistance, plant productivity, and/or plant longevity, or that results in the promotion of organisms in the plant microbiome, such as beneficial bacteria in the soil, either directly or through improving one or more physical characteristics of the soil. A biostimulatory effect can arise from the direct administration of products to plants, such as by foliar application to leaves, or indirectly through administration of products to soil to improve the environment of the plant (thereby indirectly providing benefits to the plant) and/or to result in uptake of the composition or elements of the composition by the plants to promote one or more detectable, desirable and/or beneficial biological effects/results.

The Solanaceae plant family includes a large number of agricultural crops, medicinal plants, spices, and ornamentals in it's over 2,500 species. Taxonomically classified in the Plantae kingdom, Tracheobionta (subkingdom), Spermatophyta (superdivision), Magnoliophyta (division), Manoliopsida (class), Asteridae (subclass), and Solanales (order), the Solanaceae family includes, but is not limited to, potatoes, tomatoes, eggplants, various peppers, tobacco, and petunias. Plants in the Solanaceae can be found on all the continents, excluding *Antarctica*, and thus have a widespread importance in agriculture across the globe.

The Fabaceae plant family (also known as the Leguminosae) comprises the third largest plant family with over 18,000 species, including a number of important agricultural and food plants. Taxonomically classified in the Plantae kingdom, Tracheobionta (subkingdom), Spermatophyta (superdivision), Magnoliophyta (division), Manoliopsida (class), Rosidae (subclass), and Fabales (order), the Fabaceae family includes, but is not limited to, soybeans, beans, green beans, peas, chickpeas, alfalfa, peanuts, sweet peas, carob, and liquorice. Plants in the Fabaceae family can range in size and type, including but not limited to, trees, small annual herbs, shrubs, and vines, and typically develop legumes. Plants in the Fabaceae family can be found on all the continents, excluding Antarctica, and thus have a widespread importance in agriculture across the globe. Besides food, plants in the Fabaceae family can be used to produce natural gums, dyes, and ornamentals.

The Poaceae plant family supplies food, building materials, and feedstock for fuel processing. Taxonomically classified in the Plantae kingdom, Tracheobionta (subkingdom), Spermatophyta (superdivision), Magnoliophyta (division), Liliopsida (class), Commelinidae (subclass), and Cyperales (order), the Poaceae family includes, but is not limited to, flowering plants, grasses, and cereal crops such as barely, corn, lemongrass, millet, oat, rye, rice, wheat, sugarcane, and sorghum. Types of turf grass found in Arizona include, but are not limited to, hybrid Bermuda grasses (e.g., 328 tifgrn, 419 tifway, tif sport).

The Rosaceae plant family includes flowering plants, herbs, shrubs, and trees. Taxonomically classified in the Plantae kingdom, Tracheobionta (subkingdom), Spermatophyta (superdivision), Magnoliophyta (division), Magnoliopsida (class), Rosidae (subclass), and Rosales (order), the Rosaceae family includes, but is not limited to, almond, apple, apricot, blackberry, cherry, nectarine, peach, plum, raspberry, strawberry, and quince.

The Vitaceae plant family includes flowering plants and vines. Taxonomically classified in the Plantae kingdom, Tracheobionta (subkingdom), Spermatophyta (superdivision), Magnoliophyta (division), Magnoliopsida (class), Rosidae (subclass), and Rhammales (order), the Vitaceae family includes, but is not limited to, grapes.

Particularly important in the production of fruit from plants is the beginning stage of growth where the plant emerges and matures into establishment. A method of treating a seed, seedling, or plant to directly improve the germination, emergence, and maturation of the plant; or to indirectly enhance the microbial soil community surrounding the seed or seedling is therefore valuable starting the plant on the path to marketable production. The standard typically used for assessing emergence is the achievement of the hypocotyl stage, where a stem is visibly protruding from the soil. The standard typically used for assessing maturation is the achievement of the cotyledon stage, where two leaves visibly form on the emerged stem.

Also important in the production of fruit from plants is the yield and quality of fruit, which can be quantified as the number, weight, color, firmness, ripeness, moisture, degree of insect infestation, degree of disease or rot, and degree of sunburn of the fruit. A method of treating a plant to directly improve the characteristics of the plant, or to indirectly enhance the chlorophyll level of the plant for photosynthetic capabilities and health of the plant's leaves, roots, and shoot to enable robust production of fruit is therefore valuable in increasing the efficiency of marketable production. Marketable and unmarketable designations can apply to both the plant and fruit, and can be defined differently based on the end use of the product, such as but not limited to, fresh market produce and processing for inclusion as an ingredient in a composition. The marketable determination can assess such qualities as, but not limited to, color, insect damage, blossom end rot, softness, and sunburn. The term total production can incorporate both marketable and unmarketable plants and fruit. The ratio of marketable plants or fruit to unmarketable plants or fruit can be referred to as utilization and expressed as a percentage. The utilization can be used as an indicator of the efficiency of the agricultural process as it shows the successful production of marketable plants or fruit, which will be obtain the highest financial return for the grower, whereas total production will not provide such an indication.

To achieve such improvements in emergence, maturation, and yield of plants, a method to treat such seeds and plants, and soil, a low concentration microalgae based composition, in a dried or liquid solution form, was developed. Microalgae can be grown in heterotrophic, mixotrophic, and phototrophic conditions. Culturing microalgae in heterotrophic conditions comprises supplying organic carbon (e.g., acetic acid, acetate, glucose) to cells in an aqueous culture medium comprising trace metals and nutrients (e.g., nitrogen, phosphorus). Culturing microalgae in mixotrophic conditions comprises supplying light and organic carbon (e.g., acetic acid, acetate, glucose) to cells in an aqueous culture medium comprising trace metals and nutrients (e.g., nitrogen, phosphorus). Culturing microalgae in phototrophic conditions comprises supplying light and inorganic carbon (e.g., carbon dioxide) to cells in an aqueous culture medium comprising trace metals and nutrients (e.g., nitrogen, phosphorus).

In some embodiments, the microalgae cells can be harvested from a culture and used as whole cells in a liquid composition for application to seeds and plants, while in other embodiments the harvested microalgae cells can be subjected to downstream processing and the resulting biomass or extract can be used in a dried composition (e.g., powder, pellet) or a liquid composition (e.g., suspension, solution) for application to plants, soil, or a combination thereof. Non-limiting examples of downstream processing comprise: drying the cells, lysing the cells, and subjecting the harvested cells to a solvent or supercritical carbon dioxide extraction process to isolate an oil or protein. In some embodiments, the extracted (i.e., residual) biomass remaining from an extraction process can be used alone or in combination with other microalgae or extracts in a liquid composition for application to plants, soil, or a combination thereof. By subjecting the microalgae to an extraction process the resulting biomass is transformed from a natural whole state to a lysed condition where the cell is missing a significant amount of the natural components, thus differentiating the extracted microalgae biomass from that which is found in nature. Excreted products from the microalgae can also be isolated from a microalgae culture using downstream processing methods.

In some embodiments, microalgae can be the dominate active ingredient source in the composition. In some embodiments, the microalgae population of the composition can include whole biomass, substantially extracted biomass, excreted products (e.g., EPS), extracted protein, or extracted oil. In some embodiments, microalgae include at least 99% of the active ingredient sources of the composition. In some embodiments, microalgae include at least 95% of the active ingredient sources of the composition. In some embodiments, microalgae include at least 90% of the active ingredient sources of the composition. In some embodiments, microalgae include at least 80% of the active ingredient sources of the composition. In some embodiments, microalgae include at least 70% of the active ingredient sources of the composition. In some embodiments, microalgae include at least 60% of the active ingredient sources of the composition. In some embodiments, microalgae include at least 50% of the active ingredient sources of the composition. In some embodiments, microalgae include at least 40% of the active ingredient sources of the composition. In some embodiments, microalgae include at least 30% of the active ingredient sources of the composition. In some embodiments, microalgae include at least 20% of the active ingredient sources of the composition. In some embodiments, microalgae include at least 10% of the active ingredient sources of the composition. In some embodiments, microalgae include at least 5% of the active ingredient sources of the composition. In some embodiments, microalgae include at least 1% of the active ingredient sources of the composition. In some embodiments, the composition lacks any detectable amount of any other active ingredient source other than microalgae. The term "substantially" herein means at least 95%, such as at least 96%, at least 97%, at least 98%, at least 99%, or more such as at least 99.2%, at least 99.5%, at least 99.75%, at least 99.8%, or at least 99.9%.

In some embodiments, microalgae biomass, excreted products, or extracts can also be mixed with biomass or extracts from other plants, microalgae, macroalgae, seaweeds, and kelp. In some embodiments, microalgae biomass, excreted products, or extracts can also be mixed with fish oil. Non-limiting examples of other plants, macroalgae, seaweeds, and kelp fractions that can be combined with microalgae cells can include species of *Lemna, Gracilaria, Kappaphycus, Ascophyllum, Macrocystis, Fucus, Laminaria, Sargassum, Turbinaria*, and *Durvilea*. In further embodiments, the extracts can comprise, but are not limited to, liquid extract from a species of *Kappaphycus*. In some embodiments, the extracts can include 50% or less by volume of the composition. In some embodiments, the extracts can include 40% or less by volume of the composition. In some embodiments, the extracts can include 30% or less by volume of the composition. In some embodiments, the extracts can include 20% or less by volume of the composition. In some embodiments, the extracts can include 10% or less by volume of the composition. In some embodiments, the extracts can include 5% or less by volume of the composition. In some embodiments, the extracts can include 4% or less by volume of the composition. In some embodiments, the extracts can include 3% or less by volume of the composition. In some embodiments, the extracts can include 2% or less by volume of the composition. In some embodiments, the extracts can include 1% or less by volume of the composition.

The term "microalgae" refers to microscopic single cell organisms such as microalgae, cyanobacteria, algae, diatoms, dinoflagelattes, freshwater organisms, marine organisms, or other similar single cell organisms capable of growth in phototrophic, mixotrophic, orheterotrophic culture conditions.

In some embodiments, microalgae biomass, excreted product, or extracts can also be sourced from multiple types of microalgae, to make a composition that is beneficial when applied to plants or soil. Non-limiting examples of microalgae that can be used in the compositions and methods of the present invention include microalgae m the classes: Eustigmatophyceae, Chlorophyceae, Prasinophyceae, Haptophyceae, Cyanidiophyceae, P. ymnesiophyceae, Porphyridiophyceae, Labyrinthulomycetes, Trebouxiophyceae, Bacillariophyceae, and Cyanophyceae. The class Lyanidiophyceae includes species of *Galdieria*. The class Chlorophyceae includes species of *Haematococcus, Scenedesmus, Chlamydomonas*, and *A4icractinium*. The class Prymnesiophyceae includes species of *Isochrysis* and Pavlova. The class Eustigmatophyceae includes species of *Nannochloropsis*. The class Porphyridiophyceae includes species of *Porphyridium*. The class Labyrinthulomycetes includes species of *Schizochytrium* and *Aurantiochytrium*. The class Prasinophyceae includes species of *Tetraselmis*. The class Trebouxiophyceae includes species of *Chlorella* and *Botlyococcus*. The class Bacillariophyceae includes species of *Phaeodactylum*. The class Cyanophyceae includes species of *Spirulina*.

Non-limiting examples of microalgae genus and species that can be used in the compositions and methods of the present invention include: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeeiformis* var. *tenuis, Amphora delicatissima, Amphora delicatissima* var. *capitata, Amphora* sp., *Anabaena, Ankistrodesmus, Ankistrodesmus falcatus, Aurantiochytrium* sp., *Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomonas* sp., *Chlamydomas perigranulata, Chlorella anitrata, Chlorella antarctica, Chlorella aureoviridis, Chlorella Candida, Chlorella capsulate, Chlorella desiccate, Chlorella ellipsoidea, Chlorella emersonii, Chlorella Jusca, Chlorella Jusca* var. *vacuolate, Chlorella glucotropha, Chlorella inJusionum, Chlorella inJusionum* var. *actophila, Chlorella inJusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris Jo. tertia, Chlorella vulgaris* var. *autotrophica, Chlorella vulgaris* var. *viridis, Chlorella vulgaris* var. *vulgaris, Chlorella vulgaris* var. *vulgaris Jo. tertia, Chlorella vulgaris* var. *vulgaris Jo. viridis, Chlorella xanthella, Chlorella zofingiensis, Chlorella trebouxioides, Chlorella vulgaris, Chlorococcum inJusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena* spp., *Franceia* sp., *Fragilaria crotonensis, Fragilaria* sp., *Galdieria* sp., *Gleocapsa* sp., *Gloeothamnion* sp., *Haematococcus pluvialis, Hymenomonas* sp., *Isochrysis af galbana, Isochrysis galbana, Lepocinclis, A4icractinium, Alonoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia*

*alexandrina, Nitzschia closterium, Nitzschia communis, Nitzschia dissipata, Nitzschia.frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricornutum, Phagus, Phormidium, Platymonas* sp., *Pleurochrysis camerae, Pleurochrysis dentate, Pleurochrysis* sp., *Porphyridium* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chlysophyte, Scenedesmus armatus, Schizochytrium, Spirogyra, Spirulina platensis, Stichococcus* sp., *Synechococcus* sp., *Synechocystisf, Tagetes erecta, Tagetes patula, Tetraedron, Tetraselmis* sp., *Tetraselmis suecica, Thalassiosira weis fiogii*, and *Viridiella fridericiana.*

Analysis of the DNA sequence of the strain of *Chlorella* sp. described in the specification was done in the NCBI 18s rDNA reference database at the Culture Collection of Algae at the University of Cologne (CCAC) showed substantial similarity (i.e., greater than 95%) with multiple known strains of *Chlorella* and *Micractinium*. Those of skill in the art will recognize that *Chlorella* and *Micractinium* appear closely related in many taxonomic classification trees for microalgae, and strains and species may be re-classified from time to time. Thus, for references throughout the instant specification for *Chlorella* sp., it is recognized that microalgae strains m related taxonomic classifications with similar characteristics to the reference *Chlorella* sp. strain would reasonably be expected to produce similar results.

Additionally, taxonomic classification has also been in flux for organisms in the genus *Schfaochytrium*. Some organisms previously classified as *Schizochytrium* have been reclassified as *Aurantiochytrium, Thraustochytrium,* or *Oblongichytrium*. See Yokoyama et al. Taxonomic rearrangement of the genus *Schizochytrium* sensu lato based on morphology, chemotaxonomic characteristics, and 18S rRNA gene phylogeny (Thrausochytriaceae, Labyrinthulomycetes): emendation for *Schizochytrium* and erection of *Aurantiochytrium* and *Oblongichytrium* gen. nov. *Mycoscience* (2007) 48:199-211. Those of skill in the art will recognize that *Schizochytrium, Aurantiochytrium, Thraustochytrium,* and *Oblongichytrium* appear closely related in many taxonomic classification trees for microalgae, and strains and species may be re-classified from time to time. Thus, for references throughout the instant specification for *Schizochytrium*, it is recognized that microalgae strains in related taxonomic classifications with similar characteristics to *Schizochytrium* would reasonably be expected to produce similar results.

By artificially controlling aspects of the microalgae culturing process such as the organic carbon feed (e.g., acetic acid, acetate), oxygen levels, pH, and light, the culturing process differs from the culturing process that microalgae experiences in nature. In addition to controlling various aspects of the culturing process, intervention by human operators or automated systems occurs during the non-axenic mixotrophic culturing of microalgae through contamination control methods to prevent the microalgae from being overrun and outcompeted by contaminating organisms (e.g., fungi, bacteria). Contamination control methods for microalgae cultures are known in the art and such suitable contamination control methods for non-axenic mixotrophic microalgae cultures are disclosed in WO2014/074769A2 (Ganuza, et al.), hereby incorporated by reference. By intervening in the microalgae culturing process, the impact of the contaminating microorganisms can be mitigated by suppressing the proliferation of containing organism populations and the effect on the microalgal cells (e.g., lysing, infection, death, clumping). Thus, through artificial control of aspects of the culturing process and intervening in the culturing process with contamination control methods, the microalgae culture produced as a whole and used in the described inventive compositions differs from the culture that results from a microalgae culturing process that occurs in nature.

During the mixotrophic culturing process the microalgae culture can also include cell debris and compounds excreted from the microalgae cells into the culture medium. The output of the microalgae mixotrophic culturing process provides the active ingredient for composition that is applied to plants for improving yield and quality without separate addition to or supplementation of the composition with other active ingredients not found in the mixotrophic microalgae whole cells and accompanying culture medium from the mixotrophic culturing process such as, but not limited to: microalgae extracts, macroalgae, macroalgae extracts, liquid fertilizers, granular fertilizers, mineral complexes (e.g., calcium, sodium, zinc, manganese, cobalt, silicon), fungi, bacteria, nematodes, protozoa, digestate solids, chemicals (e.g., ethanolamine, borax, boric acid), humic acid, nitrogen and nitrogen derivatives, phosphorus rock, pesticides, herbicides, insecticides, enzymes, plant fiber (e.g., coconut fiber).

In some embodiments, the microalgae can be previously frozen and thawed before inclusion in the liquid composition. In some embodiments, the microalgae may not have been subjected to a previous freezing or thawing process. In some embodiments, the microalgae whole cells have not been subjected to a drying process. The cell walls of the microalgae of the composition have not been lysed or disrupted, and the microalgae cells have not been subjected to an extraction process or process that pulverizes the cells. The microalgae whole cells are not subjected to a purification process for isolating the microalgae whole cells from the accompanying constituents of the culturing process (e.g., trace nutrients, residual organic carbon, bacteria, cell debris, cell excretions), and thus the whole output from the microalgae culturing process comprising whole microalgae cells, culture medium, cell excretions, cell debris, bacteria, residual organic carbon, and trace nutrients, is used in the liquid composition for application to plants. In some embodiments, the microalgae whole cells and the accompanying constituents of the culturing process are concentrated in the composition. In some embodiments, the microalgae whole cells and the accompanying constituents of the culturing process are diluted in the composition to a low concentration. The microalgae whole cells of the composition are not fossilized. In some embodiments, the microalgae whole cells are not maintained in a viable state in the composition for continued growth after the method of using the composition in a soil or foliar application. In some embodiments, the microalgae base composition can be biologically inactive after the composition is prepared. In some embodiments, the microalgae base composition can be substantially biologically inactive after the composition is prepared. In some embodiments, the microalgae base composition can increase m biological activity after the prepared composition is exposed to air.

In some embodiments, a liquid composition can include low concentrations of bacteria contributing to the solids percentage of the composition in addition to the microalgae cells. Examples of bacteria found in non-axenic mixotrophic conditions can be found in WO2014/074769A2 (Ganuza, et al.), hereby incorporated by reference. A live bacteria count can be determined using methods known in the art such as plate counts, plates counts using Petrifilm available from 3M (St. Paul, Minn.), spectrophotometric (turbidimetric) measurements, visual comparison of turbidity with a known standard, direct cell counts under a microscope, cell mass determination, and measurement of cellular activity. Live bacteria counts in a non-axenic mixotrophic microalgae culture can range from $10^4$ to $10^9$ CFU/mL, and can depend on contamination control measures taken during the culturing of the microalgae. The level of bacteria in the composition can be determined by an aerobic plate count which quantifies aerobic colony forming units (CFU) in a designated volume. In some embodiments, the composition includes an aerobic plate count of 40,000-400,000 CFU/mL. In some embodiments, the composition includes an aerobic plate count of 40,000-100,000 CFU/mL. In some embodiments, the composition includes an aerobic plate count of 100,000-200,000 CFU/mL. In some embodiments, the composition includes an aerobic plate count of 200,000-300,000 CFU/mL. In some embodiments, the composition includes an aerobic plate count of 300,000-400,000 CFU/mL.

In some embodiments, the microalgae based composition can be supplemented with a supplemental nutrient such as nitrogen, phosphorus, or potassium to increase the levels within the composition to at least 1% of the total composition (i.e., addition of N, P, or K to increase levels at least 1-0-0, 0-1-0, 0-0-1, or other combinations thereof). In some embodiments, the microalgae composition can be supplemented with nutrients such as, but not limited to, calcium, magnesium, silicon, sulfur, iron, manganese, zinc, copper, boron, molybdenum, chlorine, sodium, aluminum, vanadium, nickel, cerium, dysprosium, erbium, europium, gadolinium, holmium, lanthanum, lutetium, neodymium, praseodymium, promethium, samarium, scandium, terbium, thulium, ytterbium, and yttrium. In some embodiments, the supplemented nutrient is not up taken, chelated, or absorbed by the microalgae. In some embodiments, the concentration of the supplemental nutrient can include 1-50 g per 100 g of the composition.

A liquid composition comprising microalgae can be stabilized by heating and cooling in a pasteurization process. As shown in the Examples, the inventors found that the active ingredients of the microalgae based composition maintained effectiveness in at least one characteristic of a plant after being subjected to the heating and cooling of a pasteurization process. In other embodiments, liquid compositions with whole cells or processed cells (e.g., dried, lysed, extracted) of microalgae cells may not need to be stabilized by pasteurization. For example, microalgae cells that have been processed, such as by drying, lysing, and extraction, or extracts can include such low levels of bacteria that a liquid composition can remain stable without being subjected to the heating and cooling of a pasteurization process.

In some embodiments, the composition can be heated to a temperature in the range of 50-70° C. In some embodiments, the composition can be heated to a temperature in the range of 55-65° C. In some embodiments, the composition can be heated to a temperature in the range of 58-62° C. In some embodiments, the composition can be heated to a temperature in the range of 50-60° C. In some embodiments, the composition can be heated to a temperature in the range of 60-70° C. In other aspects of the invention, the composition can be heated to a temperature that is at least 65 degrees C. or higher, such as at least 75 degrees C. or higher, such as at least 80 degrees C. or higher, or at least 90 degrees or higher, such as about 95 degrees C., or the heat can be characterized as being in a range of 50-100 degrees C., such as 60-95 degrees C., e.g., 75-95 degrees C., or 80-, 85-, or 90-95 degrees C.

In some embodiments, the composition can be heated for a time period in the range of 90-150 minutes. In some embodiments, the composition can be heated for a time period in the range of 110-130 minutes. In some embodiments, the composition can be heated for a time period in the range of 90-100 minutes. In some embodiments, the composition can be heated for a time period in the range of 100-110 minutes. In some embodiments, the composition can be heated for a time period in the range of 110-120 minutes. In some embodiments, the composition can be heated for a time period in the range of 120-130 minutes. In some embodiments, the composition can be heated for a time period in the range of 130-140 minutes. In some embodiments, the composition can be heated for a time period in the range of 140-150 minutes.

After the step of heating or subjecting the liquid composition to high temperatures is complete, the compositions can be cooled at any rate to a temperature that is safe to work with. In one non-limiting embodiment, the composition can be cooled to a temperature in the range of 35-45° C. In some embodiments, the composition can be cooled to a temperature in the range of 36-44° C. In some embodiments, the composition can be cooled to a temperature in the range of 37-43° C. In some embodiments, the composition can be cooled to a temperature in the range of 38-42° C. In some embodiments, the composition can be cooled to a temperature in the range of 39-41° C. In further embodiments, the pasteurization process can be part of a continuous production process that also involves packaging, and thus the liquid composition can be packaged (e.g., bottled) directly after the heating or high temperature stage without a cooling step.

In some embodiments, the composition can include 5-30% solids by weight of microalgae cells (i.e., 5-30 g of microalgae cells/100 mL of the liquid composition). In some embodiments, the composition can include 5-20% solids by weight of microalgae cells. In some embodiments, the composition can include 5-15%> solids by weight of microalgae cells. In some embodiments, the composition can include 5-10% solids by weight of microalgae cells. In some embodiments, the composition can include 10-20% solids by weight of microalgae cells. In some embodiments, the composition can include 10-20% solids by weight of microalgae cells. In some embodiments, the composition can include 20-30% solids by weight of microalgae cells. In some embodiments, further dilution of the microalgae cells percent solids by weight can occur before application for low concentration applications of the composition.

In some embodiments, the composition can include less than 1% by weight of microalgae biomass or extracts (i.e., less than 1 g of microalgae derived product/100 mL of the liquid composition). In some embodiments, the composition can include less than 0.9% by weight of microalgae biomass or extracts. In some embodiments, the composition can include less than 0.8% by weight of microalgae biomass or extracts. In some embodiments, the composition can include less than 0.7% by weight of microalgae biomass or extracts. In some embodiments, the composition can include less than 0.6% by weight of microalgae biomass or extracts. In some embodiments, the composition can include less than 0.5% by weight of microalgae biomass or extracts. In some embodiments, the composition can include less than 0.4%> by weight of microalgae biomass or extracts. In some embodiments, the composition can include less than 0.3% by weight of microalgae biomass or extracts. In some embodiments, the composition can include less than 0.2% by weight of microalgae biomass or extracts. In some embodiments, the composition can include less than 0.1% by weight of microalgae biomass or extracts. In some embodiments, the composition can include at least 0.0001% by weight of microalgae biomass or extracts. In some embodiments, the composition can include at least 0.001% by weight of microalgae biomass or extracts. In some embodiments, the composition can include at least 0.01% by weight of microalgae biomass or extracts. In some embodiments, the composition can include at least 0.1% by weight of microalgae biomass or extracts. In some embodiments, the composition can include 0.0001-1% by weight of microalgae biomass or extracts. In some embodiments, the composition can include 0.0001-0.001% by weight of microalgae biomass or extracts. In some embodiments, the composition can include 0.001-0.01<% by weight of microalgae biomass or extracts. In some embodiments, the composition can include 0.01-0.1% by weight of microalgae biomass or extracts. In some embodiments, the composition can include 0.1-1% by weight of microalgae biomass or extracts.

In some embodiments, an application concentration of 0.1% of microalgae biomass or extract equates to 0.04 g of microalgae biomass or extract in 40 mL of a composition. While the desired application concentration to a plant can be 0.1% of microalgae biomass or extract, the composition can be packaged as a 10% concentration (0.4 mL in 40 mL of a composition). Thus a desired application concentration of 0.1% would require 6,000 mL of the 10% microalgae biomass or extract in the 100 gallons of water applied to the assumption of 15,000 plants in an acre, which is equivalent to an application rate of about 1.585 gallons per acre. In some embodiments, a desired application concentration of 0.01% of microalgae biomass or extract using a 10% concentration composition equates to an application rate of about 0.159 gallons per acre. In some embodiments, a desired application concentration of 0.001% of microalgae biomass or extract using a 10% concentration composition equates to an application rate of about 0.016 gallons per acre. In some embodiments, a desired application concentration of 0.0001% of microalgae biomass or extract using a 10% concentration composition equates to an application rate of about 0.002 gallons per acre.

In another non-limiting embodiment, correlating the application of the microalgae biomass or extract on a per plant basis using the assumption of 15,000 plants per acre, the composition application rate of 1 gallon per acre is equal to about 0.25 mL per plant=0.025 g per plant=25 mg of microalgae biomass or extract per plant. The water requirement assumption of 100 gallons per acre is equal to about 35 mL of water per plant. Therefore, 0.025 g of microalgae biomass or extract in 35 mL of water is equal to about 0.071 g of microalgae biomass or extract per 100 mL of composition equates to about a 0.07% application concentration. In some embodiments, the microalgae biomass or extract based composition can be applied at a rate in a range as low as about 0.001-10 gallons per acre, or as high as up to 150 gallons per acre.

In some embodiments, stabilizing means or stabilizers that substantially all or all (at least within the capacity of detection) are not active regarding the improvement of soil and/or plant characteristics, such as with respect to plant germination, emergence, maturation, quality, and yield, but instead aid in stabilizing the composition can be added to prevent the proliferation of unwanted microorganisms (e.g., yeast, mold) and prolong shelf life of the composition. Such inactive but stabilizing means or stabilizers can include an acid that exhibits anti-microbial or otherwise stabilizing properties in the amount that the stabilizing means/stabilizer is present in the composition, such as but not limited to phosphoric acid or citric acid, and a yeast and mold inhibitor, such as but not limited to potassium sorbate. In some embodiments, the stabilizing means are suitable for plants and do not inhibit the growth or health of the plant. In the alternative, the stabilizing means can contribute to nutritional properties of the liquid composition, such as but not limited to, the levels of nitrogen, phosphorus, or potassium.

In some embodiments, the composition can include less than 0.3% phosphoric acid. In some embodiments, the composition can include 0.01-0.3% phosphoric acid. In some embodiments, the composition can include 0.05-0.25% phosphoric acid. In some embodiments, the composition can include 0.01-0.1% phosphoric acid. In some embodiments, the composition can include 0.1-0.2% phosphoric acid. In some embodiments, the composition can include 0.2-0.3% phosphoric acid. In some embodiments, the composition can include less than 0.3% citric acid. In some embodiments, the composition can include 0.01-0.3% citric acid. In some embodiments, the composition can include 0.05-0.25% citric acid. In some embodiments, the composition can include 0.01-0.1% citric acid. In some embodiments, the composition can include 0.1-0.2% citric acid. In some embodiments, the composition can include 0.2-0.3% citric acid.

In some embodiments, the composition can include less than 0.5% potassium sorbate. In some embodiments, the composition can include 0.01-0.5% potassium sorbate. In some embodiments, the composition can include 0.05-0.4% potassium sorbate. In some embodiments, the composition can include 0.01-0.1% potassium sorbate. In some embodiments, the composition can include 0.1-0.2% potassium sorbate. In some embodiments, the composition can include 0.2-0.3% potassium sorbate. In some embodiments, the composition can include 0.3-0.4% i potassium sorbate. In some embodiments, the composition can include 0.4-0.5% potassium sorbate.

In some embodiments, the composition is a liquid and substantially includes of water. In some embodiments, the composition can include 70-99% water. In some embodiments, the composition can include 85-95% water. In some embodiments, the composition can include 70-75% water. In some embodiments, the composition can include 75-80% water. In some embodiments, the composition can include 80-85% water. In some embodiments, the composition can include 85-90 '0 water. In some embodiments, the composition can include 90-95% water. In some embodiments, the composition can include 95-99% water. The liquid nature and high-water content of the composition facilitates administration of the composition in a variety of manners, such as but not limit to: flowing through an irrigation system, flowing through an above ground drip irrigation system, flowing through a buried drip irrigation system, flowing through a central pivot irrigation system, sprayers, sprinklers, and water cans.

In some embodiments, the liquid composition can be used immediately after formulation, or can be stored in containers for later use. In some embodiments, the composition can be stored out of direct sunlight. In some embodiments, the composition can be refrigerated. In some embodiments, the composition can be stored at 1-10° C. In some embodiments, the composition can be stored at 1-3° C. In some embodiments, the composition can be stored at 3-50 C. In some embodiments, the composition can be stored at 5-8° C. In some embodiments, the composition can be stored at 8-10° C.

In some embodiments, administration of the liquid composition to a seed or plant can be in an amount effective to produce an enhanced characteristic in plants compared to a substantially identical population of untreated seeds or plants. Such enhanced characteristics can include accelerated seed germination, accelerated seedling emergence, improved seedling emergence, improved leaf formation, accelerated leaf formation, improved plant maturation, accelerated plant maturation, increased plant yield, increased plant growth, increased plant quality, increased plant health, increased fruit yield, increased fruit growth, and increased fruit quality. Non-limiting examples of such enhanced characteristics can include accelerated achievement of the hypocotyl stage, accelerated protrusion of a stem from the soil, accelerated achievement of the cotyledon stage, accelerated leaf formation, increased marketable plant weight, increased marketable plant yield, increased marketable fruit weight, increased production plant weight, increased production fruit weight, increased utilization (indicator of efficiency in the agricultural process based on ratio of marketable fruit to unmarketable fruit), increased chlorophyll content (indicator of plant health), increased plant weight (indicator of plant health), increased root weight (indicator of plant health), increased shoot weight (indicator of plant health), increased plant height, increased thatch height, increased resistance to salt stress, increased plant resistance to heat stress (temperature stress), increased plant resistance to heavy metal stress, increased plant resistance to drought, increased plant resistance to disease, improved color, reduced insect damage, reduced blossom end rot, and reduced sun burn. Such enhanced characteristics can occur individually in a plant, in soil, or in combinations of multiple enhanced characteristics.

In some embodiments, after harvest of the microalgae from the culturing vessel, the microalgae biomass can be dried or dehydrated to form a composition of dried microalgae biomass (i.e., reduced moisture content). The microalgae biomass can be dried by at least one method selected from the group consisting of: freeze drying (or lyophilization), drum (or rotary) drying, spray drying, crossflow air drying, solar drying, vacuum shelf drying, pulse combustion drying, flash drying, furnace drying, belt conveyor drying, and refractance window drying. In some embodiments, the microalgae cells can be dried by a combination of two or more methods, such as in a process with multiple drying methods in series. The process of drying the microalgae biomass can reduce the percent moisture (on a wet basis) to the range of about 1-15<% and result in a cake, flakes, or a powder, which is more uniform and more stable than the wet culture of microalgae. In some embodiments, the dried microalgae cells can be intact. In some embodiments, the dried microalgae cells can be lysed or disrupted. In some embodiments, the microalgae cells can be lysed or disrupted prior to or after drying by mechanical, electrical, acoustic, or chemical means. In some embodiments, drying the microalgae cells achieves an acceptable product stability for storage, with the reduction or elimination of chemical stabilizers. The composition can be stored in any suitable container such as, but not limited to, a bag, bucket, jug, tote, or bottle.

In some embodiments, the dried microalgae biomass can have a moisture content of 1-15% on a wet basis. In some embodiments, the dried microalgae biomass can have a moisture content of 1-2% on a wet basis. In some embodiments, the dried microalgae biomass can have a moisture content of 2-3% on a wet basis. In some embodiments, the dried microalgae biomass can have a moisture content of 3-5% on a wet basis. In some embodiments, the dried microalgae biomass can have a moisture content of 5-7% on a wet basis. In some embodiments, the dried microalgae biomass can have a moisture content of 7-10% on a wet basis. In some embodiments, the dried microalgae biomass can have a moisture content of 10-12% on a wet basis. In some embodiments, the dried microalgae biomass can have a moisture content of 12-15% on a wet basis. In some embodiments, the dried microalgae biomass can have a moisture content of 1-8% i on a wet basis. In some embodiments, the dried microalgae biomass can have a moisture content of 8-15% on a wet basis.

The various drying processes can have different capabilities such as, but not limited to, the amount of moisture that can be removed, the preservation of metabolites (e.g., proteins, lipids, pigments, carbohydrates, polysaccharides, soluble nitrogen, phytohormones), and the effect on the cell wall or membrane. For example, loss of protein in Spirulina biomass has been found to increase proportionally as the drying temperature increases. Additionally, drying at high temperatures has been shown to alter polymer chains, alter interactions between polysaccharide and glycoprotein, and increase bound water content of polysaccharides. Pigments and fatty acids are also known to oxidize and de-stabilize to different degrees in different drying processes. The effectiveness of each drying method can also vary based on the microalgae species due to different physical characteristics of the microalgae (e.g., sheer sensitivity, cell size, cell wall thickness and composition). The method of drying and drying method parameters can also result in a structural change to the microalgae cell such as, but not limited to, increased porosity in the cell wall, changes in the cell wall make up or bonds, and measurable changes in cell characteristics (e.g., elasticity, viscosity, digestibility); as wells as functional differences when applied to plants that can be measured in changes in plant performance or plant characteristics. Drying microalgae with a combination of methods in series can also result in structural and functional changes, minimize structural and functional changes, or increase the effectiveness for a particular type of microalgae.

Drum drying includes the use of sloped, rotating cylinders which use gravity to move the microalgal biomass from one end to the other. Drum drying can be conducted with direct contact between a hot gas and the microalgal biomass, or indirect heating in which the gas and microalgal biomass is separated by a barrier such as a steel shell. A non-limiting example of a drum drying process for Scenedesmus can include 10 seconds of heating at 120° C. Possible effects to the microalga biomass in a drum drying process include sterilization of the biomass, and breaking of the cell wall. Microalgal biomass that is drum dried can have higher digestibility than microalgal biomass that is spray dried.

Freeze drying includes freezing the microalgal biomass and then transferring the frozen biomass to a vacuum chamber with reduced pressure (e.g., 4.6 Torr). The ice in the microalgal biomass changes to vapor through sublimation which is collected on an extremely cold condenser and removed from the vacuum chamber. Freeze drying typically minimizes the degradation of unsaturated fatty acids and pigments (e.g., carotenoids) through oxidation, which preserves the nutritional value of the microalgal biomass. Although the targeted removal of water in the freeze drying process is beneficial, the process is very costly and time consuming which makes freeze drying impractical for many commercial applications. In some embodiments, microalgae dried by freeze drying can include 2-6% moisture (on a wet basis). A non-limiting example of a freeze drying process for *Scenedesmus* can include 24 hours at −84° C. Freeze drying is known to maintain the integrity of the microalgal cell, but is also known been known in some cases to disrupt the cell or increase the pore size in the cell wall. In *Scenedesmus*, freeze drying was found to decrease rigidity, increase surface area by 165% i, and increase pore size by 19% i of the cells (see eSEM images below). In *Phaeodactylum ricornutum*, freeze drying had no effect on the total lipid content, made the cells more susceptible to lipolysis (i.e., breakdown of lipids, hydrolysis of triglycerides into glycerol and free fatty acids) upon storage than spray dried cells, and made the cells less susceptible to oxidation than spray dried cells.

Spray drying includes atomizing an aqueous microalgae culture into droplets sprayed downwardly in a vertical tower through which hot gases pass downward. The gas stream can be exhausted through a cyclonic separator. The process of spray drying is expensive, but slightly cheaper than freeze drying. Spray drying has become the method of choice for high value products (>$1,000/ton). With the proper type of burner, oxygen can be virtually eliminated from the recycled drying gas, which prevents the oxidation of oxygen sensitive products (e.g., carotenoids). In some embodiments, microalgae dried by spray drying can include 1-7% moisture (on a wet basis). Examples of spray drying systems include: box dryers, tall-form spray dryers, fluidized bed dryers, and moving fluidized bed dryers (e.g., FilterMat spray dryer GEA Process Engineering Inc.). An open cycle spray dryer with a particular direct fired air heater can operate at elevated temperatures (e.g., 60-93° C.) and high oxygen concentrations (e.g., 19-20%). The possible effects of spray drying on microalgal biomass include rupturing the cells walls, reduction of protein content by 10-15%, significant deterioration of pigments (depending on the oxygen concentration), and a lower digestibility than drum drying. In *Phyaeadactylum ricornutum*, spray drying had no effect on the total lipid content, made the cells less susceptible to lipolysis than freeze drying, and made the cells more susceptible to oxidation than freeze drying (possibly due to the breakdown of protective carotenoids).

Crossflow air drying uses movement of heated air across a layer of microalgae on a tray, which is a modification of indirect solar and convection oven driers. Crossflow air drying is faster than solar drying, cheaper than drum drying, and is known to typically not break the microalgal cell wall. In some embodiments, microalgae dried by crossflow air drying can include 8-12% moisture (on a wet basis). Non-limiting examples of crossflow air drying for *Spirulina* can include: 1) a temperature of 62° C. for 14 hours, 2) a temperature of 50-60° C., a relative humidity of 7-10%, an air velocity of 1.5 m/s, and a duration of 150-220 minutes, 3) a temperature of 40-60° C. and an air velocity of 1.9-3.8 m/s, and 4) temperatures of 50-70° C. for layers of 3-7 mm in a perforated tray with parallel air flow. Crossflow air drying of *Spirulina* has shown a loss in protein of about 17% and a loss in phycocyanin of 37-50%. Particularly, degradation of phycocyanin was found to occur above 60° C., but there was no significant change in the fatty acid composition in the crossflow air drying methods.

Non-limiting examples of crossflow air drying of *Chlorella kessieri* and *Chlamydamonas reinhardtii* can include a temperature of 55° C. for more than 5 hours. Crossflow air drying of *Chlorella kessieri* and *Chlamdamanas reinhardtii* has produced a reduction of chlorophyll relative to the dry cell weight, an increase of total fatty acid content relative to the dry cell, a decrease of polar lipids relative to the dry cell weight, and a decrease in the availability of nutritional salts (e.g., S, N). A cell's sensitivity to air drying stress (as measured through the change in chlorophyll) can be correlated to the properties of the cell wall. For example, the crossflow air dried *Chlamydamanas reinhardtii* (hydroxyproline-rich glucoprotein based cell walls) had a larger decrease in chlorophyll than the *Chlorella kessieri* (sugar based cell walls), which can be associated with the cell wall's ability to restructure in Sand N deficient conditions. In a non-limiting example of drying 5-7 mm thick layers of *Aphanathece micrascapia Nageli* at temperatures of 40-60° C. with parallel air flow of 1.5 m/s, it was found that drying conditions influenced the concentrations of protein, carbohydrates, and lipids in the biomass.

Solar drying methods can include the use of direct solar radiation to dry microalgae on sand or a plastic sheet, or the indirect use of solar radiation to heat air that is circulated around microalgae in a dryer. Direct solar drying is strongly weather dependent, slow, and can require a short duration of high heat (e.g., 120° C.) to increase the biological value of the microalgal biomass. A non-limiting example of a direct solar drying process for *Scenedesmus* can include a 1,500 micron thickness white plastic drying bed liner, a temperature of 25-30° C., and a duration of 72 hours. The possible effects of direct solar drying on microalgal biomass include chlorophyll degradation, overheating of the biomass, and creation of an unpleasant odor. Indirect solar drying prevents overheating, has a higher drying rate than direct solar drying, but produces a less attractive profile in the final product. An indirect solar drying method for microalgae can include temperature of 65-70° C. for 0.5-6 hours.

Drying of a thin film of microalgal biomass in a convection oven is a fairly common practice performed in scientific literature to test the biomass going through further processing, but may be less practical for many commercial applications. Thin film convection oven drying has been demonstrated in the literature with species of *Chlorella, Chlamydomonas*, and *Scenedesmus*. In some embodiments, microalgae dried by oven drying can include 6-10% moisture (on a wet basis). Thin film convection oven drying methods can include temperatures of 30-90° C., and durations of 4-12 hours. Thin film convection oven dried microalgal biomass showed no significant change in the fatty acid profile and a slight decrease in the degree of unsaturation of fatty acids at higher temperature for ruptured cells (likely due to oxidation causing cleavage of unsaturated bonds).

Microalgae can be dried in thin layers with heat at a reduced pressure. Non-limiting examples of drying of *Spirulina* in layers within a vacuum can include temperatures of 50-65° C. and a pressure of 0.05-0.06 atm. Possible effects on the microalgae that may result from vacuum shelf drying include development of a hygroscopic property (i.e., ability to attract and hold water particles from the surrounding environment by absorption or adsorption) and development of a porous structure.

Pulse combustion drying uses a blast of controlled heat to flash dry the microalgae. Air is pumped into a combustion chamber, mixed with a fuel and ignited to created pressurized hot gas (e.g., at 3 psi). The dryer can automatically blast the heated gas with quench air to control the temperature of the heated gas before coming into contact with the microalgae. The process is then repeated multiple times to provide the pulses of heated gas. Pulse combustion heating is known to dry microalgae at a low heat which preserves the integrity and nutritional value of the microalgae. Flash drying includes spraying or injecting a mixture of dried and undried material into a hot gas stream, and is commonly used in wastewater sludge drying.

Drying of microalgae using an incinerator or furnace can include heating the biomass to a high temperature (e.g., 100° C.) to evaporate the water. The heating can be performed at a level below the temperature at which the microalgae will burn and can include using hot gases that proceed downwardly with the biomass in parallel flow. Microalgae that are dewatered to an appropriate solids level can be dried indirectly by heating elements lining the pathway of a belt conveyor. Refractance window drying is a dehydration method that uses infra-red light, rather than high direct temperature, to remove moisture from microalgae. Vet microalgae biomass can be translated through an evaporation chamber by a belt disposed above a circulating hot water reservoir to dry the microalgae with infra-red energy in a refractance window drying. In some embodiments, microalgae dried by refractance window drying can include 3-8% moisture (on a wet basis).

In some embodiments, the dry composition can be mixed with water and stabilized by heating and cooling in a pasteurization process, adjustment of pH, the addition of an inhibitor of yeast and mold growth, or combinations thereof. In one non-limiting example of preparing the dried microalgae composition for application to plants, the microalgae harvested from the culturing system is first held in a harvest tank before centrifuging the culture. Once the microalgae is centrifuged, the centrifuge discharges the fraction rich in microalgae whole cell solids, but also containing the accompanying constituents from the culture medium, into a container at a temperature of about 30° C. The microalgae composition is then dried.

Surprisingly, the inventors found that administration of the described composition in low concentration applications was effective in producing enhanced characteristics in plants. In some embodiments, a liquid composition can be administered before the seed is planted. In some embodiments, a liquid composition can be administered at the time the seed is planted. In some embodiments, a liquid composition can be administered after the seed is planted. In some embodiments, a liquid composition can be administered to plants that have emerged from the ground. In some embodiments, a dried composition can be applied to the soil before, during, or after the planting of a seed. In some embodiments, a dried composition can be applied to the soil before or after a plant emerges from the soil.

In some embodiments, the volume or mass of the microalgae based composition applied to a seed, seedling, or plant may not increase or decrease during the growth cycle of the plant (i.e., the amount of the microalgae composition applied to the plant will not change as the plant grows larger). In some embodiments, the volume or mass of the microalgae based composition applied to a seed, seedling, or plant can increase during the growth cycle of the plant (i.e., applied on a mass or volume per plant mass basis to provide more of the microalgae composition as the plant grows larger). In some embodiments, the volume or mass of the microalgae based composition applied to a seed, seedling, or plant can decrease during the growth cycle of the plant (i.e., applied on a mass or volume per plant mass basis to provide more of the microalgae composition as the plant grows larger).

Seed Soak Application

In one non-limiting embodiment, the administration of the liquid composition can include soaking the seed in an effective amount of the liquid composition before planting the seed. In some embodiments, the administration of the liquid composition further includes removing the seed from the liquid composition after soaking, and drying the seed before planting. In some embodiments, the seed can be soaked in the liquid composition for a time period in the range of 90-150 minutes. In some embodiments, the seed can be soaked in the liquid composition for a time period in the range of 110-130 minutes. In some embodiments, the seed can be soaked in the liquid composition for a time period in the range of 90-100 minutes. In some embodiments, the seed can be soaked in the liquid composition for a time period in the range of 100-110 minutes. In some embodiments, the seed can be soaked in the liquid composition for a time period in the range of 110-120 minutes. In some embodiments, the seed can be soaked in the liquid composition for a time period in the range of 120-130 minutes. In some embodiments, the seed can be soaked in the liquid composition for a time period in the range of 130-140 minutes. In some embodiments, the seed can be soaked in the liquid composition for a time period in the range of 140-150 minutes.

The composition can be diluted to a lower concentration for an effective amount in a seed soak application by mixing a volume of the composition in a volume of water. The concentration of microalgae sourced components resulting in the diluted composition can be calculated by the multiplying the original concentration in the composition by the ratio of the volume of the composition to the volume of water. Alternatively, the grams of microalgae source components in the diluted composition can be calculated by the multiplying the original grams of microalgae sourced components per 100 mL by the ratio of the volume of the composition to the volume of water.

Soil Application—Seed

In another non-limiting embodiment, the administration of the composition can include contacting the soil in the immediate vicinity of the planted seed with an effective amount of the composition. In some embodiments, the liquid composition can be supplied to the soil by injection into a low volume irrigation system, such as but not limited to a drip irrigation system supplying water beneath the soil through perforated conduits or at the soil level by fluid conduits hanging above the ground or protruding from the ground. In some embodiments, the liquid composition can be supplied to the soil by a soil drench method wherein the liquid composition is poured on the soil.

The composition can be diluted to a lower concentration for an effective amount in a soil application by mixing a volume of the composition in a volume of water. The percent solids of microalgae sourced components resulting in the diluted composition can be calculated by the multiplying the original concentration in the composition by the ratio of the volume of the composition to the volume of water. Alternatively, the grams of microalgae sourced components in the diluted composition can be calculated by the multiplying the original grams of microalgae sourced components per 100 mL by the ratio of the volume of the composition to the volume of water.

The rate of application of the composition at the desired concentration can be expressed as a volume per area. In some embodiments, the rate of application of the liquid composition in a soil application can include a rate in the range of 50-150 gallons/acre. In some embodiments, the rate of application of the liquid composition in a soil application can include a rate in the range of 75-125 gallons/acre. In some embodiments, the rate of application of the liquid composition in a soil application can include a rate in the range of 50-75 gallons/acre. In some embodiments, the rate of application of the liquid composition in a soil application can include a rate in the range of 75-100 gallons/acre. In some embodiments, the rate of application of the liquid composition in a soil application can include a rate in the range of 100-125 gallons/acre. In some embodiments, the rate of application of the liquid composition in a soil application can include a rate in the range of 125-150 gallons/acre.

In some embodiments, the rate of application of the liquid composition in a soil application can include a rate in the range of 10-50 gallons/acre. In some embodiments, the rate of application of the liquid composition in a soil application can include a rate in the range of 10-20 gallons/acre. In some embodiments, the rate of application of the liquid composition in a soil application can include a rate in the range of 20-30 gallons/acre. In some embodiments, the rate of application of the liquid composition in a soil application can include a rate in the range of 30-40 gallons/acre. In some embodiments, the rate of application of the liquid composition in a soil application can include a rate in the range of 40-50 gallons/acre.

In some embodiments, the rate of application of the liquid composition in a soil application can include a rate in the range of 0.01-10 gallons/acre (such as 0.02-8 gal/acre, such as 0.025-7.5 gal/acre, 0.05-5 gal/acre, 0.1-5 gal/acre, 0.2-5 gal/acre, 0.2-4 gal/acre, 0.25-4 gal/acre, 0.33-3 gal/acre, 0.5-2.5 gal/acre, 0.5-2 gal/acre, or 0.66- or 0.75-1, 1.5, 1.75, or 2 gal/acre. In some embodiments, the rate of application of the liquid composition in a soil application can include a rate in the range of 0.01-0.1 gallons/acre. In some embodiments, the rate of application of the liquid composition in a soil application can include a rate in the range of 0.1-1.0 gallons/acre (such as 0.25-1 gal/acre, 0.33-1 gal/acre, 0.5-1 gal/acre, or 0.25-0.75 gal/acre, or 0.33-0.66 gal/acre). In some embodiments, the rate of application of the liquid composition in a soil application can include a rate in the range of 1-2 gallons/acre. In some embodiments, the rate of application of the liquid composition in a soil application can include a rate in the range of 2-3 gallons/acre. In some embodiments, the rate of application of the liquid composition in a soil application can include a rate in the range of 3-4 gallons/acre. In some embodiments, the rate of application of the liquid composition in a soil application can include a rate in the range of 4-5 gallons/acre. In some embodiments, the rate of application of the liquid composition in a soil application can include a rate in the range of 5-10 gallons/acre.

In some embodiments, the rate of application of the liquid composition in a soil application can include a rate in the range of 2-20 liters/acre. In some embodiments, the rate of application of the liquid composition in a soil application can include a rate in the range of 3.7-15 liters/acre. In some embodiments, the rate of application of the liquid composition in a soil application can include a rate in the range of 2-5 liters/acre. In some embodiments, the rate of application of the liquid composition in a soil application can include a rate in the range of 5-10 liters/acre. In some embodiments, the rate of application of the liquid composition in a soil application can include a rate in the range of 10-15 liters/acre. In some embodiments, the rate of application of the liquid composition in a soil application can include a rate in the range of 15-20 liters/acre.

Capillary Action Application

In another non-limiting embodiment, the administration of the liquid composition can include first soaking the seed in water, removing the seed from the water, drying the seed, applying an effective amount of the liquid composition below the seed planting level in the soil, and planting the seed, wherein the liquid composition supplied to the seed from below by capillary action. In some embodiments, the seed can be soaked in water for a time period in the range of 90-150 minutes. In some embodiments, the seed can be soaked in water for a time period in the range of 110-130 minutes. In some embodiments, the seed can be soaked in water for a time period in the range of 90-100 minutes. In some embodiments, the seed can be soaked in water for a time period in the range of 100-110 minutes. In some embodiments, the seed can be soaked in water for a time period in the range of 110-120 minutes. In some embodiments, the seed can be soaked in water for a time period in the range of 120-130 minutes. In some embodiments, the seed can be soaked in water for a time period in the range of 130-140 minutes. In some embodiments, the seed can be soaked in water for a time period in the range of 140-150 minutes.

The composition can be diluted to a lower concentration for an effective amount in a capillary action application by mixing a volume of the composition in a volume of water. The concentration of microalgae sourced components resulting in the diluted composition can be calculated by the multiplying the original concentration in the composition by the ratio of the volume of the composition to the volume of water. Alternatively, the grams of microalgae sourced components in the diluted composition can be calculated by the multiplying the original grams of microalgae sourced components per 100 mL by the ratio of the volume of the composition to the volume of water.

Hydroponic Applications

In another non-limiting embodiment, the administration of the liquid composition to a seed or plant can include applying the microalga based composition in combination with a nutrient medium to seeds disposed in and plants growing in a hydroponic growth medium or an inert growth medium (e.g., coconut husks). The liquid composition can be applied multiple times per day, per week, or per growing season.

Foliar Application

In one non-limiting embodiment, the administration of the composition can include contacting the foliage of the plant with an effective amount of the composition. In some embodiments, the liquid composition can be sprayed on the foliage by a hand sprayer, a sprayer on an agriculture implement, or a sprinkler.

The composition can be diluted to a lower concentration for an effective amount in a foliar application by mixing a volume of the composition in a volume of water. The concentration of microalgae sourced components resulting in the diluted composition can be calculated by the multiplying the original concentration in the composition by the ratio of the volume of the composition to the volume of water. Alternatively, the grams of microalgae sourced components in the diluted composition can be calculated by the multiplying the original grams of microalgae sourced components per 100 mL by the ratio of the volume of the composition to the volume of water.

The rate of application of the composition at the desired concentration can be expressed as a volume per area. In some embodiments, the rate of application of the liquid composition in a foliar application can include a rate in the range of 10-50 gallons/acre. In some embodiments, the rate of application of the liquid composition in a foliar application can include a rate in the range of 10-15 gallons/acre. In some embodiments, the rate of application of the liquid composition in a foliar application can include a rate in the range of 15-20 gallons/acre. In some embodiments, the rate of application of the liquid composition in a foliar application can include a rate in the range of 20-25 gallons/acre. In some embodiments, the rate of application of the liquid composition in a foliar application can include a rate in the range of 25-30 gallons/acre. In some embodiments, the rate of application of the liquid composition in a foliar application can include a rate in the range of 30-35 gallons/acre. In some embodiments, the rate of application of the liquid composition in a foliar application can include a rate in the range of 35-40 gallons/acre. In some embodiments, the rate of application of the liquid composition in a foliar application can include a rate in the range of 40-45 gallons/acre. In some embodiments, the rate of application of the liquid composition in a foliar application can include a rate in the range of 45-50 gallons/acre.

In some embodiments, the rate of application of the liquid composition in a foliar application can include a rate in the range of 0.01-10 gallons/acre. In some embodiments, the rate of application of the liquid composition in a foliar application can include a rate in the range of 0.01-0.1 gallons/acre. In some embodiments, the rate of application of the liquid composition in a foliar application can include a rate in the range of 0.1-1.0 gallons/acre. In some embodiments, the rate of application of the liquid composition in a foliar application can include a rate in the range of 1-2 gallons/acre. In some embodiments, the rate of application of the liquid composition in a foliar application can include a rate in the range of 2-3 gallons/acre. In some embodiments, the rate of application of the liquid composition in a foliar application can include a rate in the range of 3-4 gallons/acre. In some embodiments, the rate of application of the liquid composition in a foliar application can include a rate in the range of 4-5 gallons/acre. In some embodiments, the rate of application of the liquid composition in a foliar application can include a rate in the range of 5-10 gallons/acre.

The frequency of the application of the composition can be expressed as the number of applications per period of time (e.g., two applications per month), or by the period of time between applications (e.g., one application every 21 days). In some embodiments, the plant can be contacted by the composition in a foliar application every 3-28 days, such as every 3-21 days, every 3-15 days, every 5-15 days, every 7-14 days, or every 6-12 days. In some embodiments, the plant can be contacted by the composition in a foliar application every 4-10 days, such as every 4-8 days, such as every 5-7 days. In some embodiments, the plant can be contacted by the composition in a foliar application every 18-24 days. In some embodiments, the plant can be contacted by the composition in a foliar application every 3-7 days. In some embodiments, the plant can be contacted by the composition in a foliar application every 7-14 days. In some embodiments, the plant can be contacted by the composition in a foliar application every 14-21 days. In some embodiments, the plant can be contacted by the composition in a foliar application every 21-28 days.

Foliar application(s) of the composition generally begin after the plant has become established, but can begin before establishment, at defined time period after planting, or at a defined time period after emergence form the soil in some embodiments. In some embodiments, the plant can be first contacted by the composition in a foliar application 5-14 days after the plant emerges from the soil. In some embodiments, the plant can be first contacted by the composition in a foliar application 5-7 days after the plant emerges from the soil. In some embodiments, the plant can be first contacted by the composition in a foliar application 7-10 days after the plant emerges from the soil. In some embodiments, the plant can be first contacted by the composition in a foliar application 10-12 days after the plant emerges from the soil. In some embodiments, the plant can be first contacted by the composition in a foliar application 12-14 days after the plant emerges from the soil.

Soil Application—Plant

In another non-limiting embodiment, the administration of the composition can include contacting the soil in the immediate vicinity of the plant with an effective amount of the composition. In some embodiments, the liquid composition can be supplied to the soil by injection into to a low volume irrigation system, such as but not limited to a drip irrigation system supplying water beneath the soil through perforated conduits or at the soil level by fluid conduits hanging above the ground or protruding from the ground. In some embodiments, the liquid composition can be supplied to the soil by a soil drench method wherein the liquid composition is poured on the soil.

The composition can be diluted to a lower concentration for an effective amount in a soil application by mixing a volume of the composition in a volume of water. The concentration of microalgae sourced components resulting in the diluted composition can be calculated by the multiplying the original concentration of microalgae sourced components in the composition by the ratio of the volume of the composition to the volume of water. Alternatively, the grams of microalgae cells in the diluted composition can be calculated by the multiplying the original grams of microalgae sourced components per 100 mL by the ratio of the volume of the composition to the volume of water.

The rate of application of the composition at the desired concentration can be expressed as a volume per area. In some embodiments, the rate of application of the liquid composition in a soil application can include a rate in the range of 50-150 gallons/acre. In some embodiments, the rate of application of the liquid composition in a soil application can include a rate in the range of 75-125 gallons/acre. In some embodiments, the rate of application of the liquid composition in a soil application can include a rate in the range of 50-75 gallons/acre. In some embodiments, the rate of application of the liquid composition in a soil application can include a rate in the range of 75-100 gallons/acre. In some embodiments, the rate of application of the liquid composition in a soil application can include a rate in the range of 100-125 gallons/acre. In some embodiments, the rate of application of the liquid composition in a soil application can include a rate in the range of 125-150 gallons/acre.

In some embodiments, the rate of application of the liquid composition in a soil application can include a rate in the range of 10-50 gallons/acre. In some embodiments, the rate of application of the liquid composition in a soil application can include a rate in the range of 10-20 gallons/acre. In some embodiments, the rate of application of the liquid composition in a soil application can include a rate in the range of 20-30 gallons/acre. In some embodiments, the rate of application of the liquid composition in a soil application can include a rate in the range of 30-40 gallons/acre. In some embodiments, the rate of application of the liquid composition in a soil application can include a rate in the range of 40-50 gallons/acre.

In some embodiments, the rate of application of the liquid composition in a soil application can include a rate in the range of 0.01-10 gallons/acre. In some embodiments, the rate of application of the liquid composition in a soil application can include a rate in the range of 0.01-0.1 gallons/acre. In some embodiments, the rate of application of the liquid composition in a soil application can include a rate in the range of 0.1-1.0 gallons/acre. In some embodiments, the rate of application of the liquid composition in a soil application can include a rate in the range of 1-2 gallons/acre. In some embodiments, the rate of application of the liquid composition in a soil application can include a rate in the range of 2-3 gallons/acre. In some embodiments, the rate of application of the liquid composition in a soil application can include a rate in the range of 3-4 gallons/acre. In some embodiments, the rate of application of the liquid composition in a soil application can include a rate in the range of 4-5 gallons/acre. In some embodiments, the rate of application of the liquid composition in a soil application can include a rate in the range of 5-10 gallons/acre.

In some embodiments, the rate of application of the liquid composition in a soil application can include a rate in the range of 0.5-20 liters/acre, such as 0.75-15 liters/acre, 1-12 liters/acre, 1.5-10 liters/acre, 2-10 liters/acre, 2-15 liters/acre, 2-20 liters/acre, 3-12 liters/acre, 3-10 liters/acre, 4-10 liters/acre, 4-12 liters/acre, or 5-10 liters/acre. In some embodiments, the rate of application of the liquid composition in a soil application can include a rate in the range of 3.5-15 liters/acre such as 3.7-15 liters/acre. In some embodiments, the rate of application of the liquid composition in a soil application can include a rate in the range of 2-5 liters/acre. In some embodiments, the rate of application of the liquid composition in a soil application can include a rate in the range of 5-10 liters/acre. In some embodiments, the rate of application of the liquid composition in a soil application can include a rate in the range of 10-15 liters/acre. In some embodiments, the rate of application of the liquid composition in a soil application can include a rate in the range of 15-20 liters/acre.

The frequency of the application of the composition can be expressed as the number of applications per period of time (e.g., two applications per month), or by the period of time between applications (e.g., one application every 21 days). In some embodiments, the plant can be contacted by the composition in a soil application every 3-28 days. In some embodiments, the plant can be contacted by the composition in a soil application every 4-10 days, but in other aspects application is every 14 days, every 21 days, or every 28 days. In some embodiments, the plant can be contacted by the liquid composition in a soil application every 18-24 days or every 14-35 days. In some embodiments, the plant can be contacted by the composition in a soil application every 3-7 days. In some embodiments, the plant can be contacted by the composition in a soil application every 7-14 days. In some embodiments, the plant can be contacted by the composition in a soil application every 14-21 days. In some embodiments, the plant can be contacted by the composition in a soil application every 21-28 days.

Soil application(s) of the composition generally begin after the plant has become established, but can begin before establishment, at defined time period after planting, or at a defined time period after emergence form the soil in some embodiments. In some embodiments, the plant can be first contacted by the composition in a soil application 5-14 days after the plant emerges from the soil. In some embodiments, the plant can be first contacted by the composition in a soil application 5-7 days after the plant emerges from the soil. In some embodiments, the plant can be first contacted by the liquid composition in a soil application 7-10 days after the plant emerges from the soil. In some embodiments, the plant can be first contacted by the composition in a soil application 10-12 days after the plant emerges from the soil. In some embodiments, the plant can be first contacted by the composition in a soil application 12-14 days after the plant emerges from the soil.

Whether in a seed soak, soil, capillary action, foliar, or hydroponic application the method of use includes relatively low concentrations of the composition. Even at such low concentrations, the described composition has been shown to be effective at producing an enhanced characteristic in plants. The ability to use low concentrations allows for a reduced impact on the environment that may result from over application and an increased efficiency in the method of use of the composition by requiring a small amount of material to produce the desired effect. In some embodiments, the use of the liquid composition with a low volume irrigation system in soil applications allows the low concentration of the liquid composition to remain effective and not be diluted to a point where the composition is no longer in at a concentration capable of producing the desired effect on the plants while also increasing the grower's water use efficiency.

In conjunction with the low concentrations of microalgae cells in the composition necessary to be effective for enhancing the described characteristics of plants, the composition does not have be to administered continuously or at a high frequency (e.g., multiple times per day, daily). The ability of the composition to be effective at low concentrations and a low frequency of application was an unexpected result, due to the traditional thinking that as the concentration of active ingredients decreases the frequency of application should increase to provide adequate amounts of the active ingredients. Effectiveness at low concentration and application frequency increases the material usage efficiency of the method of using the composition while also increasing the yield efficiency of the agricultural process.

Administration of a dry composition treatment to the soil, seed, or plant can be in an amount effective to produce an enhanced characteristic in the plant compared to a substantially identical population of untreated plant. Such enhanced characteristics can include accelerated seed germination, accelerated seedling emergence, improved seedling emergence, improved leaf formation, accelerated leaf formation, improved plant maturation, accelerated plant maturation, increased plant yield, increased plant growth, increased plant quality, increased plant health, increased flowering, increased fruit yield, increased fruit growth, and increased fruit quality. Non-limiting examples of such enhanced characteristics can include accelerated achievement of the hypocotyl stage, accelerated protrusion of a stem from the soil, accelerated achievement of the cotyledon stage, accelerated leaf formation, increased leaf size, increased leaf area index, increased marketable plant weight, increased marketable plant yield, increased marketable fruit weight, increased production plant weight, increased production fruit weight, increased utilization (indicator of efficiency in the agricultural process based on ratio of marketable fruit to unmarketable fruit), increased chlorophyll content (indicator of plant health), increased plant weight (indicator of plant health), increased root weight (indicator of plant health), increased root mass (indicator of plant health), increased shoot weight (indicator of plant health), increased plant height, increased thatch height, increased resistance to salt stress, increased plant resistance to heat stress (temperature stress), increased plant resistance to heavy metal stress, increased plant resistance to drought, increased plant resistance to disease improved color, reduced insect damage, reduced blossom end rot, and reduced sun burn. Such enhanced characteristics can occur individually in a plant, or in combinations of multiple enhanced characteristics. The characteristic of flowering has is important for not only the ornamental market, but also for fruiting plants where an increase in flowering can correlate to an increase in fruit production.

Seed Coating

In one non-limiting embodiment, the administration of the dried microalgae composition treatment can include coating a seed. In some embodiments, a seed can be coated by passing through a slurry comprising microalgae and then dried. In some embodiments, the seed can be coated with the dried microalgae composition and other components such as, but not limited to, binders and fillers known in the art to be suitable for coating seeds. The fillers can include suitable inorganic particles such as, but not limited to, silicate particles, carbonate particles, and sulphate particles, quartz, zeolites, pumice, perlite, diatomaceous earth, pyrogene silica, Sb20 3, TiO 2, lithopone, ZnO, and hydrated aluminum oxide. The binders can include, but are not limited to, water-soluble polymers, polyvinyl acetate, polyvinyl alcohol, polyvinyl pyrrolidone, polyurethane, methyl cellulose, carboxymethyl cellulose, hydroxylpropyl cellulose, sodium alginate, polyacrylate, casein, gelatin, pullulan, polyacrylamide, polyethylene oxide, polystyrene, styrene acrylic copolymers, styrene butadiene polymers, poly (N-vinylacetamide), waxes, canauba wax, paraffin wax, polyethylene wax, bees wax, polypropylene wax, and ethylene vinyl acetate. In some embodiments, the seed coating can include a wetting and dispersing additive such as, but not limited to polyacrylates, organo-modified polyacrylates, sodium polyacrylates, polyurethanes, phosphoric acid esters, star polymers, and modified polyethers.

In some embodiments, the seed coating can include other components such as, but not limited to, a solvent, thickener, coloring agent, anti-foaming agent, biocide, surfactant, and pigment. In some embodiments, the seed coating can include a hydrogel or film coating materials. In some embodiments, the concentration of dried microalgae in the seed coating can include 0.001-20% solids, such as 0.01%-15% solids, such as 0.25%-12% solids, for example 1%-12.5% solids, 2.5%-15% solids, 2.5%-12.5% solids, 3-12% solids, 5-12% solids, 5-15% solids, 7.5-12.5% solids, 8-12%> solids, or 9-11% solids, such as about 10% solids. In some embodiments, the concentration of microalgae in the seed coating can include less than 0.1% solids. In some embodiments, the concentration of dried microalgae in the seed coating can include 0.001-0.01% solids. In some embodiments, the concentration of dried microalgae in the seed coating can include 0.01-0.1% solids. In some embodiments, the concentration of dried microalgae in the seed coating can include 0.1-1% solids. In some embodiments, the concentration of dried microalgae in the seed coating can include 1-2% solids. In some embodiments, the concentration of dried microalgae in the seed coating can include 2-3% solids. In some embodiments, the concentration of dried microalgae in the seed coating can include 3-5% solids. In some embodiments, the concentration of dried microalgae in the seed coating can include 5-10% solids. In some embodiments, the concentration of dried microalgae in the seed coating can include 10-15% solids. In some embodiments, the concentration of dried microalgae in the seed coating can include 15-20% solids. In some embodiments, the seed can be coated in a single step. In some embodiments, the seed can be coated in multiple steps. Conventional or otherwise suitable coating equipment or techniques can be used to coat the seeds. Suitable equipment can include drum coaters, fluidized beds, rotary coaters, side vended pan, tumble mixers, and spouted beds. Suitable techniques can include mixing in a container, tumbling, spraying, or immersion. After coating, the seeds can be dried or partially dried.

Soil Application

In another non-limiting embodiment, the administration of the dried microalgae composition treatment can include mixing an effective amount of the composition with a solid growth medium, such as soil, potting mix, compost, or inert hydroponic material, prior to planting a seed, seedling, or plant in the solid growth medium. The dried microalgae composition can be mixed in the solid growth medium at an inclusion level of 0.001-20% by volume. In some embodiments, the effective amount in a mixed solid growth medium application of the dried microalgae composition can include a concentration in the range of 0.001-0.01% solids. In some embodiments, the effective amount in a mixed solid growth medium application of the dried microalgae composition can include a concentration in the range of 0.01-0.1% solids. In some embodiments, the effective amount in a mixed solid growth medium application of the dried microalgae composition can include a concentration in the range of 0.1-1% solids. In some embodiments, the effective amount in a mixed solid growth medium application of the dried microalgae composition can include a concentration in the range of 1-3%% solids. In some embodiments, the effective amount in a mixed solid growth medium application of the dried microalgae composition can include a concentration in the range of 3-5% solids. In some embodiments, the effective amount in a mixed solid growth medium application of the dried microalgae composition can include a concentration in the range of 5-10% solids. In some embodiments, the effective amount in a mixed solid growth medium application of the dried microalgae composition can include a concentration in the range of 10-20% solids.

In another non-limiting embodiment, the administration of the dried microalgae composition treatment can include inclusion in a solid growth medium during in-furrow plants or broadcast application to the ground. The dried microalgae composition can be applied at a rate of 50-500 grams/acre. In some embodiments, the application rate of the dried microalgae composition can include 50-100 grams/acre. In some embodiments, the application rate of the dried microalgae composition can include 100-150 grams/acre. In some embodiments, the application rate of the dried microalgae composition can include 150-200 grams/acre. In some embodiments, the application rate of the dried microalgae composition can include 200-250 grams/acre. In some embodiments, the application rate of the dried microalgae composition can include 250-300 grams/acre. In some embodiments, the application rate of the dried microalgae composition can include 300-350 grams/acre. In some embodiments, the application rate of the dried microalgae composition can include 350-400 grams/acre. In some embodiments, the application rate of the dried microalgae composition can include 400-450 grams/acre. In some embodiments, the application rate of the dried microalgae composition can include 450-500 grams/acre.

The dried microalgae composition can be applied at a rate of 10-50 grams/acre. In some embodiments, the application rate of the dried microalgae composition can include 10-20 grams/acre. In some embodiments, the application rate of the dried microalgae composition can include 20-30 grams/acre. In some embodiments, the application rate of the dried microalgae composition can include 30-40 grams/acre. In some embodiments, the application rate of the dried microalgae composition can include 40-50 grams/acre.

The dried microalgae composition can be applied at a rate of 0.001-10 grams/acre. In some embodiments, the application rate of the dried microalgae composition can include 0.001-0.01 grams/acre. In some embodiments, the application rate of the dried microalgae composition can include 0.01-0.1 grams/acre. In some embodiments, the application rate of the dried microalgae composition can include 0.1-1.0 grams/acre. In some embodiments, the application rate of the dried microalgae composition can include 1-2 grams/acre. In some embodiments, the application rate of the dried microalgae composition can include 2-3 grams/acre. In some embodiments, the application rate of the dried microalgae composition can include 3-4 grams/acre. In some embodiments, the application rate of the dried microalgae composition can include 4-5 grams/acre. In some embodiments, the application rate of the dried microalgae composition can include 5-10 grams/acre.

In another aspect, the invention provides a method of promoting an increase in the growth of a plant, comprising administering an effective amount of a composition of the invention to a plant such that growth of the treated plant is at least about 10% more than what is achieved by a control. In some cases the increase of growth is 15% or more, such as 20% or more, 25% or more, 30% or more, 35% or more, or even 40% or more (e.g., at least 45%, at least 50%, at least 55%, at least 60%, at least 65%, at least 70%, or even at least 75% increase in growth). In some aspects an effective amount to stimulate growth comprises administering a composition comprising a concentration of a microalgae composition (such as a whole cell microalgae, a post-extraction microalgae biomass, or a combination thereof) that is in a concentration of 0.001%-0.1%, such as 0.0025%-0.1%, for example 0.005%-0.1%, 0.0075%-0.1%, 0.01%-0.1%, e.g., 0.01%-0.025%, 0.01%-0.05%, 0.01%-0.075%, or 0.001%-0.025%, 0.001%-0.05%, 0.02%-0.08%, or 0.025%-0.075%. In one aspect, the microalgae composition comprises an *Aurantiochytrium* composition. In one aspect, the microalgae composition comprises a post-extraction *Aurantiochytrium* composition, such as a composition in which at least about 25%, at least about 33%, at least about 50%, at least about 75%, or even more (e.g., at least about 85%, 90%, or 95%), of the DHA and DHA-associated lipids of the *Aurantiochytrium* whole cell composition have been extracted from the biomass prior to the inclusion in the composition.

In another aspect, the invention provides a method of promoting the growth of plants under salt stress conditions, which comprises administering an effective amount of a microalgae composition to the plant and/or plant-associated soil, such that the growth of the plant is increased at least 10% as compared to an untreated control under the salt stress condition. In some aspects the increase in growth of the treated plant (whether treated directly and/or growing in treated soil) is at least 15%, at least 20%, at least 25%, at least 30%, at least 35%, at least 40%, at least 45%, at least 50%, at least 55%, at least 60% or more such as about 65% increase in growth under the high salt conditions. In some aspects, the amount of excess salt in the salt stress condition is at least 25 mM additional NaCl, such as at least 35 mM, at least 50 mM, at least 60 mM, at least 70 mM, at least 75 mM, at least 80 mM, at least 90 mM, at least 100 mM, at least 110 mM, at least 120 mM, at least 125 mM, at least 135 mM, or at least 150 mM additional NaCl. In other aspects, the amount of salt has been determined to be at least 10%, at least about 15%, at least about 20%, at least about 25%, at least about 35%, at least about 40%, at least about 50%, at least about 66%, at least about 75%, at least about 90%, or even at least 100%, 150%, 200%, 250%, or 300% greater than either a desired growing condition, a historic soil condition, or both. In some aspects, the concentration of the microalgae composition that is administered to the plant and/or soil is in the range of 0.001%-0.25%, such as 0.001%-0.1%, such as 0.01%-0.1%, or such as 0.05%-0.1%. Typically the composition will comprise 0.1%-15% solids of the microalgae composition, such as 0.25-12.5%, 0.33-12%, 0.5-12%, 1-12%, 2-11%, 5-10%, or 7.5-12.5% microalgae solids; is formulated as a liquid composition; and is administered at a rate of 0.25-2.5 gal/acre, such as 0.33-2 gal/acre, or 0.5-1.75 gal/acre, for a period of 8-20 weeks, typically every 1-6 weeks, such as every 2-6 weeks, every 2-4 weeks, every 2 weeks, every 3 weeks, or every 4 weeks, for 1-10, 1-8, 1-6, 1-4, 2-10, 2-8, 2-6, 2-4, 3-10, 3-8, 3-6, 3-4, or 4-10, 4-8, 4-6, 6-10, or 6-8 applications, depending on the plant, soil type, etc. In one aspect, the microalgae comprises *Aurantiochytrium* material, such as post-extraction *Aurantiochytrium* material, examples of which are described elsewhere herein.

In another aspect, the invention provides a method for promoting the growth of roots of a plant comprising administering to the plant and/or plant-associated soil an effective amount of a microalgae composition of the invention, such that the number of roots, size of roots, total weight of roots, or a combination of any or all thereof is increased by at least about 20%, such as at least 30%, at least 40%, at least 50%, at least 75%, or even at least 100%. In some aspects, the method can result in an increase in root growth in any of these three dimensions by at least 150%>, at least 175%, at least 200%>, at least 250%, at least 300%, at least 325%>, at least 350%, at least 375%, at least 400%, at least 425%, at least 450%, at least 475%, or even at least 500%. In some aspects, the amount of microalgae that is effective for increasing root concentration is in the concentration of 0.001%-0.25%, such as 0.001%-0.02%, 0.001%-0.01%, e.g., 0.0025%-0.009%, 0.0033%-0.009%, 0.004%-0.008%, or 0.005%-0.0075%. Typically the composition will comprise 0.1%-15%> solids of the microalgae composition, such as 0.25-12.5%, 0.33-12%, 0.5-12%, 1-12%, 2-11%, 5-10%, or 7.5-12.5% microalgae solids; is formulated as a liquid composition; and is administered at a rate of 0.25-2.5 gal/acre, such as 0.33-2 gal/acre, or 0.5-1.75 gal/acre, for a period of 8-20 weeks, typically every 1-6 weeks, such as every 2-6 weeks, every 2-4 weeks, every 2 weeks, every 3 weeks, or every 4 weeks, for 1-10, 1-8, 1-6, 1-4, 2-10, 2-8, 2-6, 2-4, 3-10, 3-8, 3-6, 3-4, or 4-10, 4-8, 4-6, 6-10, or 6-8 applications, depending on the plant, soil type, etc. In some aspects the microalgae material comprises *Aurantiochytrium* material, such as post-extraction *Aurantiochytrium* material.

In another aspect, the invention provides methods for the prevention and/or reduction of one or more biotic stress(ors) and/or one or more plant diseas(es), such as, for example, white mold (*S. sclerotiorum*). An effective amount of a microalgae composition of the invention can be administered to the plant (directly and/or to the associated soil, but more typically such methods are performed by application to the plant) in an effective manner and effective amount, such as foliar administration of an effective amount of the microalgae composition in the case of white mold treatment or prevention. "Treatment" of the biotic stress/disease in this respect means reduction in the duration and/or extent of the incidence of the condition or disease. Compositions of the invention also or alternatively can be administered for the "prevention" of the disease/condition (reduction of the severity, as measured by, e.g., lessening of the duration, amount of deleterious impact (e.g., measured terms of frequency of occurrence of death, size reduction, etc.), and/or extent (as measured by amount of impacted area in the applicable plants) of the infection/disease). In one embodiment, an effective amount means a composition comprising the microalgae in a concentration of 0.001% to 0.01% (such as 0.005%-0.01%, 0.0075%-0.01%, 0.009-0.01%, 0.001%-0.008%, 0.001%-0.006%, 0.001%-0.005%, or 0.001%-0.003%). The amount of microalgae concentration, material, and route of administration is desirably effective to reduce *S. sclerotiorum* infection in a plant between about 15% to about 100%, such as at least about 20%, at least about 25%, at least about 30%, at least about 35%, at least about 40% or greater or 50% or greater, and in certain cases even 60% or greater or even 70% or greater (e.g., about 20%-100%, such as about 25% to about 95%, about 25% to about 90%, about 30% to about 80%, about 30% to about 75%, about 30% to about 70%, or about 35% to about 70%, such as about 40% to about 65%). Such reductions in infection can be measured with respect to a particular plant or as an average reduction in a population of plants. In one aspect, the microalgae composition comprises *Aurantiochytrium* material, such as post-extraction *Aurantiochytrium* material. In other particular aspects, the microalgae compositions of the invention are combined with one or additional products that treat, prevent, or otherwise modulate one or more diseases, such as white mold and/or white mold-associated conditions in the applicable plant(s) or plant population(s). In a particular aspect, the additional product is derived from macroalgae, such as kelp extract. In another aspect, the additional product also or alternatively is an anti-fungal product, such as an amount of vinclozolin, benomyl, and/or thiophanate methyl, in a concentration, administration amount, and administration protocol that alone or in combination with the microalgae composition to treat, prevent, or otherwise detectably, and desirably by at least 10%, at least 20%, at least 25%, or more, modulate white mold infection/disease in the applicable plant or plant population. In another aspect, the composition is also or alternatively administered in association with an agent that prevents rotting such as an ozone treatment. Associated administration in this context can mean co-administration or separate (serial) administration that is near enough in time to obtain the desired impact of administering the two or more agents in concert for the desired impact. The methods of the invention that are focused on the prevention of spread of disease such as white mold disease can advantageously be performed in areas that have been associated with recent infection, such as recent *S. sclerotiorum* infection, in areas that are associated with frequent infection as determined by longer term historical data or modeling, and/or in areas where *S. sclerotiorum* infection is predicted to occur through other means. Treatment methods can be performed where *S. sclerotiorum* is identified on plants or in a population of plants.

In another aspect, the invention provides a method of promoting the amount of active carbon in a soil, which comprises administering an effective amount of a microalgae composition of the invention to a soil such that the amount of active carbon in the soil is increased at least 5%, such as at least 10%, at least 12%, at least 15%, at least 17.5%, at least 20%, at least 22.5%, or at least 25%, within a period of 3 days, 5 days, 7 days, 10 days, 12 days, 14 days, 15 days, or 20 days. In one aspect, the microalgae comprises *Chlorella* material. In another aspect, the microalgae comprises *Aurantiochytrium* material. In another aspect, the invention comprises a combination of *Chlorella* material and *Aurantiochytrium* material. In another aspect, performance of the method results in achievement of an active carbon score of at least 65, at least 70, or at least 75, within a period of 5 days, 10 days, 15 days, or 20 days.

In still another facet, the invention provides a method for increasing the proportion of soil particles of 1-2 mm in size in a soil comprising administering an effective amount of a microalgae composition of the invention to a soil such that the amount of 1-2 mm particles present in the soil are increased by at least 20%, at least 25%, at least 30%, at least 35%, at least 40%, at least 50%, at least 60%, at least 651}/o, at least 70%, at least 75%, or more (such as about 80%), within a period of 10 days, 12 days, 14 days, or 15 days. In one aspect, the microalgae comprises *Aurantiochytrium* or *Chlorella*. In some aspects, the soil that receives the administration has been determined to have a lower proportion of 1-2 mm particles than is optimal for the growth of target plants, for the area and/or soil type that characterizes the soil before the treatment, or a combination thereof.

In still another dimension, the invention provides a method for increasing the amount of beneficial bacteria in a soil comprising administering an effective amount of a microalgae composition of the invention to a soil such that the amount of one or more beneficial bacterial species in the soil are increased by at least 25%, at least 35%, at least 50%>, at least 65%, at least 75%, at least 80%, at least 90%, or more. In some cases, the amount of beneficial bacteria in the soil are at least doubled by the application of the microalgae. In some aspects, the method comprises determining that the soil contains one or more endogenous, beneficial bacteria prior to application of the microalgae. The microalgae composition is typically applied 2-8 times, such as 3-6 times, such as 4-6 times, over a period of 4-30 weeks, such as 6-24 weeks, 8-24 weeks, 9-24 weeks, e.g., 8-16 weeks. The amount of microalgae applied is typically in the range of 0.1-3.5 gal/acre, for example 0.25 gal/acre-3 gal/acre, such as 0.33 gal/acre-2.5 gal/acre, such as 0.4-2.25 gal/acre, for example 0.5-1.5 gal acre, 0.5-1.25 gal/acre, or 0.5-1 gal/acre. In one aspect the beneficial bacteria comprises *Nitrospira* bacteria. In another aspect, the beneficial bacteria also or alternatively comprises *Gaiellales* bacteria. In still a further aspect, the beneficial bacteria also or alternatively comprises *Bacillus* bacteria. The bacteria can comprise another beneficial bacteria. A "beneficial bacteria" in this context means a bacteria that promotes the growth, quality, and/or health of one or more plant species.

EXAMPLES

Embodiments of the invention are exemplified and additional embodiments are disclosed in further detail in the following Examples, which are not in any way intended to limit the scope of any aspect of the invention described herein. The strain of microalgae identified as *Aurantiochytrium* sp. in some of the following examples was isolated from marine field samples (Mangrove, Fla.—Biscayne Bay) and sequenced for 1 8S. The sequences were compared with existing sequences on the National Center for Biotechnology Information (NCBI) GenBank database via Basic Local Alignment Search Tool (BLAST). The results of the sequence comparison showed strain's sequence is positioned between two species of the genus *Aurantiochytrium* (*Schizochytrium*), with the closest BLAST hits having a 98.8% similarity to *Aurantiochytrium* (*Schizochytrium*) *limacinum* SR21 (accession number AB973564. 1). Therefore, this isolated microalgae strain is referred to in the examples as *Aurantiochytrium* sp.

Example 1—Fabaceae (Leguminosae)

Experiments are conducted to test effects of application of a microalgae based composition to crop plants of the family Fabaceae (Leguminosae). Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plant fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 2—Poaceae

Experiments are conducted to test effects of application of a microalgae based composition to crop plants of the family Poaceae. Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plant fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 3—Roasaceae

Experiments are conducted to test effects of application of a microalgae based composition to crop plants of the family Roasaceae. Application is done as in other examples herein, such that, in various treatments, (a) seeds are wetted or soaked in the composition; ((b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plant fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 4—Vitaceae

Experiments are conducted to test effects of application of a microalgae based composition to crop plants of the family Vitaceae. Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plant fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 5—Brassicaeae (Cruciferae)

Experiments reconducted to test effects of application of a microalgae based composition to crop plants of the family Brassicaeae (Cruciferae). Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plant fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 6—Caricaceae

Experiments are conducted to test effects of application of a microalgae based composition to crop plants of the family Caricaceae. Application is done as in other examples herein, such that, in various treatments, (a) seeds are wetted or soaked in the composition; ((b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plant fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 7—Malvaceae

Experiments are conducted to test effects of application of a microalgae based composition to crop plants of the family Malvaceae. Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 8—Sapindaceae

Experiments are conducted to test effects of application of a microalgae based composition to crop plants of the family Sapindaceae. Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plant fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 9—Anacardiaceae

Experiments are conducted to test effects of application of a microalgae based composition to crop plants of the family Anacardiaceae. Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plant fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 10

An experiment was performed to determine the effect of treating *Arabidopsis thaliana* with a variety of treatments made from microalgae under normal growth conditions and under salt stressed conditions. The bioassay was initiated using four-day old plantlets grown on half strength Murashige and Skoog (MS) medium, supplemented with 1% (w/v) sucrose, and solidified with 0.4% (w/v) Phytagel in square petri plates. Plates were vertically stacked in the growth chamber set at 22° C. with 16-h light/8-h dark cycle, with light intensity of 100 µmol/m$^{-2}$s−1. Each plate contained five replicate plantlets. Plantlets were transferred onto medium supplemented with concentrations of 0.1% (0.1 mL/L), 0.01% (0.01 mL/L), or 0.001% (0.001 mL/L) of non-oil treatments, or 0.01% (0.01 mL/L), 0.001% (0.001 mL/L), or 0.0001% (0.0001 mL/L) of oil treatments listed in the table and compared to an untreated control. Each concentration of each treatment was tested in triplicate.

The organic carbon uses for culturing the *Chlorella* sp. biomass is specified in the tables below. All microalgae whole biomass treatments were prepared by lysing and freeze drying the biomass. For extracted biomass and extracted oil treatments (except for *Haematococcus*), the microalgal biomass (600 g) was mixed with a solvent (ethanol, hexane, or acetone) (3,000 mL) and heated at reflux for 2 hours. The reaction mixture was then filtered while hot and the biomass was extracted again with a solvent (ethanol, hexane, or acetone) twice (2 times at 3,000 mL). The combined organic extracts from the process were concentrated to yield the extracted oil, and the resulting extracted biomass was free dried. For *Haematococcus*, the extracted oil treatment was obtained by subjecting the biomass to a super critical carbon dioxide extraction. For the high lipid *Nannochloropsis* treatments, the cells were harvested during the oil or stationary phase when the metabolic activity was primarily lipid accumulation and not cell growth (e.g., cell division). In one treatment of *Aurantiochytrium*, the oil was extracted without using a solvent (i.e., mechanical separation of the oil from the biomass).

For the *Galdieria* protein fraction treatment, *Galdieria* biomass (100 g) was added to 1,000 mL of water and was heated to 50° C. for 4 hours. The reaction mixture was cooled and centrifuged at 6,000 rpm for 15 minutes at 4° C. The crude pellet was isolated and freeze dried to form the low protein whole biomass treatment. Next ammonium sulfate was added to the supernatant (30% saturation). The resulting solution was stirred at room temperature for 2 hours and centrifuged at 6,000 rpm for 30 minutes. The supernatant solution was then saturated with ammonium sulfate a second time (30%> saturation). The resulting solution was stirred at room temperature for 2 hours and centrifuged at 6,000 rpm for 30 minutes. The pellet obtained was isolated and diluted with water (about 200 mL) and purified by ultrafiltration to remove soluble salts. The resulting solution was collected and freeze dried to produce the protein fraction. The resulting *Galdieria* biomass that was subjected to the protein extraction had less than 15% protein. The low protein whole biomass was subjected to the oil extraction method described above using ethanol to produce the low protein extracted oil and low protein extracted biomass treatments. The resulting *Galdieria* biomass that was subjected to the protein extraction and oil extraction had less than 20% protein.

For the *Porphyridium* EPS treatments, first the *Porphyridium* culture broth was centrifuged to remove the microalgae biomass. Next the supernatant was diluted with isopropanol (3 to 5 times v/v) to precipitate the EPS. The precipitated EPS was then separated from the supernatant by filtration. The "PE rich fraction" *Porphyridium* treatment was produced by lysing the biomass and subjecting the lyzed biomass at a concentration of 10% solids (w/v) to a water based extraction at 50° C. for 4 hours. The resulting solution was then diluted with water (10×) and centrifuged to produce the "PE rich fraction" liquid fraction and the "PEG 1 Lipid+EPS fraction". The "PE rich fraction" was purified using tangential flow filtration and freeze dried, resulting in a final concentration of 20-25% phycoerythrin. The "PEG 1 Lipid+EPS fraction" *Porphyridium* treatment contained primarily lipids, EPS, and water insoluble (non-extractable) protein. To produce the "LEB2+EPS" *Porphyridium* treatment, the "PEG 1 Lipid+EPS fraction" was refluxed in hexane and the lipids were extracted. The remaining solid fraction primarily comprised of EPS and protein.

The "Biomass—EPS" *Porphyridium* treatment was produced by centrifuging the culture to separate the EPS from the biomass, diluting the concentrated biomass with water (10-20×) and centrifuging a second time to remove additional EPS and salt (about 90-95%) from the resulting biomass used as the treatment. To produce the "PEB2 Lipid+PS fraction" *Porphyridium* treatment, "Biomass–EPS" fraction at a concentration of 5% solids (w/v) was subjected to a water based extraction at 50° C. for 4 hours. The resulting solution was centrifuged, and the supernatant was separated from the sediment. The supernatant was then brought to 25% saturation using ammonium sulfate to precipitate proteins that were then removed by centrifugation. The supernatant was then brought to 50% saturation using ammonium sulfate to precipitate the phycoerythrin. The precipitated phycoerythrin was collected by centrifugation, purified via dialysis using a 30 kDa filter, and freeze dried to produce the final form of the "PEB2 Lipid+PSfraction" *Porphyridium* treatment which contained 20-25% phycoerythrin.

For the *Spirulina* low protein and protein fraction treatments, the aqueous extract method as described above for *Galdieria* was performed. The resulting *Spirulina* biomass that was subjected to a protein extraction had less than 15% protein. The *Spirulina* lyzed whole biomass treatment was formed by mechanically disrupted the cells but then performing no further separations with or without solvents.

The salt stressed plantlets were also supplemented with 100 mM of NaCl. Seven days after the plantlets were treated plant dry weight, root length, amount of chlorotic leaves, and the amount of plants with chlorosis were measured. The results are shown in Tables 1-3, which display the results for each tested concentration with respect to the untreated control. For the chlorosis metric, the reduction in the effect of chlorosis with respect to the control (i.e., improvement over the control) is represented as a negative (−) value.

TABLE 1

| | | | Dry Weight % Difference vs. | Root Length % Difference vs. |
|---|---|---|---|---|
| Genus | Treatment | Concentration | Control | Control |
| | | Growth (No Salt Stress) | | |
| *Galdieria* | Whole Biomass | 0.1% | −38.2 | −81.0 |
| | | 0.01% | −30.0 | −6.4 |
| | | 0.001% | −40.6 | +4.0 |
| *Galdieria* | Extracted Biomass | 0.1% | −52.1 | −27.0 |
| | | 0.01% | −20.6 | −4.7 |
| | | 0.001% | −37.0 | −3.2 |
| *Galdieria* | Extracted Oil | 0.01% | −57.0 | −77.8 |
| | | 0.001% | −24.7 | −29.6 |
| | | 0.0001% | −45.2 | +6.9 |
| *Galdieria* | Low Protein Whole Biomass | 0.1% | −23.6 | −63.6 |
| | | 0.01% | −8.5 | +9.7 |
| | | 0.001% | +7.3 | −11.0 |
| *Galdieria* | Low Protein Extracted Biomass | 0.1% | −73.9 | −62.0 |
| | | 0.01% | −46.7 | −31.8 |
| | | 0.001% | −41.8 | −10.6 |
| *Galdieria* | Low Protein Extracted Oil | 0.01% | −58.1 | −97.2 |
| | | 0.001% | +38.7 | −37.8 |
| | | 0.0001 | +21.5 | −3.9 |
| *Galdieria* | Protein Fraction | 0.1% | −37.6 | −30.3 |
| | | 0.01% | −26.1 | −14.6 |
| | | 0.001% | −9.7 | −5.3 |
| *Chlorella* sp. (acetate) | Whole Biomass | 0.1% | −27.3 | −100.0 |
| | | 0.01% | +40.0 | +3.0 |
| | | 0.001% | +21.8 | −6.0 |
| *Chlorella* sp. (acetate) | Extracted Biomass | 0.1% | +9.1 | −99.6 |
| | | 0.01% | +32.7 | −20.0 |
| | | 0.001% | +36.4 | −30.8 |
| *Chlorella* sp. (acetate) | Extracted Oil | 0.01% | −32.4 | −63.4 |
| | | 0.001% | −23.8 | −7.7 |
| | | 0.0001% | −4.8 | +23.7 |
| *Haematococcus* | Whole Biomass | 0.1% | −49.1 | −98.8 |
| | | 0.01% | −23.6 | −8.4 |
| | | 0.001% | −40.0 | +11.5 |
| *Haematococcus* | Extracted biomass | 0.1% | −3.6 | −82.9 |
| | | 0.01% | +50.9 | +1.9 |
| | | 0.001% | +27.3 | +9.6 |
| *Haematococcus* | Extracted Oil | 0.01% | −22.6 | −71.9 |
| | | 0.001% | −10.8 | −24.9 |
| | | 0.0001% | −2.2 | −13.8 |
| *Isochrysis* | Whole Biomass | 0.1% | −52.1 | −99.4 |
| | | 0.01% | −14.5 | +1.3 |
| | | 0.001% | −30.2 | +6.1 |
| *Isochrysis* | Extracted Biomass | 0.1% | −43.6 | −100.0 |
| | | 0.01% | +41.8 | +14.9 |
| | | 0.001% | +94.5 | +12.0 |
| *Isochrysis* | Extracted Oil | 0.01% | −33.3 | −17.9 |
| | | 0.001% | +9.5 | +17.3 |
| | | 0.0001% | −16.2 | +0.2 |
| *Nannochloropsis* | Extracted Biomass | 0.1% | +16.4 | −12.3 |
| | | 0.01% | +41.8 | +21.4 |
| | | 0.001% | +69.1 | +7.9 |
| *Nannochloropsis* | Extracted Oil | 0.01% | −9.5 | −57.6 |
| | | 0.001% | +1.9 | −10.7 |
| | | 0.0001% | −29.4 | +22.1 |
| *Porphyridium* | Whole Biomass | 0.1% | −38.8 | −39.4 |
| | | 0.01% | −14.5 | −5.0 |
| | | 0.001% | −20.6 | −3.2 |
| *Porphyridium* | Extracted Biomass | 0.1% | −47.3 | −78.9 |
| | | 0.01% | −30.3 | −10.3 |
| | | 0.001% | −21.8 | −4.3 |
| *Porphyridium* | Extracted Oil | 0.01% | −16.1 | −15.8 |
| | | 0.001% | +1.1 | −21.7 |
| | | 0.0001% | −16.1 | +2.1 |
| *Porphyridium* | EPS | 0.1% | — | — |
| | | 0.01% | +27.3 | −87.2 |
| | | 0.001% | +41.8 | +14.3 |
| *Schizochytrium* | Whole Biomass | 0.1% | −61.2 | −99.8 |
| | | 0.01% | −37.6 | −78.5 |
| | | 0.001% | −38.2 | −16.5 |
| *Schizochytrium* | Extracted Biomass | 0.1% | +27.3 | −88.9 |
| | | 0.01% | +63.6 | +5.2 |
| | | 0.001% | +40.0 | +15.2 |

TABLE 1-continued

| | Growth (No Salt Stress) | | | |
|---|---|---|---|---|
| Genus | T1.eatment | Concentration | Dry Weight % Difference vs. Control | Root Length % Difference vs. Control |
| Schizochytrium | Extracted Oil | 0.01% | +3.2 | −10.8 |
| | | 0.001% | −6.7 | +2.6 |
| | | 0.0001% | −19.0 | +31.7 |
| Tetraselmis | Whole Biomass | 0.1% | −53.3 | −100.0 |
| | | 0.01% | −29.1 | −17.9 |
| | | 0.001% | −15.8 | +4.8 |
| Tetraselmis | Extracted Biomass | 0.1% | −67.9 | −100.0 |
| | | 0.01% | −18.8 | −1.4 |
| | | 0.001% | −12.7 | +15.7 |
| Tetraselmis | Extracted Oil | 0.01% | −32.3 | −89.0 |
| | | 0.001% | −14.0 | −33.9 |
| | | 0.0001% | −2.2 | −24.7 |
| Pavlova | Whole Biomass | 0.1% | −63.4 | −100.0 |
| | | 0.01% | −44.7 | −61.4 |
| | | 0.001% | −31.7 | −48.7 |
| Pavlova | Extracted Biomass | 0.1% | +73.9 | — |
| | | 0.01% | +131.5 | +159.0 |
| | | 0.001% | +118 | +175.3 |
| Pavlova | Extracted Oil | 0.01% | +18.1 | +10.6 |
| | | 0.001% | +18.7 | +11.3 |
| | | 0.0001% | +26.3 | +10.9 |
| Phaeodactylum | Whole Biomass | 0.1% | −38.9 | −90.6 |
| | | 0.01% | −29.5 | +1.0 |
| | | 0.001% | +42.1 | +26.9 |
| Phaeodactylum | Extracted Biomass | 0.1% | — | — |
| | | 0.01% | +70.3 | +21.9 |
| | | 0.001% | +148.6 | +57.6 |
| Phaeodactylum | Extracted Oil | 0.01% | −46.5 | −3.9 |
| | | 0.001% | −48.5 | −11.1 |
| | | 0.0001% | −46.5 | −0.6 |
| Nannochloropsis | High Lipid Whole Biomass | 0.1% | −31.9 | −95.6 |
| | | 0.01% | −22.5 | −26.1 |
| | | 0.001% | −22.1 | −26.0 |
| Nannochloropsis | High Lipid Extracted Biomass | 0.1% | −54.0 | +46.6 |
| | | 0.01% | −30.5 | +28.4 |
| | | 0.001% | −9.1 | +0.4 |
| Nannochloropsis | High Lipid Extracted Oil | 0.01% | −15.8 | +5.1 |
| | | 0.001% | −13.7 | +1.0 |
| | | 0.0001% | −22.1 | +7.3 |
| Porphyridium | PE rich fraction | 0.1% | −67.4 | −47.9 |
| | | 0.01% | −56.3 | +40.0 |
| | | 0.001% | −46.3 | +46.8 |
| Porphyridium | PEB 1 lipid + EPS fraction | 0.1% | −59.1 | −33.2 |
| | | 0.01% | −36.3 | +0.6 |
| | | 0.001% | −23.4 | +0.7 |
| Porphyridium | Extracted Oil | 0.01% | — | −100.0 |
| | | 0.001% | — | −15.8 |
| | | 0.0001% | — | +2.3 |
| Porphyridium | LEB2 + EPS | 0.1% | −69.7 | −78.7 |
| | | 0.01% | −52.9 | +0.3 |
| | | 0.001% | −17.3 | −2.2 |
| Porphyridium | Biomass − EPS | 0.1% | −45.9 | −6.1 |
| | | 0.01% | −27.6 | +5.8 |
| | | 0.001% | −26.3 | +0.7 |
| Porphyridium | PE rich Fraction from biomass − EPS | 0.1% | −41.5 | −93.2 |
| | | 0.01% | −33.9 | −1.5 |
| | | 0.001% | −7.6 | +5.0 |
| Porphyridium | PEB2 Lipid + PS fraction | 0.1% | −59.1 | −100.0 |
| | | 0.01% | −11.7 | −5.7 |
| | | 0.001% | −15.8 | +13.1 |
| Aurantiochytrium sp. | Whole Biomass | 0.1% | −44.4 | −90.7 |
| | | 0.01% | −8.9 | −8.8 |
| | | 0.001% | −4.8 | −0.6 |
| Aurantiochytrium sp. | Extracted Biomass (hexane) | 0.1% | −61.8 | −14.2 |
| | | 0.01% | −44.4 | +15.1 |
| | | 0.001% | +2.2 | +17.6 |
| Aurantiochytrium sp. | Extracted Oil (hexane) | 0.01% | −15.9 | +8.0 |
| | | 0.001% | +3.0 | −6.7 |
| | | 0.0001% | −3.0 | +16.1 |
| Aurantiochytrium sp. | Extracted Biomass (ethanol) | 0.1% | −46.2 | −83.4 |
| | | 0.01% | −6.2 | −2.6 |
| | | 0.001% | −0.9 | −0.4 |

TABLE 1-continued

| | Growth (No Salt Stress) | | | |
|---|---|---|---|---|
| Genus | Treatment | Concentration | Dry Weight % Difference vs. Control | Root Length % Difference vs. Control |
| *Aurantiochytrium* sp. | Extracted Oil (ethanol) | 0.01% | −18.3 | +8.0 |
| | | 0.001% | −43.3 | −6.7 |
| | | 0.0001% | −23.3 | +16.1 |
| *Aurantiochytrium* sp. | Extracted Oil (mechanical) | 0.01% | −11.1 | +10.6 |
| | | 0.001% | −0.4 | −4.0 |
| | | 0.0001% | −28.9 | +6.8 |
| *Spirulina* | Extracted Biomass (hexane) | 0.1% | −35.1 | −93.6 |
| | | 0.01% | −46.7 | +1.6 |
| | | 0.001% | +4.7 | +2.2 |
| *Spirulina* | Extracted Oil (hexane) | 0.01% | −7.0 | −58.0 |
| | | 0.001% | +13.7 | −9.9 |
| | | 0.0001% | +32.8 | +4.1 |
| *Spirulina* | Extracted Biomass (acetone) | 0.1% | −77.8 | −100.0 |
| | | 0.01% | −17.3 | +18.7 |
| | | 0.001% | −22.7 | −2.2 |
| *Spirulina* | Extracted Oil (acetone) | 0.01% | −37.4 | −77.4 |
| | | 0.001% | −13.0 | +3.1 |
| | | 0.0001% | +22.6 | +14.7 |
| *Spirulina* | Low Protein Whole Biomass | 0.1% | −79.1 | −88.2 |
| | | 0.01% | −56.4 | −18.9 |
| | | 0.001% | −29.3 | +1.2 |
| *Spirulina* | Protein Fraction | 0.1% | +36.4 | +13.8 |
| | | 0.01% | −4.9 | +10.8 |
| | | 0.001% | −18.7 | +7.7 |
| *Spirulina* | Lyzed Whole Biomass | 0.1% | −15.2 | −20.6 |
| | | 0.01% | +6.3 | +36.5 |
| | | 0.001% | −9.6 | +15.6 |
| *Scenedesmus* | Whole Biomass | 0.1% | −58.2 | |
| | | 0.01% | −37.7 | |
| | | 0.001% | −21.8 | |
| *Scenedesmus* | Extracted Biomass | 0.1% | −32.8 | |
| | | 0.01% | −28.1 | |
| | | 0.001% | −25.8 | |
| *Scenedesmus* | Extracted Oil | 0.01% | −58.7 | |
| | | 0.001% | −35.8 | |
| | | 0.0001% | −32.3 | |
| T-*Isochrysis* | Whole Biomass | 0.1% | −58.9 | |
| | | 0.01% | −31.6 | |
| | | 0.001% | −10.2 | |
| T-*Isochrysis* | Extracted Biomass (ethanol) | 0.1% | −55.2 | |
| | | 0.01% | +7.8 | |
| | | 0.001% | +23.5 | |
| T-*Isochrysis* | Extracted Oil (ethanol) | 0.01% | −42.1 | |
| | | 0.001% | −6.0 | |
| | | 0.0001% | +9.9 | |
| *Chlorella zofingiensis* | Whole Biomass | 0.1% | −54.0 | |
| | | 0.01% | −30.0 | |
| | | 0.001% | −1.8 | |
| *Chlorella zofingiensis* | Extracted Biomass (ethanol) | 0.1% | −36.5 | |
| | | 0.01% | −6.2 | |
| | | 0.001% | −3.6 | |
| *Chlorella zofingiensis* | Extracted Oil (ethanol) | 0.01% | −34.7 | |
| | | 0.001% | −12.0 | |
| | | 0.0001% | −6.4 | |
| *Chlorella* sp. (glucose) | Whole Biomass | 0.1% | −43.5 | |
| | | 0.01% | −5.5 | |
| | | 0.001% | +21.1 | |
| *Chlorella* sp. (glucose) | Extracted Biomass (ethanol) | 0.1% | +11.6 | |
| | | 0.01% | +13.6 | |
| | | 0.001% | +42.9 | |
| *Chlorella* sp. (glucose) | Extracted Oil (ethanol) | 0.01% | −42.7 | |
| | | 0.001% | −28.7 | |
| | | 0.0001% | −10.2 | |
| *Aurantiochytrium* sp. | Whole Biomass (Medium Lipid) | 0.1% | −80.0 | |
| | | 0.01% | −66.6 | |
| | | 0.001% | −33.5 | |
| *Aurantiochytrium* sp. | Extracted Biomass (High Lipid) (Mechanical Extraction) | 0.1% | −69.9 | |
| | | 0.01% | −24.5 | |
| | | 0.001% | +7.1 | |
| *Aurantiochytrium* sp. | Extracted Oil (High Lipid) (Hexane) | 0.01% | −37.7 | |
| | | 0.001% | −15.3 | |
| | | 0.0001% | −38.0 | |

TABLE 1-continued

Growth (No Salt Stress)

| Genus | Treatment | Concentration | Dry Weight % Difference vs. Control | Root Length % Difference vs. Control |
|---|---|---|---|---|
| *Aurantiochytrium* sp. | Extracted Oil (High Lipid) (Ethanol) | 0.01% | +1.7 | |
| | | 0.001% | −4.0 | |
| | | 0.0001% | −10.8 | |
| *Aurantiochytrium* sp. | Extracted Oil (High Lipid) (Mechanical,) | 0.01% | −27.7 | |
| | | 0.001% | −21.2 | |
| | | 0.0001% | −31.6 | |
| *Aurantiochytrium* sp. | Extracted Oil (Medium Lipid) (Hexane) | 0.01% | −40.2 | |
| | | 0.001% | −38.5 | |
| | | 0.0001% | −39.7 | |
| *Aurantiochytrium* sp. | Extracted Oil (Medium Lipid) (Ethanol) | 0.01% | −52.2 | |
| | | 0.001% | −25.7 | |
| | | 0.0001% | −32.5 | |
| *Aurantiochytrium* sp. | Extracted Biomass (Medium Lipid) (Hexane) | 0.1% | −55.7 | |
| | | 0.01% | −16.1 | |
| | | 0.001% | −14.1 | |
| *Aurantiochytrium* sp. | Extracted Biomass (Medium Lipid) (Ethanol) | 0.1% | −25.4 | |
| | | 0.01% | −24.4 | |
| | | 0.001% | −11.4 | |
| *Aurantiochytrium* sp. | Whole Biomass (High Lipid) | 0.1% | −65.5 | |
| | | 0.01% | −13.1 | |
| | | 0.001% | +0.4 | |
| *Aurantiochytrium* sp. | Extracted Biomass (High Lipid) (Ethanol) | 0.1% | −36.2 | |
| | | 0.01% | −10.1 | |
| | | 0.001% | +1.4 | |
| *Aurantiochytrium* sp. | Extracted Biomass (High Lipid) (Hexane) | 0.1% | −54.9 | |
| | | 0.01% | −29.1 | |
| | | 0.001% | +32.0 | |
| *Botryococcus* | Lyzed Whole Biomass | 0.1% | −55.7 | |
| | | 0.01% | −31.5 | |
| | | 0.001% | −24.0 | |
| *Botryococcus* | Extracted Oil | 0.01% | −44.1 | |
| | | 0.001% | −22.2 | |
| | | 0.0001% | −11.2 | |
| *Botryococcus* | Extracted Biomass | 0.1% | −45.2 | |
| | | 0.01% | −31.7 | |
| | | 0.001% | −28.6 | |

TABLE 2

Salt Stress

| Genus | Treatment | Concentration | Dry Weight % Difference vs. Control | Root Length % Difference vs. Control |
|---|---|---|---|---|
| *Galdieria* | Whole Biomass | 0.1% | −25.0 | −100.0 |
| | | 0.01% | −38.2 | −15.6 |
| | | 0.001% | −43.1 | −22.0 |
| *Galdieria* | Extracted Biomass | 0.1% | −20.6 | −35.2 |
| | | 0.01% | −13.7 | −3.0 |
| | | 0.001% | −50.0 | −20.7 |
| *Galdieria* | Extracted Oil | 0.01% | −41.7 | −48.1 |
| | | 0.001% | −38.3 | −37.4 |
| | | 0.0001% | −34.5 | −11.8 |
| *Galdieria* | Low Protein Whole Biomass | 0.1% | −35.3 | −98.3 |
| | | 0.01% | −51.0 | −26.6 |
| | | 0.001% | −36.3 | −10.9 |
| *Galdieria* | Low Protein Extracted Biomass | 0.1% | −32.4 | −35.4 |
| | | 0.01% | −20.6 | −17.5 |
| | | 0.001% | −28.4 | −9.0 |
| *Galdieria* | Low Protein Extracted Oil | 0.01% | −63.3 | −96.9 |
| | | 0.001% | −45.0 | −21.1 |
| | | 0.0001% | −21.7 | −56.5 |

TABLE 2-continued

| | Salt Stress | | | |
|---|---|---|---|---|
| Genus | Treatment | Concentration | Dry Weight % Difference vs. Control | Root Length % Difference vs. Control |
| *Galdieria* | Protein Fraction | 0.1% | −8.8 | −33.4 |
| | | 0.01% | −29.4 | −22.6 |
| | | 0.001% | −22.5 | −22.9 |
| *Chlorella* sp. (acetate) | Whole Biomass | 0.1% | −22.4 | −96.3 |
| | | 0.01% | +47.1 | −33.7 |
| | | 0.001% | +47.1 | +17.7 |
| *Chlorella* sp. (acetate) | Extracted Biomass | 0.1% | −11.8 | −100.0 |
| | | 0.01% | +26.5 | −80.9 |
| | | 0.001% | −20.6 | +15.3 |
| *Chlorella* sp. (acetate) | Extracted Oil | 0.01% | −9.6 | −42.8 |
| | | 0.001% | −22.8 | +0.5 |
| | | 0.0001% | −2.1 | +31.7 |
| *Haematococcus* | Whole Biomass | 0.1% | −81.7 | +0.6 |
| | | 0.01% | −75.0 | −23.0 |
| | | 0.001% | −35.0 | +2.6 |
| *Haematococcus* | Extracted Biomass | 0.1% | +8.8 | −96.4 |
| | | 0.01% | −2.9 | +2.8 |
| | | 0.001% | −20.6 | +26.7 |
| *Haematococcus* | Extracted Oil | 0.01% | −28.4 | −100.0 |
| | | 0.001% | −30.4 | −15.5 |
| | | 0.0001% | −5.9 | +8.4 |
| *Isochrysis* | Whole Biomass | 0.1% | — | −99.8 |
| | | 0.01% | −19.6 | −56.4 |
| | | 0.001% | −30.4 | −12.8 |
| *Isochrysis* | Extracted Biomass | 0.1% | −11.8 | −91.5 |
| | | 0.01% | +29.4 | −61.2 |
| | | 0.001% | +26.5 | +5.1 |
| *Isochrysis* | Extracted Oil | 0.01% | −28.4 | −63.5 |
| | | 0.001% | −19.0 | +15.8 |
| | | 0.0001% | −15.3 | +58.2 |
| *Nannochloropsis* | Extracted Biomass | 0.1% | +44.1 | −87.1 |
| | | 0.01% | +50.0 | +5.3 |
| | | 0.001% | +32.4 | +36.8 |
| *Nannochloropsis* | Extracted Oil | 0.01% | +31.8 | −30.3 |
| | | 0.001% | +9.2 | +37.3 |
| | | 0.0001% | +28.1 | +55.0 |
| *Porphyridium* | Whole Biomass | 0.1% | −34.3 | −87.2 |
| | | 0.01% | −9.8 | −3.6 |
| | | 0.001% | −28.4 | −3.8 |
| *Porphyridium* | Extracted Biomass | 0.1% | −26.5 | −55.6 |
| | | 0.01% | −20.6 | −26.5 |
| | | 0.001% | −14.7 | −16.4 |
| *Porphyridium* | Extracted Oil | 0.01% | −55.0 | −90.9 |
| | | 0.001% | −31.7 | −6.0 |
| | | 0.0001% | −55.0 | −5.2 |
| *Porphyridium* | EPS | 0.1% | — | — |
| | | 0.01% | +32.4 | −67.8 |
| | | 0.001% | +8.8 | +35.7 |
| *Schizochytrium* | Whole Biomass | 0.1% | −45.1 | −100.0 |
| | | 0.01% | −50.0 | −92.0 |
| | | 0.001% | −48.0 | −35.0 |
| *Schizochytrium* | Extracted Biomass | 0.1% | +38.2 | −100.0 |
| | | 0.01% | +8.8 | −2.6 |
| | | 0.001% | −2.9 | +10.9 |
| *Schizochytrium* | Extracted Oil | 0.01% | +46.9 | −17.1 |
| | | 0.001?,,o | +49.7 | +6.3 |
| | | 0.0001% | +24.3 | +25.8 |
| *Tetraselmis* | Whole Biomass | 0.1% | −39.7 | −96.2 |
| | | 0.01% | −32.2 | −68.1 |
| | | 0.001% | −31.2 | −17.4 |
| *Tetraselmis* | Extracted Biomass | 0.1% | −55.9 | −95.7 |
| | | 0.01% | −20.6 | −68.0 |
| | | 0.001% | −16.7 | −8.9 |
| *Tetraselmis* | Extracted Oil | 0.01 | −81.7 | −83.3 |
| | | 0.001% | −16.7 | +1.6 |
| | | 0.0001% | −1.7 | −40.7 |
| *Pavlova* | Whole Biomass | 0.1% | −66.7 | −100.0 |
| | | 0.01% | −55.6 | −95.3 |
| | | 0.001% | −53.3 | −64.7 |
| *Pavlova* | Extracted Biomass | 0.1% | 0.0 | −98.5 |
| | | 0.01% | −27.1 | −71.7 |
| | | 0.001% | +34.4 | +6.0 |

TABLE 2-continued

| | | Salt Stress | | |
|---|---|---|---|---|
| Genus | Treatment | Concentration | Dry Weight % Difference vs. Control | Root Length % Difference vs. Control |
| *Pavlova* | Extracted Oil | 0.01% | +15.2 | −5.5 |
| | | 0.001% | +5.1 | +6.2 |
| | | 0.0001% | −16.2 | −2.9 |
| *Phaeodactylum* | Whole Biomass | 0.1% | +26.3 | −100.0 |
| | | 0.01% | −30.0 | −41.7 |
| | | 0.001% | +1.3 | +12.4 |
| *Phaeodactylum* | Extracted Biomass | 0.1% | — | — |
| | | 0.01% | +129.2 | −73.8 |
| | | 0.001% | +175.0 | +37.0 |
| *Phaeodactylum* | Extracted Oil | 0.01% | −90.9 | −12.8 |
| | | 0.001% | −75.8 | +12.7 |
| | | 0.0001% | −53.5 | +38.3 |
| *Nannochloropsis* | High Lipid Whole Biomass | 0.1% | −37.5 | −94.1 |
| | | 0.01% | −52.5 | −16.2 |
| | | 0.001% | −25.0 | +53.8 |
| *Nannochloropsis* | High Lipid Extracted Biomass | 0.1% | −5.0 | +53.8 |
| | | 0.01% | −46.7 | +59.1 |
| | | 0.001% | −25.8 | +98.8 |
| *Nannochloropsis* | High Lipid Extracted Oil | 0.01% | +20.2 | +25.6 |
| | | 0.001% | −14.1 | −6.3 |
| | | 0.0001% | −2.0 | +6.7 |
| *Porphyridium* | PE rich fraction | 0.1% | −12.1 | −25.1 |
| | | 0.01% | −1.7 | +6.3 |
| | | 0.001% | −48.3 | −4.2 |
| *Porphyridium* | PEB 1 lipid + EPS fraction | 0.1% | −8.1 | −59.9 |
| | | 0.01% | +11.1 | +7.8 |
| | | 0.001% | −11.1 | +22.5 |
| *Porphyridium* | Extracted Oil | 0.01% | — | −78.9 |
| | | 0.001% | — | +4.2 |
| | | 0.0001% | — | +23.7 |
| *Porphyridium* | LEB2 + EPS | 0.1% | −14.1 | −91.5 |
| | | 0.01% | −25.3 | −1.7 |
| | | 0.001% | −41.4 | +16.0 |
| *Porphyridium* | Biomass − EPS | 0.1% | −63.6 | +17.1 |
| | | 0.01% | −70.7 | +24.5 |
| | | 0.001% | −49.5 | +24.5 |
| *Porphyridium* | PE rich fraction from biomass − EPS | 0.1% | −43.4 | −100.0 |
| | | 0.01% | −47.5 | +24.9 |
| | | 0.001% | −59.6 | +8.3 |
| *Porphyridium* | PEB2 Lipid + PS fraction | 0.1% | −24.2 | −100.0 |
| | | 0.01% | −48.5 | −33.7 |
| | | 0.001% | −33.7 | +2.4 |
| *Aurantiochytrium* sp. | Whole Biomass | 0.1% | −21.1 | −96.8 |
| | | 0.01% | −29.4 | −4.0 |
| | | 0.001% | +12.2 | +29.0 |
| *Aurantiochytrium* sp. | Extracted Biomass (hexane) | 0.1% | +46.7 | +19.0 |
| | | 0.01% | +20.0 | +4.0 |
| | | 0.001% | +61.7 | +39.7 |
| *Aurantiochytrium* sp. | Extracted Oil (hexane) | 0.01% | −1.1 | −6.8 |
| | | 0.001% | −11.1 | −6.9 |
| | | 0.0001% | −4.4 | +9.6 |
| *Aurantiochytrium* sp. | Extracted Biomass (ethanol) | 0.1% | +13.3 | −100.0 |
| | | 0.01% | −30.0 | −25.8 |
| | | 0.001% | +18.3 | −1.8 |
| *Aurantiochytrium* sp. | Extracted Oil (ethanol) | 0.01% | +3.3 | −6.8 |
| | | 0.001% | −24.4 | −6.9 |
| | | 0.0001% | −12.1 | +9.6 |
| *Aurantiochytrium* sp. | Extracted Oil (mechanical) | 0.01% | −63.3 | +11.0 |
| | | 0.001% | −23.3 | +28.3 |
| | | 0.0001% | −42.8 | +15.3 |
| *Spirulina* | Extracted Biomass (hexane) | 0.1% | −16.7 | −100.0 |
| | | 0.01% | +27.5 | −23.2 |
| | | 0.001% | −13.3 | −19.5 |
| *Spirulina* | Extracted Oil (hexane) | 0.01% | −41.1 | −100.0 |
| | | 0.001% | +2.2 | −84.1 |
| | | 0.0001% | +31.7 | −47.8 |
| *Spirulina* | Extracted Biomass (acetone) | 0.1% | +1.7 | −92.9 |
| | | 0.01% | +16.7 | +5.3 |
| | | 0.001% | +50.0 | +23.3 |
| *Spirulina* | Extracted Oil (acetone) | 0.01% | −36.7 | −100.0 |
| | | 0.001% | −7.8 | −35.1 |
| | | 0.0001% | −23.3 | −17.9 |

TABLE 2-continued

| | | Salt Stress | | |
|---|---|---|---|---|
| Genus | Treatment | Concentration | Dry Weight % Difference vs. Control | Root Length % Difference vs. Control |
| Spirulina | Low Protein Whole Biomass | 0.1% 0.01% 0.001% | −13.3 −25.0 −45.0 | −88.9 −61.9 −8.8 |
| Spirulina | Protein Fraction | 0.1% 0.01% 0.001% | −8.3 +16.7 +42.5 | +20.3 +30.5 +11.4 |
| Spirulina | Lyzed Whole Biomass | 0.1% 0.01% 0.001% | −17.8 −33.3 −15.6 | −73.3 +7.0 +0.6 |
| Scenedesmus | Whole Biomass | 0.1% 0.01% 0.001% | +41.2 −26.6 −1.1 | |
| Scenedesmus | Extracted Biomass | 0.1% 0.01% 0.001% | +168.4 +1.7 −35.0 | |
| Scenedesmus | Extracted Oil | 0.01% 0.001% 0.0001% | +4.5 +35.6 −40.7 | |
| T-Isochrysis | Whole Biomass | 0.1% 0.01% 0.001% | +188.1 +137.3 +168.4 | |
| T-Isochrysis | Extracted Biomass (ethanol) | 0.1% 0.01% 0.001% | +66.7 +126.0 +29.9 | |
| T-Isochrysis | Extracted Oil (ethanol) | 0.01% 0.001% 0.0001% | +29.9 −1.1 +18.6 | |
| Chlorella zofingiensis | Whole Biomass | 0.1% 0.01% 0.001% | +111.9 −6.8 +10.2 | |
| Chlorella zofingiensis | Extracted Biomass (ethanol) | 0.1% 0.01% 0.001% | +92.1 +15.8 +15.8 | |
| Chlorella zofingiensis | Extracted Oil (ethanol) | 0.01% 0.001% 0.0001% | +21.5 +27.1 +89.3 | |
| Chlorella sp. (glucose) | Whole Biomass | 0.1% 0.01% 0.001% | −106.2 +75.1 +13.0 | |
| Chlorella sp. (glucose) | Extracted Biomass (ethanol) | 0.1% 0.01% 0.001% | +99.7 +59.7 +28.5 | |
| Chlorella sp. (glucose) | Extracted Oil (ethanol) | 0.01% 0.001% 0.0001% | +51.0 +2.4 +9.4 | |
| Aurantiochytrium sp. | Whole Biomass (Medium Lipid) | 0.1% 0.01% 0.001% | −84.4 −25.3 −9.7 | |
| Aurantiochytrium sp. | Extracted Biomass (High Lipid) (Mechanical Extraction) | 0.1% 0.01% 0.001% | −67.0 −27.1 +25.0 | |
| Aurantiochytrium sp. | Extracted Oil (High Lipid) (Hexane) | 0.01% 0.001% 0.0001% | +33.7 −9.7 +0.7 | |
| Aurantiochytrium sp. | Extracted Oil (High Lipid) (Ethanol) | 0.01% 0.001% 0.0001% | −4.5 −41.0 −61.8 | |
| Aurantiochytrium sp. | Extracted Oil (High Lipid) (Mechanical Extraction) | 0.01% 0.001% 0.0001% | −29.8 −50.9 −31.6 | |
| Aurantiochytrium sp. | Extracted Oil (Medium Lipid) (Hexane) | 0.01% 0.001% 0.0001% | −18.2 +5.1 −17.2 | |
| Aurantiochytrium sp. | Extracted Oil (Medium Lipid) (Ethanol) | 0.01% 0.001% 0.0001% | +6.1 −5.1 +5.1 | |
| Aurantiochytrium sp. | Extracted Biomass | 0.1% 0.01% | +20.2 +49.5 | |

TABLE 2-continued

Salt Stress

| Genus | Treatment | Concentration | Dry Weight % Difference vs. Control | Root Length % Difference vs. Control |
|---|---|---|---|---|
| | (Medium Lipid) (Hexane) | 0.001% | +30.3 | |
| Aurantiochytrium sp. | Extracted Biomass (Medium Lipid) (Ethanol) | 0.1% | +29.3 | |
| | | 0.01% | −1.0 | |
| | | 0.001% | +3.0 | |
| Aurantiochytrium sp. | Whole Biomass (High Lipid) | 0.1% | −49.5 | |
| | | 0.01% | −17.2 | |
| | | 0.001% | −19.2 | |
| Aurantiochytrium sp. | Extracted Biomass (High Lipid) (Ethanol) | 0.1% | +3.0 | |
| | | 0.01% | +20.2 | |
| | | 0.001% | +37.4 | |
| Aurantiochytrium sp. | Extracted Biomass (High Lipid) (Hexane) | 0.1% | −17.2 | |
| | | 0.01% | +20.2 | |
| | | 0.001% | +8.1 | |
| Botryococcus | Lyzed Whole Biomass | 0.1% | −9.4 | |
| | | 0.01% | −28.1 | |
| | | 0.001% | −28.8 | |
| Botryococcus | Extracted Oil | 0.01% | −32.9 | |
| | | 0.001% | −35.0 | |
| | | 0.0001% | −37.8 | |
| Botryococcus | Extracted Biomass | 0.1% | +15.5 | |
| | | 0.01% | −12.2 | |
| | | 0.001% | −7.3 | |

TABLE 3

Chlorosis

| Genus | Treatment | Concentration | Chlorotic leaves % Difference vs. Control | Plants with Chlorosis % Diffe1.ence vs. Control |
|---|---|---|---|---|
| Galdieria | Whole Biomass | 0.1% | −0.5 | +25.8 |
| | | 0.01% | −78.2 | −68.6 |
| | | 0.001% | −26.4 | −21.4 |
| Galdieria | Extracted Biomass | 0.1% | +6.0 | +25.8 |
| | | 0.01% | −48.6 | −26.6 |
| | | 0.001% | −69.0 | −52.8 |
| Galdieria | Extracted Oil | 0.01% | −11.1 | −29.4 |
| | | 0.001% | 0.0 | 0.0 |
| | | 0.0001% | +33.3 | +35.3 |
| Galdieria | Low Protein Whole Biomass | 0.1% | +97.7 | +57.2 |
| | | 0.01% | +31.9 | +41.5 |
| | | 0.001% | +128.7 | +39.9 |
| Galdieria | Low Protein Extracted Biomass | 0.1% | −84.7 | −68.6 |
| | | 0.01% | −44.0 | −26.6 |
| | | 0.001% | −46.3 | −21.4 |
| Galdieria | Low Protein Extracted Oil | 0.01% | −11.1 | 0.0 |
| | | 0.001% | 0.0 | −23.5 |
| | | 0.0001% | −33.3 | +58.8 |
| Galdieria | Protein Fraction | 0.1% | +7.9 | +25.8 |
| | | 0.01% | −8.3 | −5.7 |
| | | 0.001% | +39.4 | +36.3 |
| Chlorella sp. (acetate) | Whole Biomass | 0.1% | +47.2 | +46.7 |
| | | 0.01% | −38.4 | +4.9 |
| | | 0.001% | +14.4 | +25.8 |
| Chlorella sp. (acetate) | Extracted Biomass | 0.1% | +123.1 | +57.2 |
| | | 0.01% | +51.9 | +46.7 |
| | | 0.001% | +13.0 | +46.7 |
| Chlorella sp. (acetate) | Extracted Oil | 0.01% | +55.6 | +35.3 |
| | | 0.001% | +33.3 | +17.6 |
| | | 0.0001% | 0.0 | −17.7 |
| Haematococcus | Whole Biomass | 0.1% | −8.8 | +15.3 |
| | | 0.01% | −69.0 | −47.6 |
| | | 0.001% | −27.8 | −16.2 |

TABLE 3-continued

| | | | Chlorosis | |
|---|---|---|---|---|
| Genus | Treatment | Concentration | Chlorotic leaves % Difference vs. Control | Plants with Chlorosis % Diffe1.ence vs. Control |
| Haematococcus | Extracted Biomass | 0.1% | −59.8 | −39.1 |
| | | 0.01% | −10.6 | +15.3 |
| | | 0.001% | +34.7 | +57.2 |
| Haematococcus | Extracted Oil | 0.01% | +22.2 | −17.7 |
| | | 0.001% | +11.1 | −41.2 |
| | | 0.0001% | +44.4 | +58.8 |
| Isochrysis | Whole Biomass | 0.1% | +279.6 | +57.2 |
| | | 0.01% | −27.3 | +25.8 |
| | | 0.001% | −40.7 | −37.1 |
| Isochrysis | Extracted Biomass | 0.1% | +85.2 | +57.2 |
| | | 0.01% | +54.2 | +57.2 |
| | | 0.001% | +108.8 | +57.2 |
| Isochrysis | Extracted Oil | 0.01% | +44.4 | +64.7 |
| | | 0.001% | +55.6 | +29.4 |
| | | 0.0001% | +66.7 | +64.7 |
| Nannochloropsis | Extracted Biomass | 0.1% | +31.2 | +57.2 |
| | | 0.01% | +49.2 | +57.2 |
| | | 0.001% | +54.2 | +57.2 |
| Nannochloropsis | Extracted Oil | 0.01% | +66.7 | +29.4 |
| | | 0.001% | +33.3 | +11.8 |
| | | 0.0001% | +33.3 | +35.3 |
| Porphyridium | Whole Biomass | 0.1% | +13.0 | −16.2 |
| | | 0.01% | −17.6 | −5.7 |
| | | 0.001% | +15.7 | +57.2 |
| Porphyridium | Extracted Biomass | 0.1% | +59.3 | +46.7 |
| | | 0.01% | 0.0 | +36.3 |
| | | 0.001% | +33.8 | +57.2 |
| Porphyridium | Extracted Oil | 0.01% | +55.6 | +35.3 |
| | | 0.001% | +33.3 | +47.1 |
| | | 0.0001% | +22.2 | +41.2 |
| Porphyridium | EPS | 0.1% | — | — |
| | | 0.01% | +35.6 | +36.3 |
| | | 0.001% | +25.9 | +46.7 |
| Schizochytrium | Whole Biomass | 0.1% | +34.7 | +46.7 |
| | | 0.01% | +6.5 | +36.3 |
| | | 0.001% | −4.6 | +4.9 |
| Schizochytrium | Extracted Biomass | 0.1% | −25.5 | +15.3 |
| | | 0.01% | −33.3 | +16.2 |
| | | 0.001% | +2.3 | +15.3 |
| Schizochytrium | Extracted Oil | 0.01% | +44.4 | +52.9 |
| | | 0.001% | +33.3 | +29.4 |
| | | 0.0001% | 0.0 | −11.8 |
| Tetraselmis | Whole Biomass | 0.1% | +314.8 | +57.2 |
| | | 0.01% | +53.7 | −26.6 |
| | | 0.001% | −21.3 | +15.3 |
| Tetraselmis | Extracted Biomass | 0.1% | +223.6 | +44.2 |
| | | 0.01% | −2.3 | +15.3 |
| | | 0.001% | −65.3 | −58.0 |
| Tetraselmis | Extracted Oil | 0.01% | +22.2 | 0.0 |
| | | 0.001% | 0.0 | +23.5 |
| | | 0.0001% | +22.2 | −23.5 |
| Pavlova | Whole Biomass | 0.1% | +72.8 | +19.0 |
| | | 0.01% | +60.5 | +3.2 |
| | | 0.001% | +57.4 | +11.1 |
| Pavlova | Extracted Biomass | 0.1% | +44.6 | +33.3 |
| | | 0.01% | +8.4 | +6.7 |
| | | 0.001% | −8.4 | −2.3 |
| Pavlova | Extracted Oil | 0.01% | +50.3 | +45.8 |
| | | 0.001% | +30.3 | +56.3 |
| | | 0.0001% | +115.2 | +56.3 |
| Phaeodactylum | Whole Biomass | 0.1% | −42.5 | −41.7 |
| | | 0.01% | −29.9 | −25.0 |
| | | 0.001% | +11.5 | 0.0 |
| Phaeodactylum | Extracted Biomass | 0.1% | — | — |
| | | 0.01% | −44.6 | −20.0 |
| | | 0.001% | −61.1 | −46.7 |
| Phaeodactylum | Extracted Oil | 0.01% | +58.3 | +9.4 |
| | | 0.001% | +61.5 | +25.0 |
| | | 0.0001% | +37.4 | +14.6 |
| Nannochloropsis | High Lipid Whole Biomass | 0.1% | −40.2 | 0.0 |
| | | 0.01% | −77.0 | −75.0 |
| | | 0.001% | +1.1 | −25.0 |

TABLE 3-continued

| | | | Chlorosis | |
|---|---|---|---|---|
| Genus | Treatment | Concentration | Chlorotic leaves % Difference vs. Control | Plants with Chlorosis % Diffe1.ence vs. Control |
| Nannochloropsis | High Lipid Extracted Biomass | 0.1% 0.01% 0.001% | −42.5 +1.1 −34.5 | −33.3 0.0 −33.3 |
| Nannochloropsis | High Lipid Extracted Oil | 0.01% 0.001% 0.0001% | −1.3 +66.2 +9.4 | +35.4 +25.0 −16.7 |
| Porphyridium | PE rich fraction | 0.1% 0.01% 0.001% | −94.8 −18.0 −29.7 | −88.1 −16.7 −16.7 |
| Porphyridium | PEB 1 lipid+ | 0.1% 0.01% 0.001% | −18.8 +9.0 −42.3 | −37.5 −16.7 −16.7 |
| Porphyridium | LEB2 + EPS | 0.1% 0.01% 0.001% | −92.5 −10.9 +9.0 | −79.2 −37.5 +14.6 |
| Porphyridium | Biomass − EPS | 0.1% 0.01% 0.001% | −10.9 +13.7 +88.0 | −6.2 +25.0 +4.2 |
| Porphyridium | PE rich fraction from biomass − EPS | 0.1% 0.01% 0.001% | +4.3 +44.0 −4.7 | −6.2 +56.3 +35.4 |
| Porphyridium | PEB2 Lipid + PS fraction | 0.1% 0.01% 0.001% | −79.9 −42.3 +29.9 | −58.3 −37.5 +4.2 |
| Aurantiochytrium sp. | Whole Biomass | 0.1% 0.01% 0.001% | +44.5 +57.5 +39.9 | +22.2 +66.7 +31.0 |
| Aurantiochytrium sp. | Extracted Biomass (hexane) | 0.1% 0.01% 0.001% | +15.7 +8.3 −25.7 | +25.0 −16.7 0.0 |
| Aurantiochytrium sp. | Extracted Oil (hexane) | 0.01% 0.001% 0.0001% | −26.7 −25.3 +9.6 | −22.2 −33.3 +44.4 |
| Aurantiochytrium sp. | Extracted Biomass (ethanol) | 0.1% 0.01% 0.001% | −33.9 +17.9 −6.8 | −8.3 0.0 −8.3 |
| Aurantiochytrium sp. | Extracted Oil (ethanol) | 0.01% 0.001% 0.0001% | −34.9 −58.0 −10.3 | +33.3 −48.7 −22.2 |
| Aurantiochytrium sp. | Extracted Oil (mechanical) | 0.01% 0.001% 0.0001% | −50.2 −3.3 −52.7 | −22.2 +22.2 −11.1 |
| Spirulina | Extracted Biomass (hexane) | 0.1% 0.01% 0.001% | +63.7 −6.0 +74.0 | +55.6 +11.1 +66.7 |
| Spirulina | Extracted Oil (hexane) | 0.01% 0.001% 0.0001% | +94.3 +55.0 +28.8 | +22.2 +33.3 +22.2 |
| Spirulina | Extracted Biomass (acetone) | 0.1% 0.01% 0.001% | −0.6 +21.9 −23.4 | 0.0 +8.3 −8.3 |
| Spirulina | Extracted Oil (acetone) | 0.01% 0.001% 0.0001% | +81.4 −22.8 +39.5 | +55.6 −11.1 +11.1 |
| Spirulina | Low Protein Whole Biomass | 0.1% 0.01% 0.001% | −21.1 −6.8 −12.3 | −16.7 −8.3 0.0 |
| Spirulina | Protein Fraction | 0.1% 0.01% 0.001% | −48.1 −35.3 +51.7 | −16.7 −16.7 +8.3 |
| Spirulina | Lyzed Whole Biomass | 0.1% 0.01% 0.001% | +122.3 +41.3 +56.1 | +66.7 +33.3 +54.8 |
| Scenedesmus | Whole Biomass | 0.1% 0.01% 0.001% | −24.1 −4.6 −27.0 | −5.8 +8.7 −5.8 |
| Scenedesmus | Extracted Biomass | 0.1% 0.01% 0.001% | −31.9 +6.9 +28.2 | −5.8 +8.7 +8.7 |
| Scenedesmus | Extracted Oil | 0.01% 0.001% 0.0001% | −2.4 +4.7 +34.2 | −5.8 +8.7 +8.7 |

TABLE 3-continued

| | | | Chlorosis | |
|---|---|---|---|---|
| Genus | Treatment | Concentration | Chlorotic leaves % Difference vs. Control | Plants with Chlorosis % Diffe1.ence vs. Control |
| T-*Isochrysis* | Whole Biomass | 0.1% | −79.1 | −34.8 |
| | | 0.01% | −54.5 | −27.5 |
| | | 0.001% | −41.3 | −20.3 |
| T-*Isochrysis* | Extracted Biomass (ethanol) | 0.1% | −25.5 | +8.7 |
| | | 0.01% | −32.8 | +8.7 |
| | | 0.001% | +11.8 | +8.7 |
| T-*Isochrysis* | Extracted Oil (ethanol) | 0.01% | −21.0 | +1.4 |
| | | 0.001% | +17.8 | +8.7 |
| | | 0.0001% | +12.9 | +1.4 |
| *Chlorella zofingiensis* | Whole Biomass | 0.1% | −43.4 | −5.8 |
| | | 0.01% | +17.6 | +8.7 |
| | | 0.001% | +17.0 | +8.7 |
| *Chlorella zofingiensis* | Extracted Biomass (ethanol) | 0.1% | −23.7 | −5.8 |
| | | 0.01% | +2.1 | +1.4 |
| | | 0.001% | +13.3 | +8.7 |
| *Chlorella zofingiensis* | Extracted Oil (ethanol) | 0.01% | +14.0 | +8.7 |
| | | 0.001% | +23.7 | +8.7 |
| | | 0.0001% | −30.7 | −27.5 |
| *Chlorella* sp. (glucose) | Whole Biomass | 0.1% | −20.2 | −13.0 |
| | | 0.01% | +2.4 | −5.8 |
| | | 0.001% | +13.3 | +1.4 |
| *Chlorella* sp. (glucose) | Extracted Biomass (ethanol) | 0.1% | −49.2 | 0.0 |
| | | 0.01% | −48.2 | −8.3 |
| | | 0.001% | −22.8 | −8.3 |
| *Chlorella* sp. (glucose) | Extracted Oil (ethanol) | 0.01% | −39.0 | +16.7 |
| | | 0.001% | −13.6 | 0.0 |
| | | 0.0001% | −12.6 | −8.3 |
| *Aurantiochytrium* sp. | Whole Biomass (Medium Lipid) | 0.1% | +41.3 | +16.7 |
| | | 0.01% | −43.1 | +8.3 |
| | | 0.001% | −13.6 | +25.0 |
| *Aurantiochytrium* sp. | Extracted Biomass (High Lipid) (Mechanical Extraction) | 0.1% | −33.9 | 0.0 |
| | | 0.01% | −10.6 | +8.3 |
| | | 0.001% | −81.7 | −33.3 |
| *Aurantiochytrium* sp. | Extracted Oil (High Lipid) (Hexane) | 0.01% | −59.3 | −8.3 |
| | | 0.001% | −43.1 | +16.7 |
| | | 0.0001% | −41.7 | +8.3 |
| *Aurantiochytrium* sp. | Extracted Oil (High Lipid) (Ethanol) | 0.01% | −16.7 | 0.0 |
| | | 0.001% | +7.7 | +16.7 |
| | | 0.0001% | +28.0 | +16.7 |
| *Aurantiochytrium* sp. | Extracted Oil (High Lipid) (Mechanical Extraction) | 0.01% | +52.9 | 0.0 |
| | | 0.001% | +67.9 | 0.0 |
| | | 0.0001% | +40.8 | 0.0 |
| *Aurantiochytrium* sp. | Extracted Oil (Medium Lipid) (Hexane) | 0.01% | −11.2 | −16.7 |
| | | 0.001% | −28.8 | −9.7 |
| | | 0.0001% | −15.2 | −2.8 |
| *Aurantiochytrium* sp. | Extracted Oil (Medium Lipid) (Ethanol) | 0.01% | −42.6 | −23.6 |
| | | 0.001% | −20.4 | −9.7 |
| | | 0.0001% | −8.1 | −2.8 |
| *Aurantiochytrium* sp. | Extracted Biomass (Medium Lipid) (Hexane) | 0.1% | −61.7 | −9.7 |
| | | 0.01% | −68.1 | −37.5 |
| | | 0.001% | −64.9 | −44.3 |
| *Aurantiochytrium* sp. | Extracted Biomass (Medium Lipid) (Ethanol) | 0.1% | +2.8 | −2.8 |
| | | 0.01% | +30.2 | +4.2 |
| | | 0.001% | −9.1 | −2.8 |
| *Aurantiochytrium* sp. | Whole Biomass (High Lipid) | 0.1% | +61.7 | +4.2 |
| | | 0.01% | +8.2 | −2.8 |
| | | 0.001% | +5.4 | −2.8 |
| *Aurantiochytrium* sp. | Extracted Biomass (High Lipid) (Ethanol) | 0.1% | −46.4 | −2.8 |
| | | 0.01% | −33.2 | −9.7 |
| | | 0.001% | −24.3 | −2.8 |

TABLE 3-continued

Chlorosis

| Genus | Treatment | Concentration | Chlorotic leaves % Diffe1.ence vs. Control | Plants with Chlorosis % Diffe1.ence vs. Control |
|---|---|---|---|---|
| Aurantiochytrium sp. | Extracted Biomass (High Lipid) (Hexane) | 0.1% | −3.8 | +4.2 |
| | | 0.01% | −37.7 | −16.7 |
| | | 0.001% | −10.7 | +4.2 |
| Botryococcus | Lyzed Whole Biomass | 0.1% | −52.9 | −20.0 |
| | | 0.01% | −11.6 | 0.0 |
| | | 0.001% | −8.8 | −6.7 |
| Botryococcus | Extracted Oil | 0.01% | −35.6 | −6.7 |
| | | 0.001% | −0.7 | 0.0 |
| | | 0.0001% | −1.9 | 0.0 |
| Botryococcus | Extracted Biomass | 0.1% | −60.1 | −26.7 |
| | | 0.01% | −61.2 | −26.7 |
| | | 0.001% | −36.9 | 0.0 |

Example 11

An experiment was performed to determine the effect of treating *Arabidopsis thaliana* with a variety of microalgae based treatments under normal growth conditions and under salt stressed conditions. The bioassay was initiated using two-week-old *Arabidopsis* plants grown on Jiffy pellets (peat moss pellets). Five replicates of each plant were performed for the treatments. Plants on Jiffy pellets were placed on trays with concentrations of 0.1% (0.1 mL/L), 0.01% (0.01 mL/L), or 0.001% (0.001 mL/L) of non-oil treatments, or 0.01% (0.01 mL/L), 0.001% (0.001 mL/L), or 0.0001% (0.0001 mL/L) microalgae oil at 40 mL/plant and compared to an untreated control. The treatments were prepared as described in Example 10. The salt stressed plantlets were also supplemented with 150 mM of NaCl. Five days after the first treatment the microalgae based treatment was repeated, but additional salt was not added. Ten days after the first treatment the plant dry weight was measured. The results are shown in Tables 4-5, which display the results for each tested concentration with respect to the untreated control.

TABLE 4

Growth (No Salt Stress)

| Genus | Treatment | Concentration | Dry Weight % Diffe1.ence vs. Control |
|---|---|---|---|
| Galdieria | Low Protein Extracted Biomass | 0.1% | +3.0 |
| | | 0.01% | +15.1 |
| | | 0.001% | +4.2 |
| Galdieria | Low Protein Extracted Oil | 0.01% | −12.6 |
| | | 0.001% | +7.8 |
| | | 0.0001% | +21.9 |
| Galdieria | Protein Fraction | 0.1% | −28.4 |
| | | 0.01% | −28.9 |
| | | 0.001% | +1.3 |
| Chlorella sp. (acetate) | Whole Biomass | 0.1% | −21.6 |
| | | 0.01% | +13.9 |
| | | 0.001% | +15.5 |
| Haematococcus | Extracted Biomass | 0.1% | −17.9 |
| | | 0.01% | +13.1 |
| | | 0.001% | +35.9 |
| Isochrysis | Extracted Biomass | 0.1% | −59.3 |
| | | 0.01% | −30.2 |
| | | 0.001% | −38.0 |

TABLE 4-continued

Growth (No Salt Stress)

| Genus | Treatment | Concentration | Dry Weight % Diffe1.ence vs. Control |
|---|---|---|---|
| Nannochloropsis | Extracted Biomass | 0.1% | −28.4 |
| | | 0.01% | −11.1 |
| | | 0.001% | −47.4 |
| Schizochytrium | Extracted Biomass | 0.1% | +44.2 |
| | | 0.01% | +94.3 |
| | | 0.001% | +65.0 |
| | | 0.01% | −7.7 |
| Schizochytrium | Extracted Oil | 0.001% | +9.6 |
| | | 0.0001% | +16.6 |
| T-*Isochrysis* | Whole Biomass | 0.1% | −16.4 |
| | | 0.01% | +11.9 |
| | | 0.001% | +10.3 |
| T-*Isochrysis* | Extracted Biomass (ethanol) | 0.1% | +9.0 |
| | | 0.01% | +10.9 |
| | | 0.001% | +18.0 |
| Chlorella zofingiensis | Extracted Oil (ethanol) | 0.01% | −44.8 |
| | | 0.001% | −16.1 |
| | | 0.0001% | −22.3 |
| Chlorella sp. (glucose) | Whole Biomass | 0.1% | −43.7 |
| | | 0.01% | −22.1 |
| | | 0.001% | −34.3 |
| Chlorella sp. (glucose) | Extracted Biomass (ethanol) | 0.1% | −10.9 |
| | | 0.01% | +30.8 |
| | | 0.001% | +23.7 |
| Aurantiochytrium sp. | Extracted Oil (High Lipid) (Hexane) | 0.01% | −15.7 |
| | | 0.001% | +40.7 |
| | | 0.0001% | +33.8 |
| Aurantiochytrium sp. | Extracted Biomass (Medium Lipid) (Hexane) | 0.1% | −9.1 |
| | | 0.01% | +33.5 |
| | | 0.001% | +29.6 |
| Aurantiochytrium sp. | Extracted Biomass (High Lipid) (Ethanol) | 0.1% | +7.1 |
| | | 0.01% | +30.4 |
| | | 0.001% | +19.9 |

TABLE 5

Salt Stress

| Genus | Treatment | Concentration | Dry Weight % Difforll"n < 'P vs rnntrol |
|---|---|---|---|
| Galdieria | Low Protein Extracted Biomass | 0.1% | −35.2 |
| | | 0.01% | +24.3 |
| | | 0.001% | −18.3 |

TABLE 5-continued

Salt Stress

| Genus | Treatment | Concentration | Dry Weight % Diff'n < 'P vs control |
|---|---|---|---|
| Galdieria | Low Protein Extracted Oil | 0.1% | — |
|  |  | 0.01% | — |
|  |  | 0.0001% | — |
| Galdieria | Protein Fraction | 0.1% | −40.2 |
|  |  | 0.01% | −9.7 |
|  |  | 0.001% | −24.0 |
| Chlorella sp. (acetate) | Whole Biomass | 0.1% | −27.0 |
|  |  | 0.01% | −3.9 |
|  |  | 0.001% | +6.4 |
| Haematococcus | Extracted Biomass | 0.1% | −18.3 |
|  |  | 0.01% | +27.3 |
|  |  | 0.001% | +30.5 |
| Isochrysis | Extracted Biomass | 0.1% | −60.5 |
|  |  | 0.01% | −24.6 |
|  |  | 0.001% | −25.0 |
| Nannochloropsis | Extracted Biomass | 0.1% | −28.8 |
|  |  | 0.01% | −21.1 |
|  |  | 0.001 | −33.3 |
| Schizochytrium | Extracted Biomass | 0.1% | — |
|  |  | 0.01% | — |
|  |  | 0.001% | — |
| Schizochytrium | Extracted Oil | 0.01% | −22.1 |
|  |  | 0.001% | +20.4 |
|  |  | 0.0001% | −3.0 |
| T-Isochrysis | Whole Biomass | 0.1% | −19.3 |
|  |  | 0.01% | +13.0 |
|  |  | 0.001% | +1.3 |
| T-Isochrysis | Extracted Biomass (ethanol) | 0.1% | −27.6 |
|  |  | 0.01% | +2.7 |
|  |  | 0.001% | −16.3 |
| Chlorella zofingiensis | Extracted Oil (ethanol) | 0.01% | −55.0 |
|  |  | 0.001% | −34.5 |
|  |  | 0.0001% | −27.0 |
| Chlorella sp. (glucose) | Whole Biomass | 0.1% | −64.9 |
|  |  | 0.01% | −46.4 |
|  |  | 0.001% | −29.4 |
| Chlorella sp. (glucose) | Extracted Biomass (ethanol) | 0.1% | −43.4 |
|  |  | 0.01% | −20.3 |
|  |  | 0.001% | −23.8 |
| Aurantiochytrium sp. | Extracted Oil (High Lipid) (Hexane) | 0.01% | −26.9 |
|  |  | 0.001% | +23.7 |
|  |  | 0.0001% | +48.0 |
| Aurantiochytrium sp. | Extracted Biomass (Medium Lipid) (Hexane) | 0.1% | −11.4 |
|  |  | 0.01% | +4.1 |
|  |  | 0.001% | +19.6 |
| Aurantiochytrium sp. | Extracted Biomass (High Lipid) (Ethanol) | 0.1% | −25.3 |
|  |  | 0.01% | −16.9 |
|  |  | 0.001% | −5.8 |

Example 12

An experiment was performed to determine the effect of treating *Arabidopsis thaliana* with a variety of treatments made from microalgae under normal growth conditions and under temperature stressed conditions. The bioassay was initiated using four-day old plantlets grown on half strength Murashige and Skoog (MS) medium, supplemented with 1% (w/v) sucrose and solidified with 0.7% (w/v) agar in square petri plates. Plants were vertically stacked in the growth chamber set at 22° C. with 16-h light/8-h dark cycle, with light intensity of 100 ρmol/m$^{-2}$s$^{-1}$. Each plate contained five replicate plantlets. Plantlets were transferred onto medium supplemented with concentrations of 0.01% (0.01 mL/L) or 0.001% (0.001 mL/L) of non-oil treatments, or 0.001%> (0.001 mL/L) or 0.0001% (0.0001 mL/L) of oil treatments listed in the table and compared to an untreated control. The treatments were prepared as described in Example 10.

After seven days, half of the plants were placed in a growth chamber and subjected to three days of continuous temperature stress (35° C.) while the other half were maintained at about 22° C. Following the temperature stress period, the plantlets were allowed to grow for seven additional days, and plant dry weight was measured at the end. The results are shown in Tables 6-7, which display the results for each tested concentration with respect to the untreated control.

TABLE 6

Growth (No temperature Stress)

| Genus | Treatment | Concentration | Dry Weight % Difference vs. Control |
|---|---|---|---|
| Galdieria | Whole Biomass | 0.01% | +3.5 |
|  |  | 0.001% | +15.9 |
| Galdieria | Extracted Biomass | 0.01% | −2.8 |
|  |  | 0.001% | −12.5 |
| Galdieria | Extracted Oil | 0.001% | −4.1 |
|  |  | 0.0001% | −6.3 |
| Galdieria | Low Protein Whole Biomass | 0.01% | −11.3 |
|  |  | 0.001% | −10.2 |
| Galdieria | Low Protein Extracted | 0.01% | +13.7 |
|  |  | 0.001% | +43.6 |
| Galdieria | Low Protein Extracted Oil | 0.001% | −44.9 |
|  |  | 0.0001% | −51.4 |
| Galdieria | Protein Fraction | 0.01% | +6.0 |
|  |  | 0.001% | −2.2 |
| Chlorella sp. (acetate) | Whole Biomass | 0.01% | +2.1 |
|  |  | 0.001% | +11.8 |
| Chlorella sp. (acetate) | Extracted Biomass | 0.01% | −8.1 |
|  |  | 0.001% | −5.6 |
| Chlorella sp. (acetate) | Extracted oil | 0.001% | +3.9 |
|  |  | 0.0001% | −20.7 |
| Haematococcus | Whole Biomass | 0.01% | −23.8 |
|  |  | 0.001% | +10.8 |
| Haematococcus | Extracted Biomass | 0.01% | +36.9 |
|  |  | 0.001% | +19.2 |
| Haematococcus | Extracted Oil | 0.001% | −54.0 |
|  |  | 0.0001% | −18.2 |
| Isochrysis | Whole Biomass | 0.01% | +1.0 |
|  |  | 0.001% | −14.5 |
| Isochrysis | Extracted Biomass | 0.01% | −5.9 |
|  |  | 0.001% | −16.4 |
| Isochrysis | Extracted Oil | 0.001% | −21.3 |
| Nannochloropsis | Whole Biomass | 0.0001% | +6.9 |
|  |  | 0.01% | −45.9 |
|  |  | 0.001% | −39.0 |
| Nannochloropsis | Extracted Biomass | 0.01% | −3.6 |
|  |  | 0.001% | −37.8 |
| Nannochloropsis | Extracted Oil | 0.001% | +2.0 |
|  |  | 0.0001% | −8.8 |
| Porphyridium | Whole Biomass | 0.01% | −6.0 |
|  |  | 0.001% | −13.3 |
| Porphyridium | Extracted Biomass | 0.01% | +16.5 |
|  |  | 0.001% | +2.6 |
| Porphyridium | Extracted Oil | 0.001% | +29.6 |
|  |  | 0.0001% | −0.2 |
| Porphyridium | EPS | 0.01% | −12.7 |
|  |  | 0.001% | +28.8 |
| Schizochytrium | Whole Biomass | 0.01% | −19.2 |
|  |  | 0.001% | −24.8 |
| Schizochytrium | Extracted Biomass | 0.01% | −3.4 |
|  |  | 0.001% | −4.8 |
| Schizochytrium | Extracted Oil | 0.001% | −25.3 |
|  |  | 0.0001% | −61.4 |
| Tetraselmis | Whole Biomass | 0.01% | — |
|  |  | 0.001% | −3.1 |
| Tetraselmis | Extracted Biomass | 0.01% | −32.6 |
|  |  | 0.001% | −29.7 |
| Tetraselmis | Extracted Oil | 0.001% | −32.6 |
|  |  | 0.0001% | −12.2 |
| Pavlova | Whole Biomass | 0.01% | +11.4 |
|  |  | 0.001% | −1.3 |
| Pavlova | Extracted Biomass | 0.01% | +12.4 |
|  |  | 0.001% | +13.8 |

TABLE 6-continued

Growth (No temperature Stress)

| Genus | Treatment | Concentration | Dry Weight % Difference vs. Control |
|---|---|---|---|
| Pavlova | Extracted Oil | 0.001% | −1.2 |
| | | 0.0001% | −1.1 |
| Phaeodactylum | Whole Biomass | 0.01% | −1.0 |
| | | 0.001% | −10.3 |
| Phaeodactylum | Extracted Biomass | 0.01% | +23.7 |
| | | 0.001% | −3.7 |
| Phaeodactylum | Extracted Oil | 0.001% | −4.2 |
| | | 0.0001% | −5.9 |
| Nannochloropsis | High Lipid Whole | 0.01% | −21.2 |
| | | 0.001% | −9.8 |
| Nannochloropsis | High Lipid Extracted Biomass | 0.01% | −5.6 |
| | | 0.001% | −5.3 |
| Nannochloropsis | High Lipid Extracted Oil | 0.001% | −7.1 |
| | | 0.0001% | −12.8 |
| Porphyridium | PE rich | 0.01% | +3.8 |
| Porphyridium | PE rich | 0.001% | +1.4 |
| Porphyridium | PEB 1 lipid + EPS fraction | 0.01% | +4.0 |
| | | 0.001% | +4.4 |
| Porphyridium | Extracted Oil | 0.001% | +2.0 |
| | | 0.0001% | −5.8 |
| Porphyridium | LEB2 + EPS | 0.01% | −8.9 |
| | | 0.001% | −16.6 |
| Porphyridium | Biomass − EPS | 0.01% | −15.4 |
| | | 0.001% | −24.5 |
| Porphyridium | PE rich fraction from biomass − EPS | 0.01% | +14.4 |
| | | 0.001% | −17.8 |
| Porphyridium | PEB2 Lipid + PS fraction | 0.01% | −2.6 |
| | | 0.001% | −12.9 |
| Aurantiochytrium sp. | Whole Biomass | 0.01% | −15.8 |
| | | 0.001 | −36.9 |
| Aurantiochytrium sp. | Extracted Biomass (hexane) | 0.01% | +3.0 |
| | | 0.001% | +3.3 |
| Aurantiochytrium sp. | Extracted Oil (hexane) | 0.001% | −24.3 |
| | | 0.0001% | +8.2 |
| Aurantiochytrium sp. | Extracted Biomass (ethanol) | 0.01% | +17.1 |
| | | 0.001% | +11.9 |
| Aurantiochytrium sp. | Extracted Oil (ethanol) | 0.001% | +5.3 |
| | | 0.0001% | +16.3 |
| Aurantiochytrium sp. | Extracted Oil (mechanical) | 0.001% | +5.3 |
| | | 0.0001% | +16.3 |
| Spirulina | Extracted Biomass (hexane) | 0.01% | +5.3 |
| | | 0.001% | +16.3 |
| Spirulina | Extracted Oil (hexane) | 0.001% | +21.8 |
| | | 0.0001% | +14.2 |
| Spirulina | Extracted Biomass (acetone) | 0.01% | +5.3 |
| | | 0.001% | +16.3 |
| Spirulina | Extracted Oil (acetone) | 0.001% | +21.1 |
| | | 0.0001% | +23.5 |
| Spirulina | Low Protein Whole Biomass | 0.01% | −22.6 |
| | | 0.001% | −8.1 |
| Spirulina | Protein Fraction | 0.01% | +3.4 |
| | | 0.001% | +1.7 |
| Spirulina | Lyzed − Whole Biomass | 0.01% | +5.0 |
| | | 0.001% | +0.2 |
| Scenedesmus | Whole Biomass | 0.01% | −27.6 |
| | | 0.001% | −19.0 |
| Scenedesmus | Extracted Biomass | 0.01% | +10.0 |
| | | 0.001% | 0.0 |
| Scenedesmus | Extracted Oil | 0.001% | −15.2 |
| | | 0.0001% | −2.1 |
| T-Isochrysis | Whole Biomass | 0.01% | +27.4 |
| | | 0.001% | +11.2 |
| T-Isochrysis | Extracted Biomass (ethanol) | 0.01% | +21.7 |
| | | 0.001% | +8.3 |
| T-Isochrysis | Extracted Oil (ethanol) | 0.001 | +6.4 |
| | | 0.0001% | +27.2 |
| Chlorella zofingiensis | Whole Biomass | 0.01% | −9.1 |
| | | 0.001% | +4.7 |
| Chlorella zofingiensis | Extracted Biomass (ethanol) | 0.01% | +10.2 |
| | | 0.001% | +11.4 |
| Chlorella zofingiensis | Extracted oil (ethanol) | 0.001% | +6.1 |
| | | 0.0001% | +2.5 |
| Chlorella sp. (glucose) | Whole Biomass | 0.01% | −6.3 |
| | | 0.001% | +13.6 |
| Chlorella sp. (glucose) | Extracted Biomass (ethanol) | 0.01% | −13.0 |
| | | 0.001% | −18.8 |
| Chlorella sp. (glucose) | Extracted Oil | 0.001% | −7.6 |
| | | 0.0001% | −9.6 |
| Aurantiochytrium SP. | Whole Biomass (Medium Lipid) | 0.01% | −21.1 |
| | | 0.001% | −26.0 |
| Aurantiochytrium sp. | Extracted Biomass (High Lipid) (Mechanical Extraction) | 0.01% | −29.2 |
| | | 0.001% | −21.7 |
| Aurantiochytrium sp. | Extracted Oil (High Lipid) (Hexane) | 0.001% | −11.7 |
| | | 0.0001% | +26.0 |
| Aurantiochytrium sp. | Extracted Oil (High Lipid) (Ethanol) | 0.001% | −7.0 |
| | | 0.0001% | −51.6 |
| Aurantiochytrium sp. | Extracted Oil (High Lipid) (Mechanical Extraction) | 0.001% | −6.7 |
| | | 0.0001% | −13.2 |
| Aurantiochytrium sp. | Extracted Oil (Medium Lipid) (Hexane) | 0.001% | −13.0 |
| | | 0.0001% | −14.4 |
| Aurantiochytrium sp. | Extracted Oil (Medium Lipid) (Hexane) | 0.001% | −0.5 |
| | | 0.0001% | −17.3 |
| Aurantiochytrium sp. | Extracted Biomass (Medium Lipid) (Hexane) | 0.01% | −4.7 |
| | | 0.001% | −2.1 |
| Aurantiochytrium sp. | Extracted Biomass (Medium Lipid) | 0.01% | −11.8 |
| | | 0.001% | −0.1 |
| Aurantiochytrium sp. | Whole Biomass (High Lipid) | 0.01% | −11.3 |
| | | 0.001 | −7.2 |
| Aurantiochytrium sp. | Extracted Biomass (High Lipid) | 0.01% | −6.0 |
| | | 0.001% | −8.4 |
| Aurantiochytrium sp. | Extracted Biomass (High Lipid) | 0.01% | −17.0 |
| | | 0.001% | −4.4 |
| Botryococcus | Lyzed Whole Biomass | 0.01% | −14.0 |
| | | 0.001% | −2.3 |
| Botryococcus | Extracted Oil | 0.001% | −14.4 |
| | | 0.0001% | −14.7 |
| Botryococcus | Extracted Biomass | 0.01% | −23.3 |
| | | 0.001% | −21.3 |

TABLE 7

Temperature Stress

| Genus | Treatment | Concentration | Dry Weight % Difference vs. Control |
|---|---|---|---|
| Galdieria | Whole Biomass | 0.01% | −14.1 |
| | | 0.0001% | — |
| Galdieria | Extracted Biomass | 0.01% | +1.1 |
| | | 0.001% | — |
| Galdieria | Extracted Oil | 0.001% | −34.3 |
| | | 0.0001% | −29.7 |

TABLE 7-continued

Temperature Stress

| Genus | Treatment | Concentration | Dry Weight % Difference vs. Control |
|---|---|---|---|
| *Galdieria* | Low Protein Whole Biomass | 0.01% 0.001% | −15.7 +14.7 |
| *Galdieria* | Low Protein Extracted Biomass | 0.01% 0.001% | +8.9 +32.6 |
| *Galdieria* | Low Protein Extracted Oil | 0.001% 0.0001% | −44.4 −23.6 |
| *Galdieria* | Protein Fraction | 0.01% 0.001% | +6.2 −8.9 |
| *Chlorella* sp. (acetate) | Whole Biomass | 0.01% 0.001% | +42.0 +23.6 |
| *Chlorella* sp. (acetate) | Extracted Biomass | 0.01% 0.001% | −7.2 +4.8 |
| *Chlorella* sp. (acetate) | Extracted oil | 0.001% 0.0001% | −18.6 −9.7 |
| *Haematococcus* | Whole Biomass | 0.01% 0.001% | −38.0 −17.0 |
| *Haematococcus* | Extracted Biomass | 0.01% 0.001 | −0.7 +54.8 |
| *Haematococcus* | Extracted Oil | 0.001% 0.0001% | −46.0 +18.1 |
| *Isochrysis* | Whole Biomass | 0.01% 0.001% | — −5.1 |
| *Isochrysis* | Extracted Biomass | 0.01% 0.001% | −15.2 −38.4 |
| *Isochrysis* | Extracted Oil | 0.001% 0.0001% | −13.8 +3.1 |
| *Nannochloropsis* | Whole Biomass | 0.01% 0.001% | −40.6 −22.8 |
| *Nannochloropsis* | Extracted Biomass | 0.01% 0.001% | −29.0 −5.1 |
| *Nannochloropsis* | Extracted Oil | 0.001% 0.0001% | +28.3 +IO.I |
| *Porphyridium* | Whole Biomass | 0.01% 0.001% | +13.0 −9.4 |
| *Porphyridium* | Extracted Biomass | 0.01% 0.001% | +18.4 −2.4 |
| *Porphyridium* | Extracted Oil | 0.001% 0.0001% | +21.4 −15.0 |
| *Porphyridium* | EPS | 0.01% 0.001% | +8.7 +0.5 |
| *Schizochytrium* | Whole Biomass | 0.01% 0.001% | −51.4 +17.4 |
| *Schizochytrium* | Extracted Biomass | 0.01% 0.001% | −15.9 −17.0 |
| *Schizochytrium* | Extracted Oil | 0.001% 0.0001% | −56.5 −44.9 |
| *Tetraselmis* | Whole Biomass | 0.01% 0.001% | +6.8 0.0 |
| *Tetraselmis* | Extracted Biomass | 0.01% 0.001% | −42.4 −51.8 |
| *Tetraselmis* | Extracted Oil | 0.001% 0.0001% | −12.6 −5.8 |
| *Pavlova* | Whole Biomass | 0.01% 0.001% | +18.4 +28.8 |
| *Pavlova* | Extracted Biomass | 0.01% 0.001% | +40.8 +7.2 |
| *Pavlova* | Extracted Oil | 0.001% 0.0001% | +32.2 +19.8 |
| *Phaeodactylum* | Whole Biomass | 0.01% 0.001% | +31.0 +5.0 |
| *Phaeodactylum* | Extracted Biomass | 0.01% 0.001% | +8.3 +3.4 |
| *Phaeodactylum* | Extracted Oil | 0.001% 0.0001% | +11.4 +27.9 |
| *Nannochloropsis* | High Lipid Whole Biomass | 0.01% 0.001% | −21.7 −13.1 |
| *Nannochloropsis* | High Lipid Extracted Biomass | 0.01% 0.001% | +4.8 −18.3 |
| *Nannochloropsis* | High Lipid Extracted Oil | 0.001% 0.001% | −14.3 −12.7 |
| *Porphyridium* | PE rich fraction | 0.01% 0.001% | −14.7 −7.8 |
| *Porphyridium* | PEB 1 lipid + EPS fraction | 0.01% 0.001 | +0.4 +20.7 |
| *Porphyridium* | Extracted Oil | 0.001% 0.0001% | −7.5 −13.4 |
| *Porphyridium* | LEB2 + EPS | 0.01% 0.001% | −43.4 +4.1 |
| *Porphyridium* | Biomass − EPS | 0.01% 0.001% | +1.7 −16.9 |
| *Porphyridium* | PE rich fraction from biomass − EPS | 0.01% 0.001% | −6.2 −10.0 |
| *Porphyridium* | PEB2 Lipid + PS fraction | 0.01% 0.001% | −12.4 +2.7 |
| *Aurantiochytrium* SP. | Whole Biomass | 0.01% 0.001% | −17.1 −2.4 |
| *Aurantiochytrium* sp. | Extracted Biomass (hexane) | 0.01% 0.001% | −22.0 +5.2 |
| *Aurantiochytrium* sp. | Extracted Oil (hexane) | 0.001% 0.0001% | −15.5 −1.2 |
| *Aurantiochytrium* sp. | Extracted Biomass (ethanol) | 0.01% 0.001% | +10.7 +2.6 |
| *Aurantiochytrium* sp. | Extracted Oil (ethanol) | 0.001% 0.0001% | −13.5 −7.9 |
| *Aurantiochytrium* sp. | Extracted Oil (mechanical) | 0.001% 0.0001% | −11.3 +21.1 |
| *Spirulina* | Extracted Biomass (hexane) | 0.01% 0.001% | −6.8 +25.5 |
| *Spirulina* | Extracted Oil (hexane) | 0.001% 0.0001% | +28.3 +7.9 |
| *Spirulina* | Extracted Biomass (acetone) | 0.01% 0.001% | +7.4 +3.5 |
| *Spirulina* | Extracted Oil (acetone) | 0.001% 0.0001% | +13.5 +18.4 |
| *Spirulina* | Low Protein Whole Biomass | 0.01% 0.001% | −39.4 −16.9 |
| *Spirulina* | Protein Fraction | 0.01% 0.001% | −27.7 −26.9 |
| *Spirulina* | Lyzed Whole Biomass | 0.01% 0.001% | −25.9 −17.5 |
| *Scenedesmus* | Whole Biomass | 0.01% 0.001% | −44.4 −26.7 |
| *Scenedesmus* | Extracted Biomass | 0.01% 0.001% | −35.4 −25.9 |
| *Scenedesmus* | Extracted Oil | 0.001% 0.0001% | −35.1 −28.4 |
| *T-Isochrysis* | Whole Biomass | 0.01% 0.001% | −11.4 −12.8 |
| *T-Isochrysis* | Extracted Biomass (ethanol) | 0.01% 0.001% | −15.3 −4.0 |
| *T-Isochrysis* | Extracted Oil (ethanol) | 0.001% 0.0001% | −14.2 −4.2 |
| *Chlorella zofingiensis* | Whole Biomass | 0.01% 0.001% | −38.0 −11.7 |
| *Chlorella zofingiensis* | Extracted Biomass (ethanol) | 0.01% 0.001% | +2.8 −0.4 |
| *Chlorella zofingiensis* | Extracted oil (ethanol) | 0.001% 0.0001% | −13.3 −21.2 |
| *Chlorella* sp. (glucose) | Whole Biomass | 0.01% 0.001% | −26.8 −12.6 |
| *Chlorella* sp. (glucose) | Extracted Biomass (ethanol) | 0.01% 0.001% | −15.1 −18.7 |
| *Chlorella* sp. (glucose) | Extracted oil (ethanol) | 0.001% 0.0001% | +1.4 −25.1 |
| *Aurantiochytrium* SP. | Whole Biomass (Medium Lipid) | 0.01% 0.001% | −73.8 −40.4 |
| *Aurantiochytrium* sp. | Extracted Biomass (High Lipid) | 0.01% 0.001% | −11.0 −2.3 |

TABLE 7-continued

Temperature Stress

| Genus | Treatment | Concentration | Dry Weight % Difference vs. Control |
|---|---|---|---|
| Aurantiochytrium sp. | Extracted Oil (High Lipid) (Hexane) (Mechanical Extraction) | 0.001% 0.0001% | +9.6 +29.3 |
| Aurantiochytrium sp. | Extracted Oil (High Lipid) (Ethanol) | 0.001% 0.0001% | −0.9 −16.7 |
| Aurantiochytrium sp. | Extracted Oil (High Lipid) (Mechanical Extraction) | 0.001% 0.0001% | −17.6 −12.1 |
| Aurantiochytrium sp. | Extracted Oil (Medium Lipid) (Hexane) | 0.001% 0.0001% | −13.5 −16.9 |
| Aurantiochytrium sp. | Extracted Oil (Medium Lipid) (Hexane) | 0.001% 0.0001% | 1.2 −19.0 |
| Aurantiochytrium sp. | Extracted Biomass (Medium Lipid) (Hexane) | 0.01% 0.001% | −3.7 +16.6 |
| Aurantiochytrium sp. | Extracted Biomass (Mediunl Lipid) (Ethanol) | 0.01% 0.001 | −0.5 −9.6 |
| Aurantiochytrium SP. | Whole Biomass (High Lipid) | 0.01% 0.001% | −28.6 −5.1 |
| Aurantiochytrium sp. | Extracted Biomass (High Lipid) (Ethanol) | 0.01% 0.001% | −14.0 +7.5 |
| Aurantiochytrium sp. | Extracted Biomass (High Lipid) (Hexane) | 0.01% 0.001% | −30.6 −15.3 |
| Botryococcus | Lyzed Whole Biomass | 0.01% 0.001% | −3.9 +1.8 |
| Botryococcus | Extracted Oil | 0.001% 0.0001% | −10.1 +0.3 |
| Botryococcus | Extracted Biomass | 0.01% 0.001% | −2.6 +17.7 |

Example 13

The bioassay was initiated using cut mung bean seedlings which were grown in vials supplemented with concentrations of the same microalgae based treatments of 0.1% (0.1 mL/L), 0.01% (0.01 mL/L), or 0.001% (0.001 mL/L) non-oil treatments, or 0.01% (0.01 mL/L), 0.001% (0.001 mL/L), or 0.0001% (0.0001 mL/L) oil, and compared to an untreated control. The mung bean seedlings were initially grown on vermiculite for two weeks and then cut approximately 3 cm below the cotyledons. Cut seedlings were placed in glass scintillation vials to which 15 mL of water or treatments were added. The treatments were prepared as described in Example 10. Five seedlings were used for each treatment. The root growth parameters of distance of root growth from meristem, number of roots, and root length were measured after 7 days. The results are shown in Table 8, which display the results for each tested concentration with respect to the untreated control.

TABLE 8

| Genus | Treatment | Conc. | Distance of Root Growth from Meristem % Difference vs. Control | Number of Roots % Difference vs. Control | Root Length % Difference vs. Control |
|---|---|---|---|---|---|
| Galdieria | Whole Biomass | 0.1% 0.01% 0.001% | +18.9 +54.1 +2.7 | +45.3 −15.6 −4.7 | −57.3 −32.0 −43.3 |
| Galdieria | Extracted Biomass | 0.1% 0.01% 0.001% | +89.2 +73.0 +62.2 | +18.8 +15.6 +45.3 | −65.3 −44.0 −64.0 |
| Galdieria | Extracted Oil | 0.01% 0.001% 0.0001% | −6.5 −13.0 +6.5 | −21.1 −29.5 −31.6 | +1.4 +23.9 +54.9 |
| Galdieria | Low Protein Whole Biomass | 0.1% 0.01% 0.001% | +150.0 +127.8 −11.1 | +87.2 +44.7 −25.5 | −22.7 +44.0 −32.0 |
| Galdieria | Low Protein Extracted Biomass | 0.1% 0.01% 0.001% | 0.0 −19.2 −19.2 | +42.0 +26.0 +16.0 | +24.4 −6.7 +73.3 |
| Galdieria | Low Protein Extracted Oil | 0.01% 0.001% 0.0001% | −41.3 −17.4 0.0 | −53.7 −28.4 −25.3 | −8.5 +105.6 +73.2 |
| Galdieria | Protein Fraction | 0.1% 0.01% 0.001% | +37.8 −18.9 +13.5 | −35.9 0.0 +10.9 | −84.0 −48.0 −4.0 |
| Chlorella sp. (acetate) | Whole Biomass | 0.1% 0.01% 0.001% | +83.3 +33.3 +5.6 | 0.0 +14.9 −6.4 | −40.0 −21.3 +13.3 |
| Chlorella sp. (acetate) | Extracted Biomass | 0.1% 0.01% 0.001% | +72.2 +100.0 −27.8 | +23.4 +6.4 −17.0 | −5.3 −44.0 −42.7 |
| Chlorella sp. (acetate) | Extracted Oil | 0.01% 0.001% 0.0001% | −26.1 +50.0 −23.9 | −29.5 +34.7 −29.5 | −47.9 +4.2 +40.8 |

TABLE 8-continued

| Genus | Treatment | Conc. | Distance of Root Growth from Meristem % Difference vs. Control | Number of Roots % Difference vs. Control | Root Length % Difference vs. Control |
| --- | --- | --- | --- | --- | --- |
| Haematococcus | Whole Biomass | 0.1% | +218.9 | +162.5 | −53.3 |
| | | 0.01% | +29.7 | −63.4 | −50.7 |
| | | 0.001% | +2.7 | −1.6 | −24.0 |
| Haematococcus | Extracted Biomass | 0.1% | +7.7 | +32.0 | +35.6 |
| | | 0.01% | −15.4 | +26.0 | +15.6 |
| | | 0.001% | −23.1 | +22.0 | +88.9 |
| Haematococcus | Extracted Oil | 0.01% | −10.9 | −37.9 | +40.8 |
| | | 0.001% | −34.8 | −43.4 | +106.0 |
| | | 0.0001% | +19.6 | −24.2 | +53.5 |
| Isochrysis | Extracted Biomass | 0.1% | −46.2 | −44.0 | −87.8 |
| | | 0.01% | −26.9 | +16.0 | +53.3 |
| | | 0.001% | −3.8 | −2.0 | +8.9 |
| Isochrysis | Extracted Oil | 0.01% | +107.4 | +15.9 | +87.7 |
| | | 0.001% | +34.3 | −6.5 | +28.8 |
| | | 0.0001% | +63.0 | +36.4 | +30.8 |
| Nannochloropsis | Extracted Biomass | 0.1% | −30.8 | −8.0 | +35.6 |
| | | 0.01% | −19.2 | −8.0 | +13.3 |
| | | 0.001% | −46.2 | −67.0 | −20.0 |
| Nannochloropsis | Extracted Oil | 0.01% | +103.7 | −196 | +63.1 |
| | | 0.001% | +62.0 | −13.6 | +36.5 |
| | | 0.0001% | −7.4 | −2.8 | +10.8 |
| Porphyridium | Whole Biomass | 0.1% | −64.9 | −81.2 | −93.3 |
| | | 0.01% | −8.1 | −35.9 | −62.7 |
| | | 0.001% | −13.5 | −53.1 | −60.0 |
| Porphyridium | Extracted Biomass | 0.1% | +394.4 | +61.7 | +12.0 |
| | | 0.01% | +11.1 | 0.0 | −21.3 |
| | | 0.001% | +16.7 | 0.0 | −14.7 |
| Porphyridium | Extracted Oil | 0.01% | −10.9 | −25.3 | −43.7 |
| | | 0.001% | −63.0 | −63.2 | −26.8 |
| | | 0.0001% | −37.0 | −38.9 | −21.1 |
| Porphyridium | EPS | 0.1% | −61.1 | −74.5 | −88.0 |
| | | 0.01% | −50.0 | −42.6 | −49.3 |
| | | 0.001% | +5.6 | +10.6 | −28.0 |
| Schizochytrium | Whole Biomass | 0.1% | +218.9 | +128.1 | −84.0 |
| | | 0.01% | +173.0 | +84.4 | −60.0 |
| | | 0.001% | +100.0 | +21.9 | −48.0 |
| Schizochytrium | Extracted Biomass | 0.1% | +96.2 | +38.0 | −2.2 |
| | | 0.01% | −7.7 | +40.0 | +53.3 |
| | | 0.001% | 0.0 | +54.0 | +51.1 |
| Schizochytrium | Extracted Oil | 0.01% | +21.7 | −2.1 | +22.5 |
| | | 0.001% | −26.1 | −23.2 | −1.4 |
| | | 0.0001% | −10.9 | −27.4 | +62.0 |
| Tetraselmis | Whole Biomass | 0.1% | −5.6 | −38.3 | −50.7 |
| | | 0.01% | −5.6 | +29.8 | +1.3 |
| | | 0.001% | −16.7 | −12.8 | −13.3 |
| Tetraselmis | Extracted Biomass | 0.1% | −11.5 | +32.0 | +17.8 |
| | | 0.01% | −23.1 | −16.0 | +20.0 |
| | | 0.001% | −61.5 | −52.0 | −68.9 |
| Tetraselmis | Extracted Oil | 0.01% | +170.4 | −14.0 | +84.6 |
| | | 0.001% | +40.7 | −6.5 | +15.4 |
| | | 0.0001% | +66.7 | +14.0 | +49.2 |
| Pavlova | Whole Biomass | 0.1% | +202.9 | +229.1 | +13.8 |
| | | 0.01% | +57.1 | +105.5 | +96.3 |
| | | 0.001% | +60.7 | +81.8 | −40.0 |
| Pavlova | Extracted Biomass | 0.1% | +185.7 | +1655 | +43.8 |
| | | 0.01% | +28.6 | +74.5 | +95.0 |
| | | 0.001% | +2.9 | +41.8 | −11.2 |
| Pavlova | Extracted Oil | 0.01% | 0.0 | +28.9 | +6.9 |
| | | 0.001% | +13.3 | +46.7 | +18.1 |
| | | 0.0001% | −6.7 | +37.8 | +50.0 |
| Phaeodactylum | Whole Biomass | 0.1% | +171.4 | +167.3 | +83.8 |
| | | 0.01% | +82.1 | +115.9 | +46.9 |
| | | 0.001% | +60.0 | +45.5 | — |
| Phaeodactylum | Extracted Biomass | 0.1% | +100.0 | +85.5 | +82.5 |
| | | 0.01% | +96.4 | +168.2 | +60.9 |
| | | 0.001% | −2.9 | +27.3 | −6.2 |
| Phaeodactylum | Extracted Oil | 0.01% | +80.0 | +35.6 | +18.8 |
| | | 0.001% | +6.7 | +24.4 | +26.9 |
| | | 0.0001% | +26.7 | +26.7 | +26.3 |
| Nannochloropsis | High Lipid Whole Biomass | 0.1% | +13.3 | +60.0 | +15.6 |
| | | 0.01% | +33.3 | +44.4 | +18.8 |
| | | 0.001% | +6.7 | +62.2 | +25.0 |

TABLE 8-continued

| Genus | Treatment | Conc. | Distance of Root Growth from Meristem % Difference vs. Control | Number of Roots % Difference vs. Control | Root Length % Difference vs. Control |
|---|---|---|---|---|---|
| Nannochloropsis | High Lipid Extracted Biomass | 0.1% | +100.0 | +44.4 | +56.9 |
| | | 0.01% | 0.0 | −2.2 | +15.6 |
| | | 0.001% | +6.7 | +37.8 | +34.4 |
| Nannochloropsis | High Lipid Extracted Oil | 0.01% | +73.3 | −6.7 | −2.5 |
| | | 0.001% | +20.0 | +17.8 | +18.8 |
| | | 0.0001% | +13.3 | +26.7 | +5.6 |
| Porphyridium | PE rich fraction | 0.1% | +162.2 | +271.4 | −4.5 |
| | | 0.01% | 101.9 | 175.7 | −26.4 |
| | | 0.001% | +86.1 | +111.4 | −22.7 |
| Porphyridium | PEB 1 lipid + EPS fraction | 0.1% | +142.2 | +144.3 | −34.5 |
| | | 0.01% | +122.2 | +121.4 | −26.4 |
| | | 0.001% | +44.4 | +30.0 | −13.6 |
| Porphyridium | Extracted Oil | 0.01% | +93.3 | +117.1 | −42.7 |
| | | 0.001% | +25.0 | +91.1 | −43.2 |
| | | 0.0001% | +48.9 | +57.1 | −27.3 |
| Porphyridium | LEB2 + EPS | 0.1% | +118.5 | +154.3 | −35.5 |
| | | 0.01% | +91.7 | +112.5 | −46.6 |
| | | 0.001% | +16.7 | +7.1 | −6.8 |
| Porphyridium | Biomass − EPS | 0.1% | +146.7 | +194.3 | −21.6 |
| | | 0.01% | +68.9 | +75.7 | −27.7 |
| | | 0.001% | +60.0 | +61.4 | +13.6 |
| Porphyridium | PE rich fraction from Biomass − EPS | 0.1% | −4.4 | −25.7 | −89.8 |
| | | 0.01% | +108.9 | +234.3 | −65.9 |
| | | 0.001% | +22.2 | +24.3 | −17.0 |
| Porphyridium | PEB2 Lipid + PS fraction | 0.1% | +168.9 | +240.0 | −43.2 |
| | | 0.01% | +133.3 | +221.4 | −28.4 |
| | | 0.001% | +44.4 | +54.3 | +6.8 |
| Aurantiochytrium sp. | Whole Biomass | 0.1% | +162.2 | +181.4 | +4.5 |
| | | 0.01% | +93.3 | +91.4 | −19.3 |
| | | 0.001% | +60.0 | −5.7 | +89.8 |
| Aurantiochytrium sp. | Extracted Biomass (hexane) | 0.1% | +155.6 | +210.0 | −3.4 |
| | | 0.01% | +124.4 | +82.9 | +5.7 |
| | | 0.001% | +42.2 | +30.0 | +26.1 |
| Aurantiochytrium sp. | Extracted Oil (hexane) | 0.01% | +60.0 | +72.9 | +19.3 |
| | | 0.001% | −17.8 | +20.0 | +51.1 |
| | | 0.0001% | +4.4 | +14.3 | +13.6 |
| Aurantiochytrium sp. | Extracted Biomass (ethanol) | 0.1% | +128.9 | +250.0 | −5.5 |
| | | 0.01% | +37.8 | +77.1 | −18.2 |
| | | 0.001% | +13.3 | +51.4 | 0.0 |
| Aurantiochytrium sp. | Extracted Oil (ethanol) | 0.01% | +37.8 | +51.4 | 0.0 |
| | | 0.001% | +37.0 | +2.9 | −29.1 |
| | | 0.0001% | +58.3 | +48.6 | −36.4 |
| Aurantiochytrium sp. | Extracted Oil (mechanical) | 0.01% | +62.2 | +95.7 | −31.8 |
| | | 0.001% | +36.1 | +42.9 | −21.6 |
| | | 0.0001% | +11.1 | +34.3 | −37.5 |
| Spirulina | Extracted Biomass (hexane) | 0.1% | +100.0 | +012.9 | −2.3 |
| | | 0.01% | +72.2 | +61.4 | −40.9 |
| | | 0.001% | +27.8 | +18.6 | −25.0 |
| Spirulina | Extracted Oil (hexane) | 0.01% | +102.8 | +85.7 | −14.8 |
| | | 0.001% | +44.4 | +60.0 | −1.1 |
| | | 0.0001% | +19.4 | +15.7 | −14.8 |
| Spirulina | Extracted Biomass (acetone) | 0.1% | +72.2 | +167.1 | +19.3 |
| | | 0.01% | +41.7 | +60.0 | −35.2 |
| | | 0.001% | −13.9 | +12.5 | −29.5 |
| Spirulina | Extracted Oil (acetone) | 0.01% | +58.3 | +60.0 | −53.4 |
| | | 0.001% | +11.1 | +50.0 | −12.5 |
| | | 0.0001% | −47.2 | −15.7 | +6.8 |
| Spirulina | Low Protein Whole Biomass | 0.1% | +205.6 | +385.7 | −71.6 |
| | | 0.01% | +94.4 | +152.9 | −50.0 |
| | | 0.001% | +22.2 | +52.9 | +4.5 |
| Spirulina | Protein Fraction | 0.1% | +155.6 | −12.5 | +146.4 |
| | | 0.01% | +88.9 | −20.5 | +77.1 |
| | | 0.001% | +41.7 | +25 | +60.0 |
| Spirulina | Lyzed Whole Biomass | 0.1% | +122.2 | −12.5 | +134.3 |
| | | 0.01% | +22.2 | +50.0 | +34.3 |
| | | 0.001% | +2.8 | +10.2 | +5.7 |
| Scenedesmus | Whole Biomass | 0.1% | +112.4 | +14.5 | +111.3 |
| | | 0.01% | +62.8 | +8.3 | +66.2 |
| | | 0.001% | +51.7 | −26.2 | +6.7 |
| Scenedesmus | Extracted Biomass | 0.1% | +35.2 | −10.2 | +32.3 |
| | | 0.01% | +104.1 | +42.8 | +39.5 |
| | | 0.001% | +79.3 | +26.8 | +33.3 |

TABLE 8-continued

| Genus | Treatment | Conc. | Distance of Root Growth from Meristem % Difference vs. Control | Number of Roots % Difference vs. Control | Root Length % Difference vs. Control |
|---|---|---|---|---|---|
| *Scenedesmus* | Extracted Oil | 0.01% | +98.6 | +23.1 | +109.2 |
| | | 0.001% | +109.7 | +12.0 | +51.8 |
| | | 0.0001 | +96.6 | +23.1 | +43.6 |
| *T-Isochrysis* | Whole Biomass | 0.1% | +106.9 | +87.7 | +189.7 |
| | | 0.01% | −31.0 | +34.2 | +19.0 |
| | | 0.001% | +34.5 | −27.7 | +25.6 |
| *T-Isochrysis* | Extracted Biomass (ethanol) | 0.1% | +34.5 | +144.6 | +105.1 |
| | | 0.01% | −36.6 | +158.5 | +43.6 |
| | | 0.001% | +13.1 | +50.2 | +27.2 |
| *T-Isochrysis* | Extracted Oil (ethanol) | 0.01% | +68.3 | +99.4 | +72.3 |
| | | 0.001% | +65.5 | +39.1 | +66.2 |
| | | 0.0001% | +93.1 | +2.2 | +31.3 |
| *Chlorella zofingiensis* | Whole Biomass | 0.1% | +369.0 | +12.0 | +158.5 |
| | | 0.01% | +37.9 | +21.8 | +60.0 |
| | | 0.001% | −37.9 | +4.6 | +5.1 |
| *Chlorella zofingiensis* | Extracted Biomass (ethanol) | 0.1% | +73.8 | −8.9 | +96.9 |
| | | 0.01% | +37.9 | +23.1 | +31.3 |
| | | 0.001% | −22.8 | +25.5 | +25.1 |
| *Chlorella zofingiensis* | Extracted Oil (ethanol) | 0.01% | +32.4 | −17.5 | +66.2 |
| | | 0.001% | +3.4 | −16.9 | +5.1 |
| | | 0.0001% | +17.2 | +4.6 | +66.7 |
| *Chlorella* sp. (glucose) | Whole Biomass | 0.1% | +195.2 | −37.8 | +273.3 |
| | | 0.01% | +51.7 | +10.8 | +76.9 |
| | | 0.001% | −13.8 | −18.5 | +12.8 |
| *Chlorella* sp. (glucose) | Extracted Biomass (ethanol) | 0.1% | +86.2 | −20.0 | +107.7 |
| | | 0.01% | −3.4 | +47.7 | +27.2 |
| | | 0.001% | −25.5 | −12.6 | −11.8 |
| *Chlorella* sp. (glucose) | Extracted Oil (ethanol) | 0.01% | +15.9 | −12.6 | +74.4 |
| | | 0.001% | −13.8 | +41.5 | +41.0 |
| | | 0.0001% | +13.8 | −27.7 | +25.6 |
| *Aurantiochytrium* sp. | Whole Biomass (Medium Lipid) | 0.1% | +173.3 | −7.4 | +102.0 |
| | | 0.01% | +6.7 | −27.0 | +8.0 |
| | | 0.001% | +37.5 | −26.3 | +17.5 |
| *Aurantiochytrium* sp. | Extracted Biomass (High Lipid) (Mechanical Extraction) | 0.1% | +266.7 | +12.3 | +207.5 |
| | | 0.01% | +70.8 | +26.3 | 0.0 |
| | | 0.001% | +90.0 | +51.6 | +42.0 |
| *Aurantiochytrium* sp. | Extracted Oil (High Lipid) (Hexane) | 0.01% | +91.7 | +32.6 | +50.0 |
| | | 0.001% | +91.7 | +38.6 | +32.5 |
| | | 0.0001% | +41.7 | +52.6 | +20.0 |
| *Aurantiochytrium* sp. | Extracted Oil (High Lipid) (Ethanol) | 0.01% | +143.3 | +26.3 | +68.0 |
| | | 0.001% | +112.5 | +94.7 | +55.0 |
| | | 0.0001% | +50.0 | −19.3 | +65.0 |
| *Aurantiochytrium* sp. | Extracted Oil (High Lipid) (Mechanical Extraction) | 0.01% | +20.0 | +53.0 | +24.0 |
| | | 0.001% | +40.0 | +50.2 | +16.0 |
| | | 0.0001% | +25.0 | +33.3 | +10.0 |
| *Aurantiochytrium* sp. | Extracted Oil (Medium Lipid) (Hexane) | 0.01% | +285.7 | −5.4 | +94.3 |
| | | 0.001% | −4.7 | −0.9 | +21.9 |
| | | 0.0001% | +114.3 | −27.0 | +57.1 |
| *Aurantiochytrium* sp. | Extracted Oil (Medium Lipid) (Ethanol) | 0.01% | +185.7 | −4.1 | +102.9 |
| | | 0.001% | +71.4 | −10.8 | +57.1 |
| | | 0.0001 | +174.3 | +3.8 | +50.9 |
| *Aurantiochytrium* sp. | Extracted Biomass (Medium Lipid) (Hexane) | 0.1% | +374.3 | −67.6 | +185.7 |
| | | 0.01% | +265.7 | −12.4 | +110.3 |
| | | 0.001% | +48.6 | −8.1 | +34.9 |
| *Aurantiochytrium* sp. | Extracted Biomass (Medium Lipid) (Ethanol) | 0.1% | +381.3 | −47.0 | +191.7 |
| | | 0.01% | +45.0 | −32.1 | +24.4 |
| | | 0.001% | +120.0 | −9.1 | +62.2 |
| *Aurantiochytrium* sp. | Whole Biomass (High Lipid) | 0.1% | +433.3 | −71.7 | +129.6 |
| | | 0.01% | +230.0 | −56.4 | +654.4 |
| | | 0.001% | −15.0 | −4.2 | +2.2 |
| *Aurantiochytrium* sp. | Extracted Biomass (High Lipid) (Ethanol) | 0.1% | +210.0 | −91.5 | +46.7 |
| | | 0.01% | +100.0 | −40.6 | +33.3 |
| | | 0.001% | +100.0 | +49.1 | +57.8 |

TABLE 8-continued

| Genus | Treatment | Conc. | Distance of Root Growth from Meristem % Difference vs. Control | Number of Roots % Difference vs. Control | Root Length % Difference vs. Control |
|---|---|---|---|---|---|
| Aurantiochytrium sp. | Extracted Biomass (High Lipid) (Hexane) | 0.1% | +290.0 | −73.3 | +164.4 |
| | | 0.01% | +95.0 | −62.4 | +75.6 |
| | | 0.001% | +110.0 | −52.7 | +66.7 |
| Botryococcus | Lyzed Whole Biomass | 0.1% | +520.0 | −56.4 | +417.8 |
| | | 0.01% | +66.7 | +9.1 | +25.9 |
| | | 0.001% | 0.0 | −56.4 | +417.8 |
| Botryococcus | Extracted Oil | 0.01% | +170.0 | −34.5 | +115.6 |
| | | 0.001% | −20.0 | +20.0 | +28.9 |
| | | 0.0001% | +5.0 | −40.6 | +26.7 |
| Botryococcus | Extracted Biomass | 0.1% | +435.0 | −33.3 | +304.4 |
| | | 0.01% | +115.0 | −28.5 | +95.6 |
| | | 0.001% | +30.0 | +5.5 | +40.0 |

Example 14

An experiment was performed to determine the effect of treating *Arabidopsis thaliana* with a variety of microalgae treatments under conditions where the plants are exposed to *Sclerotinia sclerotiorum*. The bioassay was initiated using four-week-old plantlets grown on Jiffy pellets (peat moss pellets). Plants on Jiffy pellets were placed on trays and the foliar was sprayed with concentrations of 0.1% (0.1 mL/L) or 0.01% (0.01 mL/L) of non-oil treatments, or 0.01% (0.01 mL/L) or 0.001% (0.001 mL/L) of microalgae oil, and compared to an untreated control. The treatments were prepared as described in Example 10. The day after the application of the treatments, the plugs of *Sclerotinia sclerotiorum* were placed on two leaves per plant. The disease severity (diameter of infected area around a plug) was recorded after 3 days. The results are shown in Table 9, which display the results for each tested concentration with respect to the untreated control.

TABLE 9

| Genus | Treatment | Concentration | Diameter of disease infected area % Difference vs. Control |
|---|---|---|---|
| Galdieria | Low Protein Extracted Biomass | 0.1% | −34.4 |
| | | 0.01% | +44.2 |
| Galdieria | Low Protein Extracted Oil | 0.01% | −1.8 |
| | | 0.001% | +31.8 |
| Galdieria | Protein Fraction | 0.1% | −29.5 |
| | | 0.01% | +0.4 |
| Chlorella sp. (acetate) | Whole Biomass | 0.1% | +66.8 |
| | | 0.01% | +2.8 |

TABLE 9-continued

| Genus | Treatment | Concentration | Diameter of disease infected area % Difference vs. Control |
|---|---|---|---|
| Haematococcus | Extracted Biomass | 0.1% | −3.6 |
| | | 0.01% | +62.6 |
| Isochrysis | Extracted Biomass | 0.1% | +57.5 |
| | | 0.01% | +28.0 |
| Nannochloropsis | Extracted Biomass | 0.1% | +3.5 |
| | | 0.01% | −15.4 |
| Schizochytrium | Extracted Biomass | 0.1% | −24.7 |
| | | 0.01% | +8.2 |
| Schizochytrium | Extracted Oil | 0.01% | +43.6 |
| | | 0.001% | +66.7 |

Example 15

An experiment was performed to determine the effect of *Chlorella* and *Aurantiochytrium* treatments on bell pepper plants when applied to the root zone during salt (NaCl) stress conditions. The treatments consisted of whole pasteurized *Chlorella* and *Aurantiochytrium* cells in addition to the normal regiment of plant nutrients. The treatments were applied to plants both receiving and not receiving salt stress at rates of 0.2 mL per plant per week or 2 mL per plant per week, and compared to a control that only received the normal regiment of plant nutrients. The plants that were under salt stress conditions received 60 mM of NaCl starting on day 2 of the experiment and 120 mM of NaCl on day 6 of the experiment in the normal plant nutrient solution. Each treatment was performed on 24 replicates. The plants were monitored and the height, circumference, leaf surface area, bud count, shoot fresh weight, shoot dry weight, root and dry weight were measured. The experiment was run for 21 days and the results are shown in the Tables 10-11 below.

TABLE 10

| | | | % Difference from Control | | | |
|---|---|---|---|---|---|---|
| Treatment | Salt Stress | Rate | Diameter (cm) | Circ. (cm) | Height (cm) | Bud Count |
| Aurantiochytrium SP. | Y | 2 mL | +1.4 | −2.8 | +3.1 | −13.5 |
| | N | 2 mL | −0.9 | −0.9 | +3.2 | −4.6 |
| Aurantiochytrium sp. | Y | 0.2 mL | +5.3 | −1.8 | +1.2 | +7.4 |
| | N | 0.2 mL | −3.6 | −3.6 | +0.3 | −2.9 |

TABLE 10-continued

| Treatment | Salt Stress | Rate | Diameter (cm) | Circ. (cm) | Height (cm) | Bud Count |
|---|---|---|---|---|---|---|
| | | | % Difference from Control | | | |
| *Chlorella* sp. (acetate) | Y | 2 mL | +8.5 | +8.5 | +6.8 | +13.3 |
| | N | 2 mL | −2.5 | −2.5 | +3.2 | +3.5 |
| *Chlorella* sp. (acetate) | Y | 0.2 mL | +12.3 | +12.3 | +7.6 | +1.7 |
| | N | 0.2 mL | −0.9 | −0.9 | +1.6 | −2.9 |

TABLE 11

| Treatment | Salt Stress | Rate | Shoot Fresh Weight (g) | Leaf Surface Area (sq. cm) | Shoot Dry Weight (g) | Root Dry Weight (g) |
|---|---|---|---|---|---|---|
| | | | % Difference from Control | | | |
| *Aurantiochytrium* sp. | Y | 2 mL | +2.0 | +5.0 | −3.4 | −3.5 |
| | N | 2 mL | −7.8 | −4.8 | −5.1 | −15.6 |
| *Aurantiochytrium* sp. | Y | 0.2 mL | +7.7 | +13.0 | +7.2 | −60.7 |
| | N | 0.2 mL | −8.4 | −1.7 | −7.7 | −13.6 |
| *Chlorella* sp. (acetate) | Y | 2 mL | +18.9 | +20.3 | +21.8 | +15.8 |
| | N | 2 mL | −4.6 | −7.3 | −0.4 | −2.8 |
| *Chlorella* sp. (acetate) | Y | 0.2 mL | +15.1 | +21.5 | +14.3 | +11.2 |
| | N | 0.2 mL | −2.6 | −3.2 | −3.7 | −8.0 |

Example 16

An experiment was performed to determine the effect of *Chlorella* and *Aurantiochytrium* treatments on snap pea plant growth and yield. The *Chlorella* treatment comprised of mixotrophically cultured cells from a non-axenic culture, which were then pasteurized and pH stabilized as whole cells without being subjected to a drying process. The *Aurantiochytrium* treatments comprised of multiple different pasteurized and pH stabilized preparations consisting of: a) whole cells from non-axenic cultures, b) disrupted cells that had been subjected to an oil extracted process, c) whole cells from axenic cultures, d) whole cells that were subjected to boiling, and e) whole cells from non-axenic cultures that were subjected to a washing process. The experiment was performed in fields located in Minnesota, USA.

All plots received a standard fertilization regimen, with the microalgae treatments added in addition standard fertilization, herbicide, and pest control practice. The microalgae treatments were irrigated into the soil in furrow at planting and via drip irrigation thereafter. The first application occurred at the time of planting and then every 14 days afterward until harvest. The treatments were applied at rates of 3.7, 7.5, and 15 L/acre. Eight replicates for each treatment were conducted in the experiment. Several metrics for the plants were measured, including pod fresh weight, pod count per plant, shoot fresh weight, root fresh weight, total pod yield, total yield, marketable yield, and utilization. The results for each treatment were averaged and compared to the untreated control, and are shown in Tables 12-13

TABLE 12

| Genus | Treatment | App. Rate (L/acre) | Pod Fresh Weight (g) | Pod count/plant | Shoot Fresh Weight (g) | Root Fresh Weight (g) | Total pod yield (lb/plot) |
|---|---|---|---|---|---|---|---|
| | | | % Difference from Control | | | | |
| *Chlorella* sp. (acetate) | Whole Biomass | 3.7 | −0.4 | +1.3 | +3.5 | +2.7 | +2.0 |
| | | 7.5 | −2.3 | +3.5 | +2.6 | +7.1 | +4.5 |
| | | 15 | −0.8 | +5.7 | +8.0 | +5.4 | +4.0 |
| *Aurantiochytrium* sp. | Whole Biomass Non-axenic | 3.7 | −2.1 | +4.4 | +7.9 | +11.6 | +2.6 |
| | | 7.5 | −3.3 | +7.0 | +8.2 | +15.2 | +3.4 |
| | | 15 | −1.6 | +5.9 | +9.1 | +17.0 | +4.1 |
| *Aurantiochytrium* sp. | Extracted Biomass | 3.7 | −4.7 | +5.5 | +8.9 | +21.4 | +3.9 |
| | | 7.5 | −1.2 | +5.7 | +8.5 | +17.9 | +4.9 |
| | | 15 | −1.0 | +4.0 | +8.1 | +27.7 | +4.7 |
| *Aurantiochytrium* sp. | Whole Biomass Axenic | 3.7 | −3.3 | +9.0 | +8.5 | +23.2 | +3.6 |
| | | 7.5 | +0.4 | +5.7 | +8.3 | +8.9 | +4.4 |
| | | 15 | −5.3 | +4.4 | +8.0 | +27.7 | +3.5 |
| *Aurantiochytrium* sp. | Whole Biomass Boiled | 3.7 | −2.1 | +6.8 | +7.6 | +19.6 | +1.0 |
| | | 7.5 | +1.4 | +7.3 | +10.2 | +30.4 | +2.2 |
| | | 15 | +0.4 | +4.0 | +10.3 | +17.0 | +4.8 |

TABLE 12-continued

|  |  | | % Difference from Control | | | | |
|---|---|---|---|---|---|---|---|
| Genus | Treatment | App. Rate (L/ acre) | Pod Fresh Weight (g) | Pod count/plant | Shoot Fresh Weight (g) | Root Fresh Weight (g) | Total pod yield (lb/plot) |
| Aurantiochytrium sp. | Whole Biomass Washed | 3.7 7.5 15 | −0.2 +1.6 −0.4 | +5.7 +5.7 +4.6 | +9.4 +9.6 +10.0 | +19.6 +24.1 +20.5 | +1.0 +3.2 +4.8 |

TABLE 13

|  |  | | % Difference from Control | | |
|---|---|---|---|---|---|
| Genus | Treatment | App. Rate (L/ acre) | Total Yield (lb/ acre) | Marketable yield (lb pod/plot) | Marketable yield (lb/ acre) | % Utilization |
| Chlorella sp. (acetate) | Whole Biomass | 3.7 7.5 15 | +2.0 +4.5 +4.0 | +0.7 +6.0 +5.5 | +0.7 +6.0 +5.5 | −1.3 +1.5 +1.4 |
| Aurantiochytrium sp. | Whole Biomass Non-axenic | 3.7 7.5 15 | +2.6 +3.4 +4.1 | +4.6 +6.2 +7.1 | +4.6 +6.2 +7.1 | +2.3 +2.7 +2.8 |
| Aurantiochytrium sp. | Extracted Biomass | 3.7 7.5 15 | +3.9 +4.9 +4.7 | +6.2 +6.5 +6.7 | +6.2 +6.5 +6.7 | +2.3 +1.6 +2.0 |
| Aurantiochytrium sp. | Whole Biomass Axenic | 3.7 7.5 15 | +3.6 +4.4 +3.5 | +5.7 +6.2 +5.5 | +5.7 +6.2 +5.5 | +2.1 +1.5 +2.0 |
| Aurantiochytrium sp. | \\-'hole Biomass Boiled | 3.7 7.5 15 | +1.0 +2.2 +4.8 | +2.6 +3.6 +6.9 | +2.6 +3.6 +6.9 | +1.8 +1.4 +1.3 |
| Aurantiochytrium sp. | \\-'hole Biomass Washed | 3.7 7.5 15 | +1.0 +3.2 +4.8 | +2.1 +4.7 +7.2 | +2.1 +4.7 +7.2 | +1.1 +1.5 +2.3 |

Example 17

An experiment was performed to determine the effect of Chlorella and Aurantiochytrium treatments on snap bean plant growth and yield. The Chlorella treatment comprised of mixotrophically cultured cells from a non-axenic culture, which were then pasteurized and pH stabilized as whole cells without being subjected to a drying process. The Aurantiochytrium treatments comprised of multiple different pasteurized and pH stabilized preparations consisting of: a) whole cells from non-axenic cultures, b) disrupted cells that had been subjected to an oil extracted process, whole cells from axenic cultures, d) whole cells that were subjected to boiling, and e) whole cells from non-axenic cultures that were subjected to a washing process. The experiment was performed in fields located in Minnesota, USA.

All plots received a standard fertilization regimen, with the microalgae treatments added in addition standard fertilization, herbicide, and pest control practice. The microalgae treatments were irrigated into the soil in furrow at planting and via drip irrigation thereafter. The first application occurred at the time of planting and then every 14 days afterward until harvest. The treatments were applied at rates of 3.7, 7.5, and 15 L/acre. Eight replicates for each treatment were conducted in the experiment. Several metrics for the plants were measured, including pod fresh weight, pod count per plant, shoot fresh weight, root fresh weight, total pod yield, total yield, marketable yield, and utilization. The results for each treatment were averaged and compared to the untreated control, and are shown in Tables 14-15.

TABLE 14

|  |  | | % Difference from Control | | | | |
|---|---|---|---|---|---|---|---|
| Genus | Treatment | App. Rate (L/ acre) | Pod Fresh Weight (g) | Pod count/plant | Shoot Fresh Weight (g) | Root Fresh Weight (g) | Total pod yield (lb/plot) |
| Chlorella sp. (acetate) | Whole Biomass | 3.7 7.5 15 | +0.6 +6.6 +2.8 | +7.2 +3.1 +5.2 | +2.5 +3.6 +2.6 | +0.9 +1.3 +1.5 | +6.7 +2.6 +2.8 |

TABLE 14-continued

| | | | % Difference from Control | | | | |
|---|---|---|---|---|---|---|---|
| Genus | Treatment | App. Rate (L/acre) | Pod Fresh Weight (g) | Pod count/plant | Shoot Fresh Weight (g) | Root Fresh Weight (g) | Total pod yield (lb/plot) |
| Aurantiochytrium sp. | Whole Biomass Non-Extracted | 3.7 | +2.8 | +4.1 | +2.6 | −0.6 | +6.4 |
| | | 7.5 | +5.5 | +7.7 | +3.2 | +2.8 | +6.4 |
| | | 15 | +2.0 | +2.6 | +1.8 | +4.5 | +6.0 |
| Aurantiochytrium sp. | Biomass | 3.7 | +5.2 | +2.6 | +3.2 | +1.5 | +4.9 |
| | | 7.5 | +4.5 | +4.6 | +2.5 | +3.1 | +4.4 |
| | | 15 | +6.0 | +3.1 | +3.2 | +4.8 | +6.5 |
| Aurantiochytrium sp. | Whole Biomass Axenic | 3.7 | +3.2 | +5.2 | +3.0 | +2.5 | +4.5 |
| | | 7.5 | +7.5 | +4.1 | +4.2 | +4.5 | +5.9 |
| | | 15 | +5.3 | +7.2 | +3.8 | +4.1 | +8.5 |
| Aurantiochytrium sp. | Whole Biomass Boiled | 3.7 | +3.6 | +1.5 | +4.0 | +1.9 | +4.7 |
| | | 7.5 | +4.7 | +5.2 | +4.2 | +6.2 | +6.4 |
| | | 15 | +6.9 | +2.1 | +3.9 | +5.5 | +6.9 |
| Aurantiochytrium sp. | Whole Biomass Washed | 3.7 | +4.9 | +1.0 | +3.8 | +2.9 | +5.5 |
| | | 7.5 | +4.2 | +5.7 | +4.1 | +3.5 | +9.2 |
| | | 15 | +6.6 | +4.6 | +4.7 | +6.3 | +7.5 |

TABLE 15

| | | | % Difference from Control | | | |
|---|---|---|---|---|---|---|
| Genus | Treatment | App. Rate (L/acre) | Total Yield (lb/acre) | Marketable yield (lb pod/plot) | Marketable yield (lb/acre) | % Utilization |
| Chlorella sp. (acetate) | Whole Biomass | 3.7 | +6.7 | +6.9 | +6.9 | +0.1 |
| | | 7.5 | +2.6 | +2.8 | +2.8 | +0.2 |
| | | 15 | +2.8 | +3.3 | +3.3 | +0.4 |
| Aurantiochytrium sp. | Whole Biomass Non-Extracted | 3.7 | +6.4 | +5.3 | +5.3 | −1.1 |
| | | 7.5 | +6.4 | +5.5 | +5.5 | −0.8 |
| | | 15 | +6.0 | +5.7 | +5.7 | −0.3 |
| Aurantiochytrium sp. | Biomass | 3.7 | +4.9 | +4.7 | +4.7 | −0.2 |
| | | 7.5 | +4.4 | +4.3 | +4.3 | −0.1 |
| | | 15 | +6.5 | +7.0 | +7.0 | +0.5 |
| Aurantiochytrium sp. | Whole Biomass Axenic | 3.7 | +4.5 | +4.0 | +4.0 | −0.5 |
| | | 7.5 | +5.9 | +6.2 | +6.2 | +0.3 |
| | | 15 | +8.5 | +7.7 | +7.7 | −0.7 |
| Aurantiochytrium sp. | Whole Biomass Boiled | 3.7 | +4.7 | +4.6 | +4.6 | −0.1 |
| | | 7.5 | +6.4 | +6.3 | +6.3 | 0.0 |
| | | 15 | +6.9 | +6.9 | +6.9 | 0.0 |
| Aurantiochytrium sp. | Whole Biomass Washed | 3.7 | +5.5 | +5.8 | +5.8 | +0.2 |
| | | 7.5 | +9.2 | +8.9 | +8.9 | −0.3 |
| | | 15 | +7.5 | +7.1 | +7.1 | −0.4 |

Example 18

An experiment was performed to determine the effect of microalgae treatments on strawberry plant growth and yield. The Chlorella treatment comprised of mixotrophically cultured cells from a non-axenic culture, which were then pasteurized and pH stabilized as whole cells without being subjected to a drying process. The Aurantiochytrium treatments comprised multiple different pasteurized and pH stabilized preparations consisting of: a) whole cells from non-axenic cultures, and b) disrupted cells that had been subjected to an oil extracted process. The Spirulina treatment comprised of cells from a non-axenic culture, which were then pasteurized and pH stabilized as whole cells without being subjected to a drying process. The Isochrysis treatment comprised of cells from a non-axenic culture, which were then pasteurized and pH stabilized as whole cells without being subjected to a drying process. The Scenedesmus treatment comprised of cells from a non-axenic polyculture primarily comprised of "demsus" microalgae with the most likely candidate being Scenedesmus, which were then pasteurized and pH stabilized as whole cells without being subjected to a drying process. The experiment was performed in fields located in California, USA.

All plots received a standard fertilization regimen, with the microalgae treatments added in addition standard fertilization, herbicide, and pest control practice. The microalgae treatments were irrigated into the soil in furrow at planting and via drip irrigation thereafter. The first application occurred at the time of planting and then every 14 days afterward until harvest. The treatments were applied at rates of 3.7, 7.5, and 15 L/acre. Eight replicates for each treatment were conducted in the experiment. Several metrics for the plants were measured, including Brix, shoot weight, total fruit number, large red fruit number, large red fruit weight, marketable yield, and marketable fruit. The results for each treatment were averaged and compared to the untreated control, and are shown in Tables 16-17.

TABLE 16

| Genus | Treatment | App. Rate (L/acre) | % Difference from Control | | | |
|---|---|---|---|---|---|---|
| | | | %, Brix | Shoot Weight (g) | Total Fruit (no.) | Large Red (no.) |
| Chlorella sp. (acetate) | Whole Biomass | 3.7 | −6.9 | +1.6 | +10.7 | +21.0 |
| | | 7.5 | −6.2 | +17.7 | −4.7 | +3.6 |
| | | 15 | −2.1 | +43.3 | −3.3 | +13.0 |
| Aurantiochytrium sp. | Whole | 3.7 | −4.6 | +41.2 | +10.2 | −2.2 |
| | Biomass | 7.5 | +0.9 | +15.1 | +9.3 | +11.6 |
| | Non-axenic | 15 | −6.2 | +13.4 | +15.1 | +31.2 |
| Aurantiochytrium sp. | Extracted Biomass | 3.7 | −2.3 | +17.5 | +8.8 | 0.0 |
| | | 7.5 | −4.6 | +2.9 | −8.2 | +1.4 |
| | | 15 | −4.7 | +3.9 | −17.0 | −15.2 |
| Spirulina | Whole | 3.7 | −4.4 | −10.1 | −0.3 | −10.9 |
| | Biomass | 7.5 | −1.7 | +29.4 | +20.1 | +18.1 |
| | | 15 | −5.1 | −15.7 | +21.2 | +16.5 |
| Isochrysis | Whole | 3.7 | +0.4 | −30.1 | +20.6 | +31.9 |
| | Biomass | 7.5 | −3.2 | −35.7 | +4.7 | −6.5 |
| | | 15 | −2.4 | +1.0 | +0.5 | +26.8 |
| Scenedesmus | Whole | 3.7 | +4.9 | −20.7 | +19.0 | +63.8 |
| | Biomass | 7.5 | −7.7 | +1.8 | +4.9 | +22.5 |
| | | 15 | −3.7 | +10.7 | +11.0 | +27.5 |

TABLE 17

| Genus | Treatment | App. Rate (L/acre) | % Difference from Control | | | |
|---|---|---|---|---|---|---|
| | | | Large Red Weight (g) | Marketable yield (lb/acre) | % Marketable Fruit (by no.) | % Marketable Fruit (by wt.) |
| Chlorella sp. (acetate) | Whole | 3.7 | +16.1 | +16.1 | +8.5 | +5.7 |
| | Biomass | 7.5 | −6.9 | −6.9 | +11.3 | +6.3 |
| | | 15 | +15.8 | +15.8 | +11.9 | +7.8 |
| Aurantiochytrium sp. | Whole | 3.7 | +9.0 | +9.0 | −1.6 | +2.2 |
| | Biomass | 7.5 | +10.9 | +10.9 | +2.8 | +2.5 |
| | Non-axenic | 15 | +35.5 | +35.5 | +8.4 | +6.4 |
| Aurantiochytrium sp. | Extracted Biomass | 3.7 | +1.6 | +1.6 | +4.9 | +5.1 |
| | | 7.5 | +6.0 | +6.0 | +24.1 | +11.9 |
| | | 15 | −6.3 | −6.3 | +9.7 | +2.2 |
| Spirulina | Whole | 3.7 | −2.1 | −2.1 | −1.7 | −1.1 |
| | Biomass | 7.5 | +7.6 | +7.6 | +3.5 | −0.2 |
| | | 15 | +15.3 | +15.3 | +2.4 | +5.3 |
| Isochrysis | Whole | 3.7 | +27.7 | +27.7 | +9.4 | +6.8 |
| | Biomass | 7.5 | −9.9 | −9.9 | −2.7 | −2.1 |
| | | 15 | +24.8 | +24.8 | +21.7 | +11.3 |
| Scenedesmus | Whole | 3.7 | +44.5 | +44.5 | +18.9 | +10.2 |
| | Biomass | 7.5 | +22.3 | +22.3 | +9.7 | +7.4 |
| | | 15 | +36.6 | +36.6 | +12.5 | +9.0 |

Example 19

An experiment was performed to determine the effect of T. Isochrysis treatments on tomato plant growth and yield. The T. Isochrysis treatment comprised of cells from a non-axenic culture, which were then pasteurized and pH stabilized as whole cells without being subjected to a drying process. The experiment was performed in fields located in California, USA.

All plots received a standard fertilization regimen, with the microalgae treatments added in addition standard fertilization, herbicide, and pest control practice. The microalgae treatments were irrigated into the soil in furrow at planting and via drip irrigation thereafter. The first application occurred at the time of planting and then every 14 days afterward until harvest. The treatments were applied at rates of 3.7, 7.5, and 15 L/acre. Eight replicates for each treatment were conducted in the experiment. Several metrics for the plants were measured, including plant height, total fruit, and marketable fruit. The results for each treatment were averaged and compared to the untreated control, and are shown in Tables 18-19.

TABLE 18

| Organism | Treatment | App. Rate (L/acre) | % Difference from Control | | | |
|---|---|---|---|---|---|---|
| | | | Plant Height (30 day) | Plant Height (60 day) | Total Fruit count per acre | Total Fruit weight (lb/acre) |
| T-Isochrysis | Whole | 3.7 | +17.5 | +16.0 | +20.6 | +21.3 |
| | Biomass | 7.5 | −2.7 | +8.7 | −15.5 | +3.9 |
| | | 15 | −0.2 | +2.0 | −30.2 | −16.2 |

TABLE 19

| | | | % Difference from Control | | | |
|---|---|---|---|---|---|---|
| Organism | Treatment | App. Rate (L/ acre) | Marketable Fruit (lb/acre) | Utilization (by wt) | Large Red Fruit per plot (kg) | Large Green Fruit per plot (kg) |
| T-Isochrysis | Whole Biomass | 3.7 | +26.6 | +6.0 | +20.2 | +70.2 |
| | | 7.5 | −3.1 | −5.6 | +14.3 | +45.9 |
| | | 15 | −18.8 | −4.8 | −19.6 | −11.2 |

Example 20

An experiment was performed to determine the effect of T-Isochrysis treatments on tomato plant growth and yield. The T-Isochrysis treatment comprised of cells from a non-axenic culture, which were then pasteurized and pH stabilized as whole cells without being subjected to a drying process. The experiment was performed in fields located in New York, USA.

All plots received a standard fertilization regimen, with the microalgae treatments added in addition standard fertilization, herbicide, and pest control practice. The microalgae treatments were irrigated into the soil in furrow at planting and via drip irrigation thereafter. The first application occurred at the time of planting and then every 14 days afterward until harvest. The treatments were applied at rates of 3.7, 7.5, and 15 L/acre. Eight replicates for each treatment were conducted in the experiment. Several metrics for the plants were measured, including plant height, total fruit, and marketable fruit. The results for each treatment were averaged and compared to the untreated control, and are shown in Tables 20-22.

TABLE 20

| | | | % Difference from Control | | | |
|---|---|---|---|---|---|---|
| Organism | Treatment | App. Rate (L/acre) | Avg. shoot wt. (g) | Root wt. per 3 plants (g) | Avg. Fruit wt. per plant (g) | Average Fruit wt. (g) |
| T-Isochrysis | Whole Biomass | 3.7 | +65.1 | +46.8 | +245.4 | +72.3 |
| | | 7.5 | +53.5 | +32.9 | +159.1 | +35.3 |
| | | 15 | +3.3 | 0.0 | +149.5 | +30.4 |

TABLE 21

| | | | % Difference from Control | | | |
|---|---|---|---|---|---|---|
| Organism | Treatment | App. Rate (L/ acre) | Marketable Yield lb/acre 1st Harvest | Marketable Yield (lb/acre) 2nd Harvest | Total Yield (lb/acre) pt Harvest | Total Yield (lb/acre) $2^{nd}$ Harvest |
| T-Isochrysis | Whole Biomass | 3.7 | +253.1 | +23.1 | +204.5 | +37.7 |
| | | 7.5 | +110.8 | +105.14 | +83.1 | +85.8 |
| | | 15 | +45.0 | +6.7 | +25.7 | +19.7 |

TABLE 22

| | | | % Difference from Control | |
| --- | --- | --- | --- | --- |
| Organism | Treatment | App. Rate (L/acre) | Utilization $1^{st}$ Harvest | Utilization $2^{nd}$ Harvest |
| T-Isochrysis | Whole Biomass | 3.7 | +29.8 | −9.6 |
| | | 7.5 | +8.0 | −66.4 |
| | | 15 | +26.0 | −44.3 |

Example 21

For the experiments described in some of the following examples, flask cultures were used to generate the biomass for the small-scale testing (*Arabidopsis* plate, seed germination), and cultures were grown in closed bag bioreactors (90-440 L) to generate larger amounts of biomass needed for the hydroponics platform testing. Throughout the specification and the following examples: the term "photo" means phototrophic conditions; the term "mixo" means mixotrophic conditions; and the term "hetero" means heterotrophic conditions. The use of the terms "acetate" or "glucose" used in combination with the terms "mixo" or "hetero" indicate the source of organic carbon supplied to the microalgae in the specified growth conditions of the microalgae culture. The same species of microalgae were grown in the flask and bag bioreactor cultures for use in treatments described in the following examples.

For the flask cultures, *Nannochloropsis* was found to tolerate glucose. *Galdieria* was found to have considerable growth on glycerol under mixotrophic and heterotrophic conditions. *Chlorella/Micractinium* (HS26) was found to grow under all conditions (Mixo Glucose, Mixo Acetate, Hetero Glucose. Photo, Hetero Acetate).

For the bag bioreactor cultures, the following yields were obtained:

*Haematococcus* pluvialis (HS36)
Photo
  Volume—440 L (produced from two 220 L cultures)
  Not axenic (i.e., some bacteria contamination)
  Harvest density—0.75 and 0.80 g/L
Mixo Acetate
  Volume—360 L
  Axenic
  Harvest density—1.93 and 2.22 g/L
  Residual organic carbon—500 mg/L
*Chlamydomonas reinhardtii* (HS206)
Photo
  Volume—440 L (produced from two 220 L cultures)
  Not axenic
  Harvest density—N/A
Mixo Acetate
  Volume—220 L
  Not axenic
  Harvest density—2.43 g/L
  Residual organic carbon—470 mg/L
*Galdieria sulphuraria* (HS130)
Photo
  Cultures died—no biomass for use in experiments
Mixo Glucose
  Volume—90 L
  Axenic
  Harvest density—5.033 g/L
  Residual organic carbon—1000 mg/L
Hetero Glucose
  Volume—90 L, 100 L
  Axenic
  Harvest density—5.24, 4.88 g/L
  Residual organic carbon—100 mg/L
*Chlorella* sp./*Micractinium* (HS26)
Photo
  Volume—220 L
  Axenic
  Harvest density—0.82, 0.78 g/L
Mixo Acetate
  Volume—360 L
  Axenic
  Harvest density—23.9 g/L
  Residual organic carbon—not measured
Mixo Glucose
  Volume—360 L
  Axenic
  Harvest density—3.46 g/L
  Residual organic carbon—1,000 mg/L
Hetero Acetate
  Volume—360 L
  Axenic
  Harvest density—1.26 g/L
  Residual organic carbon—920 mg/L
Hetero Glucose
  Volume—360 L
  Axenic
  Harvest density—2.74 g/L
  Residual organic carbon—250 mg/L
*Scenedesmus obliquus* (HS199)
Photo
  Volume—220 L
  Axenic
  Harvest density—0.52, 0.39 g/L
Mixo Acetate
  Volume—220 L
  Axenic
  Harvest density—2.3 g/L
  Residual organic carbon—1700 mg/L
Hetero Glucose
  Volume—220 L
  Axenic
  Harvest density—2.78 g/L
  Residual organic carbon—50 mg/L
Hetero Glucose
  Volume—220 L
  Axenic
  Harvest density—2.66 g/L
  Residual organic carbon—not measured Example 22 (RDT1818)

Experiments were done to test the effects of different microalgae compositions on wild type *Arabidopsis thaliana*. Wild type *Arabidopsis thaliana* seeds were surface sterilized by soaking in 70% ethanol for two minutes, followed by 2.5% bleach for 15 minutes and rinsing with sterile deionized (DI) water three times (15 plants per treatment). Seeds were vernalized by soaking in filtered reverse osmosis (RO) water at 4° C. then sown on 0.1×MS media for germination and placed on a lighting rack. Week old seedlings were transferred to experimental plates and inoculated with the described treatments.

The conditions of the experiments were as follows:
Temperature—25° C.
Day length—16 hr light/8 hr dark lighting cycle
Light irradiance—12 0-14 0 umol/m²/s.
The following treatments were tested (18 mL/gal, biomass from flask cultures):
1. *Chlorella* Hetero Acetic
2. *Chlorella* Hetero Glucose
3. *Chlorella* Mixo Acetic
4. *Chlorella* Mixo Glucose
5. *Chlorella* Photo
6. *Galdieria* Hetero Glycerol
7. *Galdieria* Mixo Glycerol
8. *Galdieria* Photo
9. Control—NTC
10. Control—Mock The NTC control consisted of plants growing on an agar plate made up of a type of media called Murashige and Skoog basal salts. It was also buffered with MES buffer at pH 6.1 This media was the base media on top of which all the treatments were added. In other words, all of the plants "received" MS media. The microalgae biomass for the treatments was obtained from axenic flask cultures as described in Example 21.

The Mock control comprised the same nutrient formulation of nutrients found in the average PhycoTerra Production Batch (i.e., *Chlorella* [HS26] Mixo Acetate) (also used in the Seed Germination studies), specifically:

1.5% of *Chlorella* (HS26) lipids
8.5% of protein and carbohydrates
128 ppb of Abscisic acid (ABA)
3.3 ppb of trans-ABA
2.8 ppb of trans-zeatin-0-glucoside (ZOG)
8.6 ppb of trans-zeatin (Z)
16.4 ppb of cis-Z
1.6 ppb of trans-zeatin riboside (ZR)
42.5 ppb of cis-ZR
9.8 ppb of isopentenyladenine (iP)
4.1 ppb of isopentenyladenine riboside (iPR)
86.3 ppb of indole acetic acid (IAA)

Leaf and root surface area (cm² were analyzed using imageJ. Root hair was also scored on a scale of 0-3 based on the following criteria: 0=no visible root hairs, 1=occasional visible root hairs in isolated areas, 2=obvious root hairs on some roots, 3=extensive root hairs across most roots.

Results from experiments are provided in Table 23.

TABLE 23

| | % Difference from Control-NTC | | |
|---|---|---|---|
| Treatment | Leaf SA | Root SA | Root Hair |
| *Chlorella* Photo | +5.2 | +43.7 | +5.6 |
| *Chlorella* Hetero Acetic | +12.9 | +57.2 | +111.1 |
| *Chlorella* Hetero Glucose | +10.8 | +46.0 | −5.6 |
| *Chlorella* Mixo Acetic | +9.5 | +14.2 | −16.7 |
| Chlorella Mixo Glucose | +37.7 | +75.3 | −33.3 |
| *Galdieria* Hetero | +9.1 | +26.1 | −28.9 |
| *Galdieria* Mixo | −1.7 | +32.7 | +4.7 |
| *Galdieria* Photo | +0.5 | +18.1 | −33.3 |
| Mock | −3.4 | +13.1 | −11.1 |

Example 23 (1818 Repeat)

The experiments described in Example 22 was repeated with the following treatments
(18 mL/gal, biomass from flask cultures):
1. *Chlorella* Hetero Acetic
2. *Chlorella* HeteroGlucose
3. *Chlorella* Mixo Acetic
4. *Chlorella* Mixo Glucose
5. *Chlorella* Photo
6. *Galdieria* Hetero
7. *Galdieria* Mixo Glycerol
8. *Galdieria* Photo
9. *Nannochloropsis* Mixo Glucose
10. *Nannochloropsis* Photo
11. *Spirulina* Mixo Glucose
12. *Spirulina* Photo
13. Control—NTC
14. Control—Mock Combined results from experiments of Example 22 and 23 are provided in Table 24.

TABLE 24

| | % Difference from Control-NTC | | |
|---|---|---|---|
| Treatment | Leaf SA | Root SA | Root Hair |
| *Chlorella* Photo | +14.9 | +41.3 | −21.7 |
| *Chlorella* Hetero Acetic | +8.2 | +78.4 | +242.7 |
| *Chlorella* Hetero Glucose | +31.1 | +49.5 | +80.3 |
| *Chlorella* Mixo Acetic | +0.3 | +42.5 | 0.0 |
| *Chlorella* Mixo Glucose | +20.9 | +33.6 | −6.7 |
| *Galdieria* Hetero | −16.4 | −4.8 | −51.0 |
| *Galdieria* Mixo | −9.6 | +14.4 | −11.9 |
| *Galdieria* Photo | +30.1 | +62.5 | +72.7 |
| Mock | +12.7 | +36.0 | −2.1 |
| *Nannochloropsis* Mixo | +15.6 | +48.4 | +36.4 |
| *Nannochloropsis* Photo | +0.3 | +13.8 | −25.8 |
| *Spirulina* Mixo | +39.5 | +57.5 | +63.6 |
| *Spirulina* Photo | +9.5 | +34.3 | +37.1 |

TABLE 25

| Experiment | Treatment | Leaf area (cm²) | Root area (cm²) |
|---|---|---|---|
| Initial | NTC | 0.424 | 0.031 |
| | Mock | 0.410 | 0.035 |
| | *Chlorella* Hetero | 0.479 | 0.049 |
| | *Chlorella* Hetero Glucose | 0.470 | 0.045 |
| | *Chlorella* Mixo Acetic | 0.464 | 0.035 |
| | *Chlorella* Mixo Glucose | 0.584 | 0.054 |
| | *Chlorella* Photo | 0.446 | 0.045 |
| | *Galdieria* Hetero | 0.463 | 0.039 |
| | *Galdieria* Mixo | 0.423 | 0.042 |
| | *Galdieria* Photo | 0.426 | 0.037 |
| Repeat | NTC | 0.257 | 0.023 |
| | Mock | 0.295 | 0.032 |
| | *Chlorella* Hetero | 0.277 | 0.043 |
| | *Chlorella* Hetero Glucose | 0.319 | 0.033 |
| | *Chlorella* Mixo Acetic | 0.255 | 0.033 |
| | *Chlorella* Mixo Glucose | 0.305 | 0.031 |
| | *Chlorella* Photo | 0.293 | 0.033 |
| | *Galdieria* Hetero | 0.192 | 0.020 |
| | *Galdieria* Mixo | 0.227 | 0.026 |
| | *Galdieria* Photo | 0.334 | 0.038 |
| | *Nannochloropsis* Mixo | 0.294 | 0.034 |
| | *Nannochloropsis* Photo | 0.253 | 0.026 |
| | *Spirulina* Mixo | 0.343 | 0.035 |
| | *Spirulina* Photo | 0.276 | 0.032 |

Example 24 (1913)

The experiments described in Example 40 was repeated with the following treatments (18 mL/gal, biomass from flask cultures):
1. *Chlorella* Photo
2. *Chlorella* Mixo Acetate
3. *Chlorella* Mixo Glucose
4. *Chlorella* Hetero Acetate
5. *Chlorella* Hetero Glucose
6. Control—NTC
7. Control—Mock Acetate
8. Control—Mock Glucose The Mock Acetate and Mock Glucose consisted of the normal Mock solution that had been supplemented with either 2 g/L sodium acetate (Acetate) or 2 g/L glucose (Glucose), respectively.

Results from experiments are provided in Table 26.

TABLE 26

| Treatment | % Difference from Control-NTC Root Hair |
|---|---|
| *Chlorella* Hetero Acetic | +151.3 |
| *Chlorella* Hetero Glucose | −15.2 |
| *Chlorella* Mixo Acetic | +16.7 |
| *Chlorella* Mixo Glucose | +32.2 |
| *Chlorella* Photo | +8.3 |
| Mock Acetic | +16.7 |
| Mock Glucose | +16.7 |

Example 25 (1914)

The experiments described in Example 22 was repeated with the following treatments (18 mL/gal, biomass from flask cultures):
1. *Galdieria* HeteroGlycerol
2. *Galdieria* MixoGlycerol
3. *Galdieria* Photo
4. *Nannochloropsis* MixoGlucose
5. NannochloropsisPhoto
6. *Spirulina* Mixo Glucose
7. *Spirulina* Photo
8. Control—NTC
9. Control—Mock Combined results from experiments of Examples 24 and 25 are provided in Table 27. Combined results from experiments of Examples 22-25 are provided in Table 28.

TABLE 27

| Treatment | Mean Root Hair Score |
|---|---|
| NTC | 0.9231 |
| Mock | 1.3636 |
| Mock Acetic | 1.0000 |
| Mock Glucose | 1.0000 |
| *Chlorella* Hetero Acetic | 2.1538 |
| *Chlorella* Hetero Glucose | 0.7273 |
| *Chlorella* Mixo Acetic | 1.0000 |
| *Chlorella* Mixo Glucose | 1.1333 |
| *Chlorella* Photo | 0.9286 |
| *Galdieria* Hetero | 1.4167 |
| *Galdieria* Mixo | 1.2222 |
| *Galdieria* Photo | 1.7000 |
| *Nannochloropsis* Mixo | 1.3333 |

TABLE 27-continued

| Treatment | Mean Root Hair Score |
|---|---|
| *Nannochloropsis* Photo | 0.7500 |
| *Spirulina* Mixo | 0.6154 |
| *Spirulina* Photo | 1.0000 |

TABLE 28

| | % Difference from Control-NTC | | |
|---|---|---|---|
| Treatment | Leaf SA | Root SA | Root Hair |
| *Galdieria* Hetero | −38.8 | −33.6 | +41.7 |
| *Galdieria* Mixo | −22.2 | −42.4 | +22.2 |
| *Galdieria* Photo | −48.8 | −57.4 | +70.0 |
| Mock | +17.1 | −15.6 | +36.4 |
| *Nannochloropsis* Mixo | +1.6 | −38.5 | +33.3 |
| *Nannochloropsis* Photo | +9.8 | −32.9 | −25.0 |
| *Spirulina* Mixo | −20.4 | −33.0 | −38.5 |
| *Spirulina* Photo | −26.7 | −22.9 | +6.7 |

Example 26 (ADT 0049)

Experiments were done to test effects of microalgae compositions on corn, bean, and pepper seed germination in soil. Seeds were planted in Sunshine Mix #4 soil in trays, and germinated in a greenhouse. Fortex Pole Beans, Hydro Peppers, and RD4AG Corn plant species were tested. Nine deep 50 cell plug trays were packed with Sunshine Mix #4. All trays were dibbled and then soaked in water until soil was visibly wet, but seed hole was still exposed. Trays were left over night to soak up water, and the next day the seeds were planted at a 2-inch depth. Solutions of treatments were made so that when 4 mL of treatment solution were applied to a single plug cell the plant received 0.02 mL of treatment. Treatment solutions were applied directly to seedosphere before the hole was covered. There was a 4 mL Carrier Volume/200 mL solution: 0.02 mL treatment/plant=1 mL treatment and 199 mL reverse osmosis water (RO). Applications of treatments were applied in a random layout. Plug trays were left in greenhouse to germinate and watered every 24 hours. Plug trays were observed multiple times daily for germination:

Corn—17 observations over a total of 141.5 hours
Beans—27 observations over a total of 233 hours
Peppers—37 observations over a total of 327.5 hours.

The following treatments were tested (0.02 mL/plant in a 4-mL carrier volume [0.25 gallon/acre in furrow], all microalgae biomass for treatments was produced in axenic flask cultures as described in Example 21):
1. *Chlorella* Hetero Acetic
2. *Chlorella* HeteroGlucose
3. *Chlorella* Mixo Acetic
4. *Chlorella* Mixo Glucose
5. *Chlorella* Photo
6. *Galdieria* HeteroGlycerol
7. *Galdieria* Mixo Glycerol
8. *Galdieria* Photo
9. Control—Reverse Osmosis (RO) water
10. Control—Mock (Mock is nutrient formulation of nutrients found in the average PhycoTerra Production Batch (i.e., *Chlorella* [HS26] Mixo Acetate)

Mock:
1.5% of *Chlorella* (HS26) lipids
8.5% i of protein and carbohydrates
128 ppb of Abscisic acid (ABA)

3.3 ppb of trans-ABA
2.8 ppb of trans-zeatin-0-glucoside (ZOG)
8.6 ppb of trans-zeatin (Z)
16.4 ppb of cis-Z
1.6 ppb of trans-zeatin riboside (ZR)
42.5 ppb of cis-ZR
9.8 ppb of isopentenyladenine (iP)
4.1 ppb of isopentenyladenine riboside (iPR)
86.3 ppb of indole acetic acid (IAA)

Results are provided in Tables 29-31.

TABLE 29

| Corn | % Difference from Control (RO) regarding % Germination at Designated Time | | | | | | |
|---|---|---|---|---|---|---|---|
| Treatment | 88.5 h | 92.5h | 95.5 h | 111.5 h | 115.5 h | 120 h | 136 h |
| Mock Control | −60.6 | +13.2 | −8.0 | −7.0 | −7.0 | −7.0 | −7.0 |
| Galdieria Photo | −18.2 | 0.0 | 0.0 | −7.0 | −7.0 | −7.0 | −7.0 |
| Galdieria Mixo Glycerol | −60.6 | +50.9 | 0.0 | 0.0 | 0.0 | 0.0 | 0.0 |
| Galdieria Hetero Glycerol | +21.2 | +37.7 | 0.0 | 0.0 | 0.0 | 0.0 | 0.0 |
| Chlorella Photo | +42.4 | 0.0 | −23.0 | −7.0 | −7.0 | −7.0 | 0.0 |
| Chlorella Mixo Glucose | 0.0 | +26.4 | 0.0 | −7.0 | −7.0 | −7.0 | 0.0 |
| Chlorella Mixo Acetate | 0.0 | +50.9 | −8.0 | 0.0 | 0.0 | 0.0 | 0.0 |
| Chlorella Hetero Glucose | +60.6 | +64.2 | 0.0 | 0.0 | 0.0 | 0.0 | 0.0 |
| Chlorella Hetero Acetate | −39.4 | +13.2 | −16.1 | 0.0 | 0.0 | 0.0 | 0.0 |

TABLE 30

| Bean | % Difference from Control (RO) regarding % Germination at Designated Time | | | | | | |
|---|---|---|---|---|---|---|---|
| Treatment | 88.5 h | 92.5 h | 95.5 h | 111.5 h | 115.5 h | 120 h | 136 h |
| Mock Control | −65.0 | −65.0 | −51.9 | −21.7 | −21.7 | −17.8 | −17.8 |
| Galdieria Photo | −65.0 | +35.0 | +22.2 | +11.7 | +21.7 | +9.6 | +9.6 |
| Galdieria Mixo Glycerol | 0.0 | +35.0 | 0.0 | −33.3 | −21.7 | 0.0 | +9.6 |
| Galdieria Hetero Glycerol | −100 | −35.0 | −25.9 | −21.7 | −11.7 | −17.8 | −8.2 |
| Chlorella Photo | −100 | −65.0 | −25.9 | −11.3 | −11.7 | −17.8 | −8.2 |
| Chlorella Mixo Glucose | +65.0 | +100 | +96.3 | +21.7 | +21.7 | +19.2 | +19.2 |
| Chlorella Mixo Acetate | −65.0 | −35.0 | −25.9 | −11.7 | −11.7 | −17.8 | −8.2 |
| Chlorella Hetero Glucose | −100 | −65.0 | +48.1 | 0.0 | 0.0 | 0.0 | +9.6 |
| Chlorella Hetero Acetate | −65.0 | −65.0 | −51.9 | 0.0 | 0.0 | −8.2 | +9.6 |

TABLE 30-continued

| Bean | % Difference from Control (RO) regarding % Germination at Designated Time | | | | | | |
|---|---|---|---|---|---|---|---|
| Treatment | 141.5 h | 145.5 h | 160.5 h | 165.5 h | 170 h | 185.5 h | 189 h |
| Mock Control | 0.0 | 0.0 | 0.0 | +9.6 | +9.6 | +9.6 | +19.2 |
| Galdieria Photo | +9.6 | +9.6 | +19.2 | +27.4 | +27.4 | +27.4 | +27.4 |
| Galdieria Mixo Glycerol | +9.6 | +9.6 | +9.6 | +19.2 | +19.2 | +19.2 | +19.2 |
| Galdieria Hetero Glycerol | −8.2 | −8.2 | 0.0 | 0.0 | 0.0 | 0. | 0.0 |
| Chlorella Photo | 0.0 | 0.0 | 0.0 | 0.0 | 0.0 | +9.6 | +9.6 |
| Chlorella Mixo Glucose | +19.2 | +19.2 | +19.2 | +19.2 | +19.2 | +19.2 | +19.2 |
| Chlorella Mixo Acetate | −8.2 | −8.2 | −8.2 | −8.2 | −8.2 | −8.2 | −8.2 |
| Chlorella Hetero Glucose | +9.6 | +9.6 | +9.6 | +9.6 | +19.2 | +19.2 | +19.2 |
| Chlorella Hetero Acetate | +9.6 | +9.6 | +9.6 | +9.6 | +9.6 | +9.6 | +9.6 |

| Bean | % Difference from Control (RO) regarding % Germination at Designated Time | | |
|---|---|---|---|
| Treatment | 192 h | 209.5 h | 216.5 h |
| Mock Control | 19.2 | +19.2 | +8.8 |
| Galdieria Photo | +27.4 | +27.4 | +16.3 |
| Galdieria Mixo Glycerol | +19.2 | +19.2 | +8.8 |
| Galdieria Hetero Glycerol | 0.0 | 0.0 | −8.7 |
| Chlorella Photo | +9.6 | +9.6 | 0.0 |
| Chlorella Mixo Glucose | +19.2 | +27.4 | +16.3 |
| Chlorella Mixo Acetate | −8.2 | −8.2 | −16.2 |
| Chlorella Hetero Glucose | +19.2 | +19.2 | +8.8 |
| Chlorella Hetero Acetate | +9.6 | +9.6 | 0.0 |

TABLE 31

| Pepper | % Difference from Control (RO) regarding % Germination at Designated Time | | | | | | |
|---|---|---|---|---|---|---|---|
| Treatment | 240.5 h | 257 h | 261.5 h | 264 h | 279.5 h | 289 h | 305 h |
| Mock Control | +42.6 | +9.6 | 0.0 | 0.0 | 0.0 | 0.0 | 0.0 |
| Galdieria Photo | −14.9 | −8.2 | +14.9 | +14.9 | +7.5 | +7.5 | +7.5 |
| Galdieria Mixo Glycerol | −42.6 | −45.2 | −23.0 | −8.0 | −1.0 | −14.0 | −14.0 |
| Galdieria Hetero Glycerol | −14.9 | −8.2 | +6.9 | +6.9 | +7.5 | +7.5 | +7.5 |
| Chlorella Photo | +12.8 | −17.8 | −23.0 | −23.0 | −6.5 | −6.5 | −6.5 |
| Chlorella Mixo Glucose | +42.6 | 0.0 | −8.0 | −8.0 | 0.0 | 0.0 | 0.0 |
| Chlorella Mixo Acetate | 0.0 | +27.4 | +6.9 | +6.9 | +7.5 | +7.5 | +7.5 |

TABLE 31-continued

| | | | | | | | |
|---|---|---|---|---|---|---|---|
| Chlorella Hetero Glucose | +12.8 | +9.6 | +6.9 | +14.9 | +7.5 | +7.5 | +7.5 |
| Chlorella Hetero Acetate | +42.6 | +19.2 | +6.9 | +6.9 | 0.0 | 0.0 | 0.0 |

| Pepper | % Difference from Control (RO) regarding % Germination at Designated Time | | |
|---|---|---|---|
| Treatment | 308 h | 313 h | 327.5 h |
| Mock Control | 0.0 | 0.0 | −7.0 |
| Galdieria Photo | 7.5 | 7.5 | 0.0 |
| Galdieria Mixo Glycerol | −14.0 | −14.0 | −13.0 |
| Galdieria Hetero Glycerol | +7.5 | +7.5 | 0.0 |
| Chlorella Photo | −6.5 | −6.5 | −13.0 |
| Chlorella Mixo Glucose | 0.0 | 0.0 | −7.0 |
| Chlorella Mixo Acetate | +7.5 | +7.5 | 0.0 |
| Chlorella Hetero Glucose | +7.5 | +7.5 | 0.0 |
| Chlorella Hetero Acetate | 0.0 | 0.0 | −7.0 |

Example 27 (ADT 0055)

Experiments were done to test effects of microalgae compositions on corn, bean, and pepper seed germination in soil. Seeds were planted in Sunshine Mix #4 soil in trays, and germinated in a greenhouse. Fortex Pole Bean, Hydro Peppers, and RD4AG Corn plant species were tested. Nine deep 50 cell plug trays were packed with Sunshine mix #4. All trays were dibbled and then soaked in water until soil was visibly wet, but seed hole was still exposed. Trays were left over night to soak up water, and the next day the seeds were planted at a 2-inch depth. Solutions of treatments were made so that when 4 mL of solution were applied to a single plug cell the plant received 0.04 mL of treatment. Treatment solutions were applied directly to seedosphere before hole was covered. There was a 4 mL Carrier Volume/200 mL solution: 0.04 mL treatment/plant=2 mL treatment and 198 mL reverse osmosis water (RO). Applications were applied in a random layout. Plug trays were left in greenhouse to germinate and watered every 24 hours. Plug trays were observed multiple times daily for germination:
  Corn—14 observations over 117 hours
  Beans—24 observations over 216.5 hours
  Peppers—33 observations over 305 hours The following treatments were tested (0.04 mL/plant in a 4-mL carrier volume [0.50 gallon/acre in furrow], all microalgae biomass for treatments was produced in axenic flask cultures as described in Example 21):
  1. Chlorella Hetero Acetic
  2. Chlorella Hetero Glucose
  3. Chlorella Mixo Acetic
  4. Chlorella Mixo Glucose
  5. Chlorella Photo
  6. Galdieria HeteroGlycerol
  7. Galdieria MixoGlycerol
  8. Galdieria Photo
  9. Control—Reverse Osmosis (RO) water
  10. Control—Mock ((Mock is nutrient formulation of nutrients found in the average PhycoTerra Production Batch (i.e., Chlorella [HS26] Mixo Acetate)

Mock:
  1.5% of Chlorella (HS26) lipids 8.5% of protein and carbohydrates 128 ppb of Abscisic acid (ABA)
  3.3 ppb of trans-ABA
  2.8 ppb of trans-zeatin-0-glucoside (ZOG)
  8.6 ppb of trans-zeatin (Z)
  16.4 ppb of cis-Z
  1.6 ppb of trans-zeatin riboside (ZR)
  42.5 ppb of cis-ZR
  9.8 ppb of isopentenyladenine (iP)
  4.1 ppb of isopentenyladenine riboside (iPR)
  86.3 ppb of indole acetic acid (IAA)
Results are provided in Tables 32-34.

TABLE 32

| Corn | % Difference from Control (RO) regarding % Germination at Designated Time | | | | | |
|---|---|---|---|---|---|---|
| Treatment | 71 h | 88 h | 94.5 h | 97.5 h | 110.5 h | 113.5 h |
| Mock Control | −10.4 | −6.5 | −6.5 | −6.5 | −6.5 | −6.5 |
| Galdieria Photo | 0.0 | 0.0 | 0.0 | 0.0 | 0.0 | 0.0 |
| Galdieria Mixo Glycerol | −20.9 | 0.0 | 0.0 | 0.0 | 0.0 | +7.5 |
| Galdieria Hetero Glycerol | −50.7 | 0.0 | +7.5 | +7.5 | +7.5 | +7.5 |
| Chlorella Photo | −10.4 | 0.0 | +7.5 | +7.5 | +7.5 | +7.5 |
| Chlorella Mixo Glucose | −20.9 | 0.0 | 0.0 | 0.0 | 0.0 | 0.0 |
| Chlorella Mixo Acetate | −40.3 | −14.0 | −6.5 | −6.5 | −6.5 | −6.5 |
| Chlorella Hetero Glucose | −40.3 | −14.0 | 0.0 | 0.0 | 0.0 | 0.0 |
| Chlorella Hetero Acetate | −10.4 | +7.5 | +7.5 | +7.5 | +7.5 | +7.5 |

TABLE 33

| Bean | % Difference from Control (RO) regarding % Germination at Designated Time | | | | | | |
|---|---|---|---|---|---|---|---|
| Treatment | 71 h | 88 h | 94.5 h | 97.5 h | 110.5 h | 113.5 h | 117 h |
| Mock Control | −35.0 | −11.7 | +9.0 | +9.0 | 0.0 | 0.0 | −8.7 |
| Galdieria Photo | +100 | −11.7 | +19.4 | +19.4 | +19.2 | +19.2 | +8.8 |
| Galdieria Mixo Glycerol | −65.0 | −33.3 | 0.0 | 0.0 | −8.2 | −8.2 | +8.7 |
| Galdieria Hetero Glycerol | −35.0 | −11.7 | +9.0 | +9.0 | +9.6 | +19.2 | +8.8 |
| Chlorella Photo | 0.0 | +11.7 | +9.0 | +9.0 | 0.0 | 0.0 | 0.0 |
| Chlorella Mixo Glucose | 0.0 | +21.7 | +19.4 | +19.4 | +9.6 | +9.6 | 0.0 |
| Chlorella Mixo Acetate | +100.0 | +11.7 | +9.0 | +9.0 | 0.0 | 0.0 | −8.7 |
| Chlorella Hetero Glucose | +100.0 | +11.7 | +19.4 | +19.4 | +19.2 | +19.2 | +8.8 |
| Chlorella Hetero Acetate | +35.0 | −21.7 | 0.0 | 0.0 | 0.0 | 0.0 | −8.7 |

TABLE 33-continued

| Bean Treatment | % Difference from Control (RO) regarding % Germination at Designated Time | | | | |
|---|---|---|---|---|---|
| | 121 h | 136.5 h | 145 h | 214 h | 216.5 h |
| Mock Control | −8.7 | −8.0 | −8.0 | −8.0 | −8.0 |
| Galdieria Photo | +8.8 | 0.0 | 0.0 | 0.0 | 0.0 |
| Galdieria Mixo Glycerol | 0.0 | −8.0 | −8.0 | −8.0 | −8.0 |
| Galdieria Hetero Glycerol | +8.8 | +6.9 | +6.9 | +6.9 | +6.9 |
| Chlorella Photo | 0.0 | −8.0 | −8.0 | −8.0 | −8.0 |
| Chlorella Mixo Glucose | 0.0 | −8.0 | 0.0 | 0.0 | 0.0 |
| Chlorella Mixo Acetate | 0.0 | −8.0 | −8.0 | −8.0 | −8.0 |
| Chlorella Hetero Glucose | +8.8 | +6.9 | +6.9 | +6.9 | +14.9 |
| Chlorella Hetero Acetate | 0.0 | −8.0 | −8.0 | −8.0 | −8.0 |

TABLE 34

| Pepper Treatment | % Difference from Control (RO) regarding % Germination at Designated Time | | | | | | |
|---|---|---|---|---|---|---|---|
| | 185 h | 192.5 h | 209.5 h | 214 h | 216.5 h | 233 h | 237 h |
| Mock Control | 0.0 | −25.9 | +12.8 | +55.0 | +27.4 | +27.4 | +37.0 |
| Galdieria Photo | 0.0 | +48.1 | +55.3 | +45.0 | +19.2 | +37.0 | +37.0 |
| Galdieria Mixo Glycerol | 0.0 | 0.0 | +12.8 | +11.7 | 0.0 | +9.6 | +9.6 |
| Galdieria Hetero Glycerol | 0.0 | 0.0 | +12.8 | +45.0 | +27.4 | +37.0 | +37.0 |
| Chlorella Photo | 0.0 | 0.0 | 0.0 | 0.0 | −8.2 | 0.0 | 0.0 |
| Chlorella Mixo Glucose | +85.7 | +96.3 | +70.2 | +45.0 | +19.2 | +27.4 | +27.4 |
| Chlorella Mixo Acetate | −100.0 | −51.9 | −29.8 | −11.7 | +8.2 | +19.2 | +19.2 |
| Chlorella Hetero Glucose | 0.0 | +48.1 | +12.8 | +11.7 | 0.0 | +27.4 | +27.4 |
| Chlorella Hetero Acetate | 0.0 | −25.9 | +42.6 | +33.3 | +19.2 | +27.4 | +37.0 |

| Pepper Treatment | % Difference from Control (RO) regarding % Germination at Designated Time | | | | |
|---|---|---|---|---|---|
| | 240 h | 256.5 h | 260.5 h | 264 h | 280 h |
| Mock Control | +25.0 | +14.9 | 0.0 | 0.0 | 0.0 |
| Galdieria Photo | +25.0 | +14.9 | 0.0 | 0.0 | 0.0 |
| Galdieria Mixo Glycerol | 0.0 | 0.0 | −7.0 | −7.0 | −7.0 |
| Galdieria Hetero Glycerol | +25.0 | +14.9 | 0.0 | 0.0 | 0.0 |
| Chlorella Photo | −8.7 | 0.0 | −13.0 | −13.0 | −13.0 |
| Chlorella Mixo Glucose | +16.3 | +6.9 | 0.0 | 0.0 | 0.0 |
| Chlorella Mixo Acetate | +8.8 | +6.9 | 0.0 | 0.0 | 0.0 |
| Chlorella Hetero Glucose | +16.3 | +6.9 | −7.0 | −7.0 | 0.0 |
| Chlorella Hetero Acetate | +25.0 | +14.9 | 0.0 | 0.0 | 0.0 |

Example 28 (ADT 0058)

Experiments were done to test effects of microalgae compositions on corn, bean, and pepper seed germination in soil. Seeds were planted in Sunshine Mix #4 soil in trays, and germinated in a greenhouse. Fortex Pole Bean Hydro Peppers, and RD4AG Corn plant species were tested. Twelve deep 50 cell plug trays were packed with Sunshine mix #4. All trays were dibbled and then soaked in water until soil was visibly wet, but seed hole was still exposed. Solutions of treatments were made so that when 4 mL of treatment solution were applied to a single plug cell the plant received 0.04 mL of treatment. Seeds were planted at a 2-inch depth and treatment solutions were applied directly to seedosphere before hole was covered. There was a 4 mL Carrier Volume/200 mL solution: 0.04 mL treatment/plant=2 mL treatment and 198 mL reverse osmosis water (RO). Applications were applied in a random layout. Plug trays were left in greenhouse to germinate and watered every 24 hours. Plug trays were observed multiple times daily for germination:

Corn—16 observations over a total of 145 hours
Beans—17 observations over a total of 161.5 hours
Peppers—32 observations over a total of 293.5 hours.

The following treatments were tested (0.04 mL/plant in a 4-mL carrier volume [0.50 gallon/acre in furrow], all microalgae biomass for treatments in axenic flask cultures as described in Example 21):

1. Chlorella Hetero Acetic
2. Chlorella Hetero Glucose
3. Chlorella Mixo Acetic
4. Chlorella Mixo Glucose
5. Chlorella Photo
6. Galdieria HeteroGlycerol
7. Galdieria Mixo Glycerol
8. Galdieria Photo
9. Nannochloropsis Photo
10. Nannochloropsis Jv1lixo Glucose
11. Spirulina Photo
12. Spirulina Mixo Glucose
13. Control—Reverse Osmosis (RO) water
14. Control—Mock The Mock is nutrient formulation of nutrients found in the average PhycoTerra Production Batch (i.e., Chlorella [HS26] Mixo Acetate)

1.5% of Chlorella (HS26) lipids
8.5% of protein and carbohydrates
128 ppb of Abscisic acid (ABA)
3.3 ppb of trans-ABA
2.8 ppb of trans-zeatin-0-glucoside (ZOG)
8.6 ppb of trans-zeatin (Z)
16.4 ppb of cis-Z
1.6 ppb of trans-zeatin riboside (ZR)
42.5 ppb of cis-ZR
9.8 ppb of isopentenyladenine (iP)
4.1 ppb of isopentenyladenine riboside (iPR)
86.3 ppb of indole acetic acid (IAA)

Results are shown in FIG. 1. Combined results from Examples 26-28 are shown in Tables 35-37.

TABLE 35

| Corn Treatment | % Difference from Control (RO) regarding % Germination at Designated Time | | | | | | |
|---|---|---|---|---|---|---|---|
| | 64.5 h | 68.5 h | 72.5 h | 89 h | 94 h | 97.5 h | 112 h |
| Mock Control | −100 | −100 | −42.0 | −8.1 | −7.5 | −14.0 | −14.0 |
| Galdieria Photo | −100 | +100 | −42.0 | +8.1 | +7.5 | 0.0 | 0.0 |
| Galdieria Mixo Glycerol | 0.0 | 0.0 | 0.0 | +8.1 | 0.0 | −7.0 | −7.0 |
| Galdieria Hetero Glycerol | −100 | −100 | −28.0 | 0.0 | 0.0 | 0.0 | 0.0 |
| Chlorella Photo | −100 | −100 | −28.0 | −8.1 | 0.0 | 0.0 | 0.0 |
| Chlorella Mixo Glucose | −100 | −100 | −28.0 | −8.1 | 0.0 | −7.0 | −7.0 |
| Chlorella Mixo Acetate | −100 | −100 | −42.0 | +16.3 | +7.5 | 0.0 | 0.0 |
| Chlorella Hetero Glucose | 0.0 | 0.0 | 0.0 | 0.0 | +7.5 | 0.0 | 0.0 |
| Chlorella Hetero Acetate | −100 | 0.0 | −28.0 | +16.3 | +7.5 | 0.0 | 0.0 |
| Nannochloropsis Photo | −100 | −100 | −28.0 | 0.0 | −6.5 | −13.0 | −13.0 |
| Nannochloropsis Mixo Glucose | −100 | 0.0 | +14.0 | +16.3 | +7.5 | 0.0 | 0.0 |
| Spirulina Photo | −100 | −100 | −28.0 | +16.3 | +7.5 | 0.0 | 0.0 |
| Spirulina Mixo Glucose | −100 | 0.0 | 0.0 | +16.3 | +7.5 | 0.0 | 0.0 |

| Corn Treatment | % Difference from Control (RO) regarding % Germination at Designated Time | |
|---|---|---|
| | 142.5 h | 145 h |
| Mock Control | −14.0 | −14.0 |
| Galdieria Photo | 0.0 | 0.0 |
| Galdieria Mixo Glycerol | −7.0 | −7.0 |
| Galdieria Hetero Glycerol | 0.0 | 0.0 |
| Chlorella Photo | 0.0 | 0.0 |
| Chlorella Mixo Glucose | −7.0 | 0.0 |
| Chlorella Mixo Acetate | 0.0 | 0.0 |
| Chlorella Hetero Glucose | 0.0 | 0.0 |
| Chlorella Hetero Acetate | 0.0 | 0.0 |
| Nannochloropsis Photo | −13.0 | −13.0 |
| Nannochloropsis Mixo Glucose | 0.0 | 0.0 |
| Spirulina Photo | 0.0 | 0.0 |
| Spirulina Mixo Glucose | 0.0 | 0.0 |

TABLE 36

| Bean Treatment | % Difference from Control (RO) regarding % Germination at Designated Time | | | | | | |
|---|---|---|---|---|---|---|---|
| | 68.5 h | 72.5 h | 89 h | 94 h | 97.5 h | 112 h | 117.5 h |
| Mock Control | 0.0 | +314.3 | +12.3 | 0.0 | −8.1 | +8.1 | +8.1 |
| Galdieria Photo | 0.0 | +100.0 | +24.6 | +17.7 | +8.1 | +16.3 | +16.3 |
| Galdieria Mixo Glycerol | +100.0 | +100.0 | +38.6 | +8.9 | 0.0 | 0.0 | 0.0 |
| Galdieria Hetero Glycerol | −100 | 0.0 | −12.3 | −10.1 | −17.4 | −17.4 | −17.4 |
| Chlorella Photo | 0.0 | +100.0 | +12.3 | +8.9 | 0.0 | 0.0 | 0.0 |
| Chlorella Mixo Glucose | +100.0 | +314.3 | +12.3 | −10.1 | −8.1 | 0.0 | 0.0 |
| Chlorella Mixo Acetate | +100.0 | +200.0 | +12.3 | 0.0 | −8.1 | −8.1 | −8.1 |
| Chlorella Hetero Glucose | −100.0 | +100.0 | +38.6 | +17.7 | +8.1 | +8.1 | +8.1 |
| Chlorella Hetero Acetate | +100.0 | +314.3 | +12.3 | +8.9 | +8.1 | +16.3 | +16.3 |
| Nannochloropsis Photo | +100.0 | +200.0 | −36.8 | −10.14 | −17.4 | −17.4 | −8.1 |
| Nannochloropsis Mixo Glucose | −100.0 | +314.3 | +24.6 | 0.0 | −8.1 | −8.1 | 0.0 |
| Spirulina Photo | 0.0 | +314.3 | +12.3 | −19.0 | −17.4 | 0.0 | 0.0 |
| Spirulina Mixo Glucose | −100.0 | −100.0 | −24.6 | 0.0 | −8.1 | 0.0 | +8.1 |

| Bean Treatment | % Difference from Control (RO) regarding % Germination at Designated Time | | | | |
|---|---|---|---|---|---|
| | 120 h | 136.5 h | 142.5 h | 145 h | 161.5 h |
| Mock Control | +8.1 | +8.1 | +8.1 | +8.1 | +8.1 |
| Galdieria Photo | +16.3 | +16.3 | +16.3 | +16.3 | +16.3 |
| Galdieria Mixo Glycerol | +8.1 | +8.1 | +8.1 | +8.1 | +8.1 |
| Galdieria Hetero Glycerol | −17.4 | −17.4 | −17.4 | −17.4 | −17.4 |
| Chlorella Photo | 0.0 | 0.0 | +8.1 | +8.1 | +8.1 |
| Chlorella Mixo Glucose | 0.0 | 0.0 | 0.0 | 0.0 | 0.0 |
| Chlorella Mixo Acetate | −8.1 | −8.1 | −8.1 | −8.1 | −8.1 |
| Chlorella Hetero Glucose | +8.1 | +8.1 | +8.1 | +8.1 | +8.1 |
| Chlorella Hetero Acetate | +16.3 | +16.3 | +16.3 | +16.3 | +16.3 |
| Nannochloropsis Photo | −8.1 | −8.1 | 0.0 | 0.0 | 0.0 |

TABLE 36-continued

|  | | | | | |
|---|---|---|---|---|---|
| Nannochloropsis Mixo Glucose | 0.0 | 0.0 | 0.0 | 0.0 | 0.0 |
| Spirulina Photo | 0.0 | 0.0 | 0.0 | 0.0 | 0.0 |
| Spirulina Mixo Glucose | +8.1 | +8.1 | +8.1 | +8.1 | +8.1 |

TABLE 37

| Pepper | % Difference from Control (RO) regarding % Germination at Designated Time | | | | | | |
|---|---|---|---|---|---|---|---|
| Treatment | 190.5 h | 193.5 h | 196.5 h | 214.5 h | 217 h | 220.5 h | 237.5 h |
| Mock Control | −10.9 | −33.7 | −17.4 | −8.1 | −15.1 | −21.0 | −21.0 |
| Galdieria Photo | −43.7 | −17.4 | −8.1 | 0.0 | 0.0 | 0.0 | 0.0 |
| Galdieria Mixo Glycerol | −33.8 | −50.0 | −41.9 | +8.1 | 0.0 | 0.0 | 0.0 |
| Galdieria Hetero Glycerol | −21.9 | −25.6 | −17.4 | 0.0 | −7.5 | −14.0 | −7.0 |
| Chlorella Photo | 0.0 | −17.4 | −8.1 | 0.0 | 0.0 | −7.0 | 0.0 |
| Chlorella Mixo Glucose | −67.2 | −33.7 | −33.7 | −8.1 | −7.5 | −14.0 | −14.0 |
| Chlorella Mixo Acetate | −21.9 | −17.4 | −8.1 | +16.3 | +7.5 | 0.0 | 0.0 |
| Chlorella Hetero Glucose | −33.8 | −41.9 | −41.9 | −8.1 | −7.5 | −7.0 | −7.0 |
| Chlorella Hetero Acetate | −54.7 | −33.7 | −33.7 | −17.4 | −23.7 | −29.0 | −29.0 |
| Nannochloropsis Photo | 0.0 | −25.6 | −25.6 | −25.6 | −23.7 | −21.0 | −21.0 |
| Nannochloropsis Mixo Glucose | −10.9 | −8.1 | −8.1 | +16.3 | +7.5 | 0.0 | 0.0 |
| Spirulina Photo | −54.7 | −50.0 | −50.0 | −17.4 | −7.5 | −14.0 | −14.0 |
| Spirulina Mixo Glucose | −54.7 | −50.0 | −33.7 | 0.0 | 0.0 | 0.0 | 0.0 |

| Pepper | % Difference from Control (RO) regarding % Germination at Designated Time | | | | | | |
|---|---|---|---|---|---|---|---|
| Treatment | 242 h | 245.5 h | 261 h | 267 h | 286.5 h | 293.5 h | 406 h |
| Mock Control | −21.0 | −21.0 | 21.0 | −21.0 | −21.0 | −21.0 | 0.0 |
| Galdieria Photo | 0.0 | 0.0 | 0.0 | 0.0 | 0.0 | 0.0 | 0.0 |
| Galdieria Mixo Glycerol | 0.0 | 0.0 | 0.0 | 0.0 | 0.0 | 0.0 | 0.0 |
| Galdieria Hetero Glycerol | −7.0 | −7.0 | 7.0 | 0.0 | 0.0 | 0.0 | 0.0 |
| Chlorella Photo | 0.0 | 0.0 | 0.0 | 0.0 | 0.0 | 0.0 | 0.0 |
| Chlorella Mixo Glucose | −14.0 | −14.0 | 14.0 | −14.0 | −14.0 | 0.0 | 0.0 |
| Chlorella Mixo Acetate | 0.0 | 0.0 | 0.0 | 0.0 | 0.0 | 0.0 | 0.0 |
| Chlorella Hetero Glucose | −7.0 | 0.0 | 0.0 | 0.0 | 0.0 | 0.0 | 0.0 |
| Chlorella Hetero Acetate | −29.0 | −21.0 | 7.0 | 0.0 | 0.0 | 0.0 | 0.0 |
| Nannochloropsis Photo | −21.0 | −1.0 | 14.0 | −14.0 | −14.0 | 0-14.0 | 0.0 |
| Nannochloropsis Mixo Glucose | 0.0 | 0.0 | 0.0 | 0.0 | 0.0 | 0.0 | 0.0 |
| Spirulina Photo | −7.0 | −7.0 | 7.0 | −7.0 | −7.0 | −7.0 | 0.0 |
| Spirulina Mixo Glucose | 0.0 | 0.0 | 0.0 | 0.0 | 0.0 | 0.0 | 0.0 |

Example 29 (ADT 0056)

Experiments were done to test the effects of microalgae-based compositions on germination of corn seeds subjected to temperature stress. In these experiments, all seeds began in 26° C. conditions for 15.5 hours; experienced a period of temperature stress (Cold period of 5° C., Heat period of 50° C., Normal always at 26° C.) for 8 hours; after the temperature stress period all seeds were moved back to 26° C. conditions. Petri plates were lined with filter paper water with 10 mL of treatment solutions (application rate/concentration of 9 mL/gallon) one time at the beginning of the experiment. The plates were located in a temperature chamber to control temperature for the temperature stress periods. Triplicate plates with 15 corn seeds were used on each plate. An application rate of 9 mL/gal was selected after comparison of 2.25 mL/gallon, 4.5 mL/gallon, 9 mL/gallon, and 18 mL/gallon and there was found to be no statistical difference for the 9 mL/gallon rate with respect to the control or other tested application rates. The biomass was produced in axenic flask cultures as described in Example 21.

1. *Chlorella* Hetero Acetate
2. *Chlorella* Hetero Glucose
3. *Chlorella* Mixo Acetate
4. *Chlorella* Mixo Glucose
5. *Chlorella* Photo
6. Control—Mock ((Mock is nutrient formulation of nutrients found in the average PhycoTerra Production Batch (i.e., *Chlorella* [HS26] Mixo Acetate)

Mock:

1.5% of *Chlorella* (HS26) lipids
8.5% of protein and carbohydrates
128 ppb of Abscisic acid (ABA)
3.3 ppb of trans-ABA
2.8 ppb of trans-zeatin-0-glucoside (ZOG)
8.6 ppb of trans-zeatin (Z)
16.4 ppb of cis-Z
1.6 ppb of trans-zeatin riboside (ZR)
42.5 ppb of cis-ZR
9.8 ppb of isopentenyladenine (iP)
4.1 ppb of isopentenyladenine riboside (iPR)
86.3 ppb of indole acetic acid (IAA)

7. Control—PhycoTerra Production Batch (*Chlorella* [HS26] Mixo Acetate produced outdoors in open culture)
8. Control—Reverse Osmosis (RO) Water Percent germination was determined with observations occurring multiple times per day. The criteria for counting germination was when the radical root was at least 1 mm in length. Percent germination was analyzed as a complete time series for each experiment and using a Dunnet's test to compare treatments to untreated control at 25 hours for normal temperatures, and 45 hours for temperature stressed experiments. Results are shown in Tables 38-40.

TABLE 38

| Treatment | Temperature | % Difference from Control (RO) of Germination at 23.5 h |
|---|---|---|
| *Chlorella* Hetero Acetate | Normal | +3.7 |
| *Chlorella* Hetero Glucose | Normal | +22.2 |
| *Chlorella* Mixo Acetate | Normal | +3.7 |
| *Chlorella* Mixo Glucose | Normal | +26.0 |
| *Chlorella* Photo | Normal | +11.2 |
| Mock | Normal | +29.7 |
| Production Batch | Normal | −14.8 |

TABLE 39

| Treatment | Temperature | % Difference from Control (RO) of % Germination at 45 h |
|---|---|---|
| *Chlorella* Hetero Acetate | Cold Stress | −4.6 |
| *Chlorella* Hetero Glucose | Cold Stress | +2.2 |
| *Chlorella* Mixo Acetate | Cold Stress | 0.0 |
| *Chlorella* Mixo Glucose | Cold Stress | +2.2 |
| *Chlorella* Photo | Cold Stress | −2.2 |
| Mock | Cold Stress | −2.2 |
| Production Batch | Cold Stress | 0.0 |

TABLE 40

| Treatment | Temperature | % Difference from Control (RO) of % Germination at 45 h |
|---|---|---|
| *Chlorella* Hetero Acetate | Heat Stress | +13.7 |
| *Chlorella* Hetero Glucose | Heat Stress | +18.2 |
| *Chlorella* Mixo Acetate | Heat Stress | +18.2 |
| *Chlorella* Mixo Glucose | Heat Stress | +40.9 |
| *Chlorella* Photo | Heat Stress | +9.0 |
| Mock | Heat Stress | +4.5 |
| Production Batch | Heat Stress | +9.2 |

Example 30 (ADT 0061)

Experiments were done to test the effects of microalgae-based compositions on germination of corn seed subjected to temperature stress. In these experiments, all seeds began in 26° C. conditions for 6 hours; experienced a period of temperature stress (Cold period of 0° C., Heat period of 45° C., Normal always at 26° C.) for 15 hours; after the temperature stress period all seeds were moved back to 26° C. conditions. Petri plates were lined with filter paper water with 10 mL of treatment solutions (application rate/concentration of 9 mL/gallon) one time at the beginning of the experiment. The plates were located in a temperature chamber to control temperature for the temperature stress periods. Triplicate plates with 15 corn seeds were used on each plate. The biomass was produced in axenic flask cultures as described in Example 21.

1. *Chlorella* Hetero Acetate
2. *Chlorella* HeteroGlucose
3. *Chlorella* Mixo Acetate
4. *Chlorella* Mixo Glucose
5. *Chlorella* Photo
6. Control—Mock ((Mock is nutrient formulation of nutrients found in the average PhycoTerra Production Batch (i.e., *Chlorella* [HS26] Mixo Acetate)

Mock:

1.5% of *Chlorella* (HS26) lipids
8.5% of protein and carbohydrates
128 ppb of Abscisic acid (ABA)
3.3 ppb of trans-ABA
2.8 ppb of trans-zeatin-0-glucoside (ZOG)
8.6 ppb of trans-zeatin (Z)
16.4 ppb of cis-Z
1.6 ppb of trans-zeatin riboside(ZR)
42.5 ppb of cis-ZR
9.8 ppb of isopentenyladenine (iP)
4.1 ppb of isopentenyladenine riboside (iPR)
86.3 ppb of indole acetic acid (IAA)

7. Control—PhycoTerra Production Batch (*Chlorella* Mixo Acetate produced outdoors in open culture)
8. Control—Reverse Osmosis (RO) Water Percent germination was determined with observations occurring multiple times per day. The criteria for counting germination was when the radical root was at least 1 mm in length. Percent germination was analyzed as a complete time series for each experiment and using a Dunnet's test to compare treatments to untreated control at 25 hours for normal temperatures, and 45 hours for temperature stressed experiments. Dry Weight (g) of plants was determined in heat stress experiments. Results are shown in Tables 41-43.

TABLE 41

| Treatment | Temperature | 0/o Difference from Control (RO) of % Germination at 21 h |
|---|---|---|
| Chlorella Hetero Acetate | Normal | −22.2 |
| Chlorella Hetero Glucose | Normal | +11.1 |
| Chlorella Mixo Acetate | Normal | +44.5 |
| Chlorella Mixo Glucose | Normal | +55.6 |
| Chlorella Photo | Normal | +33.4 |
| Mock | Normal | +44.5 |
| Production Batch | Normal | +88.9 |

TABLE 42

| Treatment | Temperature | % Difference from Control (RO) of % Germination at 45 h |
|---|---|---|
| Chlorella Hetero Acetate | Cold Stress | +35.7 |
| Chlorella Hetero Glucose | Cold Stress | +35.7 |
| Chlorella Mixo Acetate | Cold Stress | +10.7 |
| Chlorella Mixo Glucose | Cold Stress | +10.7 |
| Chlorella Photo | Cold Stress | +39.3 |
| Mock | Cold Stress | +39.3 |
| Production Batch | Cold Stress | +32.1 |

TABLE 43

| Treatment | Temperature | % Difference from Control (RO) of % Germination at 45 h |
|---|---|---|
| Chlorella Hetero Acetate | Heat Stress | −12.5 |
| Chlorella Hetero Glucose | Heat Stress | −40.6 |
| Chlorella Mixo Acetate | Heat Stress | −12.5 |
| Chlorella Mixo Glucose | Heat Stress | −34.4 |
| Chlorella Photo | Heat Stress | +6.3 |
| Mock | Heat Stress | −25.0 |
| Production Batch | Heat Stress | −43.7 |

TABLE 44

| Treatment | Dry Weight (g) | |
|---|---|---|
| | ADT0061 | ADT0063 |
| RO Control | 2.71 | 2.15 |
| Mock | 2.23 | 2.55 |
| Production Batch | 2.02 | no test |
| Chlorella Photo | 2.80 | 2.31 |
| Chlorella Hetero Acetate | 2.21 | 2.27 |
| Chlorella Hetero Glucose | 2.07 | 3.09 |
| Chlorella Mixo Acetate | 2.65 | 2.40 |
| Chlorella Mixo Glucose | 2.05 | 2.78 |
| Nanno Photo | no test | 2.95 |
| Nano Mixo Glucose | no test | 2.46 |
| Spirulina Mixo Glucose | no test | 2.71 |
| Spirulina Photo | no test | 2.88 |

Example 31 (ADT 0063)

Experiments were done to test the effects of microalgae-based compositions on germination of corn seed subjected to temperature stress. In these experiments, all seeds began in 26° C. conditions for 6 hours; experienced a period of temperature stress (Cold period of 24 hours at 0° C., Heat period of 15 hours at 45° C., Normal always at 26° C.); after the temperature stress period all seeds were moved back to 26° C. conditions. Petri plates were lined with filter paper water with 10 mL of treatment solutions (application rate/concentration of 9 mL/gallon) one time at the beginning of the experiment. The plates were located in a temperature chamber to control temperature for the temperature stress periods. Triplicate plates with 15 corn seeds were used on each plate. The biomass was produced in axenic flask cultures as described in Example 21.

1. Chlorella Hetero Acetate
2. Chlorella Hetero Glucose
3. Chlorella Mixo Acetate
4. Chlorella Mixo Glucose
5. Chlorella Photo
6. Nannochloropsis Mixo Glucose
7. Nannochloropsis Photo
8. Spirulina Mixo Glucose
9. Spirulina Photo
10. Control—Mock (Mock is nutrient formulation of nutrients found in the average PhycoTerra Production Batch (i.e., Chlorella [HS26] Mixo Acetate)

Mock:
1.5% of Chlorella (HS26) lipids
8.5% of protein and carbohydrates
128 ppb of Abscisic acid (ABA)
3.3 ppb of trans-ABA
2.8 ppb of trans-zeatin-0-glucoside (ZOG)
8.6 ppb of trans-zeatin (Z)
16.4 ppb of cis-Z
1.6 ppb of trans-zeatin riboside (ZR)
42.5 ppb of cis-ZR
9.8 ppb of isopentenyladenine (iP)
4.1 ppb of isopentenyladenine riboside (iPR)
86.3 ppb of indole acetic acid (IAA)

11. Control—Reverse Osmosis (RO) Water

Percent germination was determined with observations occurring multiple times per day. The criterion for counting germination was when the radical root was at least 1 mm in length. Dry Weight (g) of plants was determined in heat stress experiments. Combined results from Examples 30 and 31 are shown in Tables 45-47.

TABLE 45

| Treatment | Temperature | % Difference from Control (RO) of % Germination at 28 h |
|---|---|---|
| Spirulina Photo | Normal | −22.5 |
| Spirulina Mixo Glucose | Normal | −12.5 |
| Nannochloropsis Photo | Normal | −25.0 |
| Nannochloropsis Mixo Glucose | Normal | −25.0 |
| Chlorella Hetero Acetate | Normal | −12.5 |
| Chlorella Hetero Glucose | Normal | −32.5 |
| Chlorella Mixo Acetate | Normal | −5.0 |
| Chlorella Mixo Glucose | Normal | −20.0 |
| Chlorella Photo | Normal | −22.5 |
| Mock | Normal | −20.0 |

TABLE 46

| Treatment | Temperature | % Difference from Control (RO) of % Germination at 44.5 h |
|---|---|---|
| Spirulina Photo | Cold Stress | +75.0 |
| Spirulina Mixo Glucose | Cold Stress | +33.3 |
| Nannochloropsis Photo | Cold Stress | +83.3 |
| Nannochloropsis Mixo Glucose | Cold Stress | +83.3 |
| Chlorella Hetero Acetate | Cold Stress | +25.0 |
| Chlorella Hetero Glucose | Cold Stress | +41.7 |
| Chlorella Mixo Acetate | Cold Stress | +50.0 |
| Chlorella Mixo Glucose | Cold Stress | +41.7 |
| Chlorella Photo | Cold Stress | +25.0 |
| Mock | Cold Stress | +16.6 |

TABLE 47

| Treatment | Temperature | % Difference from Control (RO) of % Germination at 44.5 h |
|---|---|---|
| *Spirulina* Photo | Heat Stress | +27.3 |
| *Spirulina* Mixo Glucose | Heat Stress | +40.9 |
| *Nannochloropsis* Photo | Heat Stress | +13.6 |
| *Nannochloropsis* Mixo Glucose | Heat Stress | −18.2 |
| *Chlorella* Hetero Acetate | Heat Stress | +18.2 |
| *Chlorella* Hetero Glucose | Heat Stress | +63.6 |
| *Chlorella* Mixo Acetate | Heat Stress | +27.3 |
| *Chlorella* Mixo Glucose | Heat Stress | +22.7 |
| *Chlorella* Photo | Heat Stress | +18.2 |
| Mock | Heat Stress | +18.2 |

Example 32 (ADT 0066)

Experiments were done to test the effects of microalgae-based compositions on germination of corn seed subjected to temperature stress. In these experiments, all seeds began in 26° C. conditions for 6 hours; experienced a period of temperature stress (Cold period of 24 hours at 0° C., Heat period of 15 hours at 45° C., Normal always at 26° C.); after the temperature stress period all seeds were moved back to 26° C. conditions. Petri plates were lined with filter paper water with 10 mL of treatment solutions (application rate/concentration of 9 mL/gallon) one time at the beginning of the experiment. The plates were located in a temperature chamber to control temperature for the temperature stress periods. Triplicate plates with 15 corn seeds were used on each plate. The biomass was produced in axenic flask cultures as described in Example 21.
1. *Chlorella* Hetero Acetate
2. *Chlorella* Hetero Glucose
3. *Chlorella* Mixo Acetate
4. *Chlorella* Mixo Glucose
5. *Chlorella* Photo
6. *Nannochloropsis* Mixo Glucose
7. *Nannochloropsis* Photo
8. *Spirulina* Mixo Glucose
9. *Spirulina* Photo
10. Control—Mock (Mock is nutrient formulation of nutrients found in the average PhycoTerra Production Batch (i.e., *Chlorella* [HS26] Mixo Acetate)

Mock:
1.5% of *Chlorella* (HS26) lipids
8.5% of protein and carbohydrates
128 ppb of Abscisic acid (ABA)
3.3 ppb of trans-ABA
2.8 ppb of trans-zeatin-0-glucoside (ZOG)
8.6 ppb of trans-zeatin (Z)
16.4 ppb of cis-Z
1.6 ppb of trans-zeatin riboside (ZR)
42.5 ppb of cis-ZR
9.8 ppb of isopentenyladenine (iP)
4.1 ppb of isopentenyladenine riboside (iPR)
86.3 ppb of indole acetic acid (IAA)

11. Control—Reverse Osmosis (RO) \\Tater

Figure 2:
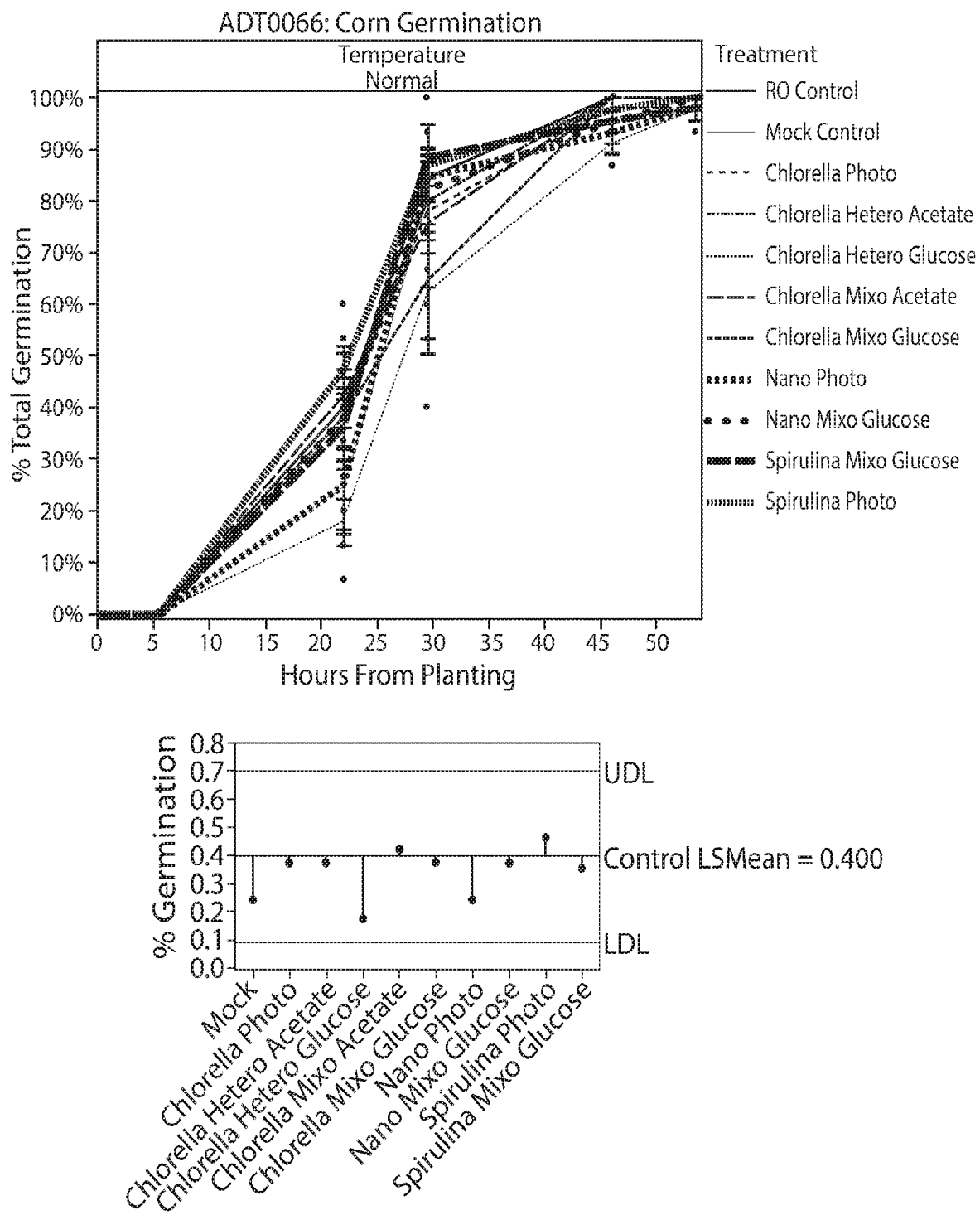
FIG. 2 depicts results of experiments involving microalgae-based compositions on corn, bean and pepper seed germination.
Figure 2:
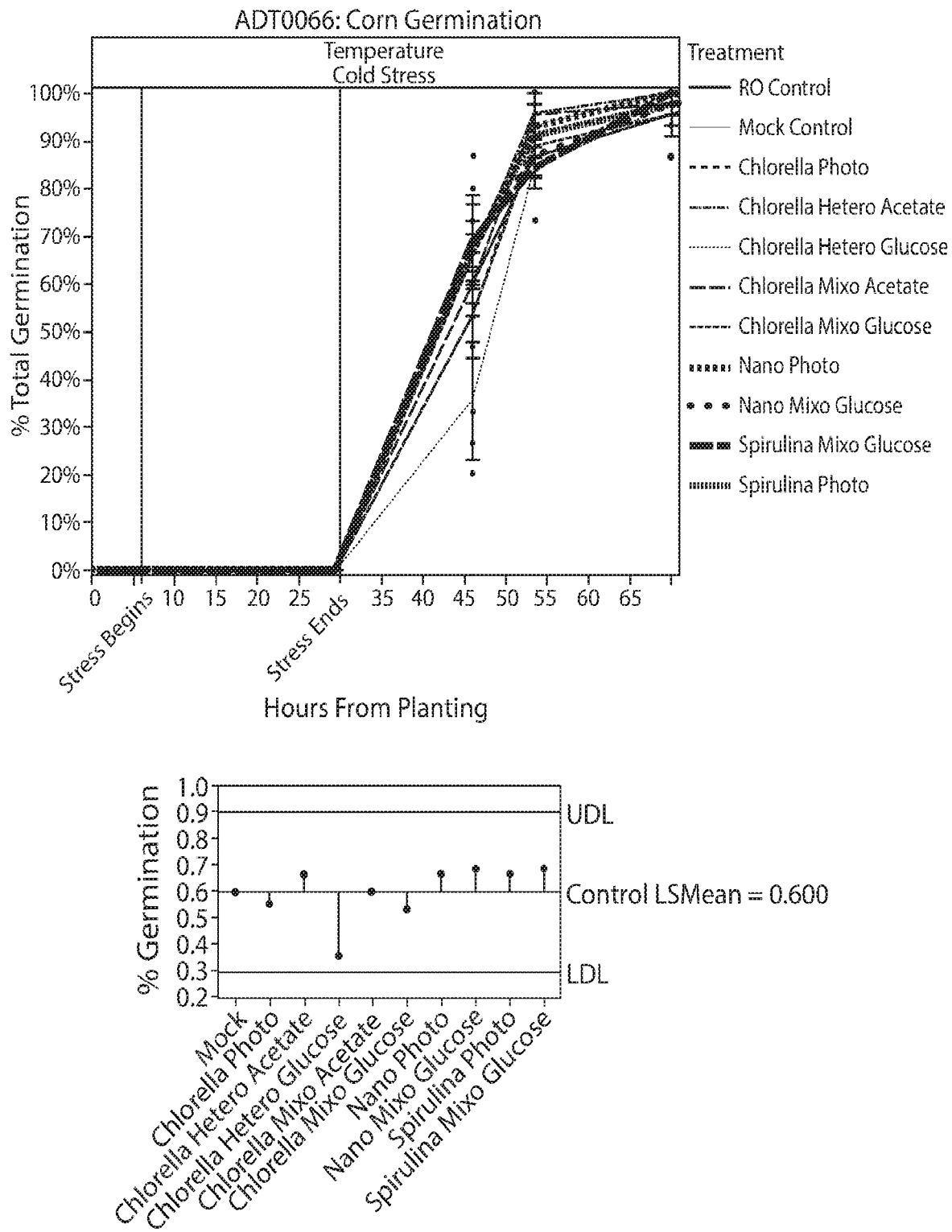
Figure 2:
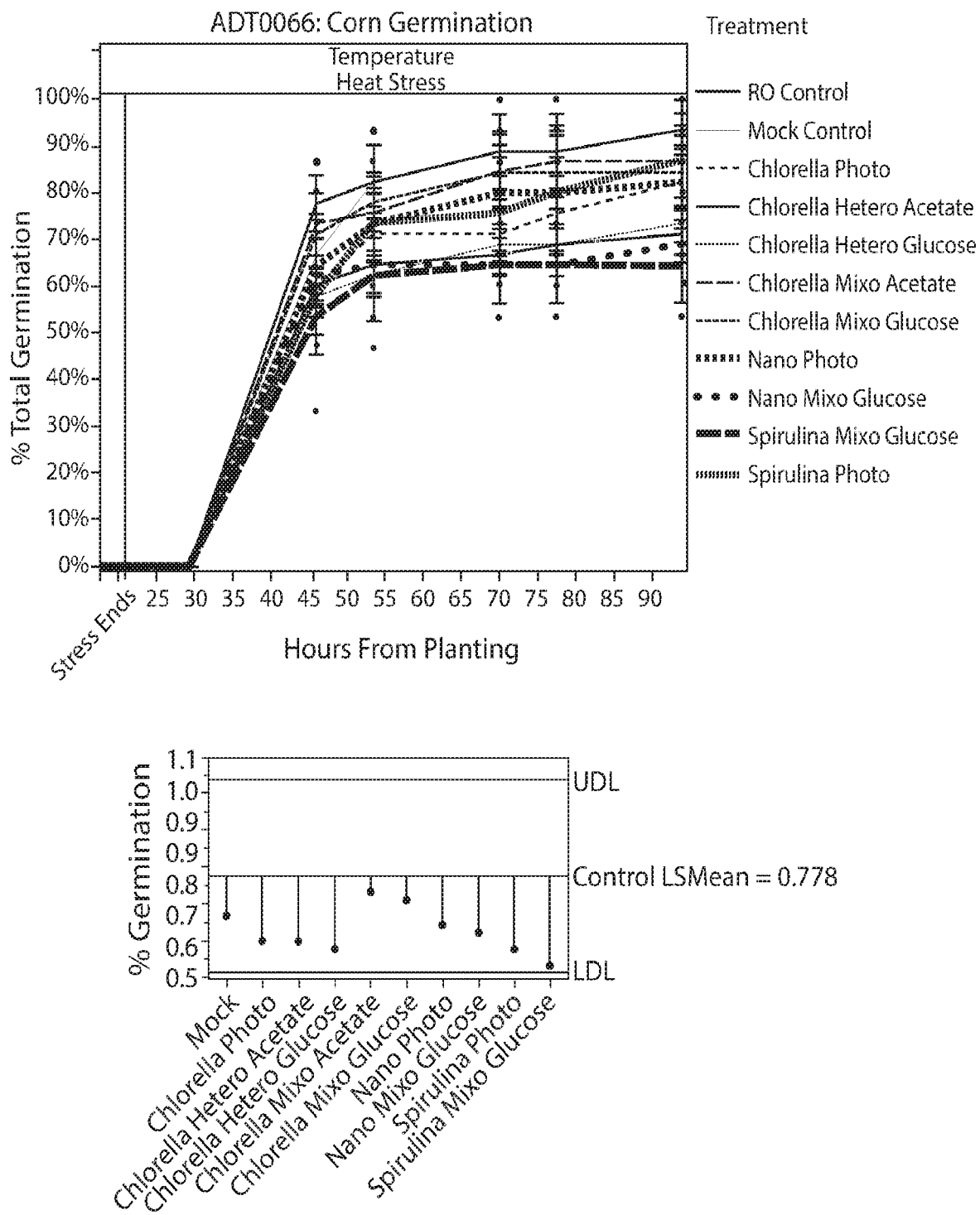

Percent germination was determined with observations occurring multiple times per day. The criteria for counting germination was when the radical root was at least 1 mm in length. Percent germination was analyzed as a complete time series for each experiment and using a Dunnet's test to compare treatments to untreated control at 25 hours for normal temperatures, and 45 hours for temperature stressed experiments. Results are shown in FIG. 2. Combined results from Examples 29-31 standardized to the RO Control are shown in Tables 48-50.

TABLE 48

| Treatment | Temperature | % Difference from Control (RO) of % Germination at 22 h |
|---|---|---|
| *Spirulina* Photo | Normal | +16.7 |
| *Spirulina* Mixo Glucose | Normal | −11.1 |
| *Nannochloropsis* Photo | Normal | −38.9 |
| *Nannochloropsis* Mixo Glucose | Normal | −5.5 |
| *Chlorella* Hetero Acetate | Normal | −5.5 |
| *Chlorella* Hetero Glucose | Normal | −55.5 |
| *Chlorella* Mixo Acetate | Normal | +5.6 |
| *Chlorella* Mixo Glucose | Normal | −5.5 |
| *Chlorella* Photo | Normal | −5.5 |
| Mock | Normal | −38.9 |

TABLE 49

| Treatment | Temperature | % Difference from Control (RO) of % Germination at 46 h |
|---|---|---|
| *Spirulina* Photo | Cold Stress | +11.1 |
| *Spirulina* Mixo Glucose | Cold Stress | +14.8 |
| *Nannochloropsis* Photo | Cold Stress | +11.1 |
| *Nannochloropsis* Mixo Glucose | Cold Stress | +14.8 |
| *Chlorella* Hetero Acetate | Cold Stress | +11.1 |
| *Chlorella* Hetero Glucose | Cold Stress | −40.7 |
| *Chlorella* Mixo Acetate | Cold Stress | 0.0 |
| *Chlorella* Mixo Glucose | Cold Stress | −11.1 |
| *Chlorella* Photo | Cold Stress | −7.4 |
| Mock | Cold Stress | 0.0 |

TABLE 50

| Treatment | Temperature | % Difference from Control (RO) of % Germination at 46 h |
|---|---|---|
| *Spirulina* Photo | Heat Stress | −25.7 |
| *Spirulina* Mixo Glucose | Heat Stress | −31.4 |
| *Nannochloropsis* Photo | Heat Stress | −17.2 |
| *Nannochloropsis* Mixo Glucose | Heat Stress | −20.0 |
| *Chlorella* Hetero Acetate | Heat Stress | −22.9 |
| *Chlorella* Hetero Glucose | Heat Stress | −25.7 |
| *Chlorella* Mixo Acetate | Heat Stress | −5.7 |
| *Chlorella* Mixo Glucose | Heat Stress | −8.6 |
| *Chlorella* Photo | Heat Stress | −22.9 |
| Mock | Heat Stress | −14.3 |

Example 33 (ADT 0069)

Experiments were done to test the effects of microalgae-based compositions on germination of corn seed subjected to temperature stress. In these experiments, all seeds began in 26° C. conditions for 6 hours; experienced a period of temperature stress (Cold period of 24 hours at 0° C., Heat period of 15 hours at 45° C., Normal always at 26° C.); after the temperature stress period all seeds were moved back to 26° C. conditions. Petri plates were lined with filter paper water with 10 mL of treatment solutions (application rate/concentration of 9 mL/gallon) one time at the beginning of the experiment. The plates were located in a temperature chamber to control temperature for the temperature stress periods. Triplicate plates with 15 corn seeds were used on each plate. The biomass was produced in axenic flask cultures as described in Example 21.

1. *Chlorella* Hetero Acetate
2. *Chlorella* Hetero Glucose
3. *Chlorella* Mixo Acetate
4. *Chlorella* Mixo Glucose
5. *Chlorella* Photo
6. *Galdieria* Hetero Glucose
7. *Galdieria* Mixo Glucose
8. *Haematococcus* Mixo Acetate
9. *Haematococcus* Photo
10. Control—Mock Mock is nutrient formulation of nutrients found in the average PhycoTerra Production Batch (i.e., *Chlorella* [HS26] Mixo Acetate)

1.5% of *Chlorella* (HS26) lipids 8.5% of protein and carbohydrates 128 ppb of Abscisic acid (ABA)

3.3 ppb of trans-ABA 2.8 ppb of trans-zeatin-0-glucoside (ZOG)

8.6 ppb of trans-zeatin 16.4 ppb of cis-Z 1.6 ppb of trans-zeatin riboside (ZR)

42.5 ppb of cis-ZR 9.8 ppb of isopentenyladenine (iP)

4.1 ppb of isopentenyladenine riboside (iPR)

86.3 ppb of indol acetic acid (IAA)

Percent germination was determined once for each temperature, 24 hours after seeding for normal temperatures and 45 hours after seeding for cold and heat stress; The criteria for counting germination was when the radical root was at least 1 mm in length. Results are shown in tables 51-53.

TABLE 51

| Treatment | Temperature | % Difference from Control (RO) of % Germination at 24 h |
| --- | --- | --- |
| Mock | Normal | −18.7 |
| *Chlorella* Photo | Normal | −40.6 |
| *Chlorella* Mixo Glucose | Normal | −25.0 |
| *Chlorella* Mixo Acetate | Normal | −9.4 |
| *Chlorella* Hetero Glucose | Normal | −6.2 |
| *Chlorella* Hetero Acetate | Normal | −15.6 |
| *Haematococcus* Photo | Normal | −15.6 |
| *Haematococcus* Mixo Acetate | Normal | −12.5 |
| *Galdieria* Mixo Glucose | Normal | −25.0 |
| *Galdieria* Hetero Glucose | Normal | −12.5 |

TABLE 52

| Treatment | Temperature | % Difference from Control (RO) of % Germination at 45 h |
| --- | --- | --- |
| Mock | Cold Stress | −30.3 |
| *Chlorella* Photo | Cold Stress | −34.8 |
| *Chlorella* Mixo Glucose | Cold Stress | −26.0 |
| *Chlorella* Mixo Acetate | Cold Stress | −30.3 |

TABLE 52-continued

| Treatment | Temperature | % Difference from Control (RO) of % Germination at 45 h |
| --- | --- | --- |
| *Chlorella* Hetero Glucose | Cold Stress | +4.3 |
| *Chlorella* Hetero Acetate | Cold Stress | −21.7 |
| *Haematococcus* Photo | Cold Stress | +17.4 |
| *Haematococcus* Mixo Acetate | Cold Stress | −21.7 |
| *Galdieria* Mixo Glucose | Cold Stress | 0.0 |
| *Galdieria* Hetero Glucose | Cold Stress | −13.1 |

TABLE 53

| Treatment | Temperature | % Difference from Control (RO) of % Germination at 45 h |
| --- | --- | --- |
| Mock | Heat Stress | −61.2 |
| *Chlorella* Photo | Heat Stress | −41.9 |
| *Chlorella* Mixo Glucose | Heat Stress | −38.8 |
| *Chlorella* Mixo Acetate | Heat Stress | −22.6 |
| *Chlorella* Hetero Glucose | Heat Stress | −3.2 |
| *Chlorella* Hetero Acetate | Heat Stress | −19.3 |
| *Haematococcus* Photo | Heat Stress | −3.2 |
| *Haematococcus* Mixo Acetate | Heat Stress | −22.6 |
| *Galdieria* Mixo Glucose | Heat Stress | −12.9 |
| *Galdieria* Hetero Glucose | Heat Stress | −35.6 |

Example 34 (ADT 0064)

Experiments were done to test the effects of microalgae-based compositions on germination of corn seeds subjected to salt stress. In these experiments, petri plates were lined with filter paper water with 10 mL of treatment solutions (application rate/concentration of 9 mL/gallon) one time at the beginning of the experiment. The plates located in a temperature chamber to control the temperature conditions. Triplicate plates with 15 corn seeds were used on each plate. The seeds in the soak treatment were soaked for two hours.

1. Control—Reverse Osmosis (RO) Water
2. Control—RO water+PhycoTerra Production Batch (*Chlorella* Mixo [HS26] Acetate produced outdoors in open culture)
3. 200 mM salt ((NaCl in RO water)
4. 200 mM salt (NaCl in RO water)+PhycoTerra Production Batch
5. 220 mM salt (NaCl in RO water)
6. 220 mM salt (NaCl in RO water)+PhycoTerra Production Batch
7. PhycoTerra Production Batch Soak/220 mM salt (NaCl in RO water)

Percent germination was determined with observations occurring multiple times per day. The criteria for counting germination was when the radical root was at least 1 mm in length. Results are shown in Table 54.

TABLE 54

| | % O/o Difference from Treatment with no Microalgae for % Germination at Designated Time | | | | | | | |
|---|---|---|---|---|---|---|---|---|
| Treatment | 20.5 h | 28 h | 44.5 h | 52 h | 68.5 h | 76 h | 92.5 h | Points of largest spread |
| RO + microalgae | −36.3 | −23.1 | −4.4 | −2.2 | −2.2 | −2.2 | −2.2 | −23.1 |
| 200 mMol salt + microalgae | — | +200.5 | −33.3 | 0.0 | −5.9 | −8.6 | −8.6 | −33.3 |
| 220 mMol Salt | — | −33.3 | −15.4 | −9.1 | 0.0 | 0.0 | 0.0 | −15.4 |

TABLE 55

| Treatment | Tissue Water Content (%) | Fresh Weight (g) | Dry Weight (g) |
|---|---|---|---|
| RO Water | 55% | 7.25 | 3.24 |
| RO + PT | 56% | 7.53 | 3.27 |
| 200 mMol salt | 50% | 5.14 | 2.55 |
| 200 mMol salt + PT | 55% | 5.11 | 2.34 |
| 220 mMol salt | 52% | 5.15 | 2.48 |
| 220 mMol salt + PT | 50% | 5.15 | 2.55 |
| PT soak/220 mMol salt | 60% | 4.97 | 2.02 |

Example 35 (ADT 0067)

Experiments were done to test the effects of microalgae-based compositions on germination of corn seeds subjected to salt stress. In these experiments, petri plates were lined with filter paper water with 10 mL of treatment solutions (application rate/concentration of 9 mL/gallon) one time at the beginning of the experiment. The plates located in a temperature chamber to control the temperature conditions. The triplicate plates with 15 corn seeds were on each plate. The seeds in the soak treatment were soaked for two hours.
1. Control—Reverse Osmosis (RO) Water
2. Control—RO water+PhycoTerra Production Batch (*Chlorella* [HS26] Mixo Acetate produced outdoors in open culture)
3. 200 mM salt ((NaCl in RO water)
4. 200 mM salt (NaCl in RO water)+PhycoTerra Production Batch
5. 220 mM salt (NaCl in RO water)
6. 220 mM salt (NaCl in RO water)+PhycoTerra Production Batch
7. PhycoTerra Production Batch Soak/220 mM salt (NaCl in RO water)

Percent germination was determined with observations occurring multiple times per day. The criteria for counting germination was when the radical root was at least 1 mm in length. Results are shown in Tables 56-57.

TABLE 56

| | % Difference from Treatment with no Microalgae for % Germination at Designated Time | | | | | | | |
|---|---|---|---|---|---|---|---|---|
| Treatment | 29 h | 45.5 h | 53 h | 69.5 h | 77 h | 93.5 h | 101 h | 117.5 h |
| RO + microalgae | −7.4 | 0.0 | 0.0 | 0.0 | 0.0 | 0.0 | 0.0 | 0.0 |
| 200 mMol salt + microalgae | −33.1 | −56.7 | −51.4 | −44.2 | −41.3 | −41.3 | −34.3 | −34.3 |
| 220 mMol salt + microalgae | −40.4 | −27.2 | −23.2 | −11.2 | −12.9 | −12.8 | −18.1 | −18.1 |

TABLE 57

| Treatment | % Difference from Treatment with no Microalgae | | | | |
|---|---|---|---|---|---|
| | Seed Weight | Fresh Weight | Dry Weight | STD Dry Weight | Water Content |
| RO + microalgae | −1.2 | −18.5 | +0.1 | +0.1 | −16.9 |
| 200 mMol salt + microalgae | −1.8 | −17.5 | −0.7 | −38.1 | +7.8 |
| 220 mMol salt + microalgae | −1.2 | −15.7 | −2.1 | −21.2 | +0.2 |

Example 36 (Hydroponic 1)

Experiments were done to test the effects of microalgae-based compositions administered hydroponically on bell peppers. In these experiments, the microalgae biomass for the identified treatments was produced in bag bioreactors (Example 21). Germinated pepper seedlings were grown in 4-inch pots with Turface-a calcined clay substrate. Everyday all plants were fertilized with 150 mL of nutrient solution (i.e., the Veg Only composition) to which various microalgae treatments were added at a concentration of 9 mL/gallon. The trays were randomized and location switched within the testing platform on one-week schedules. All the trays were harvested 22 days after the start of the experiment due to a pest infestation. The treatments tested comprised:

1. Control—Veg Only 1
2. Control—Veg Only 2

Both Veg Only Controls comprise the following nutrients:
KH2PO4
KNO3
Ca(N03)2 4H20
MgSO4 7H20
NaFe(III)EDTA
H3H03
MnC124H20
ZnSO4 7H20
CuSO4 5H20
Na2Mo03

3. Control—PhycoTerra Production Batch #HG 160303 (*Chlorella* [HS26] Mixo Acetate produced outdoors in open culture)
4. *Chlorella* Photo
5. *Chlorella* Mixo Acetate
6. *Chlorella* Mixo Glucose
7. *Chlorella* Hetero Acetate
8. *Chlorella* HeteroGlucose
9. *Haematococcus* Photo
10. *Haematococcus* Mixo Acetate
11. *Galdieria* Hetero Glucose
12. *Galdieria* Mixo Glucose
13. *Scenedesmus* Photo
14. *Scenedesmus* Mixo Acetate
15. *Scenedesmus* MixoGlucose
16. *Scenedesmus* Hetero Glucose
17. *Chlamydomonas* Mixo Acetate
18. *Chlamydomonas* Photo A damage score at the time of harvest was observed for all plants, as well as a plant dry weight (g). The *Chlamydomonas* treatments were not applied to plants but were analyzed for micronutrient content. Below is a table of Micronutrient analysis of microalgal biomass used in treatments (questionable values are shaded).

TABLE 58

| Trtmnt | pH (SU) | Chloride, Cl (ppm) | Cobalt, Co (ppb) | Molybdenum, Mo (ppb) | Phosphorus, P2O5 (%) | Potassium, K2O (%) | Calcium, Ca (%) | Magnesium, Mg (%) | Sodium, Na (%) | Sulfur, S (%) |
|---|---|---|---|---|---|---|---|---|---|---|
| Veg Only | 5.9 | 7.74 | <10 | 10 | 0.0072 | 0.019 | 0.016 | 0.0052 | 0.0012 | 0.0067 |
| HG160303 | 3 | 141 | 130 | 170 | 0.86 | 0.16 | 0.045 | 0.017 | 0.052 | 0.047 |
| Photo *Chlorella* | 3.8 | 66 | 250 | 150 | 0.82 | 0.27 | 0.045 | 0.042 | 0.037 | 0.067 |
| Mixo Acetate *Chlorella* | 3.8 | 34 | 20 | 240 | 0.25 | 0.13 | 0.031 | 0.0083 | 0.022 | 0.005 |
| Mixo Glucose *Chlorella* | 3.8 | 123 | 190 | 930 | 0.68 | 0.21 | 0.038 | 0.022 | 0.065 | 0.036 |
| Hetero Acetate *Chlorella* | 3.8 | 111 | 120 | 200 | 0.4 | 0.14 | 0.036 | 0.017 | 0.061 | 0.039 |
| Hetero Glucose *Chlorella* | 3.9 | 90 | 120 | 480 | 0.8 | 0.29 | 0.037 | 0.028 | 0.093 | 0.068 |
| Photo *Haematococcus* | 4 | 85 | <10 | 800 | 0.9 | 0.25 | 0.041 | 0.048 | 0.0093 | 0.054 |
| Mixo *Haematococcus* | 4.2 | 133 | 10 | 1270 | 0.63 | 0.21 | 0.033 | 0.029 | 0.015 | 0.05 |
| Mixo *Galdieria* | 3.9 | 246 | 440 | 570 | 0.36 | 0.11 | 0.028 | 0.013 | 0.047 | 0.026 |
| Hetero Glucose *Galdieria* | 3.8 | 208 | 1150 | 890 | 0.72 | 0.14 | 0.032 | 0.027 | 0.04 | 0.068 |
| Photo *Scenedesmus* | 4.1 | 55 | 100 | 310 | 0.82 | 0.25 | 0.031 | 0.038 | 0.036 | 0.059 |
| Mixo Acetate *Scenedesmus* | 4 | 147 | 120 | 5150 | 0.73 | 0.16 | 0.029 | 0.026 | 0.049 | 0.057 |
| Mixo Glucose *scenedesmus* | 3.8 | 159 | 140 | 2780 | 0.6 | 0.18 | 0.028 | 0.019 | 0.031 | 0.04 |
| Hetero Gluose *Scenedesmus* | 3.8 | 47 | 80 | 1690 | 0.63 | 0.19 | 0.028 | 0.017 | 0.029 | 0.04 |
| Mixo Acetate *Chlamydomonas* | 3.5 | 66 | 10 | 220 | 0.95 | 0.14 | 0.038 | 0.027 | 0.031 | 0.057 |
| Photo *Chlamydomonas* | 3.7 | 93 | <10 | 140 | 0.93 | 0.13 | 0.077 | 0.042 | 0.012 | 0.056 |

| Trtmnt | Iron, Fe (ppm) | Zinc, Zn (ppm) | Manganese, Mn (ppm) | Copper, Cu (ppm) | Boron, B (ppm) | Ammonium-Nitrogen, NH4—N (ppm) | Nitrate-Nitrogen, NO3—N (ppm) | Insoluble Nitrogen (ppm) | Total Nitrogen, N (ppm) | Moisture (%) | Dry Matter (%) |
|---|---|---|---|---|---|---|---|---|---|---|---|
| Veg Only | 2.2 | 0.46 | 0.26 | 0.026 | 0.61 | 22.5 | 201 | 811 | 1,034 | 99.9 | 0.1 |
| HG160303 | 29 | 1.5 | 3 | 1.2 | 0.77 | 270 | 105 | 4,448 | 4,823 | 88.2 | 11.8 |
| Photo *Chlorella* | 38 | 6 | 13 | 2.7 | 0.62 | 81.6 | 203 | 6,830 | 7,115 | 88.8 | 11.2 |
| Mixo Acetate *Chlorella* | 45 | 1.1 | 1.2 | 1.2 | 0.39 | 43.8 | 124 | 2,415 | 2,583 | 95.2 | 11.3 |
| Mixo Glucose *Chlorella* | 18 | 3.2 | 12 | 1.9 | 1.2 | 88.9 | 101 | 9,249 | 9,301 | 89.1 | 10.9 |
| Hetero Acetate *Chlorella* | 22 | 3.5 | 9.6 | 1.8 | 1 | 60.1 | 167 | 1,259 | 1,486 | 90.8 | 14 |
| Hetero Glucose *Chlorella* | 23 | 3.3 | 5.1 | 3.2 | 1 | 51 | 198 | 6,879 | 7,128 | 86.3 | 11.7 |
| Photo *Haematococcus* | 52 | 6.4 | 18 | 7.6 | 0.028 | 281 | 375 | 8,193 | 8,849 | 88.7 | 11.3 |
| Mixo *Haematococcus* | 19 | 3.8 | 4.3 | 4.2 | 0.17 | 75.8 | 57.7 | 892 | 1,025 | 89.2 | 10.8 |

TABLE 58-continued

| | | | | | | | | | | |
|---|---|---|---|---|---|---|---|---|---|---|
| Mixo *Galdieria* | 62 | 36 | 19 | 2.5 | 4.5 | 149 | 15.9 | 6,736 | 6,901 | 97 | 12 |
| Hetero Glucose *Galdieria* | 45 | 49 | 27 | 2.1 | 5.4 | 488 | 12.8 | 12,438 | 12,939 | 88.2 | 11.8 |
| Photo *Scenedesmus* | 36 | 11 | 11 | 6.6 | 0.71 | 73.8 | 183 | 9,504 | 9,761 | 89.7 | 10.3 |
| Mixo Acetate *Scenedesmus* | 42 | 4 | 7.9 | 1.3 | 0.84 | 274 | 122 | 4,805 | 5,201 | 88.5 | 11.5 |
| Mixo Glucose *scenedesmus* | 25 | 2.7 | 9.3 | 1.2 | 0.37 | 133 | 75.5 | 10,408 | 10,616 | 88.5 | 11.5 |
| Hetero Gluose *Scenedesmus* | 22 | 2.8 | 11 | 1.4 | 0.45 | 92.6 | 75.2 | 8,831 | 8,999 | 88.3 | 11.7 |
| Mixo Acetate *Chlamydomonas* | 27 | 3.7 | 4.4 | 5.2 | 0.5 | 487 | 3.08 | 6,241 | 6,731 | 88.5 | 11.5 |
| Photo *Chlamydomonas* | 34 | 3.9 | 6.2 | 5.9 | 0.12 | 240 | 3.52 | 8,667 | 8,911 | 90 | 10 |

TABLE 59

Damage score for plants at termination of experiment
Damage LSMeans Differences Tukey HSD

| Level | | | | Least Sq Mean |
|---|---|---|---|---|
| Veg Only1 | A | | | 2.100000 |
| Mixo Acetic *Chlorella* | A | | | 2.100000 |
| Mixo glucose *Galdieria* | A | | | 2.100000 |
| Hetero glucose *Chlorella* | A | B | | 2.066667 |
| Hetero glucose *Galdieria* | A | B | | 2.066667 |
| Hetero Glucose *Scenedemus* | A | B | | 2.066667 |
| Hetero acetic *Chlorella* | A | B | | 2.033333 |
| Mixo Acetic *Haematococus* | A | B | | 2.033333 |
| Photo *Haematococus* | A | B | | 2.033333 |
| Photo *Scenedesmus* | A | B | | 2.033333 |
| Photo *Chlorella* | A | B | | 2.000000 |
| Mixo Glucose *Chlorella* | A | B | | 1.933333 |
| Veg Only 2 | A | B | | 1.833333 |
| Mixo Acetate *Scenedemus* | A | B | | 1.766667 |
| HG160303 | | B | | 1.733333 |
| Mixo Glucose *Scenedesmus* | | | C | 1.133333 |

TABLE 60

Dry Weight for plants at termination of experiment
DW LSMeans Differences Tukey HSD

| Level | | | | | Least Sq Mean |
|---|---|---|---|---|---|
| Mixo Glucose *Scenedesmus* | A | | | | 0.067933 |
| HG160303 | A | B | | | 0.623000 |
| Mixo Acetate *Scenedemus* | A | B | C | | 0.599667 |
| Photo *Chlorella* | | B | C | D | 0.540667 |
| Photo *Haematococus* | | B | C | D | 0.521667 |
| Hetero glucose *Galdieria* | | B | C | D | 0.505667 |
| Photo *Scenedesmus* | | B | C | D | 0.504333 |
| Mixo acetic *Haematococus* | | B | C | D | 0.502333 |
| Hetero Glucose *Scenedesmus* | | B | C | D | 0.498667 |
| Veg Only 2 | | B | C | D | 0.496000 |
| Mixo Glucose *Chlorella* | | B | C | D | 0.495667 |
| Mixo Acetic *Chlorella* | | | C | D | 0.476000 |
| Hetero glucose *Chlorella* | | | | D | 0.447667 |
| Veg Only 1 | | | | D | 0.439333 |
| Hetero acetic *Chlorella* | | | | D | 0.438333 |
| Mixo glucose *Galdieria* | | | | D | 0.431000 |

Example 37 (ADT0059—Hydroponic 2)

Experiments were done to test the effects of microalgae-based compositions administered hydroponically on be 11 peppers. In these experiments, the biomass for the identified treatments were produced in bag bioreactors (Example 21). Germinated pepper seedlings were grown in 4-inch pots with Turface-a calcined clay substrate. Everyday all plants were fertilized with 150 mL of nutrient solution (i.e., the Veg Only composition) to which various microalgae treatments were added at a concentration of 9 mL/gallon. The trays randomized and location switched within the testing platform on one-week schedules. Half of the trays were harvested 22 days after the start of the experiment to collect vegetative growth data. Non-destructive measurements (e.g., height, circumference) were taken on the remaining plants 31 days after the start of the experiment. The remaining plants were harvested 44 days after the start of the experiment to collect additional vegetative growth andyield data.

Control—Veg Only 1

Control—Veg Only

Both Veg Only Controls comprise the following nutrients

KH2PO4

KN03

Ca(N03)2 4H20

MgSO4 7H20

NaFe(III)EDTA

H3H03

MnC124H20

ZnSO47H20

CuSO4 5H20

Na2Mo03

Control—PhycoTerra Production Batch #HG 160303 (*Chlorella* [HS26] Mixo Acetate produced outdoors in open culture)

*Chlorella* Photo

*Chlorella* Mixo Acetate

*Chlorella* Mixo Glucose

*Chlorella* Hetero Acetate

*Chlorella* Hetero Glucose

*Haematococcus* Photo

*Haematococcus* Mixo Acetate

*Galdieria* Hetero Glucose

*Galdieria* Mixo Glucose

*Scenedesmus* Photo

*Scenedesmus* Mixo Acetate

*Scenedesmus* Mixo Glucose

*Scenedesmus* Hetero Glucose

Plant height, plant circumference, plant fresh weight, plant dry weight, bud count and fruit count were observed. Results are shown in Tables 61-67.

TABLE 61

| DAY 22 | % Difference from Control 1 | | | | % Difference from Control 2 | | | |
|---|---|---|---|---|---|---|---|---|
| Treatment | Dia. | Circ. | Height | Bud count | Dia. | Circ. | Height | Bud count |
| Control 1 | | | | | +1.3 | +1.3 | −11.2 | +8.9 |
| Control 2 | −1.3 | −1.3 | +12.6 | −8.2 | | | | |
| Production Batch HG160303 | +4.9 | +4.9 | −1.0 | +5.5 | +6.2 | +6.2 | −12.1 | +14.9 |
| *Chlorella* Photo | +3.8 | +3.8 | +11.5 | −0.9 | +5.1 | +5.1 | −1.0 | +7.9 |
| *Chlorella* Mixo Glucose | +0.3 | +0.3 | −2.3 | +5.5 | +1.6 | +1.6 | −13.2 | +14.9 |
| *Chlorella* Mixo Acetate | −6.8 | −6.8 | +1.5 | +8.2 | −5.6 | −5.6 | −9.9 | +17.8 |
| *Chlorella* Hetero Glucose | +4.2 | +4.2 | −1.8 | +24.5 | +5.6 | +5.6 | −12.8 | +35.6 |
| *Chlorella* Hetero Acetate | +4.6 | +4.6 | +12.3 | −6.4 | +5.9 | +5.9 | −0.3 | +2.0 |
| *Scenedesmus* Photo | +3.8 | +3.8 | +14.8 | −3.6 | +5.2 | +5.2 | +1.9 | +5.0 |
| *Scenedesmus* Mixo Glucose | +0.3 | +0.3 | +10.8 | 0.0 | +1.6 | +1.6 | −1.6 | +8.9 |
| *Scenedesmus* Mixo Acetate | +5.1 | +5.1 | −0.1 | +9.1 | +6.4 | +6.4 | −11.2 | +18.8 |
| *Scenedesmus* Hetero Glucose | +6.3 | +6.3 | +2.0 | +11.8 | +7.6 | +7.6 | −9.4 | +21.8 |
| *Haematococcus* Photo | −1.1 | −1.1 | −3.6 | −3.6 | +0.2 | +0.2 | −14.4 | +5.0 |
| *Haematococcus* Mixo Acetate | −2.4 | −2.4 | +14.1 | −5.5 | −1.2 | −1.2 | +1.3 | +3.0 |
| *Galdieria* Mixo Glucose | +3.0 | +3.0 | +0.9 | +18.2 | +4.3 | +4.3 | −10.4 | +28.7 |
| *Galdieria* Hetero | +2.8 | +2.8 | +11.0 | 0.0 | +4.1 | +4.1 | −1.4 | +8.9 |

TABLE 62

| | % Difference from Control 1 | | | | % Difference from Control 2 | | | |
|---|---|---|---|---|---|---|---|---|
| DAY 22 Treatment | Shoot FW | Root FW | Shoot DW | Root DW | Shoot FW | Root FW | Shoot DW | Root DW |
| Control 1 | | | | | +15.8 | +6.5 | +0.2 | −3.7 |
| Control 2 | −13.6 | −6.1 | −0.2 | +3.8 | | | | |
| Production Batch HG160303 | −0.5 | −44.8 | −1.2 | −8.5 | +15.2 | −41.2 | −0.9 | −11.9 |
| *Chlorella* Photo | +2.3 | −14.0 | +3.4 | +3.0 | +18.5 | −8.4 | +3.6 | −0.8 |
| *Chlorella* Mixo Glucose | −9.6 | −33.2 | −12.3 | +2.3 | +4.7 | −28.9 | −12.1 | −1.5 |
| *Chlorella* Mixo Acetate | −2.4 | +15.7 | +17.5 | +23.5 | +13.0 | +23.3 | +17.8 | +19.0 |
| *Chlorella* Hetero Glucose | −3.1 | −24.0 | −3.0 | −5.1 | +12.2 | −19.1 | −2.7 | −8.6 |
| *Chlorella* Hetero Acetate | +1.8 | −31.4 | −0.8 | −3.5 | +17.9 | −26.9 | −0.5 | −7.0 |
| *Scenedesmus* Photo | +8.8 | +18.0 | +22.5 | +31.2 | +26.0 | +25.7 | +22.8 | +26.3 |
| *Scenedesmus* Mixo Glucose | −6.0 | −20.4 | −4.8 | +2.1 | +8.8 | −15.2 | −4.6 | −1.7 |
| *Scenedesmus* Mixo Acetate | −10.3 | −34.2 | −3.8 | −4.7 | +3.9 | −29.9 | −3.6 | −8.2 |
| *Scenedesmus* Hetero Glucose | +0.4 | −1.0 | +0.4 | −11.1 | +16.3 | +5.5 | +0.7 | −14.4 |
| *Haematococcus* Photo | −12.2 | −36.5 | −9.7 | −6.4 | +1.7 | −33.4 | −9.5 | −9.9 |
| *Haematococcus* Mixo Acetate | +5.9 | +10.5 | +23.4 | +28.4 | +22.6 | +17.7 | +23.7 | +23.7 |
| *Galdieria* Mixo Glucose | −8.1 | −11.0 | −4.1 | −3.0 | +6.4 | −5.2 | −3.9 | −6.5 |
| *Galdieria* Hetero Glucose | +5.3 | −2.4 | +5.9 | +11.3 | +22.0 | +4.0 | +6.1 | +7.2 |

TABLE 63

| | % Difference from Control 1 | | | % Difference from Control 2 | | |
|---|---|---|---|---|---|---|
| DAY 31 Treatment | Dia. | Circ. | Height | Dia. | Circ. | Height |
| Control 1 | | | | −4.7 | −4.7 | −10.3 |
| Control 2 | +4.9 | +4.9 | +11.5 | | | |
| Production Batch HG160303 | −0.9 | −0.9 | +10.2 | −5.5 | −5.5 | −1.1 |
| *Chlorella* Photo | −1.7 | −1.7 | +5.2 | −6.3 | −6.3 | −5.7 |
| *Chlorella* Mixo Glucose | −2.6 | −2.6 | −4.8 | −7.1 | −7.1 | −14.6 |
| *Chlorella* Mixo Acetate | +3.0 | +3.0 | +7.0 | −1.9 | −1.9 | −4.0 |
| *Chlorella* Hetero Glucose | −4.5 | −4.5 | +1.2 | −9.0 | −9.0 | −9.3 |
| *Chlorella* Hetero Acetate | +0.1 | +0.1 | +9.1 | −4.6 | −4.6 | −2.1 |
| *Scenedesmus* Photo | +1.7 | +1.7 | −1.7 | −3.1 | −3.1 | −11.8 |
| *Scenedesmus* Mixo Glucose | +0.9 | +0.9 | +4.3 | −3.8 | −3.8 | −6.4 |
| *Scenedesmus* Mixo Acetate | −5.1 | −5.1 | +4.6 | −9.5 | −9.5 | −6.2 |
| *Scenedesmus* Hetero Glucose | −1.8 | −1.8 | +5.1 | −6.4 | −6.4 | −5.7 |
| *Haematococcus* Photo | −0.2 | −0.2 | +7.3 | −4.9 | −4.9 | −3.7 |
| *Haematococcus* Mixo Acetate | +5.3 | +5.3 | +6.1 | +0.4 | +0.4 | −4.9 |
| *Galdieria* Mixo Glucose | −2.0 | −2.0 | +4.3 | −6.6 | −6.6 | −6.5 |
| *Galdieria* Hetero Glucose | +3.5 | +3.5 | +0.2 | −1.4 | −1.4 | −10.1 |

TABLE 64

| DAY 44 | % Difference from Control 1 | | | | % Difference from Control 2 | | | |
|---|---|---|---|---|---|---|---|---|
| Treatment | Dia. | Circ. | Height | Bud count | Dia. | Circ. | Height | Bud count |
| Control 1 | | | | | +8.1 | +8.1 | +2.9 | +29.9 |
| Control 2 | −7.5 | −7.5 | −2.9 | −23.0 | | | | |
| Production Batch HG160303 | −4.3 | −4.3 | −14.6 | −10.7 | +3.4 | +3.4 | −12.1 | +16.0 |
| *Chlorella* Photo | −7.4 | −7.4 | −10.2 | −20.7 | +0.1 | +0.1 | −7.5 | +3.1 |
| *Chlorella* Mixo Glucose | +0.8 | +0.8 | −10.0 | +2.6 | +8.9 | +8.9 | −7.4 | +33.3 |
| *Chlorella* Mixo Acetate | −5.2 | −5.2 | −4.1 | −12.8 | +2.5 | +2.5 | −1.3 | +13.3 |
| *Chlorella* Hetero Glucose | −4.1 | −4.1 | +10.2 | +11.1 | +3.6 | +3.6 | +13.5 | +44.4 |
| *Chlorella* Hetero Acetate | +2.4 | +2.4 | +3.7 | −4.2 | +10.7 | +10.7 | +6.7 | +24.5 |
| *Scenedesmus* Photo | +1.6 | +1.6 | 0.0 | 0.0 | +9.8 | +9.8 | +2.9 | +29.9 |
| *Scenedesmus* Mixo Glucose | −2.5 | −2.5 | −.03 | −9.7 | +5.4 | +5.4 | +2.6 | +17.3 |
| *Scenedesmus* Mixo Acetate | −3.0 | −3.0 | +76 | +6.8 | +4.8 | +4.8 | +10.8 | +38.8 |
| *Scenedesmus* Hetero Glucose | −2.4 | −2.4 | +7.5 | −6.3 | +5.5 | +5.5 | +10.6 | +21.8 |
| *Haematococcus* Photo | +0.5 | +0.5 | −1.9 | −1.2 | +8.7 | +8.7 | +1.0 | +28.2 |
| *Haematococcus* Mixo Acetate | −0.7 | −0.7 | 0.0 | −6.3 | +7.4 | +7.4 | +2.9 | +21.8 |
| *Galdieria* Mixo Glucose | −0.1 | −0.1 | +12.8 | −9.7 | +8.0 | +8.0 | +16.1 | +17.3 |
| *Galdieria* Hetero Glucose | −1.4 | −1.4 | −2.5 | −16.0 | +6.6 | +6.6 | +0.3 | +9.2 |

TABLE 65

| | % Difference from Control 1 | | | | % Difference from Control 2 | | | |
|---|---|---|---|---|---|---|---|---|
| DAY 44 Treatment | Flower Count | Micro Fruit | Inter. Fruit | Pepper Count | Flower Count | Micro Fruit | Inter. Fruit | Pepper Count |
| Control 1 | | | | | +53.6 | +51.6 | −50.0 | +50.0 |
| Control 2 | −34.9 | −34.0 | +100 | −33.3 | | | | |
| Production Batch HG160303 | −18.6 | −4.3 | −100 | 0.0 | +25.0 | +45.2 | −100 | +50.0 |
| *Chlorella* Photo | −43.0 | −21.3 | +200.0 | −12.5 | −12.5 | +19.4 | +50.0 | +31.3 |
| *Chlorella* Mixo Glucose | −22.1 | −2.1 | +100 | 0.0 | +19.6 | +48.4 | 0.0 | +50.0 |
| *Chlorella* Mixo Acetate | −18.6 | −27.7 | +200.0 | −22.9 | +25.0 | +9.7 | +50.0 | +15.6 |
| *Chlorella* Hetero Glucose | −27.6 | −22.0 | +11.1 | −21.3 | +11.1 | +18.3 | −44.4 | +18.1 |
| *Chlorella* Hetero Acetate | −37.2 | −34.0 | +100.0 | −33.3 | −3.6 | 0.0 | 0.0 | 0.0 |
| *Scenedesmus* Photo | −19.8 | −44.7 | 0.0 | −39.6 | +23.2 | −16.1 | −50.0 | −9.4 |
| *Scenedesmus* Mixo Glucose | −45.3 | −8.5 | −100 | −8.3 | −16.1 | +38.7 | −100 | +37.5 |
| *Scenedesmus* Mixo Acetate | −33.6 | −40.4 | 0.0 | −39.6 | +3.6 | −9.7 | −50.0 | −9.4 |
| *Scenedesmus* Hetero Glucose | −27.9 | −38.3 | 0.0 | −35.4 | +10.7 | −6.5 | −50.0 | −3.1 |
| *Haematococcus* Photo | −23.3 | −17.0 | −100 | −16.7 | +17.9 | +25.8 | −100 | +25.0 |
| *Haematococcus* Mixo Acetate | −26.7 | −51.1 | −100 | −52.1 | +12.5 | −25.8 | −100 | −28.1 |
| *Galdieria* Mixo Glucose | −25.6 | −2.1 | −100 | −4.2 | +14.3 | +48.4 | −100 | +43.8 |
| *Galdieria* Hetero Glucose | −37.2 | −36.2 | +100.0 | −35.4 | −3.6 | −3.2 | 0.0 | −3.1 |

TABLE 66

| DAY 44 Treatment | % Difference from Control 1 | | | % Difference from Control 2 | | |
|---|---|---|---|---|---|---|
| | Shoot DW | Root DW | Corrected Root DW | Shoot DW | Root DW | Corrected Root DW |
| Control 1 | | | | +25.2 | −25.4 | −2.9 |
| Control 2 | −20.1 | +34.1 | +2.9 | | | |
| Production Batch HG160303 | −9.1 | +25.9 | +5.2 | +13.9 | −6.1 | +2.2 |
| Chlorella Photo | −21.1 | +23.5 | +9.8 | −1.2 | −7.9 | +6.7 |
| Chlorella Mixo Glucose | +4.6 | +22.4 | +4.2 | +31.0 | −8.7 | +1.2 |
| Chlorella Mixo Acetate | −14.7 | +80.8 | −0.6 | +6.9 | +34.8 | −3.4 |
| Chlorella Hetero Glucose | +1.3 | −5.1 | −0.3 | +26.8 | −29.2 | −3.1 |
| Chlorella Hetero Acetate | −1.5 | +4.1 | +0.3 | +23.3 | −22.4 | −2.6 |
| Scenedesmus Photo | +1.0 | +5.7 | −10.2 | +26.4 | −21.2 | −12.7 |
| Scenedesmus Mixo Glucose | −3.2 | +19.7 | −7.4 | +21.2 | −10.7 | −10.1 |
| Scenedesmus Mixo Acetate | +1.1 | −26.5 | −12.8 | +26.6 | −45.2 | −15.3 |
| Scenedesmus Hetero Glucose | +4.0 | +8.3 | +5.7 | +30.3 | −19.3 | +2.6 |
| Haematococcus Photo | +4.2 | +81.4 | +0.8 | +30.5 | +35.2 | −2.1 |
| Haematococcus Mixo Acetate | −2.9 | +72.3 | +0.3 | +21.6 | +28.5 | −2.6 |
| Galdieria Mixo Glucose | +6.1 | −6.6 | +7.9 | +32.8 | −30.4 | +4.8 |
| Galdieria Hetero Glucose | −15.7 | +7.0 | −20.0 | +5.5 | −20.2 | −22.3 |

TABLE 67

| DAY 44 Treatment | % Difference from Control 1 | | | % Difference from Control 2 | | |
|---|---|---|---|---|---|---|
| | Tray Micro Fruit Count | Tray Int. Fruit Count | Tray Total | Tray Micro Fruit Count | Tray Int. Fruit Count | Tray Total |
| Control 1 | | | | +51.6 | −50.0 | +45.5 |
| Control 2 | −34.0 | +100.0 | −31.2 | | | |
| Production Batch HG160303 | −4.3 | −100 | 0.0 | +45.2 | −100 | +45.5 |
| Chlorella Photo | −21.3 | +200.0 | −12.5 | +19.4 | +50.0 | +27.3 |
| Chlorella Mixo Glucose | −2.1 | +100.0 | 0.0 | +48.4 | 0.0 | +45.5 |
| Chlorella Mixo Acetate | −27.7 | +200.0 | −22.9 | +9.7 | +50.0 | +12.1 |
| Chlorella Hetero Glucose | −29.8 | 0.0 | −29.2 | +6.5 | −50.0 | +3.0 |
| Chlorella Hetero Acetate | −34.0 | +100 | −31.2 | 0.0 | 0.0 | 0.0 |
| Scenedesmus Photo | −44.7 | 0.0 | −39.6 | −16.1 | −50.0 | −12.1 |
| Scenedesmus Mixo Glucose | −8.5 | −100 | −8.3 | +38.7 | −100 | +33.3 |
| Scenedesmus Mixo Acetate | −40.4 | 0.0 | −39.6 | −9.7 | −50.0 | −12.1 |
| Scenedesmus Hetero Glucose | −38.3 | 0.0 | −35.4 | −6.5 | −50.0 | −6.1 |
| Haematococcus Photo | −17.0 | −100 | −16.7 | +25.8 | −100 | +21.2 |
| Haematococcus Mixo Acetate | −51.1 | −100 | −52.1 | −25.8 | −100 | −30.3 |
| Galdieria Mixo Glucose | −2.1 | −100 | −4.2 | +48.4 | −100 | +39.4 |
| Galdieria Hetero Glucose | −36.2 | +100.0 | −33.3 | −3.2 | 0.0 | −3.0 |

Example 38

Below is a table of Micronutrient analysis of microalgal biomass used in treatments (questionable values are shaded).

TABLE 68

| Trtmnt | pH (SU) | Chloride, Cl (ppm) | Phosphorus, P2O5 (%) | Potassium, K2O (%) | Calcium, Ca (%) | Magnesium, Mg (%) | Sodium, Na (%) | Sulfur, S (%) |
|---|---|---|---|---|---|---|---|---|
| Veg Only | 5.9 | 7.74 | 0.0072 | 0.019 | 0.016 | 0.0052 | 0.0012 | 0.0067 |
| HG160303 | 3.0 | 141 | 0.86 | 0.16 | 0.045 | 0.017 | 0.052 | 0.047 |
| Photo Chlorella | 3.8 | 66 | 0.82 | 0.27 | 0.045 | 0.042 | 0.037 | 0.067 |
| Mixo Acetate Chlorella | 3.8 | 34 | 0.25 | 0.13 | 0.031 | 0.0083 | 0.022 | 0.005 |
| Mixo Glucose Chlorella | 3.8 | 123 | 0.68 | 0.21 | 0.038 | 0.022 | 0.065 | 0.036 |
| Hetero Acetate Chlorella | 3.8 | 111 | 0.4 | 0.14 | 0.036 | 0.017 | 0.061 | 0.039 |
| Hetero Glucose Chlorella | 3.9 | 90 | 0.8 | 0.29 | 0.037 | 0.028 | 0.093 | 0.068 |
| Photo Haematococcus | 4.0 | 85 | 0.9 | 0.25 | 0.041 | 0.048 | 0.0093 | 0.054 |
| Mixo Haematococcus | 4.2 | 133 | 0.63 | 0.21 | 0.033 | 0.029 | 0.015 | 0.05 |
| Mixo Galdieria | 3.9 | 246 | 0.36 | 0.11 | 0.028 | 0.013 | 0.047 | 0.026 |
| Hetero Glucose Galdieria | 3.8 | 208 | 0.72 | 0.14 | 0.032 | 0.027 | 0.04 | 0.068 |
| Photo Scenedesmus | 4.1 | 55 | 0.82 | 0.25 | 0.031 | 0.038 | 0.036 | 0.059 |
| Mixo Acetate Scenedesmus | 4.0 | 147 | 0.73 | 0.16 | 0.029 | 0.026 | 0.049 | 0.057 |
| Mixo Glucose scenedesmus | 3.8 | 159 | 0.6 | 0.18 | 0.028 | 0.019 | 0.031 | 0.04 |
| Hetero Gluose Scenedesmus | 3.8 | 47 | 0.63 | 0.19 | 0.028 | 0.017 | 0.029 | 0.04 |
| Mixo Acetate Chlamydomonas | 3.5 | 66 | 0.95 | 0.14 | 0.038 | 0.027 | 0.031 | 0.057 |
| Photo Chlamydomonas | 3.7 | 93 | 0.93 | 0.13 | 0.077 | 0.042 | 0.012 | 0.056 |

TABLE 68-continued

| Trtmnt | Iron, Fe (ppm) | Zinc, Zn (ppm) | Manganese, Mn (ppm) | Copper, Cu (ppm) | Boron, B (ppm) | Insoluble Nitrogen (ppm) | Total Nitrogen, N (ppm) | Moisture (%) | Dry Matter (%) |
|---|---|---|---|---|---|---|---|---|---|
| Veg Only | 2.2 | 0.46 | 0.26 | 0.026 | 0.61 | 811 | 1,034 | 99.9 | 0.1 |
| HG160303 | 29 | 1.5 | 3.0 | 1.2 | 0.77 | 4,448 | 4,823 | 88.2 | 11.8 |
| Photo *Chlorella* | 38 | 6.0 | 13 | 2.7 | 0.62 | 6,830 | 7,115 | 88.8 | 11.2 |
| Mixo Acetate *Chlorella* | 45 | 1.1 | 1.2 | 1.2 | 0.39 | 2,415 | 2,583 | 95.2 | 11.3 |
| Mixo Glucose *Chlorella* | 18 | 3.2 | 12 | 1.9 | 1.2 | 9,249 | 9,301 | 89.1 | 10.9 |
| Hetero Acetate *Chlorella* | 22 | 3.5 | 9.6 | 1.8 | 1.0 | 1,259 | 1,486 | 90.8 | 14 |
| Hetero Glucose *Chlorella* | 23 | 3.3 | 5.1 | 3.2 | 1.0 | 6,879 | 7,128 | 86.3 | 11.7 |
| Photo *Haematococcus* | 52 | 6.4 | 18 | 7.6 | 0.028 | 8,193 | 8,849 | 88.7 | 11.3 |
| Mixo *Haematococcus* | 19 | 3.8 | 4.3 | 4.2 | 0.17 | 892 | 1,025 | 89.2 | 10.8 |
| Mixo *Galdieria* | 62 | 36 | 19 | 2.5 | 4.5 | 6,736 | 6,901 | 97.0 | 12.0 |
| Hetero Glucose *Galdieria* | 45 | 49 | 27 | 2.1 | 5.4 | 12,438 | 12,939 | 88.2 | 11.8 |
| Photo *Scenedesmus* | 36 | 11 | 11 | 6.6 | 0.71 | 9,504 | 9,761 | 89.7 | 10.3 |
| Mixo Acetate *Scenedesmus* | 42 | 4.0 | 7.9 | 1.3 | 0.84 | 4,805 | 5,201 | 88.5 | 11.5 |
| Mixo Glucose *scenedesmus* | 25 | 2.7 | 9.3 | 1.2 | 0.37 | 10,408 | 10,616 | 88.5 | 11.5 |
| Hetero Gluose *Scenedesmus* | 22 | 2.8 | 11 | 1.4 | 0.45 | 8,831 | 8,999 | 88.3 | 11.7 |
| Mixo Acetate *Chlamydomonas* | 27 | 3.7 | 4.4 | 5.2 | 0.50 | 6,241 | 6,731 | 88.5 | 11.5 |
| Photo *Chlamydomonas* | 34 | 3.9 | 6.2 | 5.9 | 0.12 | 8,667 | 8,911 | 90.0 | 10.0 |

Figure 3:
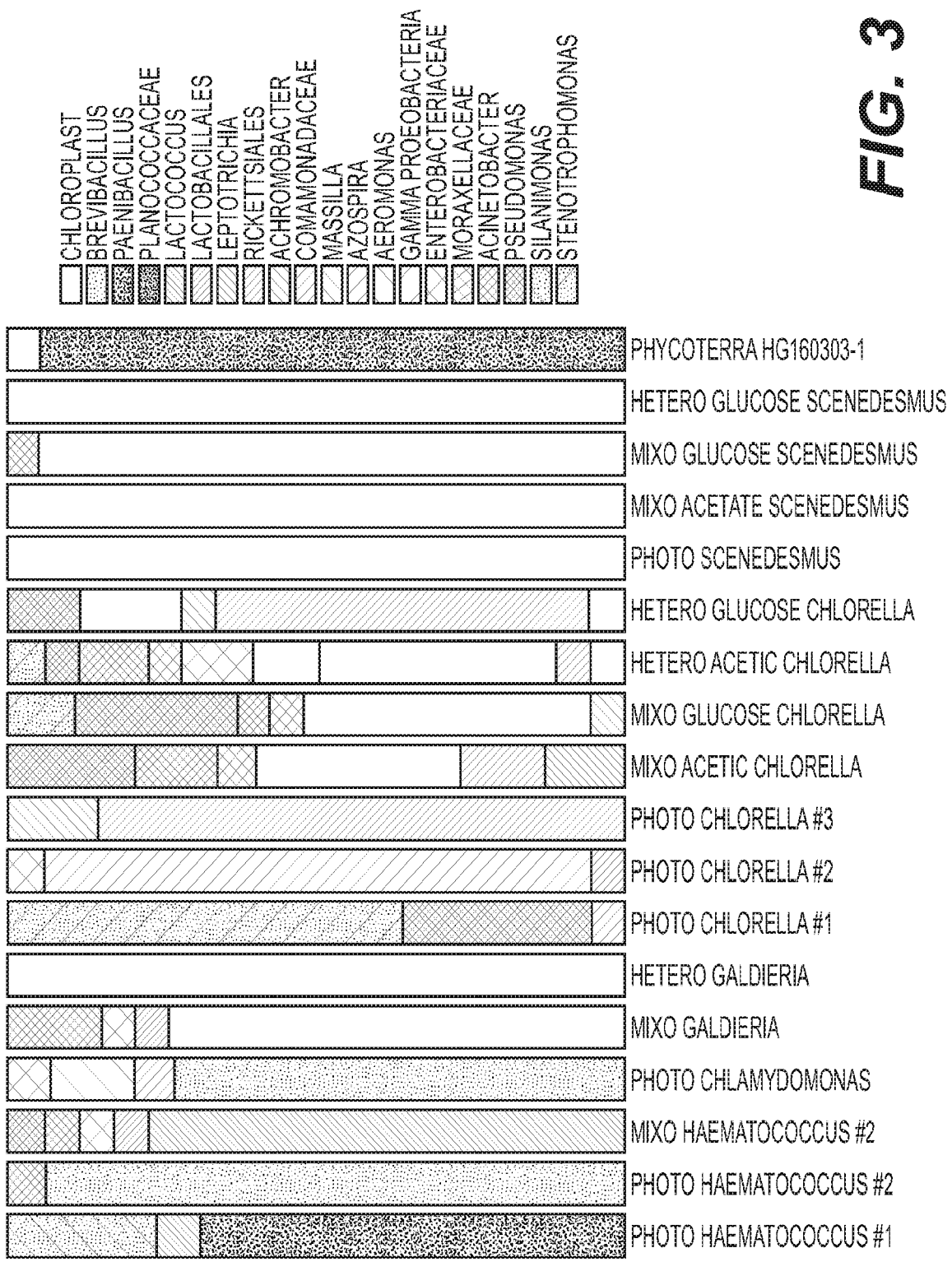
FIG. 3 depicts a composition analyses of example microalgae-based compositions.

Results of analyses of phytohormone and bacterial communities in an example of the composition are provide in Table 69 and FIG. 3.

TABLE 69

| Treatment | Phytohormone | Concentration (ng/g FW) |
|---|---|---|
| HG160303 | c-Z | 8.7 |
| | c-ZR | 0.6 |
| | IAA | 21.1 |
| | t-ABA | |
| | t-ZR | 0.2 |
| | iP | 6 |
| | iPR | 0.5 |
| *Chlorella* HA | c-Z | 0.1 |
| | c-ZR | 41.3 |
| | IAA | |
| | t-ABA | |
| | t-ZR | 1.1 |
| | iP | 0.1 |
| | iPR | 25 |
| *Chlorella* HG | c-Z | |
| | c-ZR | 15.6 |
| | IAA | 3.9 |
| | t-ABA | |
| | t-ZR | 3.4 |
| | iP | |
| | iPR | 3 |
| *Chlorella* MA | c-Z | |
| | c-ZR | 0.8 |
| | IAA | 1.3 |
| | t-ABA | |
| | t-ZR | |
| | iP | |
| | iPR | 0.2 |
| *Chlorella* MG | c-Z | |
| | c-ZR | 34.7 |
| | IAA | 5.7 |
| | t-ABA | |
| | t-ZR | 2.6 |
| | iP | |
| | iPR | 32.1 |
| *Chlorella* Photo | c-Z | |
| | c-ZR | 0.9 |
| | IAA | 9.9 |
| | t-ABA | |
| *Galdi* HG | t-ZR | 0.3 |
| | iP | |
| | iPR | 0.5 |
| | c-Z | |
| | c-ZR | |
| | IAA | 10.7 |
| | t-ABA | |
| | t-ZR | |
| *Galdi* MG | iP | 3.9 |
| | iPR | 18.8 |
| | c-Z | |
| | c-ZR | |
| | IAA | 16.5 |
| | t-ABA | |
| | t-ZR | |
| | iP | 1.7 |
| | iPR | 6.9 |
| *Haemy* MA | c-Z | 0.8 |
| | c-ZR | 7.1 |
| | IAA | 96.4 |
| | t-ABA | |
| | t-ZR | 0.2 |
| | iP | 0.8 |
| | iPR | 3.4 |
| *Haemy* Photo | c-Z | 11 |
| | c-ZR | 1.1 |
| | IAA | 1830.8 |
| | t-ABA | 0.4 |
| | t-ZR | |
| | iP | 18 |
| | iPR | 2.2 |
| Seen HG | c-Z | 1.7 |
| | c-ZR | 4.6 |
| | IAA | 5.2 |
| | t-ABA | |
| | t-ZR | |
| | iP | 0.6 |
| | iPR | 0.6 |
| Seen MA | e-Z | 7.5 |
| | e-ZR | 12.5 |
| | IAA | 12.4 |
| | t-ABA | 0.4 |
| | t-ZR | 0.4 |

TABLE 69-continued

| Treatment | Phytohormone | Concentration (ng/g FW) |
|---|---|---|
|  | iP | 4.6 |
|  | iPR | 1.5 |
| Seen MG | e-Z | 2.1 |
|  | e-ZR | 27.6 |
|  | IAA | 2 |
|  | t-ABA |  |
|  | t-ZR | 2 |
|  | iP | 0.6 |
|  | iPR | 2.5 |
| Seen Photo | e-Z | 0.7 |
|  | e-ZR | 4.8 |
|  | IAA | 6.7 |
|  | t-ABA | 0.8 |
|  | t-ZR | 0.4 |
|  | iP | 0.5 |
|  | iPR | 2.2 |

Example 39

This experiment exemplifies how formulations of microalgae materials can be prepared for purpose of treating plants and/or soil in accordance with the principles of the invention described herein.

For the purpose of several experiments that follow, the following exemplary formulations were prepared based on either *Aurantiochytrium* intact cells (whole biomass or "WB"), *Aurantiochytrium* cells/biomass that had been subjected to extraction of lipids/oils (extracted biomass, "EB", or "defatted" biomass), alone or in combination with *Yucca* extract as specified in Table 70 and the more detailed description that follows.

TABLE 70

*Aurantiochytrium* Derived Test Formulations

| Code | Formulation Number | Short Summary |
|---|---|---|
| HEL17-0205 | Formulation 1 | 98.5% WB + 1% FP (French Press) Oil + 0.5% *Yucca* extract (Blend) |
| HEL17-0206 | Formulation 2 | 76% EB (mech) + 9.5% EB Haem + 9.5% FP oil + 4.8% *Yucca* extract |
| HEL17-0207 | Formulation 3 | 98.5% EB (mech) + 1% FP oil + 0.5% *Yucca* extract |
| HEL17-0208 | Formulation 4 | 98.5% WB + 1% FP Oil + 0.5% *Yucca* extract |
| HEL17-0209 | Formulation 5 | 98.5% EB (FP) + 1% FP Oil + 0.5% *Yucca* extract |
| HEL17-0210 | Formulation 6 | 65 Deg. C. pasteurized WB (citric acid formulation) |
| HEL17-0211 | Formulation 7 | 95 Deg. C. pasteurized WB (citric acid formulation) |

Preparation Procedures:

Formulation 1/HEL17-0205: 98.5 g of whole cell ("whole" or "WB") *Aurantiochytrium* biomass was mixed with 1 g French press extracted *Aurantiochytrium* oil and 0.5 g of *yucca* extract. The sample was blended for 5 minutes to finish.

Formulation 2/HEL17-0206: 80 g of defatted *Aurantiochytrium* biomass (mechanically extracted, but not French press extracted) and 10 g of extracted *haematococcus* biomass ("EB") were suspended in 750 mL of water. "Defatted biomass" (also referred to by the abbreviations "DF" or "EB") means microalgae (here, *Aurantiochytrium*) biomass that has been subjected to one or more extractions, typically of lipids, such as oils (e.g., the extraction of omega-3 and omega-3-associated oils/lipids). This initially prepared solution was heated at 60-65 deg C for 2 h, and pH adjusted to 3.5-4.0 by the addition of citric acid. To the solution was then added 10 g of crude *Aurantiochytrium* French press oil and 5 g of *yucca* extract. The volume of the solution was adjusted to 1000 mL by the addition of water to finish.

Formulation 3/HEL 17-0207: 98.5 g of defatted *Aurantiochytrium* biomass (mechanically extracted by means other than French press) was mixed with 1 g French press extracted *Aurantiochytrium* oil and 0.5 g of *yucca* extract. The sample was blended 5 minutes to finish.

Formulation 4/HEL 17-0208: 98.5 g of whole cell *Aurantiochytrium* biomass was suspended in 750 mL of water. The solution heated at 60-65 deg C for 2 h, pH adjusted to 3.5-4.0 by the addition of citric acid. To the solution was then added 1 g of crude 399 French press oil and 5 g of *yucca* extract. The volume was adjusted to 1000 mL by the addition of water.

Formulation 5/HEL17-0209: 98.5 g of defatted *Aurantiochytrium* biomass (left after French press extraction) was mixed with 1 g French press extracted *Aurantiochytrium* oil and 0.5 g of *yucca* extract. The sample was blended 5 minutes to finish.

Formulation 6/HEL 17-0210: 1000 mL of a whole cell (WB) *Aurantiochytrium* suspension in water (~87-89%) containing—10.5% solids was stirred at 65 deg C for 2 h, thereby pasteurizing the *Aurantiochytrium* WB material. The pH of the formulation was then adjusted to 3.8-4.0 by the addition of citric acid (0.1-2% citric acid) to finish.

Formulation 7/HEL17-0211: 1000 mL of a whole biomass/cell *Aurantiochytrium* suspension in water (~87-89%) containing ~10-5<% solids was stirred at 95 deg C for 2 h (providing a more rigorous (higher temperature) pasteurization step than that performed in the preparation of Formulation 6). The pH of the suspension was then adjusted to 3.8-4.0 by the addition of citric acid (0.1-2% citric acid) to finish.

Example 40

To exemplify the ability of *Aurantiochytrium* compositions to promote plant growth, the following experiment was performed.

Seed surface sterilization of *A. thalania* seed used in this experiment was performed by washing the seeds in a 1.5 ml Eppendorf tube for 10 minutes in 2% v/v bleach (sodium hypochlorite, NaOCl). Seeds were rinsed two times with sterile water to ensure that the bleach was removed. Seeds were placed on the plates containing half strength Murashige and Skoog (MS) medium, supplemented with 1% (w/v) sucrose and solidified with 0.4% (w/v) Phytagel (or 0.7<% w/v bacto agar). Plates were vertically stacked in the grow 1 h chamber set at 22° C. with 16-h light/8-h dark cycle, with light intensity of 100 $\rho$mol/m$^{-2}$ s$^{-1}$. After 4 or 5 days, plants were transferred to plates containing half strength MS medium with 1% (w/v) sucrose, and 0.4% (w/v) Phytagel (control plates) and supplemented with different concentrations of test compounds as described below (test plates).

Solutions containing different concentrations of Formulation 4/HEL 17-208 were prepared as follows: 0.1 ml/L (0.01% concentration), (the "Hi" concentration) 0.01 ml/L (0.001% concentration) (the "Med" concentration) and 0.001 ml/L (0.0001% concentration) (the "Low" concentration).

Five plants were placed in each square Petri dish. Each concentration of each formulation was tested in triplicate. Plates were vertically stacked in the growth chamber and maintained at 22° C. with 16-h light/8-h dark cycle, with light intensity of 100 µmol·m$^{-2}$s$^{-1}$. Plants were dried in a hot air oven at 70° C. for 48 hrs and the dry weight was recorded for each plant. Data for the calculated percent dry weight as compared with that of the wild type (Col-0) plants grown without application of the formulation was determined. The results of this experiment are presented in Table 71.

TABLE 71

| | In vivo Growth | | |
|---|---|---|---|
| | Hi | Med | Low |
| | % Dry weight | | |
| Control | 100.00 | | |
| HEL17-0208 | | 135.36 | 176.37 | 156.26 |

These results demonstrate that various concentrations of *Aurantiochytrium* formulations, such as Formulation 4, are capable of inducing significant increases in the growth of plants.

Example 41

To illustrate the ability of *Aurantiochytrium* to promote plant growth under high salinity conditions, the following experiment was performed.

In general, the methods of Example 40 were employed in the preparation of *A. thalania* seed, initial growth of plants, etc. After 4-5 days of growth, plants were transferred to plates containing half strength MS medium with 1% (w/v) sucrose, 0.4% (w/v) Phytagel and 100 mM NaCl (control plates) and supplemented with different concentrations of Formulation HEL 17-0208 or HEL 17-0209 (using "Hi", "Med", and "Low" concentrations as described above (0.01%, 0.001%, and 0.0001% concentration of *Aurantiochytrium* formulation, respectively). The number of plants and replications were the same as described for the growth testing. Plates treated with NaCl were vertically stacked in the growth chamber and maintained at 22° C. with 16-h light/8-h dark cycle, with light intensity of 100 pmol·m$^{-2}$s$^{-1}$. The results of this experiment are provided in Table 72.

TABLE 72

| | In vivo Growth | | |
|---|---|---|---|
| | Hi | Med | Low |
| | % Dry weight | | |
| Control | 100.00 | | |
| HEL17-0208 | | 102.56 | 166.28 | 99.54 |
| HEL17-0209 | | 64.56 | 127.33 | 64.36 |

As can be seen from these results, at the "Med" concentration, both *Aurantiochytrium* formulations tested were able to significantly enhance plant growth as compared to the control until high salinity conditions. This result reflects the ability of compositions of the invention to promote plant growth in high salinity environments.

Example 42

This example illustrates the ability of compositions of the invention, such as the *Aurantiochytrium* formulations described above, to promote root growth.

Mung beans plants were grown on vermiculite for two weeks and then cut approximately 3 cm below cotyledons. Cut plantlets were placed in glass scintillation vials to which 15 ml of water (control) or different concentrations ("Hi", "Med", and "Low" concentrations, as described above) of the selected *Aurantiochytrium* formulations were added. Five plantlets were used for each concentration and for controls. After 7 days, the effects of compounds on root growth were assessed by determining the distance of root growth from meristem, longest root length and the number of roots. The results of this experiment are provided in Table 73.

TABLE 73

| | Mung bean root assay | | |
|---|---|---|---|
| | Hi | Med | Low |
| | Average no. of roots | | |
| Control | | 5.8 | |
| HEL17-0205 | 40.8 | 13.6 | 18.8 |
| HEL17-0206 | 22.2 | 18.8 | 18.8 |
| HEL17-0207 | 27.2 | 16.2 | 18.6 |
| HEL17-0208 | 21.2 | 19.2 | 21 |
| HEL17-0209 | 7.8 | 23.6 | 18 |
| HEL17-0210 | 21.8 | 12.8 | 16.8 |
| HEL17-0211 | 22.4 | 21.6 | 13.6 |

As can be seen from the results provided in Table 73, *Aurantiochytrium* compositions, such as the several different and exemplary formulations used in this experiment, are capable of significantly promoting root growth in terms of the number of roots of a treated plant, reaching increases of 1.5× (150%>), over 2× (200%+), 3× (300%), in several cases 4×-5× (400-500%), and in some cases achieving even more than a 600% (6×) increase in the number of roots obtained via treatment.

Example 43

This example illustrates the ability of compositions of the invention to protect plants against plant disease, such as white mold disease caused by the plant pathogen *S. sclerotiorum*.

Specifically, the impact of *S. sclerotiorum* on *Arabidopsis thaliana* Col-0 plants were assessed by determining disease severity in both control and *Aurantiochytrium* composition-treated plants. The experiment employed treatment with 2 ml of water/plant (control sample) or 2 ml of the tested *Aurantiochytrium* formulations at two concentrations ("Hi" and "Med" (in Table 73 presented as "Lo"), as described above (Hi=0.01% and Lo=0.001% concentration of *Aurantiochytrium* composition in the final formulation, respectively). Foliar treatments were applied 24 h before the infection with *S. sclerotiorum*. Six plants were used for each treatment. For infection, *S. sclerotiorum* was grown on PDA medium for 3 days. At the time of infection plants were around 21 days old. At this stage, all the plants had well developed leaves and they were infected by placing a plug with a diameter of 5 mm on the middle of the adaxial side of one leaf of each plant. Disease progression was observed for 3 days, from 1 dpi (days post inoculation) to 3 dpi. The results of this experiment are presented in Table 74.

TABLE 74

Sclerotinia assay

| | 48 h | | 72 h | |
|---|---|---|---|---|
| | Hi | Lo | Hi | Lo |
| | | % Infection | | |
| Control | 100% | 100% | 100% | 100% |
| HEL17-0205 | 53% | 50% | 68% | 86% |
| HEL17-0206 | 40% | 49% | 61% | 50% |
| HEL17-0207 | 36% | 52% | 38% | 75% |
| HEL17-0208 | 23% | 10% | 21% | 27% |
| HEL17-0209 | 42% | 53% | 44% | 43% |
| HEL17-0210 | 65% | 52% | 35% | 59% |
| HEL17-0211 | 47% | 75% | 79% | 59% |

The results of this experiment demonstrate that *Aurantiochytrium* formulations of the invention are very capable of reducing the severity of *S. sclerotiorum* infection in infected plants. In some cases, the reduction in % infection (as determined by amount of infected tissue in the plants) was often 20% or greater, frequently 30% or greater, and in numerous cases about 40% or greater or 50% or greater, and in certain cases even 60% or greater or even 70%> or greater.

Example 44

A greenhouse experiment was performed to determine the effect of *Schizochytrium*- and *Chlorella*-based compositions on active carbon level and dry soil aggregate size distribution. Soil was collected from a fallow field previously planted with corn from Gilbert, Ariz. Soil was diluted by 40% with a peat based soil mix and perlite.

Quart pots were filled and drenched with *Schizochytrium*- or *Chlorella*-based compositions in concentrations ranging from 0.03-3% volume/volume in water. Water alone was included as the untreated control. Pots were kept moist by watering with water alone every 2 days. Soil samples were collected every 5 days for 2 weeks and assayed for active carbon and dry soil aggregate size distribution.

To obtain active carbon scores, soil samples were air dried and sieved to 2 mm. A 2.5 g sample of air-dried soil was placed in a 50-mL centrifuge tube filled with 20 mL of a 0.02 M potassium permanganate ($KMnO_4$) solution, which is deep purple in color. The soil and $KMnO_4$ were shaken for exactly 2 minutes to oxidize the active carbon in the sample. The purple color becomes lighter as a result of the oxidation reaction. The sample tube was then allowed to settle for 8 minutes, pipetted into a second tube, and diluted with distilled water. Absorbance was measured at 550 nm. The absorbance of a standard dilution series of the $KMnO_4$ was measured to create a calibration curve for interpreting the sample absorbance data. A formula was used to convert sample absorbance value to active carbon units of mg carbon per kg of soil (assay as published by Cornell University at https://blogs.cornell.edu/healthvsoil/files/2016/12/011_ActiveCarbon040517-llinulc.pdf).

Dry soil aggregate size distribution was analyzed through use of a stacked sieve assay with each level of sieve containing a different sized mesh screen. A dry soil sample of approximately 50 g (exact weight obtained) was poured through a 4 mm sieve. Soil that passed through that sieve was then added to the top sieve pan in a set of 5 stacked pans, with each layer of the stack having progressively smaller screens and the bottom pan being a collection pan (5 layers: 2 mm sieve, 1 mm sieve, 0.5 mm sieve, 0.25 mm sieve, and catch pan). The stack of sieves was then shaken on an orbital shaker for 5 minutes. Larger aggregates were caught in the higher sieves with only dust passing through to the bottom catch pan. The amount of material caught on each sieve level was then weighed and a simple calculation used to determine the percent of total soil content, represented by each aggregate size.

Figure 4:
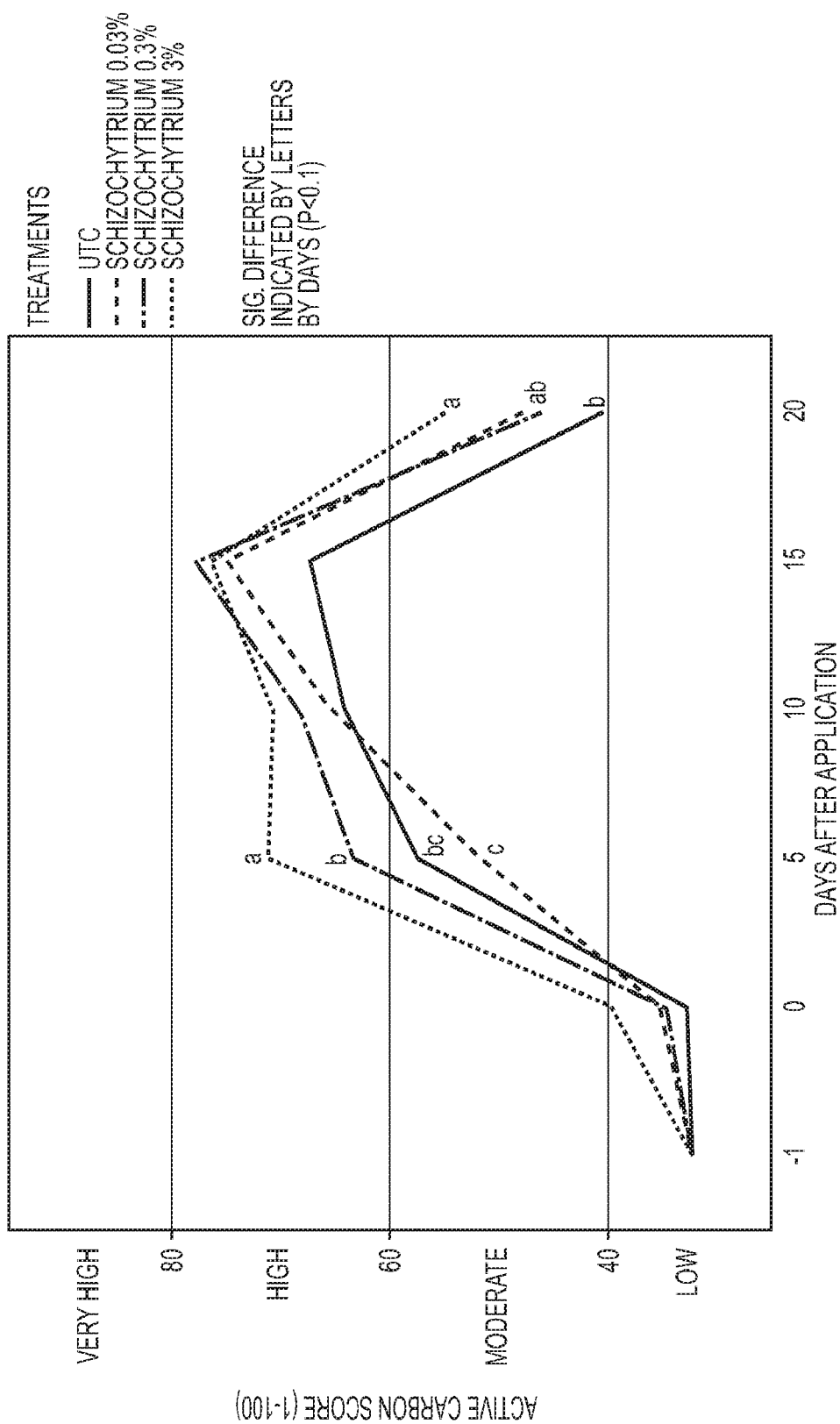
FIG. 4 depicts results of an experiment analyzing the effect of *Schizochytrium* compositions on soil active carbon score.
Figure 5:
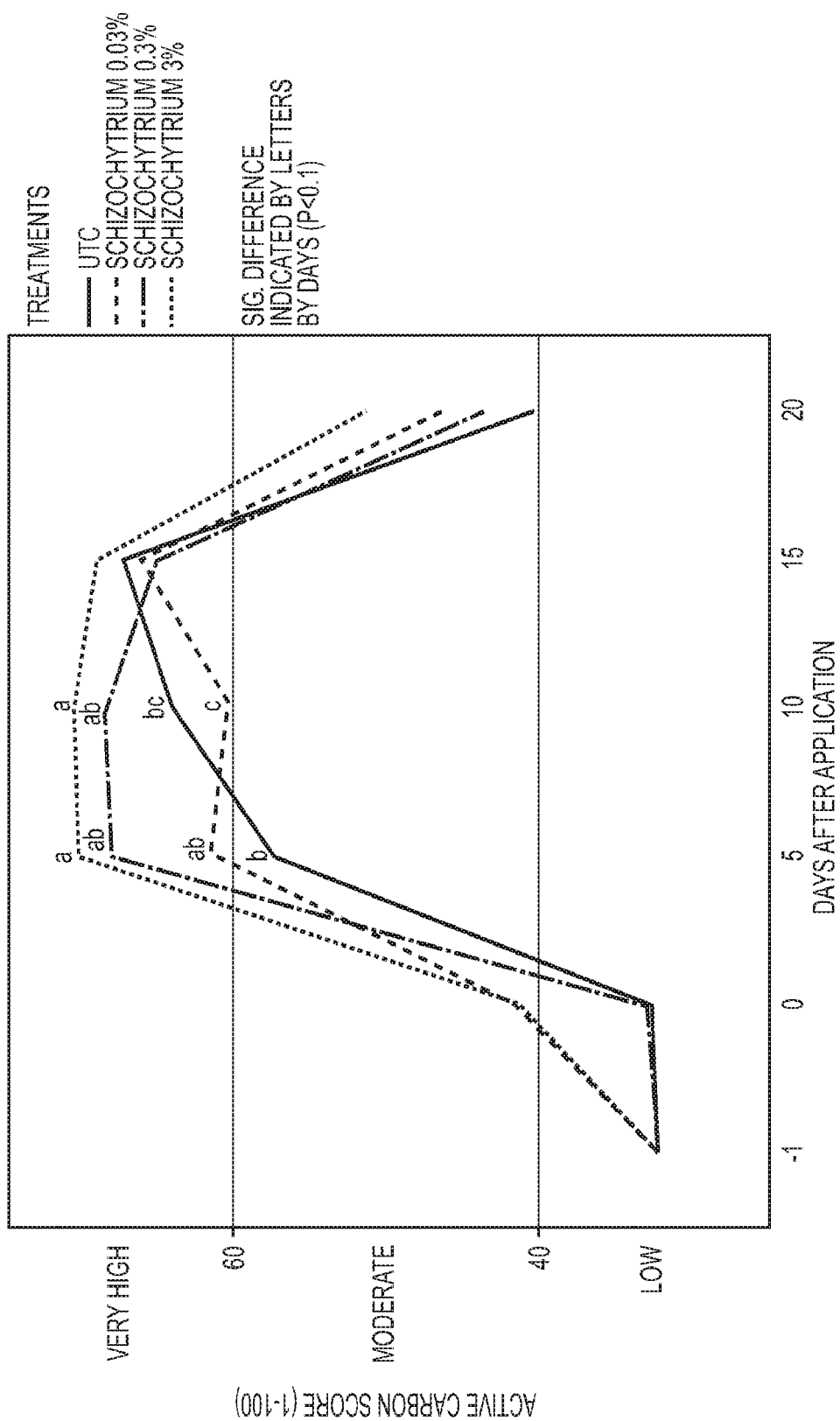
FIG. 5 depicts results of an experiment analyzing the effect of *Schizochytrium* compositions on soil active carbon score.
Figure 6:
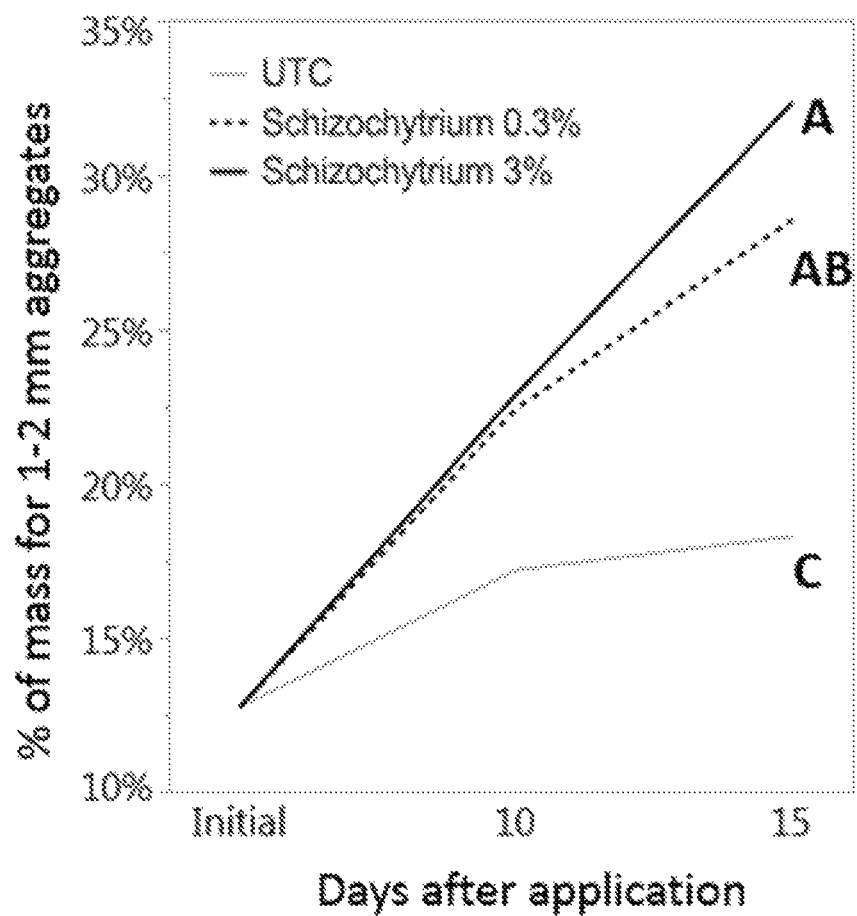
FIG. 6 depicts results of an experiment analyzing the effects of *Schizochytrium* compositions on soil aggregation.
Figure 7:
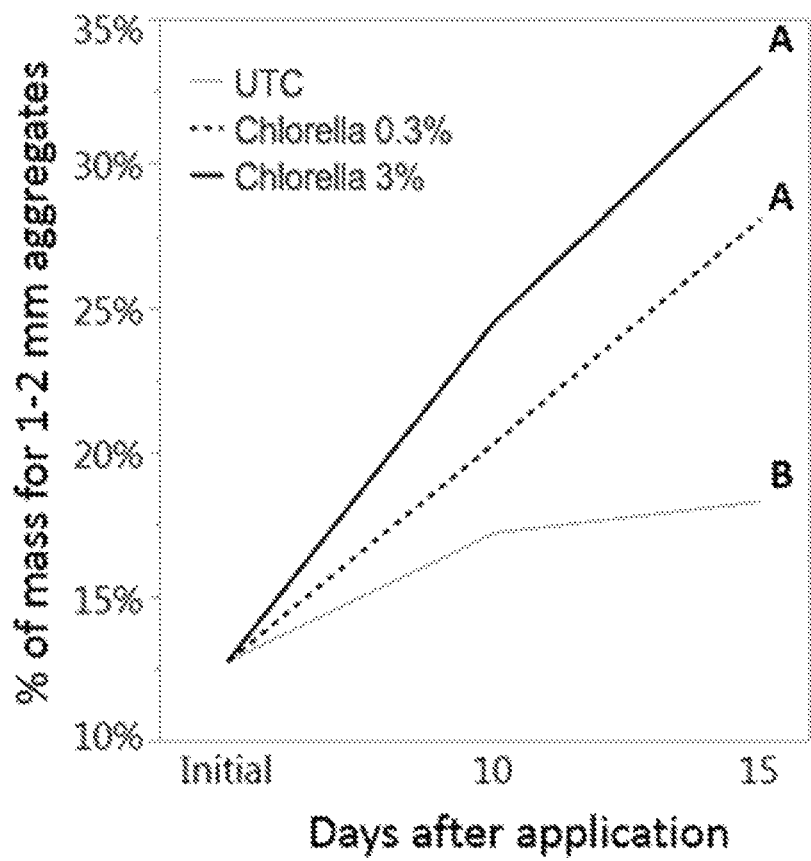
FIG. 7 depicts results of an experiment analyzing the effects of *Chlorella* on soil aggregation.

Results of active carbon assays for *Schizochytrium*-based compositions are shown in FIGS. 4 and 5 and Table 75. Results of active carbon assays for *Chlorella*-based compositions are shown in Table 75. Results of dry soil aggregate size distribution for *Schizochytrium*-based compositions are shown in FIG. 6 and Table 76. Results of dry soil aggregate size distribution for *Chlorella*-based compositions are shown in FIG. 7 and Table 76.

TABLE 75

| | Active Carbon Score | | | | | |
|---|---|---|---|---|---|---|
| Treatment | Initial Sample (−1 days) | Immediately after application (0 days) | Day 5 | Day 10 | Day 15 | Day 20 |
| *Schizochytrium*, 3% | 32 | 39 | 73 | 71 | 76 | 56 |
| *Schizochytrium*, 0.3% | 32 | 35 | 64 | 68 | 77 | 47 |
| *Schizochytrium*, 0.03% | 32 | 35 | 52 | 65 | 74 | 48 |
| *Chlorella*, 3% | 32 | 42 | 70 | 70.5 | 69 | 52 |
| *Chlorella*, 0.3% | 32 | 33 | 68 | 68.5 | 65 | 44 |
| *Chlorella*, 0.03% | 32 | 41 | 62 | 61 | 66 | 47 |
| UTC | 32 | 33 | 57 | 64 | 66 | 40 |

TABLE 76

| | % of Mass for 1-2 mm Aggregates | | |
|---|---|---|---|
| Treatment | Initial | Day 10 | Day 15 |
| *Schizochytrium*, 3% | 13 | 23 | 32.5 |
| *Schizochytrium*, 0.3% | 13 | 22.5 | 28 |
| *Chlorella*, 3% | 13 | 24 | 33 |
| *Chlorella*, 0.3% | 13 | 20 | 28 |
| UTC | 13 | 17 | 18 |

As shown in FIGS. 4, 5, and Table 75, the *Schizochytrium*- and *Chlorella*-based compositions with the highest concentrations of 3% demonstrated a statistically significant increase in active carbon over untreated control. After a single application of both the *Schizochytrium*- and *Chlorella*-based compositions, active carbon in the soil increased from a score falling in the 'low' health range to the 'high' health range. The 'high' range score was maintained by both microalgae compositions at the highest concentration (3%) for approximately 10 days. The rate of increase in active carbon followed a dose-dependent pattern, with the compositions at 3% showing the fastest score increases, followed by the 0.3% composition and finally by the 0.03% composition. While water alone also increased the active carbon level over time, it did not do so as quickly as the algae compositions at 0.3% and 3% concentrations, nor did it reach the same peak active carbon score of any of the *Schizochytrium*-based compositions. In addition, water alone failed to maintain an active carbon score in the 'high' range for as long as either the 3% or 0.3% *Schizochytrium*- based compositions and was outperformed by all *Chlorella*-based compositions in this regard.

As shown in FIGS. 6, 7 and Table 76, both *Schizochytrium*- and *Chlorella*-based compositions at both 0.3% and 3% demonstrated statistically significant increases in the percent (by mass) of the desirable dry soil aggregate size 1-2 mm over untreated control. The percent mass of dry soil aggregates of 1-2 mm increased for 15 days after algae-based compositions were applied. The algae-based compositions at a concentration of 3% more than doubled the percent mass of dry soil aggregates of 1-2 mm over the course of the 15-day study.

Example 45

Field trial experiments were conducted on sweet corn, snap peas, and snap beans to evaluate the effects of *Schizochytrium*- and *Chlorella*-based compositions on soil microbial communities.

Sweet corn, snap beans, and snap peas were transplanted in adjacent fields in Paynesville, Minn. All plots were managed according to grower standard practice (see Table 77). Soil from treated and untreated plots was collected from the root zone of each plot during harvest and evaluated for bacterial community changes and bacterial community structure using next-generation Illumina MiSeq™ sequencing. Sequences were analyzed using the QIHvIE-2 software package; DADA2 pipeline for sequence variant annotation. Beta-diversity using PERMANOVA of unweighted unifrac distances. Differential abundance of sequence variants using the QIIJVIE-1 implementation of the DESeq2 algorithm as well as the QIIJ\IE-1 "group-significance.py" script. Sequence variants showing significant differential abundance were analyzed for further phylogenetic placement with a bootstrapped neighbor joining tree of curated 16S sequences and an outgroup of *Aquifex aeolicus*.

TABLE 77

STUDY PARAMETERS

| Crop & variety | Sweet corn, Temptation | Snap bean, Provider | Snap pea, Sugar Sprint |
|---|---|---|---|
| Location | Crow River Research Farm, Paynesville MN | | |
| Transplanting date | Jun. 24, 2016 | Jun. 25, 2016 | Jun. 23, 2016 |
| Harvest dates | Sep. 11, 2016 | Sep. 8, 2016 | Aug. 25, 2016 |
| Planting density | 34,800 plants/A | 8,800 plants/A | 8,600 plants/A |
| Irrigation | Via pivot as needed | | |
| Fertilizer at planting | 120 lbs/A Urea | | 80 lbs/A Urea |
| | 30 lbs/AK, 30 lbs/AP, lib/A Zn, lib/AB | | |
| Soil type | Estherville sandy loam, silt loam | | |
| Plot size | 5' W × 20' L | | |
| Replication | 8 plots per treatment, RCB design | | |
| Product applied via temporary drip at planting: | then every 2 wks (6 total) | | then every 2 wks (5 total) |

Figure 8:
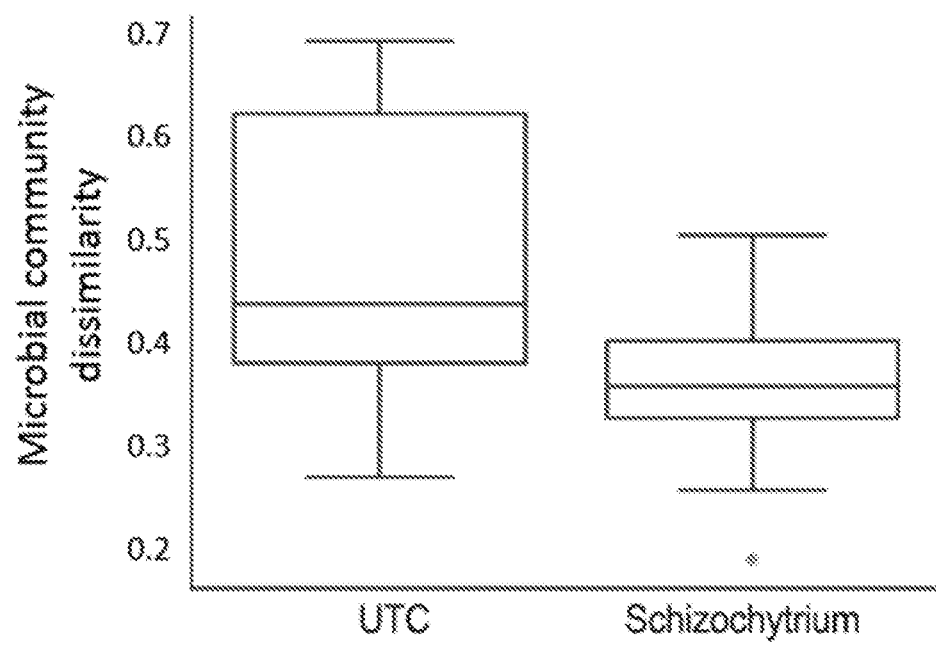
FIG. 8 depicts the results of an experiment analyzing the effects of *Schizochytrium* compositions on soil microbial communities.
Figure 9:
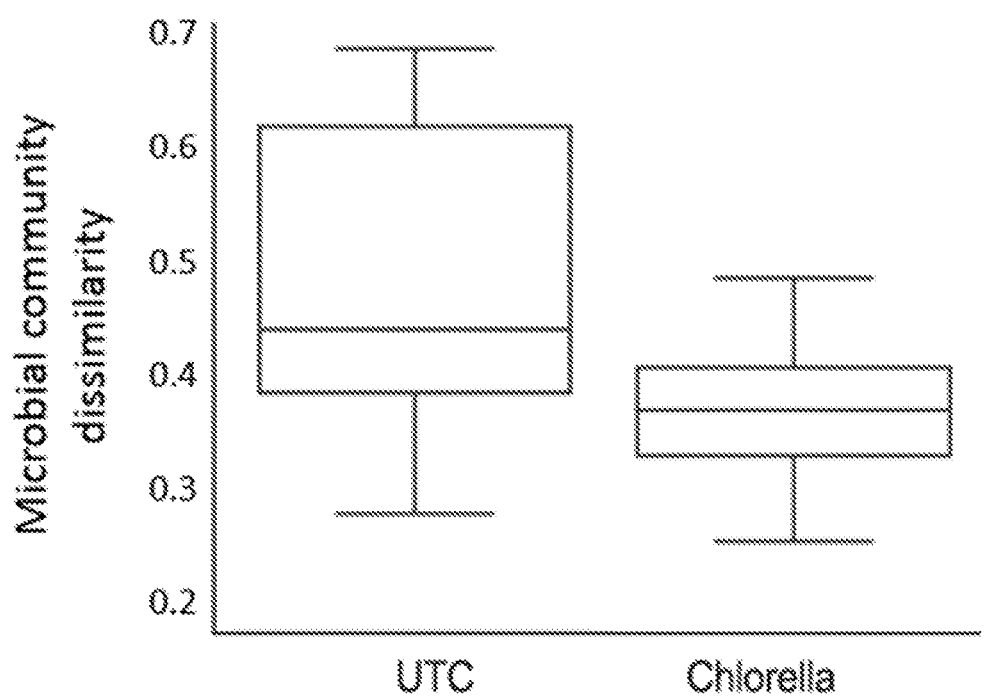
FIG. 9 depicts the results of an experiment analyzing the effects of *Chlorella* compositions on soil microbial communities.
Figure 10:
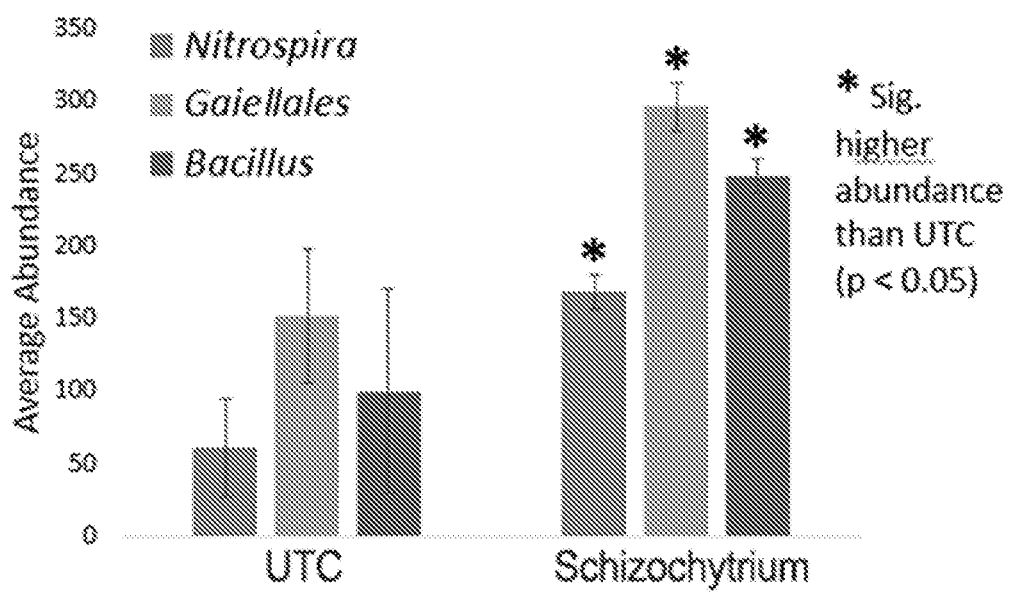
FIG. 10 depicts the results of an experiment analyzing the effects of *Schizochytrium* compositions on the beneficial soil bacteria *Nitrospira, Gaiellales*, and *Bacillus*.
Figure 11:
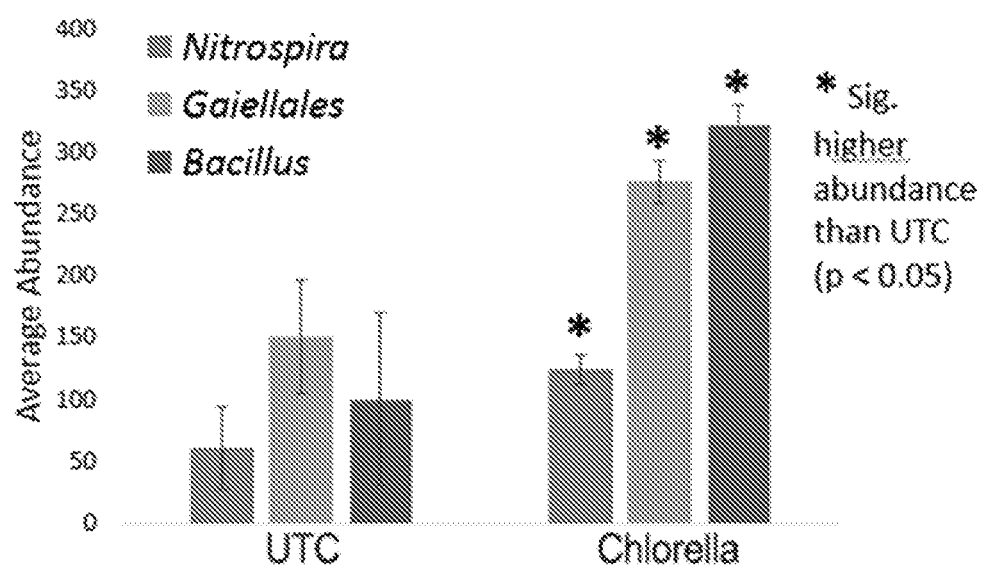
FIG. 11 depicts the results of an experiment analyzing the effects of *Chlorella* compositions on the beneficial soil bacteria *Nitrospira, Gaiellales*, and *Bacillus*.

Results of soil community similarity analysis are shown as dissimilarity plots in FIGS. 8 and 9. Results from the analysis of levels of beneficial soil bacteria are shown in FIGS. 10 and 11.

Results show that both *Schizochytrium*- and *Chlorella*-based compositions standardized the bacterial community and increased the population of specific bacterial populations known to be beneficial to plants. Community dissimilarity analysis performed across all crops and all application rates showed that both *Schizochytrium*- and *Chlorella*-based compositions increased similarity among plots compared to control (FIGS. 5-6). In addition, both *Schizochytrium*- and *Chlorella*-based compositions demonstrated at least a 2-fold increase in abundances of two bacteria known to be beneficial to plants: *Bacillus*, a plant growth promoter and *Nitrospira*, a complete nitrifier (FIGS. 7-8). Phylogenetic analysis placed the unknown *Bacillus* sp. as *B. megaterium* (99%—425 bp amplicon). This strain is commonly used as a direct additive in microbial plant products to improve plant performance. A third rhizosphere-associated bacterium, *Gaiellales* also increased in dominance.

It will be apparent to one skilled in the art that various substitutions and modifications can be made to the invention disclosed herein without departing from the scope and spirit of the invention.

Those skilled in the art recognize that the aspects and embodiments of the invention set forth herein can be practiced separate from each other or in conjunction with each other. Therefore, combinations of separate embodiments are within the scope of the invention as disclosed herein.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). All provided ranges of values are intended to include the end points of the ranges, as well as values between the end points.

The description herein of any aspect or embodiment of the invention using terms such as "comprising", "having," "including," or "containing" with reference to an element or elements is intended to provide support for a similar aspect or embodiment of the invention that "consists of," consists essentially of, or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims and/or aspects appended hereto as permitted by applicable law.

What is claimed is:

1. A method of enhancing the active carbon score of a soil, comprising administering an amount of a microalgae material to the soil,
wherein the amount of microalgae material is effective to increase the active carbon score of the soil by at least 10% over a period of 10-15 days;
the microalgae material comprises *Chlorella* cells and/or *Parachlorella kessleri* cells that have been lysed; and
the microalgae material is provided as a liquid formulation composition comprising 0.1-15% solids from one or more cultures of the microalgae that is applied in a concentration of 0.25 gal/acre to 4 gal/acre for a period of 8-20 weeks.

2. The method of claim 1, wherein the amount of solids in the composition is in the range of 1-15%.

3. The method of claim 2, wherein the amount of solids in the composition is in the range of 5-12.5%.

4. The method of claim 1, wherein the microalgae material comprises lysed *Chlorella* cells.

5. The method of claim 1, wherein the microalgae material comprises lysed *Parachlorella kessleri* cells.

6. The method of claim 1, wherein the microalgae material comprises excreted products.

7. The method of claim 6, wherein the excreted products are excreted polysaccharides (EPS).

8. The method of claim 1, wherein a single application of microalgae material is made to the soil.

9. The method of claim 1, wherein multiple applications of microalgae material are made to the soil.

10. The method of claim 1, wherein the microalgae material is administered to soil associated with a plant.

11. The method of claim 1, wherein the microalgae material is administered by irrigation into the soil in-furrow, via drip irrigation, and/or with a broadcast application.

12. A method of enhancing the active carbon score of a soil, comprising administering an amount of a microalgae material to soil associated with a plant,
wherein the amount of microalgae material is effective to increase the active carbon score of the soil by at least 10% over a period of 10-15 days;
the microalgae material comprises *Chlorella* cells and/or *Parachlorella kessleri* cells that have been lysed; and
the microalgae material is administered at a concentration of microalgae biomass in the range of 0.001% to 0.1% by weight.

13. The method of claim 12, wherein the microalgae material comprises lysed *Chlorella* cells.

14. The method of claim 12, wherein the microalgae material comprises lysed *Parachlorella kessleri* cells.

15. The method of claim 12, wherein the microalgae material comprises excreted products.

16. The method of claim 15, wherein the excreted products are excreted polysaccharides (EPS).

17. The method of claim 12, wherein a single application of microalgae material is made to the soil.

18. The method of claim 12, wherein multiple applications of microalgae material are made to the soil.

19. The method of claim 12, wherein the microalgae material is administered to soil associated with a plant.

20. The method of claim 12, wherein the microalgae material is administered by irrigation into the soil in-furrow, via drip irrigation, and/or with a broadcast application.

* * * * *